US008329667B2

(12) United States Patent
Christiano

(10) Patent No.: US 8,329,667 B2
(45) Date of Patent: Dec. 11, 2012

(54) INHIBITION OF HAIRLESS PROTEIN MRNA

(75) Inventor: Angela M. Christiano, Upper Saddle River, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 26 days.

(21) Appl. No.: 11/333,748

(22) Filed: Jan. 17, 2006

(65) Prior Publication Data

US 2007/0269395 A1 Nov. 22, 2007

Related U.S. Application Data

(63) Continuation of application No. 11/113,423, filed on Apr. 22, 2005, now abandoned.

(60) Provisional application No. 60/565,127, filed on Apr. 23, 2004.

(51) Int. Cl.
A61K 48/00 (2006.01)
C07H 21/02 (2006.01)
C07H 21/04 (2006.01)
C12N 15/85 (2006.01)

(52) U.S. Cl. ......... 514/44; 536/23.1; 536/24.5; 435/325

(58) Field of Classification Search .................. None
See application file for complete search history.

(56) References Cited

U.S. PATENT DOCUMENTS

| 5,160,328 | A | 11/1992 | Cartmell |
| 5,230,896 | A | 7/1993 | Yeh |
| 5,254,346 | A | 10/1993 | Tucker |
| 5,260,066 | A | 11/1993 | Wood |
| 5,334,711 | A | 8/1994 | Sproat |
| 5,627,053 | A | 5/1997 | Usman |
| 5,667,798 | A | 9/1997 | Royds |
| 5,672,695 | A | 9/1997 | Eckstein |
| 5,714,162 | A | 2/1998 | Muller |
| 5,716,824 | A | 2/1998 | Beigelman |
| 5,804,683 | A | 9/1998 | Usman |
| 5,831,071 | A | 11/1998 | Usman |
| 5,854,038 | A | 12/1998 | Sullenger |
| 5,914,126 | A | 6/1999 | Li |
| 5,998,203 | A | 12/1999 | Matulic-Adamic |
| 6,001,311 | A | 12/1999 | Brennan |
| 6,008,400 | A | 12/1999 | Scaringe |
| 6,080,127 | A | 6/2000 | Li |
| 6,087,341 | A | 7/2000 | Khavari |
| 6,111,086 | A | 8/2000 | Scaringe |
| 6,117,657 | A | 9/2000 | Usman |
| 6,248,878 | B1 | 6/2001 | Matulic-Adamic |
| 6,300,074 | B1 | 10/2001 | Gold |
| 6,348,348 | B1 | 2/2002 | Thompson |
| 6,353,098 | B1 | 3/2002 | Usman |
| 6,362,323 | B1 | 3/2002 | Usman |
| 6,437,117 | B1 | 8/2002 | Usman |
| 6,469,158 | B1 | 10/2002 | Usman |
| 6,506,559 | B1 * | 1/2003 | Fire et al. ............ 435/6 |
| 6,989,442 | B2 | 1/2006 | Vargeese |
| 2004/0086945 | A1 * | 5/2004 | Sreekrishna et al. ......... 435/7.1 |
| 2005/0054598 | A1 * | 3/2005 | McSwiggen .................. 514/44 |

FOREIGN PATENT DOCUMENTS

| WO | WO 89/02439 | 3/1989 |
| WO | WO 91/01362 | 2/1991 |
| WO | WO 92/07065 | 4/1992 |
| WO | WO 93/15187 | 8/1993 |
| WO | WO 93/23569 | 11/1993 |
| WO | WO 95/06731 | 3/1995 |
| WO | WO 95/11910 | 5/1995 |
| WO | WO 97/26270 | 7/1997 |
| WO | WO 98/13526 | 4/1998 |
| WO | WO 99/07409 | 2/1999 |
| WO | WO 99/14226 | 3/1999 |
| WO | WO 99/32619 | 7/1999 |
| WO | WO 99/38965 | 8/1999 |
| WO | WO 99/49029 | 9/1999 |
| WO | WO 99/53050 | 10/1999 |
| WO | WO 99/54459 | 10/1999 |
| WO | WO 00/01846 | 1/2000 |
| WO | WO 00/44895 | 4/2000 |
| WO | WO 00/44914 | 8/2000 |
| WO | WO 00/63364 | 10/2000 |
| WO | WO 00/66604 | 11/2000 |
| WO | WO 01/04313 | 1/2001 |
| WO | WO 01/29058 | 4/2001 |
| WO | WO 01/36646 | 5/2001 |
| WO | WO 01/38551 | 5/2001 |
| WO | WO 01/42443 | 6/2001 |
| WO | WO 01/49844 | 7/2001 |
| WO | WO 01/53475 | 7/2001 |
| WO | WO 01/68836 | 9/2001 |
| WO | WO 01/70944 | 9/2001 |
| WO | WO 01/70949 | 9/2001 |
| WO | WO 01/72774 | 10/2001 |

(Continued)

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Bertrand et al. (Biochemical and Biophysical Research Communications, 2002, 296, pp. 1000-1004).*
U.S. Appl. No. 60/311,865, Vargeese.
U.S. Appl. No. 60/082,404, filed Apr. 20, 1998, Thompson.
GenBank Accession No. NM_005144.3 4981 by mRNA linear Definition: *Homo sapiens* hairless homolog (mouse) (HR), transcript variant 1.

(Continued)

*Primary Examiner* — Amy Bowman
(74) *Attorney, Agent, or Firm* — Baker Botts L.L.P.

(57) ABSTRACT

Methods for inhibition of hairless protein mRNA using RNA interference is described, in particular methods for hair removal. Also described are nucleic acid constructs for RNAi-mediated inhibition of hairless protein mRNA and compositions including such constructs.

37 Claims, 4 Drawing Sheets

FOREIGN PATENT DOCUMENTS

| | | |
|---|---|---|
| WO | WO 01/75164 | 10/2001 |
| WO | WO 01/92513 | 12/2001 |
| WO | WO 02/38805 | 5/2002 |
| WO | WO 02/44321 | 6/2002 |
| WO | WO 02/055692 | 7/2002 |
| WO | WO 02/055693 | 7/2002 |
| WO | WO 02/083891 | 10/2002 |
| WO | WO 03/070918 | 8/2003 |
| WO | WO 03/074654 | 9/2003 |
| WO | WO 2005/045036 | 5/2005 |

OTHER PUBLICATIONS

GenBank Accession No. NM_005144. 5699 by mRNA linear Definition: *Homo sapiens* hairless homolog (mouse) transcript variant 1, mRNA.

GenBank Accession No. NM_021877. Definition: *Mus musculus* hairless (Hr), mRNA.

GenBank Accession No. 024364. Definition: *Rattus norvegicus* hairless homolog (mouse) (hr), mRNA.

GenBank Accession No. AY130969. Definition: *Ovis aries* hairless mRNA, partial cds.

GenBank Accession No. AY279972. Definition: *Sus scrofa* hairless mRNA, partial cds.

GenBank Accession No. AF361864. Definition: *Macaca mulatta* hairless mRNA, complete cds.

Beaucage and Iyer. 1993. The functionalization of oligonucleotides via phosphoramidite derivative. Tetrahedron 49:1925-63.

Beigelman et al. 1995. Chemical modification of hammerhead ribozymes. Catalytic activity and nuclease resistance. J. Biol. Chem. 27:25702-8.

Bellon et al. 1997. Amino linked ribozymes: post-synthetic conjugation of half-ribozymes. Nucleosides & Nucleotides. 16:951-54.

Bellon et al. 1997. Post-synthetically ligated ribozymes: an alternative approach to iterative solid-phase synthesis. Bioconjug. Chem. 8:204-12.

Bergeron et al. 2003. Ribozyme-based gene-inactivation systems require a fine comprehension of their substrate specificities; the case of delta ribozyme. Curr. Med. Chem. 10:2589-97.

Bernard et al. 1997. Importance of sebaceous glands in cutaneous penetration of an antiandrogen: target effect of liposomes. J. Pharm. Sci. 86:573-8.

Bernstein et al. 2001. Role for a bidentate ribonuclease in the initiation step of RNA interference. Nature 409:363-6.

Branch. 1998. A good antisense molecule is hard to find. Trends Biochem. Sci. 23:45-50.

Brennan et al. 1998. Two-dimensional parallel array technology as a new approach to automated combinatorial solid-phase organic synthesis. Biotechnol. Bioeng. 61:33-45.

Brody and Gold. 2000. Aptamers as therapeutic and diagnostic agents. J. Biotechnol. 74:5-13.

Burgin et al. 1996. Chemically modified hammerhead ribozymes with improved catalytic rates. Biochemistry. 35:14090-7.

Burlina et al. 1997. Chemical engineering of RNase resistant and catalytically active hammerhead ribozymes. Bioorg. Med. Chem. 5:1999-2010.

Caplen. 2000. dsRNA-mediated gene silencing in cultured *Drosophila* cells: a tissue culture model for the analysis of RNA interference. Gene. 252:95-105.

Caruthers et al. 1992. Chemical synthesis of deoxyoligonucleotides and deoxyoligonucleotide analogs. Meth. Enzymol. 211:3-19.

Cload and Schepartz. 1991. Polyether tethered oligonucleotide probes. J. Am. Chem. Soc. 113:6324-6326.

Cserhalmi-Friedman et al. 2004. Recapitulation of the hairless phenotype using catalytic oligonucleotides: implications for permanent hair removal. Exp. Dermatol. 13:255-263.

De Oliveira et al. 1998. pH-sensitive liposomes as a carrier for oligonucleotides: a physico-chemical study of the interaction between DOPE and a 15-mer oligonucleotide in quasi-anhydrous samples. Biochim. Biophys. Acta 1372:301-10.

Durand et al. 1990. Circular dichroism studies of an oligodeoxyribonucleotide containing a hairpin loop made of a hexaethylene glycol chain: conformation and stability. Nucleic Acids Res. 18:6353-9.

Earnshaw and Gait. 1998. Modified oligoribonucleotides as site-specific probes of RNA structure and function. Biopolymers (Nucleic Acid Sciences). 48:39-55.

Elbashir et al. 2001. Duplexes of 21-nucleotide RNAs mediate RNA interference in cultured mammalian cells. Nature 411:494-8.

Elbashir et al. 2001. RNA interference is mediated by 21- and 22-nucleotide RNAs. Genes Dev. 15:188-200.

Elbashir et al. 2001. Functional anatomy of siRNAs for mediating efficient RNAi in *Drosophila melanogaster* embryo lysate. EMBO J. 20:6877-88.

Ferentz and Verdine. 1991. Disulfide cross-linked oligonucleotides. J. Am. Chem. Soc. 113:4000.

Fire et al. 1998. Potent and specific genetic interference by double-stranded RNA in *Caenorhabditis elegans*. Nature 391:806-11.

Fire. 1999. RNA-triggered gene silencing. Trends Genet. 15:358-63.

Gold et al. 1995. Diversity of oligonucleotide functions. Annu. Rev. Biochem. 64:763-97.

Hammond et al. 2000. An RNA-directed nuclease mediates post-transcriptional gene silencing in *Drosophila* cells. Nature Mar. 16;404(6775):293-6.

Hardy. 1992. The secret life of the hair follicle. Trends Genet. 8:55-61.

Hermann and Patel. 2000. Adaptive recognition by nucleic acid aptamers. Science 287:820-5.

Hudson et al. 1999. Cellular delivery of hammerhead ribozymes conjugated to a transferrin receptor antibody. Int. J. Phann. 182:49-58.

Hughes et al. 2000. In vitro transport and delivery of antisense oligonucleotides. Meth. Enzymol. 313:342-58.

Hunziker and Leumann. 1995. Nucleic acid analogues: synthesis and properties. In *Modern Synthetic Methods*, VCH, 331-417.

Hutvagner et al. 2001. A cellular function for the RNA-interference enzyme Dicer in the maturation of the let-7 small temporal RNA. Science. 293:834-8. Epub Jul. 12, 2001.

Irvine et al. 1996. An autosomal dominant syndrome of acromegaloid facial appearance and generalised hypertrichosis terminalis. J. Med. Genet. 33:972-4.

Jaschke et al. 1993. Automated incorporation of polyethylene glycol into synthetic oligonucleotides. Tetrahedron Lett. 34:301-304.

Jayasena. 1999. Aptamers: an emerging class of molecules that rival antibodies in diagnostics. Clin. Chem. 45:1628-50.

Jen et al. 2000. Suppression of gene expression by targeted disruption of messenger RNA: available options and current strategies. Stem Cells 18:307-319.

Karande et al. 2004. Discovery of transdermal penetration enhancers by high-throughput screening. Nat. Biotechnol. 22:192-7. Epub Jan. 4, 2004.

Karpeisky et al. 1998. Highly efficient synthesis of 2'-O-amino nucleosides and their incorporation in hammerhead ribozymes. Tetrahedron Lett. 39:1131-34.

Kashani-Sabet. 2004. Non-viral delivery of ribozymes for cancer gene therapy. Expert Opin. Biol. Ther. 4:1749-55.

Kusser. 2000. Chemically modified nucleic acid aptamers for in vitro selections: evolving evolution. J. Biotechnol. 74:27-38.

Lewis et al. 1998. Development of a sustained-release biodegradable polymer delivery system for site-specific delivery of oligonucleotides: characterization of P(LA-GA) copolymer microspheres in vitro. J. Drug Target. 5:291-302.

Li et al. 1992. Product-delivering liposomes specifically target hair follicles in histocultured intact skin. In Vitro Cell. Dev. Biol. 28A:679-81.

Lieb et al. 1992. Topical delivery enhancement with multilamellar liposomes into pilosebaceous units: I. In vitro evaluation using fluorescent techniques with the hamster ear model. J. Invest. Dermatol. 99:108-13.

Limbach et al. 1994. Summary: the modified nucleosides of RNA. Nucleic Acids Res. 22):2183-96.

Lin and Matteucci. 1998. A cytosine analogue capable of claim-like binding to a guanine in helical nucleic acids. J. Am. Chem. Soc., 120:8531-8532.

Liu and Saint. 2002. A new quantitative method of real time reverse transcription polymerase chain reaction assay based on simulation of polymerase chain reaction kinetics. Anal. Biochem. 302:52-59.

Ma et al. 1993. Design and synthesis of RNA miniduplexes via a synthetic linker approach. 2. Generation of covalently closed, double-stranded cyclic HIV-1 TAR RNA analogs with high Tat-binding affinity. Nucleic Acids Res. 21:2585-9.

Ma et al. 1993. Design and synthesis of RNA miniduplexes via a synthetic linker approach. Biochemistry. 32:1751-8.

McCurdy et al. 1991. Deoxyoligonucleotides with inverted polarity: synthesis and use in triple-helix formation. Nucleosides & Nucleotides. 10:287-290.

Mesmaeker et al. 1994. Novel backbone replacements for oligonucleotides, In *Carbohydrate Modifications in Antisense Research,* Am. Chem. Soc. 24-39.

Moore and Sharp. 1992. Site-specific modification of pre-mRNA: the 2'-hydroxyl groups at the splice sites. Science. 256:992-7.

Mullins. 1996. Perspective Series: Molecular medicine in genetically engineered animals. J. Clin. Invest. 98 (Supplement):S37-S40.

Nykanen et al. 2001. ATP requirements and small interfering RNA structure in the RNA interference pathway. Cell. 107:309-21.

Ono et al. 1991. DNA triplex formation of oligonucleotide analogues consisting of linker groups and octamer segments that have opposite sugar-phosphate backbone polarities. Biochemistry. 30:9914-2.

Panteleyev et al. 2000. Patterns of hairless (hr) gene expression in mouse hair follicle morphogenesis and cycling. Am. J. Pathol. 157:1071-9.

Panteleyev et al. 1998. Molecular and functional aspects of the hairless (hr) gene in laboratory rodents and humans. Exp. Dermatol. 7:249-67.

Parrish et al. 2000. Functional anatomy of a dsRNA trigger: differential requirement for the two trigger strands in RNA interference. Mol. Cell 6:1077-87.

Perreault et al. 1990. Mixed deoxyribo- and ribo-oligonucleotides with catalytic activity. Nature 344:565-7.

Pieken et al. 1991. Kinetic characterization of ribonuclease-resistant 2'-modified hammerhead ribozymes. Science 253:314-7.

Remington. 1995. The Science and Practice of Pharmacy, 19th Ed. (Easton, Pa.: Mack Publishing Co.), pp. 1399-1404.

Richardson and Schepartz. 1991. Tethered oligonucleotide probes. A strategy for the recognition of structured RNA. J. Am. Chem. Soc. 113:5109.

Rosenquist and Martin. 1996. Fibroblast growth factor signalling in the hair growth cycle: expression of the fibroblast growth factor receptor and ligand genes in the murine hair follicle. Dev. Dyn. 205:379-86.

Saenger. 1984. Principles of Nucleic Acid Structure Springer-Verlag NY. (TOC Only).

Scaringe et al. 1990. Chemical synthesis of biologically active oligoribonucleotides using beta-cyanoethyl protected ribonucleoside phosphoramidites. Nucleic Acids Res. 18:5433-41.

Seela and Kaiser. 1987. Oligodeoxyribonucleotides containing 1,3-propanediol as nucleoside substitute. Nucleic Acids Res. 15:3113-29.

Segre et al. 1995. Positional cloning of the nude locus: genetic, physical, and transcription maps of the region and mutations in the mouse and rat. Genomics 28: 549-559.

Shabarova et al. 1991. Chemical ligation of DNA: the first non-enzymatic assembly of a biologically active gene, Nucleic Acids Res. 19:4247-4251.

Sun. 2000. Technology evaluation: SELEX, Gilead Sciences Inc. Curr. Opin. Mo.1 Ther. 2:100-5.

Tuschl et al. 1999. Targeted mRNA degradation by double-stranded RNA in vitro. Genes Dev. 1999 13:3191-7.

Tuschl. 2001. RNA interference and small interfering RNAs. Chem. Biochem. 2001 2:239-45.

Uhlmann and Peyman. 1990. Antisense oligonucleotides: a new therapeutic principle. Chem. Revs. 90:544-584.

Usman et al. 1994. Chemical modification of hammerhead ribozymes: activity and nuclease resistance. Nucleic Acids Symp. Ser. 31:163.

Usman and Cedergren. 1992. Exploiting the chemical synthesis of RNA. Trends Biochem Sci. 17:334-9.

Usman et al. 1987. Automated chemical synthesis of long oligoribonucleotides using 2'-O-silylated ribonucleotide 3'-O-phosphoramidites on a controlled-pore glass support: Synthesis of a 43-nucleotide sequence similar to the 3' half molecule of an *E. coli* formylmethionine tRNA. J. Am. Chem. Soc. 109:7845-7854.

Verma and Eckstein. 1998. Modified oligonucleotides: synthesis and strategy for users. Annu. Rev. Biochem. 67:99-134.

Wall. 1996. Transgenic livestock: progress and prospects for the future. Theriogenology 45:57-68.

Wianny and Zernicka-Goetz. 2000. Specific interference with gene function by double-stranded RNA in early mouse development. Nat. Cell Biol. 2:70-5.

Wincott et al. 1995. Synthesis, deprotection, analysis and purification of RNA and ribozymes. Nucleic Acids Res. 23:2677-84.

Wincott and Usman. 1997. A practical method for the production of RNA and ribozymes. Methods Mol. Biol. 74:59-68.

Zamore et al. 2000. RNAi: double-stranded RNA directs the ATP-dependent cleavage of mRNA at 21 to 23 nucleotide intervals. Cell 101:25-33.

Zlotogorski et al. 2002. Clinical and molecular diagnostic criteria of congenital atrichia with papular lesions. J. Invest. Dermatol. 118:887-90.

U.S. Appl. No. 11/113,423, filed Apr. 22, 2005.

U.S. Appl. No. 11/113,423, filed Feb. 21, 2006 Notice of Abandonment.

Macron, 2008, "Former Sirna Derm head says technical hurdles hindered hair removal drug." *RNAi News.* Retrieved from the internet; URL: <www.genomeweb.com> on Feb. 20, 2010.

Carrnell, et al., 2003, "Germline transmission of RNAi in mice." *Nature Structural Biology* 10(2):91-92.

* cited by examiner

FIGURE 1

LOCUS       NM_005144    5699 bp    mRNA    linear    PRI 02-MAR-2005
DEFINITION  Homo sapiens hairless homolog (mouse) (HR), transcript variant 1, mRNA
ACCESSION   NM_005144

```
   1 tctcccggga gccactccca tgggcgcctc tccagcccct ggcctggaag caccaggaac
  61 cctggggatg gggcagaccc tcacagcccg gggtctggag ccggtgtcgg agctcatctg
 121 ggcccatgac ctctccagac atttggcaaa atcaaggccc ttagaccagg gacagaccca
 181 agcccaggcc ctcccagagg tcctaggacg caacccttg tgcccttggg ctctggaaga
 241 ggtttgggaa gggtttgggg tggaagatgg caaagagcag cttggccagg tgaggatgag
 301 gcagggcaga cacaggccag tggggcgtgc catgtgccac agatggagag gaccaggagc
 361 cagtggcccg gcaggcacag cccggttggc gtgggccaga gcgcccatca ctgacccgtg
 421 agaactcgac tgccccctgcc agctctggca ctgccccctt ccagccgccc cgccctagca
 481 ccctgggggg caccccgccc aaccgtggcc tggtccggcc cctcccgccc tttgctccag
 541 ttcccgggct tggcacctat agtggggtg ccgcccgcct gccaggctcc ggggccgggc
 601 ccacgggagg gtggggcggc tgggaagctg gcacgctgcc ccggggagc ctctctcggc
 661 aggcgcccgg gtgccgcggg gggaggggg aacaaagggc tcattctccc cgtgcgcagc
 721 cggtggcatc gccggggcgt tggcggaagc ccccggggcc cggggaggggg caggcccagg
 781 cgcggccgcc gaatcacggg ctcctgtttc ccgcagggtg ctggaggagg aaaccggcgg
 841 agcagcttcc ccactctcag ttgcgcttct ggcgatggcg atcagaggtc ctgctgcgct
 901 ctccgccgcg ctctacctcc attagccgcg ctgcgcggtg ctgcgccctc gccggtgcct
 961 ctctcctggg tcccaggatc ggccccacc atccaggcac gacccccttc cccggcccct
1021 cggcctttcc cccaactcgg ccatctccga cccggggcgc gtgttccccc cggcccggcg
1081 ccttctctcc ctccgggggc acccgctccc tagccccggc ccggccctcc ccgcggcgca
1141 gcacggagtc tcggcgtccc atggcgcaac ctacggcctc ggcccagaag ctggtgcggc
1201 cgatccgcgc cgtgtgccgc atcctgcaga tcccggagtc cgacccctcc aacctgcggc
1261 cctagagcgc ccccgccgcc ccggggaag gagagcgcga gcgcgctgag cagacagagc
1321 gggagaacgc gtcctcgccc gccggccggg aggccccgga gctggcccat ggggagcagg
1381 cgcccggtgc cggccacgac gaccgccacc gccgcgccg cgaccggccg gtgaagccca
1441 gggacccccc tctgggagag cccccatgagg gcaggagagt gatggagagt acgcccagct
1501 tcctgaaggg caccccaacc tgggagaaga cggcccccaga gaacggcatc gtgagacagg
1561 agcccggcag cccgcctcga gatggactgc accatgggcc gctgtgcctg ggagagcctg
1621 ctccctttg gagggcgtc ctgagcaccc cagactcctg gcttccccct ggcttccccc
1681 agggccccaa ggacatgctc ccacttgtgg agggcgaggg cccccagaat ggggagagga
1741 aggtcaactg gctggcagc aaagagggac tgcgctggaa ggaggccatg cttaccccatc
1801 cgctggcatt ctgcgggcca gcgtgcccac ctcgctgtgg ccccctgatg cctgagcata
1861 gtggtggcca tctcaagagt gaccctgtgg ccttccggcc ctggcactgc cttttccttc
1921 tggagaccaa gatcctggag cgagctccct tctgggtgcc cacctgcttg ccacccctacc
1981 tagtgtctgg cctgccccca gagcatccat gtgactggcc cctgaccccg caccctggg
2041 tatactccgg gggccagccc aaagtgccct ctgccttcag cttaggcagc aagggctttt
2101 actacaagga tccgagcatt cccaggttgg caaggagcc cttggcagct gcggaacctg
2161 ggttgtttgg cttaaactct ggtgggcacc tgcagagagc cggggaggcc gaacgccctt
2221 cactgcacca gagggatgga gagatgggag ctggccggca gcagaatcct tgcccgctct
2281 tcctgggca gccagacact gtgccctgga cctcctggcc cgcttgtccc ccaggccttg
2341 ttcatactct tggcaactc tgggctgggc caggcgatgg gaaccttggg taccagctgg
2401 ggccaccagc aacaccaagg tgcccctctc ctgagccgcc tgtcacccag cggggctgct
2461 gttcatccta cccacccact aaaggtgggg gtcttggccc ttgctggaag tgccaggagg
2521 gcctgagggg gggtgccagt ggagccagcg aacccagcga ggaagtgaac aaggcctctg
2581 gccccagggc ctgtcccccc agccaccaca ccaagctgaa gaagacatgg ctcacacggc
```

FIGURE 1 (cont)

```
2641 actcggagca gtttgaatgt ccacgcggct gccctgaggt cgaggagagg ccggttgctc
2701 ggctccgggc cctcaaaagg gcaggcagcc ccgaggtcca gggagcaatg ggcagtccag
2761 cccccaagcg gccaccggac ccttttccag gcactgcaga acaggggget ggggttggc
2821 aggaggtgcg ggacacatcg ataggaaca aggatgtgga ctcgggacag catgatgagc
2881 agaaaggacc ccaagatggc caggccagtc tccaggaccc gggacttcag gacataccat
2941 gcctggctct ccctgcaaaa ctggctcaat gccaaagttg tgcccaggca gctggagagg
3001 gaggagggca cgcctgccac tctcagcaag tgcggagatc gcctctggga ggggagctgc
3061 agcaggagga agacacagcc accaactcca gctctgagga aggcccaggg tccggccctg
3121 acagccggct cagcacaggc ctcgccaagc acctgctcag tggtttgggg gaccgactgt
3181 gccgcctgct gcggagggag cgggaggccc tggcttgggc ccagcgggaa ggccaagggc
3241 cagccgtgac agaggacagc ccaggcattc cacgctgctg cagccgttgc caccatggac
3301 tcttcaacac ccactggcga tgtccccgct gcagccaccg gctgtgtgtg gcctgtggtc
3361 gtgtggcagg cactgggcgg gccagggaga aagcaggctt tcagagcag tccgcggagg
3421 agtgcacgca ggaggccggg cacgctgcct gttccctgat gctgacccag tttgtctcca
3481 gccaggcttt ggcagagctg agcactgcaa tgcaccaggt ctgggtcaag tttgatatcc
3541 gggggcactg cccctgccaa gctgatgccc gggtatgggc cccggggat gcaggccagc
3601 agaaggaatc aacacagaaa acgccccaa ctccacaacc ttcctgcaat ggcgacaccc
3661 acaggaccaa gagcatcaaa gaggagaccc ccgattccgc tgagacccca gcagaggacc
3721 gtgctggccg agggcccctg ccttgtcctt ctctctgcga actgctggct tctaccgcgg
3781 tcaaactctg cttgggccat gagcgaatac acatggcctt cgccccgtc actccggccc
3841 tgcccagtga tgaccgcatc accaacatcc tggacagcat tatcgcacag gtggtggaac
3901 ggaagatcca ggagaaagcc ctggggccgg ggcttcgagc tggcccgggt ctgcgcaagg
3961 gcctgggcct gcccctctct ccagtgcggc cccggctgcc tcccccaggg gctttgctgt
4021 ggctgcagga gccccagcct tgccctcggc gtggcttcca cctcttccag gagcactgga
4081 ggcagggcca gcctgtgttg gtgtcaggga tccaaaggac attgcagggc aacctgtggg
4141 ggacagaagc tcttggggca cttggaggcc aggtgcaggc gctgagcccc ctcggacctc
4201 cccagcccag cagcctgggc agcacaacat tctgggaggg cttctcctgg cctgagcttc
4261 gcccaaagtc agacgagggc tctgtcctcc tgctgcaccg agctttgggg gatgaggaca
4321 ccagcagggt ggagaaccta gctgccagtc tgccacttcc ggagtactgc gccctccatg
4381 gaaaactcaa cctgcttcc tacctcccac cgggccttgc cctgcgtcca ctggagcccc
4441 agctctgggc agcctatggt gtgagcccgc accggggaca cctggggacc aagaacctct
4501 gtgtggaggt ggccgacctg gtcagcatcc tggtgcatgc cgacacacca ctgcctgcct
4561 ggcaccgggc acagaaagac ttcctttcag gcctggacgg ggaggggctc tggtctccgg
4621 gcagccaggt cagcactgtg tggcacgtgt tccgggcaca ggacgcccag cgcatccgcc
4681 gctttctcca gatggtgtgc ccggccgggg caggcgccct ggagcctggc gccccaggca
4741 gctgctacct ggatgcaggg ctgcggcggc gcctgcggga ggagtggggc gtgagctgct
4801 ggaccctgct ccaggccccc ggagaggccg tgctggtgcc tgcaggggct ccccaccagg
4861 tgcagggcct ggtgagcaca gtcagcgtca ctcagcactt cctctcccct gagacctctg
4921 ccctctctgc tcagctctgc caccagggac ccagccttcc ccctgactgc cacctgcttt
4981 atgcccagat ggactgggct gtgttccaag cagtgaaggt ggccgtgggg acattacagg
5041 aggccaaata gagggatgct aggtgtctgg gatcggggtg gggacaggta gaccaggtgc
5101 tcagcccagg cacaacttca gcagggatg gcgctagggg acttggggat ttctggtcaa
5161 ccccacaagc accactctgg gcacaagcag ggcactctgt tcccctcccc cttaagccaa
5221 caaccacagt gccaccaagc tcacacctgt ccttctcagg ctggcatctc ccccaccctg
5281 tgcccctttt catggtacca ggcccgcact ggggggcaatt gacttcctcc aatccccact
5341 cctccgagac ccaggagaca aacagccctt ccttggggaa acttgggaat cattctggct
5401 taaacaacac ctcctcctgc tgctcactcc cgctgagccc actctactgc cccagctccg
5461 tttctaccac cgcatcctca ctgggctcac tgcaggcatg ctgaacaagg ggcctccaac
5521 cttctgccct cctgccaaaa gatctgggga gtgtgaggag agggtggcat caggagctgc
5581 tcaggcttgg cggagggagc ggcatgggcg atgtcactca gccccttccc ggtccgcccg
5641 cttccctcct tcatgatttc cattaaagtc tgttgttttg tgaaaaaaaa aaaaaaaa
```

FIGURE 2

LOCUS NM_005144 4981 bp mRNA linear PRI 19-APR-2005
DEFINITION Homo sapiens hairless homolog (mouse) (HR), mRNA
ACCESSION NM_005144 VERSION NM_005144.3 GI:62750351

```
   1 ggccccggag ctggcccatg gggagcaggc gcccggtgcc ggccacgacg accgccaccg
  61 cccgcgccgc gaccggccgg tgaagcccag ggacccccct ctgggagagc cccatgaggg
 121 caggagagtg atggagagta cgcccagctt cctgaagggc accccaacct gggagaagac
 181 ggccccagag aacggcatcg tgagacagga gcccggcagc ccgcctcgag atggactgca
 241 ccatgggccg ctgtgcctgg gagagcctgc tcccttttgg aggggcgtcc tgagcacccc
 301 agactcctgg cttccccctg gcttccccca gggcccaag gacatgctcc cacttgtgga
 361 gggcgaggc ccccagaatg gggagaggaa ggtcaactgg ctgggcagca aagagggact
 421 gcgctggaag gaggccatgc ttacccatcc gctggcattc tgcgggccag cgtgcccacc
 481 tcgctgtggc ccctgatgc ctgagcatag tggtggccat ctcaagagtg accctgtggc
 541 cttccggccc tggcactgcc ctttccttct ggagaccaag atcctggagc gagctccctt
 601 ctgggtgccc acctgcttgc caccctacct agtgtctggc ctgccccag agcatccatg
 661 tgactggccc ctgacccgc accctgggt atactccggg ggccagccca aagtgccctc
 721 tgccttcagc ttaggcagca agggctttta ctacaaggat ccgagcattc ccaggttggc
 781 aaaggagccc tggcagctg cggaacctgg gttgtttggc ttaaactctg gtgggcacct
 841 gcagagagcc ggggaggccg aacgcccttc actgcaccag agggatggag agatgggagc
 901 tggccggcag cagaatcctt gcccgctctt cctggggcag ccagacactg tgccctggac
 961 ctcctggccc gcttgtcccc caggccttgt tcatactctt ggcaacgtct gggctgggcc
1021 aggcgatggg aaccttgggt accagctggg gccaccagca acaccaaggt gccctctcc
1081 tgagccgcct gtcacccagc ggggctgctg ttcatcctac ccacccacta aggtgggg
1141 tcttggccct tgtgggaagt gccaggaggg cctggagggg ggtgccagtg gagccagcga
1201 acccagcgag gaagtgaaca aggcctctgg ccccagggcc tgtccccca gccaccacac
1261 caagctgaag aagacatggc tcacacggca ctcggagcag tttgaatgtc cacgcggctg
1321 ccctgaggtc gaggagaggc cggttgctcg gctccgggcc ctcaaaaggg caggcagccc
1381 cgaggtccag ggagcaatgg gcagtccagc ccccaagcgg ccaccggacc cttttccagg
1441 cactgcagaa caggggctg ggggttggca ggaggtgcgg gacacatcga tagggaacaa
1501 ggatgtggac tcgggacagc atgatgagca gaaaggaccc caagatggcc aggccagtct
1561 ccaggacccg ggacttcagg acataccatg cctggctctc cctgcaaaac tgctcaatg
1621 ccaaagttgt gcccaggcag ctggagaggg aggagggcac gcctgccact ctcagcaagt
1681 gcggagatcg cctctgggag gggagctgca gcaggaggaa gacacagcca ccaactccag
1741 ctctgaggaa ggcccagggt ccggccctga cagccggctc agcacaggcc tgccaagca
1801 cctgctcagt ggtttggggg accgactgtg ccgcctgctg cggagggagc gggaggccct
1861 ggcttgggcc cagcggttaag gccaagggcc agccgtgaca gaggacagcc caggcattcc
1921 acgctgctgc agccgttgcc accatggact cttcaacacc cactggcgat gtccccgctg
1981 cagccaccgg ctgtgtgtgg cctgtggtcg tgtggcaggc actgggcggg cagggagaa
2041 agcaggcttt caggagcagt ccgcggagga gtgcacgcag gaggccgggc acgctgcctg
2101 ttccctgatg ctgacccagt ttgtctccag ccaggctttg gcagagctga gcactgcaat
2161 gcaccaggtc tgggtcaagt ttgatatccg ggggcactgc ccctgccaag ctgatgcccg
2221 ggtatgggcc cccggggatg caggccagca gaaggaatca acacagaaaa cgcccccaac
2281 tccacaacct tcctgcaatg gcgacaccca caggaccaag agcatcaaag aggagacccc
2341 cgattccgct gagacccag cagaggaccg tgctggccga gggcccctgc cttgtccttc
2401 tctctgcgaa ctgctggctt ctaccgcggt caaactctgc ttgggccatg agcgaataca
2461 catggccttc gcccccgtca ctccggccct gcccagtgat daccgcatca ccaacatcct
2521 ggacagcatt atcgcacagg tggtggaacg gaagatccag gagaaagccc tggggccggg
```

FIGURE 2 (cont)

```
2581 gcttcgagct ggcccgggtc tgcgcaaggg cctgggcctg ccctctctc cagtgcggcc
2641 ccggctgcct cccccagggg ctttgctgtg gctgcaggag ccccagcctt gccctcggcg
2701 tggcttccac ctcttccagg agcactggag gcagggccag cctgtgttgg tgtcagggat
2761 ccaaaggaca ttgcagggca acctgtgggg gacagaagct cttggggcac ttggaggcca
2821 ggtgcaggcg ctgagccccc tcggacctcc ccagcccagc agcctgggca gcacaacatt
2881 ctgggagggc ttctcctggc ctgagcttcg cccaaagtca gacgagggct ctgtcctcct
2941 gctgcaccga gctttggggg atgaggacac cagcagggtg gagaacctag ctgccagtct
3001 gccacttccg gagtactgcg ccctccatgg aaaactcaac ctggcttcct acctcccacc
3061 gggccttgcc ctgcgtccac tggagcccca gctctgggca gcctatggtg tgagcccgca
3121 ccggggacac ctggggacca agaacctctg tgtggaggtg gccgacctgg tcagcatcct
3181 ggtgcatgcc gacacaccac tgcctgcctg gcaccgggca cagaaagact tcctttcagg
3241 cctggacggg gaggggctct ggtctccggg cagccaggtc agcactgtgt ggcacgtgtt
3301 ccgggcacag gacgcccagc gcatccgccg ctttctccag atggtgtgcc cggccggggc
3361 aggcgccctg gagcctggcg ccccaggcag ctgctacctg gatgcaggc tgcggcggcg
3421 cctgcgggag gagtggggcg tgagctgctg gaccctgctc caggcccccg gagaggccgt
3481 gctggtgcct gcaggggctc cccaccaggt gcagggcctg gtgagcacag tcagcgtcac
3541 tcagcacttc ctctcccctg agacctctgc cctctctgct cagctctgcc accagggacc
3601 cagccttccc cctgactgcc acctgcttta tgcccagatg gactgggctg tgttccaagc
3661 agtgaaggtg gccgtgggga cattacagga ggccaaatag agggatgcta ggtgtctggg
3721 atcggggtgg ggacaggtag accaggtgct cagcccaggc acaacttcag caggggatgg
3781 cgctagggga cttggggatt tctggtcaac cccacaagca ccactctggg cacaagcagg
3841 gcactctgtt cccctccccc ttaagccaac aaccacagtg ccaccaagct cacacctgtc
3901 cttctcaggc tggcatctcc cccaccctgt gcccttttc atggtaccag gcccgcactg
3961 ggggcaattg acttcctcca atccccactc ctccgagacc caggagacaa acagcccttc
4021 cttgggaaa cttgggaatc attctggctt aaacaacacc tcctcctgct gctcactccc
4081 gctgagccca ctctactgcc ccagctccgt ttctaccacc gcatcctcac tgggctcact
4141 gcaggcatgc tgaacaaggg gcctccaacc ttctgccctc ctgccaaaag atctggggag
4201 tgtgaggaga gggtggcatc aggagctgct caggcttggc ggagggagcg gcatgggcga
4261 tgtcactcag ccccttcccg gtccgcccgc ttccctcctt catgatttcc attaaagtct
4321 gttgttttgt gactgctgcc agtgtggttg gccctgcccc tgcaggccac atggtccagg
4381 gagggagggg gacatggaaa tctgccttag agacaaatgg agtagggcag cccggagctg
4441 gggcccaagg gacaggacac cactgcctgc tcttcgtctg gggcctgggg ccttgcctcc
4501 cactgaggag actttgggtg gggtggggg ctgtccccca aagatgctcc tgagtgcaag
4561 agcaggcaag gcagagtcct ggggcacagc cacgaggtga cctccctgtg cagagactcc
4621 cgagccctac tccacccagc aagctccagt ccgcccatc tctccgtct accctgacct
4681 ggagatccag aagtatggcc cagaagagcc cttgccccgc ctgtctgccc ttggtggcag
4741 tggccatggc cgacgccagg cccagccacc ctgggactga gcctgactgc ttcagacagc
4801 cgacccctcc ttgtccccgc tccacgcccg cagcctcctg gtggcgctcc gccctctccc
4861 gcttcctttg tgtatctcag ccctacaaag aaaaacactc ccactcttgt catacctaat
4921 tgttcctgct gtggtttggg gaatttttt tattaaataa agttttttat tataagggta
4981 a
```

INHIBITION OF HAIRLESS PROTEIN MRNA

CROSS-REFERENCE TO RELATED PATENT APPLICATIONS

This application is a continuation of U.S. application Ser. No. 11/113,423 filed Apr. 22, 2005, now abandoned which is based on U.S. Provisional Application Ser. No. 60/565,127 filed Apr. 23, 2004, the contents of each of which are incorporated by reference herein, and to each of which priority is claimed.

SEQUENCE LISTING

The specification further incorporates by reference a substitute Sequence Listing submitted via EFS on Jul. 2, 2007. Pursuant to 37 C.F.R. §1.52(e)(5), the substitute Sequence Listing text file, identified as 700503051.txt, is 2.0 Mb and was created on Jul. 2, 2007. The substitute Sequence Listing, electronically filed herewith, does not extend beyond the scope of the specification and thus does not contain new matter.

The sequence listing, submitted in duplicate on compact disk (CD), in lieu of a paper copy in compliance with 37 C.F.R. §§1.821(c) and 1.52(e), and in duplicate on CD (CRF copy), in compliance with 37 C.F.R. §1.821 (e) has been generated from the specification and figures and does not constitute new matter. The Sequence Listing has been prepared using FastSeq for Windows Version 4.0 software. Four identical CDs, labeled COPY 1, COPY 2, CRF of Sequence Listing submitted under 37 C.F.R. §1.821(e)—COPY 1 and CRF of Sequence Listing submitted under 37 C.F.R. §1.821 (e)—COPY 2, (total four (4) CDs), created on Apr. 22, 2005 each contain file: "AP36462_SEQLIST.TXT", of size 2.28 MB (2,398,842 bytes). The specification incorporates herein by reference, the CD copies of the Sequence Listing submitted under 37 C.F.R §§1.821(c) and 1.52(e). The sequence listing, submitted herewith, does not extend beyond the scope of the specification, and thus, does not contain new matter.

BACKGROUND OF THE INVENTION

The following is a discussion of some relevant art relating to hairless protein, and to RNAi. This discussion is provided only to assist the understanding of the reader, and does not constitute an admission that any of the information provided or references cited constitutes prior art to the present invention.

As described in Christiano et al., PCT/US99/02128, WO 99/38965, The human hair follicle is a dynamic structure which generates hair through a complex and highly regulated cycle of growth and remodeling. Hardy, 1992, *Trends Genet.* 8:159; Rosenquist and Martin, 1996, *Dev. Dynamics* 205: 379. Hair growth is typically described as having three distinct phases. In the first phase, knows as anagen, the follicle is generated and new hair grows.

During the second phase, known as catagen, the follicle enters the stage where elongation ceases and the follicle regresses because the matrix cells stop proliferating. At this stage, the lower, transient half of the follicle is eliminated due to terminal differentiation and keratinization, and programmed cell death. Rosenquist and Martin, 1996, *Dev. Dynamics* 205:379. Also during catagen, although the dermal papilla remains intact, it undergoes several remodeling events, including degradation of the extracellular matrix that is deposited during anagen. At the close of catagen, the hair is only loosely anchored in a matrix of keratin, with the dermal papilla located just below. The catagen stage occurs at a genetically predetermined time, which is specific for each hair type in a species.

The third phase, known as telogen, is characterized by the follicle entering a quiescent phase, during which the hair is usually shed. When a new hair cycle is initiated, it is thought that a signal from the dermal papilla stimulates the stem cells, which are thought to reside in the permanent portion of the follicle, to undergo a phase of downward proliferation and genesis of a new bulbous base containing matrix cells which then surround the dermal papilla. As the new anagen state progresses, these hair matrix cells produce a new hair, the cycle begins again. Each follicle appears to be under completely asynchronous control, resulting in a continuum of follicles in anagen, catagen, and telegen phases, leading to a relatively homogeneous hair distribution. Hardy, 1992, *Trends Genet.* 8:159; Rosenquist and Martin, 1996, *Dev. Dynamics* 205:379.

Christiano et al., PCT/US99/02128, WO 99/38965 describes isolated nucleic acid encoding human hairless protein, the isolated protein, and methods for identifying a compound that is capable of enhancing or inhibiting expression of a human hairless protein, and states that "A therapeutic approach using antisense to human hairless can be used to directly interfere with the translation of Human hairless protein messenger RNA into protein." It further states that "antisense nucleic acid or ribozymes could be used to bind to the Human hairless protein mRNA or to cleave it."

Thompson, U.S. Pat. No. 6,348,348, issued Feb. 19, 2002, describes human hairless gene and protein, and screening methods to identify agents that affect expression of the human hairless gene.

Christiano, U.S. patent application Ser. No. 10/122,013, publication 20030077614 (and corresponding Internation Application PCT/US02/11683, WO 02/083891), indicates that "The present invention provides DNAzymes and ribozymes that specifically cleave Hairless Protein mRNA." The present invention also provides antisense oligonucleotides that specifically inhibit translation of Hairless Protein mRNA. (Abstract.) Also, it states that "This invention provides a nucleic acid molecule that specifically hybridizes to Hairless Protein mRNA so as to inhibit the translation thereof in a cell"; (Specification ¶ 0099) and that "Antisense oligodeoxynucleotides were synthesized as directed to the inhibition of Hairless expression based on the Hairless mRNA sequence."

SUMMARY OF THE INVENTION

The present invention concerns the use of RNA interference (RNAi) to inhibit mRNA's involved in hair growth, resulting in inhibition of hair growth. For many applications, short interfering RNA (siRNA) are used. Thus, inhibition of hairless protein mRNA, particularly during catagen phase, can result in permanent or at least long term inhibition of hair growth, and thus provides a method for hair removal. Consequently, inhibition of hairless protein mRNA can be used for hair removal and/or hair growth inhibition in cosmetic, therapeutic, and industrial applications.

Thus, in a first aspect, the invention provides a method for hair removal from a mammal, e.g., a human. The method involves applying to a human in an area comprising hair follicles a double stranded nucleic acid molecule that includes a sequence of at least a portion of human hairless protein mRNA and a sequence complementary thereto.

In particular embodiments, the inhibition of hair growth in the treated area persists at least 1, 2, 4, 6, 8, 10, 12, or 24 months, or longer, or permanently.

In certain embodiments, the method also involves synchronizing hair growth cycles for hair follicles in the treated area, e.g., by extracting hairs such as by waxing. Such extraction causes follicles in anagen to transition into catagen thereby making those follicles susceptible to inhibition using this invention, and triggers new hair growth of follicles in telogen and thus makes those follicles suitable for transitioning into catagen. Thus, these methods synchronize hair follicles in the hair cycle.

As used in connection with this invention, the term "hair removal" refers to physical removal and continuing inhibition of hair growth from one or more hair follicles. Typically the hair removal applies to a plurality of hair follicles in a skin area on a subject. For example, the area can be up to 2, 5, 10, 20, 50, 100, 200, 400, or more $cm^2$. For hair removal in an area, the hair removal may apply to all or a fraction of the hair follicles in the area.

The term "hair follicle" is used conventionally to refer to a biological hair producing structure.

As used in connection with the present methods, the term "applying" indicates that a substance is placed such that the substance is physically present on or in an area.

The term "nucleic acid molecule" refers to a polymer that includes a plurality of linked nucleotides or nucleotide analogs, and may include one or more modified internucleotidic linkages.

The term "hairless gene" refers to a mammalian gene that corresponds to reference human cDNA GenBank reference number NM_005144, FIG. 1 (SEQ ID NO: 11412) and version NM_005144.3, GI:62750351, FIG. 2 (SEQ ID NO:11413), recognizing that polymorphisms and potentially sequencing errors may be present, or a species homolog of that sequence, e.g., mouse homolog cDNA sequence NM_021877. Similarly the terms "hairless protein mRNA" and "hairless mRNA" refer to an mRNA encoding a hairless gene protein, and "human hairless mRNA" refers to a human homolog of such mRNA.

The phrase "inhibition of hair growth" is used to refer to a reduction or stoppage of hair growth caused at least in part by an agent not normally present in cells in a hair follicle.

As used herein, the phrase "synchronizing hair growth cycles" means that at least 10% of hair follicles in catagen or telogen phase in a particular area are caused to enter anagen phase essentially simultaneously (i.e., within 2 weeks). Such synchronizing can be accomplished, for example, with a physical action such as hair extraction or with one or more chemical or biomolecular agents.

As used herein, the term "hair extraction" refers to pulling of individual hair shafts out of their follicles.

A related aspect concerns a method for hair removal from an area of a mammal comprising hair follicles, where the method involves applying to the area a composition that includes at least one double stranded nucleic acid molecule able to inhibit hairless mRNA translation in vitro.

In certain embodiments, the method also includes synchronizing hair growth cycles for hair follicles in the treated area, such as by hair extraction, e.g., using waxing; the mammal is a human; the mammal is a mouse; the mammal is a rat; the mammal is a bovine.

In another aspect, the invention provides a method of inhibiting expression of hairless protein in a mammal. The method involves administering a double stranded nucleic acid molecule to the mammal, where the double stranded nucleic acid molecule includes a sequence selected from the group consisting of oligonucleotides 1-5664 and their respective antisense sequences, or the species homology of such sequences, and a sequence complementary thereto.

As used in the context of this invention, the term "inhibiting expression" indicates that the level of mRNA and/or corresponding protein or rate of production of the corresponding protein in a cell that would otherwise produce the mRNA and/or protein is reduced as compared to a non-inhibited but otherwise equivalent cell. Reduction in the rate of production can be at various levels, including stopping such production.

The term "species homolog" refers to a form of a gene, or corresponding nucleic acid molecule, or polypeptide from a particular species that is sufficiently similar in sequence to the gene, corresponding nucleic acid, or polypeptide from a reference species that one skilled in the art recognizes a common evolutionary origin.

Thus, as used in connection with a molecule or composition, the phrase "able to inhibit hairless mRNA translation" indicates that the molecule or composition has the property that when present in a cell that would translate hairless mRNA to produce protein in the absence of an inhibitor, the molecule or composition reduces the rate of biosynthesis of hairless protein (or even eliminate such biosynthesis). Such reduction can occur in various ways, for example, by reducing the amount of mRNA available for translation or by at least partially blocking translation of mRNA that is present.

Reference to Oligonucleotides by number utilizes the oligonucleotide numbering in Table 1, and therefore, specifies a nucleotide sequence.

In particular embodiments, the mammal is a human, a mouse, a rat, a bovine (such as a cow), an ovine (such as a sheep), a monkey, a porcine (such as domestic pig).

The term "bovine" is used conventionally to refer to cattle, oxen, and closely related ruminants.

Another aspect concerns a method for treating a human desirous of losing hair. The method involves administering to the human a composition that includes a double stranded nucleic acid molecule that includes a sequence of at least a portion of human hairless protein mRNA and a sequence complementary thereto.

As used herein, the phrase "desirous of losing hair" refers to an objective indication of consent or request for a process to remove hair from a body area in a manner reducing or eliminating future hair growth in that area for a period of time, e.g., at least 1 week, 2 weeks, 1 month, 2 months, or longer.

A further aspect concerns a method for marketing a composition for hair removal, which includes providing for sale to medical practitioners (e.g., doctors, nurse practitioners, doctor's assistants, and nurses) or to the public (e.g., spas and other body care businesses, and individuals) a packaged pharmaceutical composition that includes a double stranded nucleic acid molecule containing a sequence of at least a portion of human hairless protein mRNA and a sequence complementary thereto; and a package label or insert indicating that the pharmaceutical composition can be used for hair removal.

In particular embodiments, the pharmaceutical composition is approved by the U.S. Food and Drug Administration, and/or by an equivalent regulatory agency in Europe or Japan, for hair removal in humans; the pharmaceutical composition is packaged with a hair removal wax or other component adapted for hair removal.

The term "pharmaceutical composition" refers to a substance that contains at least one biologically active component. The composition typically also contains at least one pharmaceutically acceptable carrier or excipient.

As used herein, the term "packaged" means that the referenced material or composition is enclosed in a container or containers in a manner suitable for storage or transportation. For example, a pharmaceutical composition may be sealed in a vial, bottle, tube, or the like, which may itself be inside a box. Typically, a label on the container identifies the contents and may also provide instructions for use and/or cautions to prevent misuse.

The term "hair removal wax" refers to refer to a substance that is adapted for removal of hair by embedding hair in the substance and then pulling the material away, thereby pulling embedded hairs out of the hair follicles. The substance may be used with a backing material such as paper or cloth. Both hot and cold waxes are commonly available. Unless clearly indicated, the term is not limited to substances that are chemically waxes; for example, the term will generally include substances such as caramel-based substances that are used for "sugaring".

The term "other component adapted for hair removal" refers to a material or device that can be used for physically removing hairs and is either generally recognized as suitable for such use, of instructions are provided indicating that the component can be used for physical hair removal or providing instructions on performing such removal.

Another aspect concerns an isolated double stranded nucleic acid molecule that includes a nucleotide sequence corresponding to 19-25 contiguous nucleotides from human hairless mRNA, where the nucleotide sequence contains a nucleotide sequence selected from the group consisting of oligonucleotides 1-5664; and a nucleotide sequence complementary thereto, where the double stranded nucleic acid molecule induces RNA interference in a human cell in vitro.

Indication that a molecule or material of interest "induces RNA interference in a human cell in vitro" means that when present in cultured cells that are capable of RNA interference and under conditions such that a molecule or molecules that will normally induce RNA interference do induce RNAi in the cell, the molecule or material of interest will induce such RNA interference.

Likewise, in another aspect the invention provides a pharmaceutical composition that includes a double stranded nucleic acid molecule that contains a nucleotide sequence corresponding to 14-50, 17-40, 17-30, 17-25, 19-30, 19-29, 19-28, 19-26, 19-25, 19-24, 19-23, 20-23, 20-22, or 21-22 contiguous nucleotides from human hairless mRNA including a nucleotide sequence selected from the group consisting of oligonucleotides 1-5664, and a sequence complementary thereto, wherein said double stranded nucleic acid molecule induces RNA interference in a human cell in vitro.

In yet another aspect, the invention provides a kit that includes a pharmaceutical composition that contains a double stranded nucleic acid molecule that includes a sequence of at least a portion of human hairless protein mRNA and a sequence complementary thereto; and a package label or insert indicating that said pharmaceutical composition can be used for hair removal.

In certain embodiments, the kit is approved by the U.S. Food and Drug Administration or equivalent regulatory agency in Europe or Japan, for human hair removal.

In certain embodiments of the above aspects or other aspects described herein, the double stranded nucleic acid includes at least one (i.e., one or two) 3'-overhang, e.g., a 1, 2, or 3 nucleotide overhang. In certain embodiments, such overhang includes one or more non-ribonucleotides; includes 1, 2, or 3 deoxynucleotide; includes a modified linkage; each strand has a 1, 2, or 3 nucleotide overhang.

In certain embodiments of the above aspects, at least one strand of the double stranded nucleic acid includes at least one nucleotide analog or internucleotidic linkage different from unmodified RNA; each strand includes at least one nucleotide analog or internucleotidic linkage different from unmodified RNA; at least one strand includes at least one modified nucleotide; each strand includes at least one modified nucleotide.

In certain embodiments of the above aspects, the double stranded nucleic acid molecule induces RNA interference in a cell in vitro and includes the RNA sense sequence of Oligonucleotide 131, namely 5'-CUCUCCAGACAUUUG-GCAA-3' (SEQ ID NO: 11329), and its complementary RNA sequence 5'-TTGCCAAATGTCTGGAGAG-3' (SEQ ID NO:262); includes the RNA sense sequence of Oligonucleotide 1194, namely 5'-GUGCGGCCGAUCCGCGCCG-3' (SEQ ID NO: 11330), and its complementary RNA sequence 5'-CGGCGCGGAUCGGCCGCAC-3' (SEQ ID NO:11331); includes the RNA sense sequence of Oligonucleotide 1521, namely 5'-TGGGAGAAGACGGCCCCAG-3' (SEQ ID NO:3041) its complementary RNA sequence 5'-CTGGGGC-CGTCTTCTCCCA-3' (SEQ ID NO: 3042); includes an RNA sense sequence and a complementary RNA antisense sequence selected from the group consisting of oligonucleotides 1-5664; is targeted to hairless mRNA corresponding to a site in the coding sequence (CDS) covering nucleotides 1482 to 5051; includes a nucleotide sequence corresponding to an oligonucleotide selected from Oligonucleotides 1482 to 5032; includes a nucleotide sequence corresponding to an oligonucleotide selected from Oligonucleotides 1482 to 4032; includes a nucleotide sequence corresponding to an oligonucleotide selected from Oligonucleotides 1482 to 3032; includes a nucleotide sequence corresponding to an oligonucleotide selected from Oligonucleotides 1482 to 2032; includes a nucleotide sequence corresponding to an oligonucleotide selected from Oligonucleotides 1582 to 1732.

In certain embodiments of the above aspects, in the double stranded nucleic acid molecule, the sense sequence and the antisense sequence each include 19, 20, 21, 22, 23, 24, 25, 26, 27, 28, or 29 complementary nucleotides and 1 to 3 non-complementary 3'-nucleotides.

In certain embodiments of the above aspects, chemically modified nucleic acids are used, e.g., chemically modified siRNAs (siNAs) as described in McSwiggen et al., PCT/US03/05346, WO 03/070918, which is incorporated herein by reference.

As used herein, the terms "siRNA" and "siNA" both refer to double stranded nucleic acid that induces RNAi, and includes unmodified RNA oligonucleotides and chemically modified oligonucleotides. When unmodified RNA is intended, the term "unmodified RNA" is expressly used.

The term "RNAi inducing oligonucleotide" or "RNA interference inducing oligonucleotide" refers to an oligonucleotide, generally a double stranded molecule (usually an siRNA molecule), that is able to induce RNA interference in a suitable cell.

In certain embodiments of the above aspects involving application of the present oligonucleotides to a mammal, the oligonucleotides are applied at 0.01 to 0.1 microgram/cm$^2$, 0.1 to 0.2 microgram/cm$^2$, 0.2 to 0.5 microgram/cm$^2$, 0.5 to 1.0 microgram/cm$^2$, 1.0 to 2.0 microgram/cm$^2$, 2.0 to 5.0 microgram/cm$^2$, or 5.0 to 10.0 microgram/cm$^2$; a combination of different RNAi inducing oligonucleotides is applied, which application can be as a mixture or mixtures or separately, e.g., 2, 3, 4, 5, 6, 7, 8, 9, 10, or more different oligonucleotides; one or more different RNAi inducing oligonucleotides (e.g., all targeted to hairless, e.g., siRNA) is applied in combination (as a mixture or separately) with one or more different agents that inhibit hairless translation or hairless activity; one or more different RNAi inducing oligonucleotides is applied in combination with one or more other hair removal agents, such as chemical depilatories and/or enzymatic hair removal agents. In accordance with the preceding description of embodiments, certain of the present pharmaceutical compositions also include at least one hairless inhibiting agent different from an RNAi inducing agent, at least one chemical depilatory; at least one enzymatic hair removal agent.

In certain embodiments, the present RNAi inducing oligonucleotides are applied once; applied daily for at least 7 days; applied daily for at least 14 days; applied on at least 4 days within a one month period; applied on at least 7 days within a one month period; applied at least 4 days per week for at least a four week period.

In particular embodiments, the RNAi inducing oligonucleotide does not include the sequence of a siRNA as shown in the Examples; the RNAi oligonucleotide includes the sequence of an siRNA shown in the Examples and the method of use includes synchronizing hair cycles, e.g., as described herein.

In particular embodiments involving mammalian mRNAs, the RNAi inducing oligonucleotide (e.g., siRNA) includes a sequence 17, 18, 19, 20, 21, 22, 23, 24, or 25 nucleotides in length (or at least one of those lengths) of one of the sequences shown in Table 3, or a sequence complementary thereto; the RNAi inducing oligonucleotide targets a mammalian hairless mRNA sequence corresponding to a sequence shown in Table 3.

In particular embodiments, the RNAi inducing oligonucleotide (e.g., siRNA) targets a human hairless mRNA sequence as identified in Table 4; the RNAi inducing oligonucleotide contains a sequence of 17, 18, 19, 20, 21, 22, 23, 24, 25, 26, 27, 28, 29, or 30 nucleotides in length (or at least one of those lengths).

In particular embodiments, the RNAi inducing oligonucleotide (e.g., siRNA) targets a mouse hairless mRNA sequence as identified in Table 5; the RNAi inducing oligonucleotide contains a sequence of 17, 18, 19, 20, 21, 22, 23, 24, 25, 26, 27, 28, 29, or 30 nucleotides in length (or at least one of those lengths).

Additional embodiments will be apparent from the Detailed Description and from the claims.

BRIEF DESCRIPTION OF THE FIGURES

FIG. 1. NM005144 (SEQ ID NO:11412)
FIG. 2. NM005144.3 (SEQ ID NO: 11413)

DETAILED DESCRIPTION OF THE PREFERRED EMBODIMENTS

The present invention concerns methods for inhibiting hair growth, by inhibiting particular mRNAs using RNAi, e.g., using siRNA. In particular non-limiting embodiments, the present invention provides for siRNA molecules, e.g., double stranded RNA oligonucleotides (which optionally may be chemically modified and/or comprise at least one 3' overhang, as set forth below), comprising a nucleotide sequence that is complementary to a target nucleotide sequence which may be 17, 18, 19, 20, 21, 22, 23, 24 or 25 nucleotides in length, where the siRNA contains a sequence 17, 18, 19, 20, 21, 22, 23, 24, 25, 26, 27, 28, 29 or 30 base pairs in length. Preferably, the hairless in RNA target nucleotide sequence comprises a 17, 18, 19, 20, 21, 22, 23, 24 or 25 nucleotide portion of the human hairless mRNA sequence set forth in FIG. 1 (SEQ ID NO: 11412) and/or FIG. 2 (SEQ ID NO: 11413). Non-limiting examples of target sequences may be identified as loops identified in secondary mRNA structure using software designed for such purpose (e.g. RnaDraw, RnaMotif, Rnaview-RnaMLView, RnaViz, Vienna RNA Package, etc.).

A. RNAi and siRNA

RNA interference (RNAi) refers to the process of sequence-specific post-transcriptional gene silencing in animals mediated by short interfering RNAs (siRNAs) (Fire et al., 1998, *Nature*, 391, 806). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, *Trends Genet.*, 15, 358). The presence of dsRNA in cells triggers the RNAi response though a mechanism that appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of the enzyme, dicer, a ribonuclease III. Dicer is involved in the processing of the dsRNA into short pieces of dsRNA known as short interfering RNAs (siRNAs) (Berstein et al., 2001, *Nature*, 409, 363). The resulting RNAs are typically about 21 to about 23 nucleotides in length, with complementary sequences of about 19 base pairs. Dicer has also been implicated in the excision of 21- and 22-nucleotide small temporal RNAs (stRNAs) from precursor RNA of conserved structure that are implicated in translational control (Hutvagner et al., 2001, *Science*, 293, 834). The RNAi response also involves an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, *Genes Dev.*, 15, 188).

RNAi has been studied in a variety of systems. Fire et al., 1998, *Nature*, 391, 806, described RNAi in *C. elegans*. Wianny and Goetz, 1999, *Nature Cell Biol.*, 2, 70, describe RNAi mediated by dsRNA in mouse embryos. Hammond et al., 2000, *Nature*, 404, 293, describe RNAi in *Drosophila* cells transfected with dsRNA. Elbashir et al., 2001, *Nature*, 411, 494, describe RNAi induced by introduction of duplexes of synthetic 21-nucleotide RNAs in cultured mammalian cells including human embryonic kidney and HeLa cells.

Work in *Drosophila* embryonic lysates (Elbashir et al., 2001, *EMBO J*, 20, 6877) has revealed certain factors of siRNA length, structure, chemical composition, and sequence that are significantly affect efficient RNAi activity. These studies have shown that 21-nucleotide siRNA duplexes are most active when containing 3'-terminal nucleotide overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with 2'-deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end of the guide sequence (Elbashir et al., 2001, *EMBO J.*, 20, 6877). Other studies have suggested that a 5'-phosphate on the target-complementary strand of a siRNA duplex is important for siRNA activity and that ATP is utilized to maintain the 5'-phosphate moiety on the siRNA (Nykanen et al., 2001, *Cell*, 107, 309).

Studies have shown that replacing the 3'-terminal nucleotide overhanging segments of a 21-mer siRNA duplex having two 2-nucleotide 3'-overhangs with deoxyribonucleotides does not have an adverse effect on RNAi activity. Replacing up to 4 nucleotides on each end of the siRNA with deoxyribonucleotides has been reported to be well-tolerated whereas complete substitution with deoxyribonucleotides results in no RNAi activity, but that substitution of siRNA with 2'-O-methyl nucleotides completely abolishes RNAi activity. (Elbashir et al., 2001, *EMBO J.*, 20, 6877.)

Li et al., International PCT Publication No. WO 00/44914, and Beach et al., International PCT Publication No. WO 01/68836 both suggest that siRNA "may include modifications to either the phosphate-sugar backbone or the nucleoside . . . to include at least one of a nitrogen or sulfur heteroatom."

Kreutzer and Limmer, Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge Parrish et al., 2000, *Molecular Cell*, 6, 1977-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two [phosphorothioate] modified bases also had substantial decreases in effectiveness as RNAi triggers (data not shown); [phosphorothioate] modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity," especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl)uracil for uracil, and inosine for guanosine. They found that whereas 4-thiouracil and 5-bromouracil were all well-tolerated, inosine "produced a substantial decrease in interference activity" when incorporated in either strand. Incorporation of 5-iodouracil and 3-(aminoallyl)uracil in the antisense strand resulted in substantial decrease in RNAi activity as well.

Beach et al., International PCT Publication No. WO 01/68836, describes specific methods for attenuating gene expression using endogenously-derived dsRNA.

Tuschl et al., International PCT Publication No. WO 01/75164, describe a *Drosophila* in vitro RNAi system and the use of specific siRNA molecules for certain functional genomic and certain therapeutic applications; although Tuschl, 2001, *Chem. Biochem.*, 2, 239-245, doubts that RNAi can be used to cure genetic diseases or viral infection due "to the danger of activating interferon response."

Li et al., International PCT Publication No. WO 00/44914, describe the use of specific dsRNAs for use in attenuating the expression of certain target genes.

Zernicka-Goetz et al., International PCT Publication No. WO 01/36646, describe certain methods for inhibiting the expression of particular genes in mammalian cells using certain dsRNA molecules.

Fire et al., International PCT Publication No. WO 99/32619, describe particular methods for introducing certain dsRNA molecules into cells for use in inhibiting gene expression.

Plaetinck et al., International PCT Publication No. WO 00/01846, describe certain methods for identifying specific genes responsible for conferring a particular phenotype in a cell using specific dsRNA molecules.

Mello et al., International PCT Publication No. WO 01/29058, describe the identification of specific genes involved in dsRNA-mediated RNAi.

Deschamps Depaillette et al., International PCT Publication No. WO 99/07409, describe specific compositions consisting of particular dsRNA molecules combined with certain anti-viral agents.

Waterhouse et al., International PCT Publication No. 99/53050, describe certain methods for decreasing the phenotypic expression of a nucleic acid in plant cells.

Driscoll et al., International PCT Publication No. WO 01/49844, describe specific DNA constructs for use in facilitating gene silencing in targeted organisms.

Parrish et al., 2000, *Molecular Cell*, 6, 1977-1087, describe specific chemically-modified siRNA constructs targeting the unc-22 gene of *C. elegans*.

Grossniklaus, International PCT Publication No. WO 01/38551, describes certain methods for regulating polycomb gene expression in plants.

Churikov et al., International PCT Publication No. WO 01/42443, describe certain methods for modifying genetic characteristics of an organism.

Cogoni et al., International PCT Publication No. WO 01/53475, describe certain methods for isolating a *Neurospora* silencing gene and uses thereof.

Reed et al., International PCT Publication No. WO 01/68836, describe certain methods for gene silencing in plants.

Honer et al., International PCT Publication No. WO 01/70944, describe certain methods of drug screening using transgenic nematodes as Parkinson's Disease models.

Deak et al., International PCT Publication No. WO 01/72774, describe certain *Drosophila*-derived gene products.

Arndt et al., International PCT Publication No. WO 01/92513, describe certain methods for mediating gene suppression by using factors that enhance RNAi.

Tuschl et al., International PCT Publication No. WO 02/44321, describe certain synthetic siRNA constructs.

Pachuk et al., International PCT Publication No. WO 00/63364, and Satishchandran et al., International PCT Publication No. WO 01/04313, describe certain methods and compositions for inhibiting the function of certain oligonucleotide sequences.

Echeverri et al., International PCT Publication No. WO 02/38805, describe certain *C. elegans* genes identified via RNAi.

Kreutzer et al., International PCT Publications Nos. WO 02/055692, WO 02/055693, and EP 1144623 B1 describes certain methods for inhibiting gene expression using RNAi.

Graham et al., International PCT Publications Nos. WO 99/49029 and WO 01/70949, and AU 4037501 describe certain vector expressed long double stranded RNA molecules.

McSwiggen et al., PCT/US03/05028, WO 03/074654 describes RNA interference mediated inhibition of gene expression using short interfering nucleic acid (siNA), and provides a table listing thousands of mRNAs, which is believed to include hairless protein mRNA, as potential targets for such siNA.

McSwiggen et al., PCT/US03/05346, WO 03/070918 describes synthetic chemically modified small nucleic acid molecules capable of mediating RNA interference against target nucleic acid sequences. The reference reports that up to all of the nucleotides in the RNA strands can be replaced with moieties that are not ribonucleotides.

B. Hairless Protein mRNA

Applicant's have found that RNAi can be used to inhibit translation from hairless protein mRNA, resulting in hair removal. This hair removal is long term, or even permanent, thus providing cosmetic and therapeutic methods, as well as methods useful for laboratory experimental mammals, and for de-hairing in the leather industry.

The Hairless Protein gene is expressed during a narrow window during the hair cycle, just at the transition to catagen (the regression phase). (Panteleyev et al. 1998, *Exp Dermatol.* 7:249-67; Panteleyev et al. 2000, *Am J Pathol.* 157:1071-9). In both humans and mice with mutations in the hairless gene, the cardinal finding is a wave of hair shedding shortly after birth, and no subsequent hair growth throughout life. The phenotype results from permanent structural damage to the hair follicle, after which no further hair cycling can occur. In addition, humans and mice which are genetically deficient in hairless gene expression exhibit no other phenotypic manifestations or abnormalities that might be associated with a deleterious effect (Zlotogorski et al., 2002, *J Invest Dermatol.* 118:887-90), suggesting that hairless is specifically involved and indispensable in regulating the hair cycle, and that its functions elsewhere in the body (if any) are compensated by other factors.

As a result, hair removal using RNAi targeted to hairless mRNA provides an advantageous approach, as any inadvertent, non-localized inhibition of hairless mRNA will not adversely affect the subject.

C. Applications and Conditions to be Treated

As indicated above, the present invention concerns inhibition of hair growth, and consequent hair removal, and is applicable to a number of different therapeutic, cosmetic, and industrial applications. The methods can be readily adapted to any of the various mammals having hairless protein analogs, for example, human, mouse, rat, cattle (and other bovines), equines.

1. Long Term (Permanent) Hair Removal

Permanent, or at least long term, hair removal can involve inhibition of hairless protein. Such hair removal is useful for both cosmetic and therapeutic applications. Exemplary cosmetic applications can include, for example, back and chest hair for men and upper lip, eyebrow, leg, arm, underarm, and pubic hair for women.

In addition to cosmetic applications, permanent or long term hair removal is also useful in certain conditions, e.g., trachoma, the various forms of hypertrichosis, and hirsutism.

Hypertrichosis

Hypertrichosis describes all forms of hair growth that are excessive for the bodily location and age of an individual, and which do not result from androgen stimulation. The present invention can be used for the various forms and causes of hypertrichosis, e.g., those described herein.

Hypertrichosis is usually categorized on the basis of the age of onset (at birth or during later years), the extent of distribution (universal or localized), the site of involvement (elbows, anterior or posterior neck), and the cause (genetic or acquired).

Acquired hypertrichosis may result from the use of particular drugs, for example, oral minoxidil, phenyloin, and cyclosporin. Acquired hypertrichosis lanuginosa may also be a manifestation of an underlying malignancy. In the dermatological literature, this is known as "malignant down". Additional causes of acquired hypertrichosis include hormonal imbalances, malnutrition, HIV and local inflammation.

In addition, some forms of hypertrichosis are clearly hereditary but the genes involved generally remain unknown. Genetic forms of hypertrichosis are very rare human disorders.

There are only a small number of human disorders that have generalized congenital hypertrichosis as the leading phenotypic feature. These include:

Hypertrichosis universalis (MIM145700)
Hypertrichosis universalis congenita, Ambras type (MIM145701)
Gingival fibromatosis with hypertrichosis (MIMI 35400)
Barber-Say syndrome (MIM209885)
Amaurosis congenita, cone-rod type, with hypertrichosis (MIM204110),
CAHMR syndrome (MIM21770)
Cantu syndrome (MIM239850)
Gingival fibromatosis with hypertrichosis and mental retardation MIM605400)
X-linked hypertrichosis (MIM307150)
Acromegaly and hypertrichosis (Irvine et al, 1996).

Of these, only Hypertrichosis universalis, Ambras type hypertrichosis, and X-linked hypertrichosis have excessive hair as the predominant feature. In all the other listed syndromes hypertrichosis is associated with additional more prominent abnormalities. The present invention can be used to treat hypertrichosis, e.g., in any of the conditions listed above, as well as in other conditions in which trichosis occurs.

Trachoma

Trachoma is the leading cause of blindness worldwide. The World Health Organization estimates that there are 146 million people with trachoma and that the disease has caused blindness in 5.9 million people, 15% of the world's blindness. Trachoma is caused by the gram-negative bacterium *Chlamydia trachomatis*, an intracellular parasite transmitted by fly infestation. In trachoma, the conjunctival lining of the eyelids becomes infected with the bacterium, which over the long term, causes an inflammatory response. The inflammation can lead to scarring, shortening of the lid and in-turning of the eyelashes. Trichiasis, the condition when eyelashes rub on the cornea, can lead to blindness. An estimated 10.6 million adults have inturned eyelashes that require surgery.

While it is advantageous of the *Chlamydia* infection is prevented, or treated before in-turning of the eyelashes, there is a need for non-surgical approaches to treatment that can at least reduce the corneal scarring. Thus, removal of the eyelash hairs (without leaving stubble) using the present invention can substantially slow, or even prevent such corneal damage, thereby preserving the individual's vision.

Trichiasis

In addition to trachoma, in-turned eyelashes (trichiasis) can have other causes, and are a common source of recurrent ocular irritation for some patients. The in-turned lash (or lashes) in contact with the conjunctiva and/or cornea may lead to a foreign body sensation, localized conjunctival injection, pain and photophobia.

Trichiasis is the term used for misdirection or aberrant placement of eyelashes along the eyelid margin resulting in lash growth toward the cornea. Trichiasis is an acquired condition that may be caused by the following inflammatory or traumatic processes involving the eyelids. The present invention can be used in all cases of trichiasis, including those in the following causal situations:

Chronic blepharitis with meibomianitis—chronic inflammatory changes within the tarsal plate and posterior eyelid margin may cause destruction and misdirection of lash follicles, resulting in chronic trichiasis.

Lid lacerations and thermal burns to the lid margin—may cause redirection of the lash roots with resultant trichiasis.

Previous surgery on eyelids—For example, lid adhesions (tarsorrhaphys) done to prevent exposure in some patients with seventh nerve palsies may cause misdirection of lashes. Similarly, in many reconstructive eyelid procedures, the new eyelid margin may contain fine skin hairs (lanugo-type) that rub on the cornea.

Mucocutaneous diseases—Stevens-Johnson syndrome and Ocular Cicatricial Pemphigoid result not only in the destruction of the eyelid margins and trichiasis but also in the formation of new lashes from the meibomian gland orifices (a condition referred to as distichiasis).

Other cicatricial conjunctival diseases—Herpes Simplex conjunctivitis and Herpes Zoster may cause a cicatrizing conjunctivitis with destruction of the lid margin and lash follicles. Trachoma may also cause a chronic tarsitis with cicatrizing conjunctivitis in the upper or lower eyelid and resultant trichiasis (as well as a cicatricial entropion).

Irradiation and chemical burns—Therapeutic irradiation for eyelid cancers or alkali burns may lead to a disruption of the normal eyelid margin anatomy and resultant misdirection of eyelashes. Both of these processes may also lead to metaplasia of squamous epithelium of the mucocutaneous margin of the eyelid with resultant keratinization, a source of ocular irritation. In addition, destruction of the goblet cells, accessory lacrimal glands, and lacrimal gland will disrupt the normal tear flow, compounding the above problems.

Other conditions in which eyelashes contact the cornea also exist, and the present invention can be used in those cases also. For example:

A condition similar to trichiasis is Eyelid entropion—True entropion (e.g. involutional type seen in the aging population) is characterized by a normal eyelid margin architecture: the eyelid inverts as a result of eyelid laxity, allowing the eyelashes to rub on the cornea. Several of the entities mentioned above (Ocular Pemphigoid, Stevens-Johnson Syndrome) may cause a cicatrization of the conjunctiva as well as the lid margin and create a cicatricial entropion with trichiasis (i.e. the eyelid is inverted due to a cicatricial process). In addition, eyelashes may be misdirected not only due to the lid position, but also due to the inflammatory process involving the actual lash follicles. Therefore, sometimes there may be two problems present (entropion and trichiasis) both of which may require treatment.

Epiblepharon—Epiblepharon is a congenital condition commonly seen in the lower Asian eyelid. A fold of skin and muscle roll upwards and presses the lashes toward the cornea. This does not represent true trichiasis.

Distichiasis—is an abnormality in which an aberrant second row of lashes, (usually from the meibomian gland orifices) grows behind the normal lash line. It may be congenital or acquired. Any process causing chronic inflammation of the lid margin and meibomian glands may transform the meibomian glands into pilosebaceous units capable of producing hair (e.g. chronic blepharitis).

Combined eyelid margin process—Several of the eyelid processes mentioned (Stevens-Johnson syndrome, Ocular Pemphigoid, irradiation, chemical burns) not only may cause entropion and trichiasis, but in addition may lead to squamous metaplasia and keratinization of the non-keratinizing squamous epithelium of the eyelid margin. Keratinized tissue is very irritating to the eye. Therefore, several factors may contribute to the ocular irritation, and as a result, several types of treatment could be required.

Marginal entropion—Is a subtle form of entropion that is seen only at the lid margin. Usually there is chronic inflammation at the eyelid margin with a mild cicatricial process that is starting to roll the lid margin inward. The eyelashes appear more vertical with some truly trichiatic lashes. The clinical clue is the meibomian gland orifices. Normally they should be vertical and not covered by conjunctival epithelium. If the openings are rolled inward and conjunctiva is growing over the opening, then marginal entropion is present in addition to trichiasis. It is important to distinguish this condition when considering treatment.

Hirsutism

Hirsutism is excessive hair growth on a female in a male growth pattern, typically excessive facial hair. Hirsutism is usually caused by an increased sensitivity of the skin to a group of hormones called androgens (testosterone and androstenedione) or increased production of these hormones. Androgen disorders (hyperandrogenism) affects between 5% to 10% of all women. Hair from this condition can be removed in full or part using the present invention.

Pseudofolliculitis barbae

Pseudofolliculitis barbae (razor bumps) is a common condition of the beard area occurring in African American men and other people with curly hair. The problem results when highly curved hairs grow back into the skin causing inflammation and a foreign body reaction. Over time, this can cause keloidal scarring which looks like hard bumps of the beard area and neck. Currently this is usually addressed by attempting to prevent the hair from curving back and growing into the skin with altered shaving practices and the like. The present invention can be used to eliminate hairs causing such difficulties.

Experimental Animals

Permanent hair removal as described herein can also be used with experimental animals to remove hair from all or a portion of the body of an experimental animal. Thus, for example, a hairless spot can be created on a mouse, rat, sheep, monkey, chimpanzee, rabbit or other animal for application over an extended period of time of topically applied pharmaceutical compounds or other materials. Thus, the present invention can be used for this purpose, either with or without shaving shaveing, waxing, or depilation, or other such treatment. In some cases, the hairless spot or area on the animal is initially created with shaving, waxing, or other hair removal method, and the present invention allows the bare area to be maintained (which may be after a sustained period of application of the present compositions, e.g., at least 2, 4, 7, or 10 days, or 2, 3, 4, 5, 6, 8, 10, 12, weeks or even longer).

Industrial Applications

In addition, permanent hair removal as described herein can also be useful to remove hair from mammals whose hides will be used for leather. Dehairing is one of the main initial steps in leather production. Five methods of dehairing are commonly used: i.e., (i) clipping process, (ii) scalding process, (iii) chemical process, (iv) sweating process, and (v) enzymatic process. Of these, the most commonly practiced method of dehairing of hides and skins is the chemical process using lime and sodium sulphide. However, the use of high concentrations of lime and sodium sulphide creates an extremely alkaline environment resulting in the pulping of hair and its subsequent removal, and presents substantial pollution problems. Thus, removal of hairs using the present invention allows hides to be prepared for leather production while eliminating or at least reducing the use of the pollution-causing methods.

D. Use of RNAi and Oligo Sequences

The use of RNAi to reduce or eliminate translation from a targeted mRNA has been described in a number of patents and published patent applications, e.g., as mentioned in the Background of the Invention. In the present invention, particular target sites in hairless protein mRNA can be identified experimentally and/or using software programs to identify accessible sites. For example, procedures such as those described below can be used to identify sites, and to select an optimal site and active oligonucleotide.

Identification of Potential RNAi (e.g., siRNA) Target Sites in any RNA Sequence

The sequence of an RNA target of interest, such as a viral or human mRNA transcript, is screened for target sites, for example by using a computer folding algorithm. In a non-limiting example, the sequence of a gene or RNA gene transcript derived from a database, such as Genbank, is used to generate siNA targets having complementarity to the target. Such sequences can be obtained from a database, or can be determined experimentally as known in the art. Target sites that are known, for example, those target sites determined to be effective target sites based on studies with other nucleic acid molecules, for example ribozymes or antisense, or those targets known to be associated with a disease or condition such as those sites containing mutations or deletions, can be used to design siNA molecules targeting those sites as well. Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siNA molecules for efficacy, for example by using in vitro RNA cleavage assays, cell culture, or animal models. In a non-limiting example, anywhere from 1 to 1000 target sites are chosen within the transcript based on the size of the siNA construct to be used. High throughput screening assays can be developed for screening siNA molecules using methods known in the art, such as with multi-well or multi-plate assays or combinatorial/siNA library screening assays to determine efficient reduction in target gene expression.

Selection of siNA Molecule Target Sites in a RNA

The following non-limiting steps can be used to carry out the selection of siNAs targeting a given gene sequence or transcript.

1 The target sequence is parsed in silico into a list of all fragments or subsequences of a particular length, for example 23 nucleotide fragments, contained within the target sequence. This step is typically carried out using a custom Perl script, but commercial sequence analysis programs such as Oligo, MacVector, or the GCG Wisconsin Package can be employed as well.

2 In some instances the siNAs correspond to more than one target sequence; such would be the case for example in targeting different transcripts of the same gene, targeting different transcripts of more than one gene, or for targeting both the human gene and an animal homolog. In this case, a subsequence list of a particular length is generated for each of the targets, and then the lists are compared to find matching sequences in each list. The subsequences are then ranked according to the number of target sequences that contain the given subsequence; the goal is to find subsequences that are present in most or all of the target sequences. Alternately, the ranking can identify subsequences that are unique to a target sequence, such as a mutant target sequence. Such an approach would enable the use of siNA to target specifically the mutant sequence and not effect the expression of the normal sequence.

3 In some instances the siNA subsequences are absent in one or more sequences while present in the desired target sequence; such would be the case if the siNA targets a gene with a paralogous family member that is to remain untargeted. As in case 2 above, a subsequence list of a particular length is generated for each of the targets, and then the lists are compared to find sequences that are present in the target gene but are absent in the untargeted paralog.

4 The ranked siNA subsequences can be further analyzed and ranked according to GC content. A preference can be given to sites containing 30-70% GC, with a further preference to sites containing 40-60% GC.

5 The ranked siNA subsequences can be further analyzed and ranked according to self-folding and internal hairpins. Weaker internal folds are preferred; strong hairpin structures are to be avoided.

6 The ranked siNA subsequences can be further analyzed and ranked according to whether they have runs of GGG or CCC in the sequence. GGG (or even more Gs) in either strand can make oligonucleotide synthesis problematic and can potentially interfere with RNAi activity, so it is avoided whenever better sequences are available. CCC is searched in the target strand because that will place GGG in the antisense strand.

7 The ranked siNA subsequences can be further analyzed and ranked according to whether they have the dinucleotide UU (uridine dinucleotide) on the 3'-end of the sequence, and/or AA on the 5'-end of the sequence (to yield 3' UU on the antisense sequence). These sequences allow one to design siNA molecules with terminal TT thymidine dinucleotides.

8 Four or five target sites are chosen from the ranked list of subsequences as described above. For example, in subsequences having 23 nucleotides, the right 21 nucleotides of each chosen 23-mer subsequence are then designed and synthesized for the upper (sense) strand of the siNA duplex, while the reverse complement of the left 21 nucleotides of each chosen 23-mer subsequence are then designed and synthesized for the lower (antisense) strand of the siNA duplex. If terminal TT residues are desired for the sequence (as described in paragraph 7), then the two 3' terminal nucleotides of both the sense and antisense strands are replaced by TT prior to synthesizing the oligos.

9 The siNA molecules are screened in an in vitro, cell culture or animal model system to identify the most active siNA molecule or the most preferred target site within the target RNA sequence.

In an alternate approach, a pool of siNA constructs specific to a target sequence is used to screen for target sites in cells expressing target RNA, such as human lung HeLa cells. A non-limiting example of such as pool is a pool comprising sequences having antisense sequences complementary to the target RNA sequence and sense sequences complementary to the antisense sequences. Cells (e.g., HeLa cells) expressing the target gene are transfected with the pool of siNA constructs and cells that demonstrate a phenotype associated with gene silencing are sorted. The pool of siNA constructs can be chemically modified as described herein and synthesized, for example, in a high throughput manner. The siNA from cells demonstrating a positive phenotypic change (e.g., decreased target mRNA levels or target protein expression), are identified, for example by positional analysis within the assay, and are used to determine the most suitable target site(s) within the target RNA sequence based upon the complementary sequence to the corresponding siNA antisense strand identified in the assay.

Exemplary siNA Design siNA target sites are chosen by analyzing sequences of the target RNA target and optionally prioritizing the target sites on the basis of folding (structure of any given sequence analyzed to determine siNA accessibility to the target), by using a library of siNA molecules as described, or alternately by using an in vitro siNA system as described herein. siNA molecules were designed that could bind each target and are optionally individually analyzed by computer folding to assess whether the siNA molecule can interact with the target sequence. Varying the length of the siNA molecules can be chosen to optimize activity. Generally, a sufficient number of complementary nucleotide bases are chosen to bind to, or otherwise interact with, the target RNA, but the degree of complementarity can be modulated to accommodate siNA duplexes or varying length or base composition. By using such methodologies, siNA molecules can be designed to target sites within any known RNA sequence, for example those RNA sequences corresponding to the any gene transcript.

Chemically modified siNA constructs are designed to provide nuclease stability for systemic administration in vivo and/or improved pharmacokinetic, localization, and delivery properties while preserving the ability to mediate RNAi activity. Chemical modifications as described herein are introduced synthetically using synthetic methods described herein and those generally known in the art. The synthetic siNA constructs are then assayed for nuclease stability in serum and/or cellular/tissue extracts (e.g. liver extracts). The synthetic siNA constructs are also tested in parallel for RNAi activity using an appropriate assay, such as a luciferase reporter assay as described herein or another suitable assay that can quantity RNAi activity. Synthetic siNA constructs that possess both nuclease stability and RNAi activity can be further modified and re-evaluated in stability and activity assays. The chemical modifications of the stabilized active siNA constructs can then be applied to any siNA sequence targeting any chosen RNA and used, for example, in target screening assays to pick lead siNA compounds for therapeutic development.

RNAi In Vitro Assay to Assess siNA Activity

An in vitro assay that recapitulates RNAi in a cell free system is used to evaluate siNA constructs specific to target RNA. The assay comprises the system described by Tuschl et al., 1999, Genes and Development, 13, 3191-3197 and Zamore et al., 2000, Cell, 101, 25-33 adapted for use with a specific target RNA. A Drosophila extract derived from syncytial blastoderm is used to reconstitute RNAi activity in vitro. Target RNA is generated via in vitro transcription from an appropriate plasmid using T7 RNA polymerase or via chemical synthesis as described herein. Sense and antisense siNA strands (for example 20 uM each) are annealed by incubation in buffer (such as 100 mM potassium acetate, 30 mM HEPES-KOH, pH 7.4, 2 mM magnesium acetate) for 1 min. at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two hour old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol] lysis buffer containing siNA (10 nM final concentration). The reaction mixture also contains 10 mM creatine phosphate, 10 ug.ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and preincubated at 25° C. for 10 minutes before adding RNA, then incubated at 25° C. for an additional 60 minutes. Reactions are quenched with 4 volumes of 1.25× Passive Lysis Buffer (Promega). Target RNA cleavage is assayed by RT-PCR analysis or other methods known in the art and are compared to control reactions in which siNA is omitted from the reaction.

Alternately, internally-labeled target RNA for the assay is prepared by in vitro transcription in the presence of $[a-^{32}P]$ CTP, passed over a G 50 Sephadex column by spin chromatography and used as target RNA without further purification. Optionally, target RNA is 5'-$^{32}$P-end labeled using T4 oligonucleotide kinase enzyme. Assays are performed as described above and target RNA and the specific RNA cleavage products generated by RNAi are visualized on an autoradiograph of a gel. The percentage of cleavage is determined by Phosphor Imager® quantitation of bands representing intact control RNA or RNA from control reactions without siNA and the cleavage products generated by the assay.

In one embodiment, this assay is used to determine target sites in the RNA target for siNA mediated RNAi cleavage, wherein a plurality of siNA constructs are screened for RNAi mediated cleavage of the RNA target, for example by analyzing the assay reaction by electrophoresis of labeled target RNA, or by northern blotting, as well as by other methodology well known in the art.

Specific hairless protein target sequences and the complementary sequences are provided as 19-mers in Table 1 following the Examples. In the table, the oligo number (first column on the left), e.g., 1, 2, 3, etc. matches the $1^{st}$ (5') nucleotide in the reference sense cDNA sequence. Thus, Oligonucleotide 1 begins at nucleotide 1 in the reference hairless cDNA sequence, Oligonucleotide 2, begins at nucleotide 2 in the reference sequence, and so on. Thus, one skilled in the art recognizes that the nucleotide position of each nucleotide in each oligonucleotide in Table 1 is specified as if each nucleotide were marked with the respective number.

The sequences shown in Table 1 are provided as DNA sequences, but one skilled in the art understands that Table 1 also describes the matching RNA sequence. One skilled in the art understands that the RNA sequence has a U replacing each T shown in the DNA sequence. For example, for Oligonucleotide 1 in Table 1, the DNA sequence is 5'-TCTCCCGG-GAGCCACTCCC-3' (SEQ ID NO: 1), and the matching RNA sequence is 5'-UCUCCCGGGAGCCACUCCC-3' (SEQ ID NO: 11332).

While oligonucleotides are shown in Table 1 as 19-mers, this description expressly includes the additional 20-mer, 21-mer, 22-mer, 23-mer, 24-mer, 25-mer, 26-mer, 27-mer, 28-mer, and 29-mer oligonucleotides as if they were included in the table. The sequence descriptions of those 20-29-mers is provided by taking a starting 19-mer that has the same 5'-nucleotide as the respective 20-29-mer, and adding the next 1, 2, 3, 4, 5, 6, 7, 8, 9, or 10 3'-nucleotides from the subsequent 19-mer oligonucleotides from the table. Thus, for example, the 19-mer sense RNA Oligonucleotide 4 has the sequence:

5'-CCCGGGAGCCACUCCCAUG-3'    (SEQ ID NO: 11333)

and the complementary 19-mer RNA described has the sequence

5'-CAUGGGAGUGGCUCCCGGG-3'.    (SEQ ID NO: 11334)

Further, a 20-mer RNA that includes the Oligonucleotide 4 sequence is described by the Oligo 4 sequence with the next nucleotide 3', i.e., the 3'-terminal G from Oligo 5. Thus, the 20-mer RNA described has the sequence

5'-CCCGGGAGCCACUCCCAUGG-3'    (SEQ ID NO: 11335)

and the complementary 20-mer RNA described has the sequence

5'-CCAUGGGAGUGGCUCCCGGG-3'.    (SEQ ID NO: 11336)

Similarly, a 21-mer RNA that includes the Oligonucleotide 4 sequence is described by the Oligo 4 sequence with the next two nucleotides 3', i.e., the 3'-terminal GG from Oligo 6. Thus, the 21-mer RNA described has the sequence

5'-CCCGGGAGCCACUCCCAUGGG-3'    (SEQ ID NO: 11337)

and the complementary 21-mer RNA described has the sequence

5'-CCCAUGGGAGUGGCUCCCGGG-3'.    (SEQ ID NO: 11338)

As the next oligonucleotide described, a 22-mer RNA that includes the Oligonucleotide 4 sequence is described by the Oligo 4 sequence with the next three nucleotides 3', i.e., the 3'-terminal GGC from Oligo 7. Thus, the 22-mer RNA described has the sequence

5'-CCCGGGAGCCACUCCCAUGGGC-3'    ((SEQ ID NO: 11339)

and the complementary 22-mer RNA described has the sequence

5'-GCCCAUGGGAGUGGCUCCCGGG-3'.    (SEQ ID NO: 11340)

A 23-mer RNA that includes the Oligonucleotide 4 sequence is described by the Oligo 4 sequence with the next four nucleotides 3', i.e., the 3'-terminal GGCG from Oligo 8. Thus, the 23-mer RNA described has the sequence

5'-CCCGGGAGCCACUCCCAUGGGCG-3'    (SEQ ID NO: 11341)

and the complementary 23-mer RNA described has the sequence

5'-CGCCCAUGGGAGUGGCUCCCGGG-3'.    (SEQ ID NO: 11342)

A 24-mer RNA that includes the Oligonucleotide 4 sequence is described by the Oligo 4 sequence with the next five nucleotides 3', i.e., the 3'-terminal GGCGC from Oligo 9. Thus, the 24-mer RNA described has the sequence

5'-CCCGGGAGCCACUCCCAUGGGCGC-3'    (SEQ ID NO: 11343)

and the complementary 24-mer RNA described has the sequence

5'-GCGCCCAUGGGAGUGGCUCCCGGG-3'.    (SEQ ID NO: 11344)

In similar fashion, a 25-mer that includes the Oligonucleotide 4 sequence is described as

5'-CCCGGGAGCCACUCCCAUGGGCGCC-3'    (SEQ ID NO: 11345)

and the complementary 25-mer RNA described has the sequence

5'-GGCGCCCAUGGGAGUGGCUCCCGGG-3'.    (SEQ ID NO: 11346)

A 26-mer that includes the Oligonucleotide 4 sequence is described as

5'-CCCGGGAGCCACUCCCAUGGGCGCCU-3'    (SEQ ID NO: 11347)

and the complementary 26-mer RNA described has the sequence (SEQ ID NO: 11348)
5'-AGGCGCCCAUGGGAGUGGCUCCCGGG-3'.

A 27-mer that includes the Oligonucleotide 4 sequence is described as (SEQ ID NO: 11349)
5'-CCCGGGAGCCACUCCCAUGGGCGCCUC-3' and the complementary 27-mer RNA described has the sequence (SEQ ID NO: 11350)
5'-GAGGCGCCCAUGGGAGUGGCUCCCGGG-3'.

A 28-mer that includes the Oligonucleotide 4 sequence is described as (SEQ ID NO: 11351)
5'-CCCGGGAGCCACUCCCAUGGGCGCCUCU-3' and the complementary 28-mer RNA described has the sequence (SEQ ID NO: 11352)
5'-AGAGGCGCCCAUGGGAGUGGCUCCCGGG-3'.

A 29-mer that includes the Oligonucleotide 4 sequence is described as (SEQ ID NO: 11353)
5'-CCCGGGAGCCACUCCCAUGGGCGCCUCUC-3' and the complementary 29-mer RNA described has the sequence (SEQ ID NO: 11354)
5'-GAGAGGCGCCCAUGGGAGUGGCUCCCGGG-3'.

Thus, Table 1 describes each of the 19-mers shown in Table 1 as DNA and RNA, and the corresponding 20-mers and longer.

In addition, the Table describes double stranded oligonucleotides with the sense and antisense oligonucleotide strands hybridized, as well as such double stranded oligonucleotides with one or both strands having a 3'-overhang. Such an overhang consists of one or more 3'-terminal nucleotides of an oligonucleotide strand in a double stranded molecule that are not hybridized with the complementary strand. In the present case, such overhang nucleotides often match the corresponding nucleotides from the target mRNA sequence, but can be different.

Table 1 also describes oligonucleotides that contain known polymorphisms. Those polymorphic sites are described in Table 2 along with the replacement nucleotide. Thus, Table 1 with Table 2 describes the oligonucleotides with the alternate nucleotides at a polymorphic site.

Chemical Modifications

As indicated above, for many applications it is advantageous to use chemically modified oligonucleotides rather than unmodified RNA for RNAi (e.g., siRNA). Such modification can dramatically increase the cellular and/or serum lifetime of the modified oligonucleotide compared to the unmodified form.

Description of such chemical modification is provided in McSwiggen et al., PCT/US03/05346, WO 03/070918. Thus, the introduction of chemically modified nucleotides into nucleic acid molecules assists in overcoming potential limitations of in vivo stability and bioavailability inherent to native RNA molecules that are delivered exogenously. For example, the use of chemically modified nucleic acid molecules can enable a lower dose of a particular nucleic acid molecule for a given therapeutic effect since chemically modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically modified nucleic acid molecule is reduced as compared to a native nucleic acid molecule, for example when compared to an all RNA nucleic acid molecule, the overall activity of the modified nucleic acid molecule can be greater than the native molecule due to improved stability and/or delivery of the molecule. Unlike native unmodified siRNA, chemically modified siNA can also minimize the possibility of activating interferon activity in humans.

Thus, in some embodiments of the present invention, the nucleic acid molecules that act as mediators of the RNA interference gene silencing response are chemically modified double stranded nucleic acid molecules, generally about 19-29 nucleotides in length. The most active siRNA molecules are thought to have such duplexes with overhanging ends of 1-3 nucleotides, for example 21 nucleotide duplexes with 19 base pairs and 2 nucleotide 3'-overhangs. These overhanging segments are readily hydrolyzed by endonucleases in vivo. Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, *EMBO J.*, 20, 6877). In addition, Elbashir et al. also report that full substitution of siRNA with 2'-O-methyl nucleotides completely abolishes RNAi activity.

In some embodiments, the chemically modified siNA constructs having specificity for target nucleic acid molecules in a cell. Non-limiting examples of such chemical modifications include without limitation phosphorothioate internucleotide linkages, 2'-O-methyl ribonucleotides, 2'-deoxy-2'-fluoro ribonucleotides, "universal base" nucleotides, 5-C-methyl nucleotides, and inverted deoxyabasic residue incorporation. These chemical modifications, when used in various siNA constructs, are shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise modified nucleotides at between 5 and 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands. In addition, the actual percentage of modified nucleotides present in a given siNA molecule can also depend on the total number of purine and pyrimidine nucleotides present in the siNA, for example wherein all pyrimidine nucleotides and/or all purine nucleotides present in the siNA molecule are modified.

In a non-limiting example, the introduction of chemically-modified nucleotides into nucleic acid molecules will provide a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

The antisense region of a siNA molecule of the invention can comprise a phosphorothioate internucleotide linkage at the 3'-end of said antisense region. The antisense region can comprise between about one and about five phosphorothioate internucleotide linkages at the 5'-end of said antisense region. The 3'-terminal nucleotide overhangs of a siNA molecule of the invention can comprise ribonucleotides or deoxyribonucleotides that are chemically-modified at a nucleic acid sugar, base, or backbone. The 3'-terminal nucleotide overhangs can comprise one or more universal base ribonucleotides. The 3'-terminal nucleotide overhangs can comprise one or more acyclic nucleotides.

In certain embodiments, the chemically-modified short interfering nucleic acid (siNA) molecule capable of mediating RNA interference (RNAi) inside a cell or reconstituted in vitro system, includes one or more chemically modified nucleotides (e.g., about 1, 2, 3, 4, 5, 6, 7, 8, 9, 10, or more) comprising a backbone modified internucleotide linkage having Formula I:

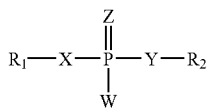

wherein each R1 and R2 is independently any nucleotide, non-nucleotide, or oligonucleotide which can be naturally-occurring or chemically-modified, each X and Y is independently O, S, N, alkyl, or substituted alkyl, each Z and W is independently O, S, N, alkyl, substituted alkyl, O-alkyl, S-alkyl, alkaryl, or aralkyl, and wherein W, X, Y, and Z are optionally not all O.

The chemically-modified internucleotide linkages having Formula I, for example wherein any Z, W, X, and/or Y independently comprises a sulphur atom, can be present in one or both oligonucleotide strands of the siNA duplex, for example in the sense strand, the antisense strand, or both strands. The siNA molecules of the invention can comprise one or more (e.g., about 1, 2, 3, 4, 5, 6, 7, 8, 9, 10, or more) chemically-modified internucleotide linkages having Formula I at the 3'-end, the 5'-end, or both of the 3' and 5'-ends of the sense strand, the antisense strand, or both strands. For example, an exemplary siNA molecule of the invention can comprise between about 1 and about 5 or more (e.g., about 1, 2, 3, 4, 5, or more) chemically-modified internucleotide linkages having Formula I at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine nucleotides with chemically-modified internucleotide linkages having Formula I in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine nucleotides with chemically-modified internucleotide linkages having Formula I in the sense strand, the antisense strand, or both strands. In another embodiment, a siNA molecule of the invention having internucleotide linkage(s) of Formula I also comprises a chemically-modified nucleotide or non-nucleotide having any of Formulae I-VII.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides or non-nucleotides having Formula II:

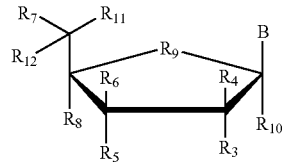

wherein each R3, R4, R5, R6, R7, R8, R10, R1 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula II can be present in one or both oligonucleotide strands of the siNA duplex, for example in the sense strand, the antisense strand, or both strands. The siNA molecules of the invention can comprise one or more chemically-modified nucleotide or non-nucleotide of Formula II at the 3'-end, the 5'-end, or both of the 3' and 5'-ends of the sense strand, the antisense strand, or both strands. For example, an exemplary siNA molecule of the invention can comprise between about 1 and about 5 or more (e.g., about 1, 2, 3, 4, 5, or more) chemically-modified nucleotides or non-nucleotides of Formula II at the 5'-end of the sense strand, the antisense strand, or both strands. In anther non-limiting example, an exemplary siNA molecule of the invention can comprise between about 1 and about 5 or more (e.g., about 1, 2, 3, 4, 5, or more) chemically-modified nucleotides or non-nucleotides of Formula II at the 3'-end of the sense strand, the antisense strand, or both strands.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides or non-nucleotides having Formula III:

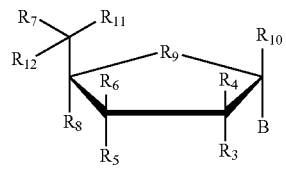

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be employed to be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula III can be present in one or both oligonucleotide strands of the siNA duplex, for example in the sense strand, the antisense strand, or both strands. The siNA molecules of the invention can comprise one or more chemically-modified nucleotide or non-nucleotide of Formula III at the 3'-end, the 5'-end, or both of the 3' and 5'-ends of the sense strand, the antisense strand, or both strands. For example, an exemplary siNA molecule of the invention can comprise between about 1 and about 5 or more (e.g., about 1, 2, 3, 4, 5, or more) chemically-modified nucleotide(s) or non-nucleotide(s) of Formula III at the 5'-end of the sense strand, the antisense strand, or both strands. In anther non-limiting example, an exemplary siNA molecule of the invention can comprise between about 1 and about 5 or more (e.g., about 1, 2, 3, 4, 5, or more) chemically-modified nucleotide or non-nucleotide of Formula III at the 3'-end of the sense strand, the antisense strand, or both strands.

In another embodiment, a siNA molecule of the invention comprises a nucleotide having Formula II or III, wherein the nucleotide having Formula II or III is in an inverted configuration. For example, the nucleotide having Formula II or III is connected to the siNA construct in a 3'-3',3'-2',2'-3', or 5'-5' configuration, such as at the 3'-end, the 5'-end, or both of the 3' and 5'-ends of one or both siNA strands.

In one embodiment, the invention features a chemically-modified short interfering nucleic acid (siNA) molecule capable of mediating RNA interference (RNAi) inside a cell or reconstituted in vitro system, wherein the chemical modification comprises a 5'-terminal phosphate group having Formula IV:

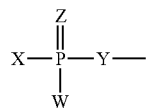

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, or alkylhalo; and wherein W, X, Y and Z are not all O.

In one embodiment, the invention features a siNA molecule having a 5'-terminal phosphate group having Formula IV on the target-complementary strand, for example a strand complementary to a target RNA, wherein the siNA molecule comprises an all RNA siNA molecule. In another embodiment, the invention features a siNA molecule having a 5'-terminal phosphate group having Formula IV on the target-complementary strand wherein the siNA molecule also comprises about 1-3 (e.g., about 1, 2, or 3) nucleotide 3'-terminal nucleotide overhangs having between about 1 and about 4 (e.g., about 1, 2, 3, or 4) deoxyribonucleotides on the 3'-end of one or both strands. In another embodiment, a 5'-terminal phosphate group having Formula IV is present on the target-complementary strand of a siNA molecule of the invention, for example a siNA molecule having chemical modifications having any of Formulae I-VII.

In one embodiment, the invention features a chemically-modified short interfering nucleic acid (siNA) molecule capable of mediating RNA interference (RNAi) inside a cell or reconstituted in vitro system, wherein the chemical modification comprises one or more phosphorothioate internucleotide linkages. For example, in a non-limiting example, the invention features a chemically-modified short interfering nucleic acid (siNA) having about 1, 2, 3, 4, 5, 6, 7, 8 or more phosphorothioate internucleotide linkages in one siNA strand. In yet another embodiment, the invention features a chemically-modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phosphorothioate internucleotide linkages at the 3'-end, the 5'-end, or both of the 3'- and 5'-ends of the sense strand, the antisense strand, or both strands. For example, an exemplary siNA molecule of the invention can comprise between about 1 and about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

In one embodiment, the invention features a siNA molecule, wherein the sense strand comprises one or more, for example about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3' end, the 5'-end, or both of the 3'- and 5'-ends of the sense strand; and wherein the antisense strand comprises any of between 1 and 10 or more, specifically about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In another embodiment, the invention features a siNA molecule, wherein the sense strand comprises between about 1 and about 5, specifically about 1, 2, 3, 4, or 5 phosphorothioate internucleotide linkages, and/or one or more (e.g., about 1, 2, 3, 4, 5, or more) 2'-deoxy, 2'-O-methyl, 2'-deoxy-2'-fluoro, and/or one or more (e.g., about 1, 2, 3, 4, 5, or more) universal base modified nucleotides, and optionally a terminal cap molecule at the 3-end, the 5'-end, or both of the 3'- and 5'-ends of the sense strand; and wherein the antisense strand comprises any of between about 1 and about 5 or more, specifically about 1, 2, 3, 4, 5, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl and/or 2'-deoxy-2'-fluoro nucleotides, with or without between about 1 and about 5 or more, for example about 1, 2, 3, 4, 5, or more phosphorothioate internucleotide linkages and/or a terminal cap molecule at the 3'-end, the 5'-end, or both of the 3'- and 5'-ends, being present in the same or different strand.

In one embodiment, the invention features a siNA molecule, wherein the antisense strand comprises one or more, for example about 1, 2, 3, 4, 5, 6, 7, 8, 9, 10, or more phosphorothioate internucleotide linkages, and/or between one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises any of between about 1 and about 10, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In another embodiment, the invention features a siNA molecule, wherein the antisense strand comprises between about 1 and about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises any of between about 1 and about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl and/or 2'-deoxy-2'-fluoro nucleotides, with or without between about 1 and about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In one embodiment, the invention features a chemically-modified short interfering nucleic acid (siNA) molecule having between about 1 and about 5, specifically about 1, 2, 3, 4, 5 or more phosphorothioate internucleotide linkages in each strand of the siNA molecule.

In another embodiment, the invention features a siNA molecule comprising 2'-5' internucleotide linkages. The 2'-5' internucleotide linkage(s) can be at the 3'-end, the 5'-end, or both of the 3'- and 5'-ends of one or both siNA sequence strands. In addition, the 2'-5' internucleotide linkage(s) can be present at various other positions within one or both siNA sequence strands, for example, about 1, 2, 3, 4, 5, 6, 7, 8, 9, 10, or more including every internucleotide linkage of a pyrimidine nucleotide in one or both strands of the siNA molecule can comprise a 2'-5' internucleotide linkage, or about 1, 2, 3, 4, 5, 6, 7, 8, 9, 10, or more including every internucleotide linkage of a purine nucleotide in one or both strands of the siNA molecule can comprise a 2'-5' internucleotide linkage.

In another embodiment, a chemically-modified siNA molecule of the invention comprises a duplex having two strands, one or both of which can be chemically-modified, wherein each strand is between about 18 and about 27 (e.g., about 18, 19, 20, 21, 22, 23, 24, 25, 26, or 27) nucleotides in length, wherein the duplex has between about 18 and about 23 (e.g., about 18, 19, 20, 21, 22, or 23) base pairs, and wherein the chemical modification comprises a structure having any of Formulae I-VII. For example, an exemplary chemically-modified siNA molecule of the invention comprises a duplex having two strands, one or both of which can be chemically-modified with a chemical modification having any of Formulae I-VII or any combination thereof, wherein each strand consists of about 21 nucleotides, each having a 2-nucleotide 3'-terminal nucleotide overhang, and wherein the duplex has about 19 base pairs. In another embodiment, a siNA molecule of the invention comprises a single stranded hairpin structure, wherein the siNA is between about 36 and about 70 (e.g., about 36, 40, 45, 50, 55, 60, 65, or 70) nucleotides in length having between about 18 and about 23 (e.g., about 18, 19, 20, 21, 22, or 23) base pairs, and wherein the siNA can include a chemical modification comprising a structure having any of Formulae I-VII or any combination thereof. For example, an exemplary chemically-modified siNA molecule of the invention comprises a linear oligonucleotide having between about 42 and about 50 (e.g., about 42, 43, 44, 45, 46, 47, 48, 49, or 50) nucleotides that is chemically-modified with a chemical modification having any of Formulae I-VII or any combination thereof, wherein the linear oligonucleotide forms a hairpin structure having about 19 base pairs and a 2-nucleotide 3'-terminal nucleotide overhang. In another embodiment, a linear hairpin siNA molecule of the invention contains a stem loop motif, wherein the loop portion of the siNA molecule is biodegradable. For example, a linear hairpin siNA molecule of the invention is designed such that degradation of the loop portion of the siNA molecule in vivo can generate a double-stranded siNA molecule with 3'-terminal overhangs, such as 3'-terminal nucleotide overhangs comprising about 2 nucleotides.

In another embodiment, a siNA molecule of the invention comprises a circular nucleic acid molecule, wherein the siNA is between about 38 and about 70 (e.g., about 38, 40, 45, 50, 55, 60, 65, or 70) nucleotides in length having between about 18 and about 23 (e.g., about 18, 19, 20, 21, 22, or 23) base pairs, and wherein the siNA can include a chemical modification, which comprises a structure having any of Formulae I-VII or any combination thereof. For example, an exemplary chemically-modified siNA molecule of the invention comprises a circular oligonucleotide having between about 42 and about 50 (e.g., about 42, 43, 44, 45, 46, 47, 48, 49, or 50) nucleotides that is chemically-modified with a chemical modification having any of Formulae I-VII or any combination thereof, wherein the circular oligonucleotide forms a dumbbell shaped structure having about 19 base pairs and 2 loops.

In another embodiment, a circular siNA molecule of the invention contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

In one embodiment, a siNA molecule of the invention comprises at least one (e.g., about 1, 2, 3, 4, 5, 6, 7, 8, 9, 10, or more) abasic moiety, for example a compound having Formula V:

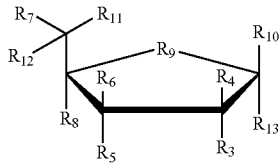

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I; R9 is O, S, CH2, S=O, CHF, or CF2.

In one embodiment, a siNA molecule of the invention comprises at least one (e.g., about 1, 2, 3, 4, 5, 6, 7, 8, 9, 10, or more) inverted abasic moiety, for example a compound having Formula VI:

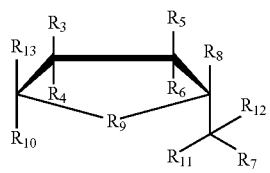

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I; R9 is O, S, CH2, S=O, CHF, or CF2, and either R2, R3, R8 or R13 serve as points of attachment to the siNA molecule of the invention.

In another embodiment, a siNA molecule of the invention comprises at least one (e.g., about 1, 2, 3, 4, 5, 6, 7, 8, 9, 10, or more) substituted polyalkyl moieties, for example a compound having Formula VII:

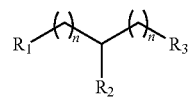

wherein each n is independently an integer from 1 to 12, each R1, R2 and R3 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or a group having Formula I, and R1, R2 or R3 serves as points of attachment to the siNA molecule of the invention.

In another embodiment, the invention features a compound having Formula VII, wherein R1 and R2 are hydroxyl (OH) groups, n=1, and R3 comprises O and is the point of attachment to the 3'-end, the 5'-end, or both of the 3' and 5'-ends of one or both strands of a double-stranded siNA molecule of the invention or to a single-stranded siNA molecule of the invention. This modification is referred to herein as "glyceryl".

In another embodiment, a moiety having any of Formula V, VI or VII of the invention is at the 3'-end, the 5'-end, or both of the 3' and 5'-ends of a siNA molecule of the invention. For example, a moiety having Formula V, VI or VII can be present at the 3'-end, the 5'-end, or both of the 3' and 5'-ends of the antisense strand, the sense strand, or both antisense and sense strands of the siNA molecule. In addition, a moiety having Formula VII can be present at the 3'-end or the 5'-end of a hairpin siNA molecule as described herein.

In another embodiment, a siNA molecule of the invention comprises an abasic residue having Formula V or VI, wherein the abasic residue having Formula VI or VI is connected to the siNA construct in a 3'-3',3'-2',2'-3', or 5'-5' configuration, such as at the 3'-end, the 5'-end, or both of the 3' and 5'-ends of one or both siNA strands.

In one embodiment, a siNA molecule of the invention comprises one or more (e.g., about 1, 2, 3, 4, 5, 6, 7, 8, 9, 10, or more) locked nucleic acid (LNA) nucleotides, for example at the 5'-end, the 3'-end, both of the 5' and 3'-ends, or any combination thereof, of the siNA molecule.

In another embodiment, a siNA molecule of the invention comprises one or more (e.g., about 1, 2, 3, 4, 5, 6, 7, 8, 9, 10, or more) acyclic nucleotides, for example at the 5'-end, the 3'-end, both of the 5' and 3'-ends, or any combination thereof, of the siNA molecule.

In one embodiment, the invention features a chemically-modified short interfering nucleic acid (siNA) molecule of the invention, wherein the chemically-modified siNA comprises a sense region, where any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention, wherein the chemically-modified siNA comprises a sense region, where any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), wherein any nucleotides comprising a 3'-terminal nucleotide overhang that are present in said sense region are 2'-deoxy nucleotides.

In one embodiment, the invention features a chemically-modified short interfering nucleic acid (siNA) molecule of the invention, wherein the chemically-modified siNA comprises an antisense region, where any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically-modified short interfering nucleic acid (siNA) molecule of the invention, wherein the chemically-modified siNA comprises an antisense region, where any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), wherein any nucleotides comprising a 3'-terminal nucleotide overhang that are present in said antisense region are 2'-deoxy nucleotides.

In one embodiment, the invention features a chemically-modified short interfering nucleic acid (siNA) molecule of the invention, wherein the chemically-modified siNA comprises an antisense region, where any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention capable of mediating RNA interference (RNAi) inside a cell or reconstituted in vitro system, wherein the chemically-modified siNA comprises a sense region, where one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where one or more purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), and inverted deoxy abasic modifications that are optionally present at the 3'-end, the 5'-end, or both of the 3' and 5'-ends of the sense region, the sense region optionally further comprising a 3'-terminal overhang having between about 1 and about 4 (e.g, about 1, 2, 3, or 4) 2'-deoxyribonucleotides; and wherein the chemically-modified short interfering nucleic acid molecule comprises an antisense region, where one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein, that is optionally present at the 3'-end, the 5'-end, or both of the 3' and 5'-ends of the antisense sequence, the antisense region optionally further comprising a 3'-terminal nucleotide overhang having between about 1 and about 4 (e.g, about 1, 2, 3, or 4) 2'-deoxynucleotides, wherein the overhang nucleotides can further comprise one or more (e.g., 1, 2, 3, or 4) phosphorothioate internucleotide linkages.

In one embodiment, the invention features a chemically-modified short interfering nucleic acid (siNA) molecule of the invention capable of mediating RNA interference (RNAi) inside a cell or reconstituted in vitro system, wherein the siNA comprises a sense region, where one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where one or more purine nucleotides present in the sense region are purine ribonucleotides (e.g., wherein all purine nucleotides are purine ribonucleotides or alternately a plurality of purine nucleotides are purine ribonucleotides), and inverted deoxy abasic modifications that are optionally present at the 3'-end, the 5'-end, or both of the 3' and 5'-ends of the sense region, the sense region optionally further comprising a 3'-terminal overhang having between about 1 and about 4 (e.g, about 1, 2, 3, or 4) 2'-deoxyribonucleotides; and wherein the siNA comprises an antisense region, where one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein, that is optionally present at the 3'-end, the 5'-end, or both of the 3' and 5'-ends of the antisense sequence, the antisense region optionally further comprising a 3'-terminal nucleotide overhang having between about 1 and about 4 (e.g, about 1, 2, 3, or 4) 2'-deoxynucleotides, wherein the overhang nucleotides can further comprise one or more (e.g., 1, 2, 3, or 4) phosphorothioate internucleotide linkages.

In one embodiment, the invention features a chemically-modified short interfering nucleic acid (siNA) molecule of the invention capable of mediating RNA interference (RNAi) inside a cell or reconstituted in vitro system, wherein the chemically-modified siNA comprises a sense region, where one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and for example where one or more purine nucleotides present in the sense region are selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides), and wherein inverted deoxy abasic modifications are optionally present at the 3'-end, the 5'-end, or both of the 3' and 5'-ends of the sense region, the sense region optionally further comprising a 3'-terminal overhang having between about 1 and about 4 (e.g, about 1, 2, 3, or 4) 2'-deoxyribonucleotides; and wherein the chemically-modified short interfering nucleic acid molecule comprises an antisense region, where one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein one or more purine nucleotides present in the antisense region are selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides), and a terminal cap modification, that is optionally present at the 3'-end, the 5'-end, or both of the 3' and 5'-ends of the antisense sequence, the antisense region optionally further comprising a 3'-terminal nucleotide overhang having between about 1 and about 4 (e.g, about 1, 2, 3, or 4) 2'-deoxynucleotides, wherein the overhang nucleotides can further comprise one or more (e.g., 1, 2, 3, or 4) phosphorothioate internucleotide linkages.

In another embodiment, any modified nucleotides present in the siNA molecules of the invention, preferably in the antisense strand of the siNA molecules of the invention, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, Principles of Nucleic Acid Structure, Springer-Verlag ed., 1984). As such, chemically modified nucleotides present in the siNA molecules of the invention, preferably in the antisense strand of the siNA molecules of the invention, are preferably resistant to nuclease degradation while at the same time maintaining the capacity to mediate RNAi. Non-limiting examples of nucleotides having a northern configuration include locked nucleic acid (LNA) nucleotides (e.g., 2'-O,4'-C-methylene-(D-ribofuranosyl) nucleotides); 2'-methoxyethoxy (MOE) nucleotides; 2'-deoxy-2'-fluoro nucleotides, 2'-deoxy-2'-chloro nucleotides, 2'-azido nucleotides, and 2'-O-methyl nucleotides.

In one embodiment, the invention features a chemically-modified short interfering nucleic acid molecule (siNA) capable of mediating RNA interference (RNAi) inside a cell or reconstituted in vitro system, wherein the chemical modification comprises one or more conjugates covalently attached to the chemically-modified siNA molecule. In another embodiment, the conjugate is covalently attached to the chemically-modified siNA molecule via a biodegradable linker. In one embodiment, the conjugate molecule is attached at the 3'-end of either the sense strand, the antisense strand, or both strands of the chemically-modified siNA molecule. In another embodiment, the conjugate molecule is attached at the 5'-end of either the sense strand, the antisense strand, or both strands of the chemically-modified siNA molecule. In yet another embodiment, the conjugate molecule is attached both the 3'-end and 5'-end of either the sense strand, the antisense strand, or both strands of the chemically-modified siNA molecule, or any combination thereof. In one embodiment, a conjugate molecule of the invention comprises a molecule that facilitates delivery of a chemically-modified siNA molecule into a biological system such as a cell. In another embodiment, the conjugate molecule attached to the chemically-modified siNA molecule is a poly ethylene glycol, human serum albumin, or a ligand for a cellular receptor that can mediate cellular uptake. Examples of specific conjugate molecules contemplated by the instant invention that can be attached to chemically-modified siNA molecules are described in Vargeese et al., U.S. Ser. No. 60/311,865, incorporated by reference herein. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

In one embodiment, the invention features a short interfering nucleic acid (siNA) molecule of the invention, wherein the siNA further comprises a nucleotide, non-nucleotide, or mixed nucleotide/non-nucleotide linker that joins the sense region of the siNA to the antisense region of the siNA. In another embodiment, a nucleotide linker of the invention can be a linker of ≧2 nucleotides in length, for example 3, 4, 5, 6, 7, 8, 9, or 10 nucleotides in length. In yet another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that is comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art, see for example Gold et al., 1995, Annu. Rev. Biochem., 64, 763; Brody and Gold, 2000, J. Biotechnol., 74, 5; Sun, 2000, Curr. Opin. Mol. Ther., 2, 100; Kusser, 2000, J. Biotechnol., 74, 27; Hermann and Patel, 2000, Science, 287, 820; and Jayasena, 1999, Clinical Chemistry, 45, 1628.

In yet another embodiment, a non-nucleotide linker of the invention comprises abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000, all hereby incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In one embodiment, the invention features a short interfering nucleic acid (siNA) molecule capable of mediating RNA interference (RNAi) inside a cell or reconstituted in vitro system, wherein one or both strands of the siNA molecule that are assembled from two separate oligonucleotides do not comprise any ribonucleotides. All positions within the siNA can include chemically modified nucleotides and/or non-nucleotides such as nucleotides and or non-nucleotides having Formula I, II, III, IV, V, VI, or VII or any combination thereof to the extent that the ability of the siNA molecule to support RNAi activity in a cell is maintained.

In one embodiment, a siNA molecule of the invention is a single stranded siNA molecule that mediates RNAi activity in a cell or reconstituted in vitro system, wherein the siNA molecule comprises a single stranded oligonucleotide having complementarity to a target nucleic acid sequence. In another embodiment, the single stranded siNA molecule of the invention comprises a 5'-terminal phosphate group. In another embodiment, the single stranded siNA molecule of the invention comprises a 5'-terminal phosphate group and a 3'-terminal phosphate group (e.g., a 2',3'-cyclic phosphate). In another embodiment, the single stranded siNA molecule of the invention comprises between 19 and 29 nucleotides. In yet another embodiment, the single stranded siNA molecule of the invention comprises one or more chemically modified nucleotides or non-nucleotides described herein. For example, all the positions within the siNA molecule can include chemically-modified nucleotides such as nucleotides having any of Formulae I-VII, or any combination thereof to the extent that the ability of the siNA molecule to support RNAi activity in a cell is maintained.

In one embodiment, a siNA molecule of the invention is a single stranded siNA molecule that mediates RNAi activity in a cell or reconstituted in vitro system, wherein the siNA molecule comprises a single stranded oligonucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein, that is optionally present at the 3'-end, the 5'-end, or both of the 3' and 5'-ends of the antisense sequence, the siNA optionally further comprising between about 1 and about 4 (e.g, about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded oligonucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, such as any modification described herein, that is optionally present at the 3'-end, the 5'-end, or both of the 3' and 5'-ends of the antisense sequence, the siNA optionally further comprising between about 1 and about 4 (e.g, about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded oligonucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are locked nucleic acid (LNA) nucleotides (e.g., wherein all purine nucleotides are LNA nucleotides or alternately a plurality of purine nucleotides are LNA nucleotides), and a terminal cap modification, such as any modification described herein, that is optionally present at the 3'-end, the 5'-end, or both of the 3' and 5'-ends of the antisense sequence, the siNA optionally further comprising between about 1 and about 4 (e.g, about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded oligonucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-methoxyethyl purine nucleotides (e.g., wherein all purine nucleotides are 2'-methoxyethyl purine nucleotides or alternately a plurality of purine nucleotides are 2'-methoxyethyl purine nucleotides), and a terminal cap modification, such as any modification described herein, that is optionally present at the 3'-end, the 5'-end, or both of the 3' and 5'-ends of the antisense sequence, the siNA optionally further comprising between about 1 and about 4 (e.g, about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded oligonucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are purine ribonucleotides (e.g., wherein all purine nucleotides are purine ribonucleotides or alternately a plurality of purine nucleotides are purine ribonucleotides), and a terminal cap modification, such as any modification described herein, that is optionally present at the 3'-end, the 5'-end, or both of the 3' and 5'-ends of the antisense sequence, the siNA optionally further comprising between about 1 and about 4 (e.g, about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In another embodiment, any modified nucleotides present in the single stranded siNA molecules of the invention comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, Principles of Nucleic Acid Structure, Springer-Verlag ed., 1984). As such, chemically modified nucleotides present in the single stranded siNA molecules of the invention are preferably resistant to nuclease degradation while at the same time maintaining the capacity to mediate RNAi.

E. Preparation of Oligonucleotides

The present oligonucleotides can be prepared by methods available to those skilled in the art. For example, unmodified RNA can be prepared by transcription, e.g., in vitro, using methods and constructs available in the art. The sequence for the particular target, and its complementary sequence can be inserted into a selected vector, and transcribed to produce the desired oligonucleotides by conventional methods.

In many cases, it will be desirable to chemically synthesize the oligonucleotides, e.g., for chemically modified oligonucleotides. Such syntheses are known in the art, and are described, for example, below.

Thus, siNA molecules can be designed to interact with various sites in the RNA message, for example target sequences within the RNA sequences described herein. The sequence of one strand of the siNA molecule(s) is complementary to the target site sequences described above. The siNA molecules can be chemically synthesized using methods described herein. Inactive siNA molecules that are used as control sequences can be synthesized by scrambling the sequence of the siNA molecules such that it is not complementary to the target sequence. Generally, siNA constructs can by synthesized using solid phase oligonucleotide synthesis methods as described herein (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086). Modification of synthesis conditions can be used to optimize coupling efficiency, for example by using differing coupling times, differing reagent/phosphoramidite concentrations, differing contact times, differing solid supports and solid support linker chemistries depending on the particular chemical composition of the siNA to be synthesized. Deprotection and purification of the siNA can be performed as is generally described in Vargeese et al., U.S. Ser. No. 10/194,875, incorporated by reference herein in its entirety. Additionally, deprotection conditions can be modified to provide the best possible yield and purity of siNA constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Synthesis of Nucleic Acid Molecules

In greater detail, synthesis of nucleic acids greater than 100 nucleotides in length is difficult using automated methods, and the therapeutic cost of such molecules is prohibitive. In this invention, small nucleic acid motifs, "small" refers to nucleic acid motifs no more than 100 nucleotides in length, preferably no more than 80 nucleotides in length, and most preferably no more than 50 nucleotides in length; e.g., individual siNA oligonucleotide sequences or siNA sequences synthesized in tandem) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 2.5 min coupling step for 2'-O-methylated nucleotides and a 45 sec coupling step for 2'-deoxy nucleotides or 2'-deoxy-2'-fluoro nucleotides. Alternatively, syntheses at the 0.2 μmol scale can be performed on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. A 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention follows the procedure as described in Usman et al., 1987, J. Am. Chem. Soc., 109, 7845; Scaringe et al., 1990, Nucleic Acids Res., 18, 5433; and Wincott et al., 1995, Nucleic Acids Res. 23, 2677-2684 Wincott et al., 1997, Methods Mol. Bio., 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA•3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 min. The vial is brought to r.t. TEA•3HF (0.1 mL) is added and the vial is heated at 65° C. for 15 min. The sample is cooled at −20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 min. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 Nucleic Acids Res. 23, 2677-2684). Those of ordinary skill in the art will recognize that the scale of synthesis can be adapted to be larger or smaller than the example described above including but not limited to 96-well format.

Alternatively, the nucleic acid molecules of the present invention can be synthesized separately and joined together post-synthetically, for example, by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204), or by hybridization following synthesis and/or deprotection.

The siNA molecules of the invention can also be synthesized via a tandem synthesis methodology as described below, where both siNA strands are synthesized as a single contiguous oligonucleotide fragment or strand separated by a cleavable linker which is subsequently cleaved to provide separate siNA fragments or strands that hybridize and permit purification of the siNA duplex. The linker can be a oligonucleotide linker or a non-nucleotide linker. The tandem synthesis of siNA as described herein can be readily adapted to both multiwell/multiplate synthesis platforms such as 96 well or similarly larger multi-well platforms. The tandem synthesis of siNA as described herein can also be readily adapted to large scale synthesis platforms employing batch reactors, synthesis columns and the like.

A siNA molecule can also be assembled from two distinct nucleic acid strands or fragments wherein one fragment includes the sense region and the second fragment includes the antisense region of the RNA molecule.

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, TIBS 17, 34; Usman et al., 1994, Nucleic Acids Symp. Ser. 31, 163). siNA constructs can be purified by gel electrophoresis using general methods or can be purified by high pressure liquid chromatography (HPLC; see Wincott et al., supra, the totality of which is hereby incorporated herein by reference) and re-suspended in water.

In another aspect of the invention, siNA molecules of the invention are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules.

Tandem Synthesis of siNA Constructs

Exemplary siNA molecules are synthesized in tandem using a cleavable linker, for example a succinyl-based linker. Tandem synthesis as described herein is followed by a one-step purification process that provides RNAi molecules in high yield. This approach is highly amenable to siNA synthesis in support of high throughput RNAi screening, and can be readily adapted to multi-column or multi-well synthesis platforms.

After completing a tandem synthesis of an siNA oligo and its complement in which the 5'-terminal dimethoxytrityl (5'-O-DMT) group remains intact (trityl on synthesis), the oligonucleotides are deprotected as described above. Following deprotection, the siNA sequence strands are allowed to spontaneously hybridize. This hybridization yields a duplex in which one strand has retained the 5'-O-DMT group while the complementary strand comprises a terminal 5'-hydroxyl. The newly formed duplex behaves as a single molecule during routine solid-phase extraction purification (Trityl-On purification) even though only one molecule has a dimethoxytrityl group. Because the strands form a stable duplex, this dimethoxytrityl group (or an equivalent group, such as other trityl groups or other hydrophobic moieties) is all that is required to purify the pair of oligos, for example by using a C18 cartridge.

Standard phosphoramidite synthesis chemistry is used up to point of introducing a tandem linker, such as an inverted deoxy abasic succinate or glyceryl succinate linker or an equivalent cleavable linker. A non-limiting example of linker coupling conditions that can be used includes a hindered base such as diisopropylethylamine (DIPA) and/or DMAP in the presence of an activator reagent such as Bromotripyrrolidinophosphoniumhexafluororophosphate (PyBrOP). After the linker is coupled, standard synthesis chemistry is utilized to complete synthesis of the second sequence leaving the terminal the 5'-O-DMT intact. Following synthesis, the resulting oligonucleotide is deprotected according to the procedures described herein and quenched with a suitable buffer, for example with 50 mM NaOAc or 1.5M $NH_4H_2CO_3$.

Purification of the siNA duplex can be readily accomplished using solid phase extraction, for example using a Waters C18 SepPak 1 g cartridge conditioned with 1 column volume (CV) of acetonitrile, 2 CV H2O, and 2 CV 50 mM NaOAc: The sample is loaded and then washed with 1 CV H2O or 50 mM NaOAc. Failure sequences are eluted with 1 CV 14% ACN (Aqueous with 50 mM NaOAc and 50 mM NaCl). The column is then washed, for example with 1 CV H2O followed by on-column detritylation, for example by passing 1 CV of 1% aqueous trifluoroacetic acid (TFA) over the column, then adding a second CV of 1% aqueous TFA to the column and allowing to stand for approx. 10 minutes. The remaining TFA solution is removed and the column washed with H2O followed by 1 CV 1 M NaCl and additional H2O. The siNA duplex product is then eluted, for example using 1 CV 20% aqueous CAN.

Optimizing Activity of the Nucleic Acid Molecules.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siNA nucleic acid molecules of the instant invention so long as the ability of siNA to promote RNAi is cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

Short interfering nucleic acid (siNA) molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., 1995, Nucleic Acids Res. 23, 2677; Caruthers et al., 1992, Methods in Enzymology 211, 3-19 (incorporated by reference herein)) have expanded the ability to modify nucleic acid molecules by introducing nucleotide modifications to enhance their nuclease stability, as described above.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, J. Am. Chem. Soc., 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2',4'-C mythylene bicyclo nucleotide (see for example Wengel et al., International PCT Publication No. WO 00/66604 and WO 99/14226).

In another embodiment, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable linker" as used herein, refers to a nucleic acid or non-nucleic acid linker molecule that is designed as a biodegradable linker to connect one molecule to another molecule, for example, a biologically active molecule to a siNA molecule of the invention or the sense and antisense strands of a siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siNA molecules either alone or in combination with other molecules contemplated by the instant invention include therapeutically active molecules such as antibodies, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

Therapeutic nucleic acid molecules (e.g., siNA molecules) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In yet another embodiment, siNA molecules having chemical modifications that maintain or enhance enzymatic activity of proteins involved in RNAi are provided. Such nucleic acids are also generally more resistant to nucleases than unmodified nucleic acids. Thus, in vitro and/or in vivo the activity should not be significantly lowered.

Use of the nucleic acid-based molecules of the invention will lead to better treatment of the disease progression by affording the possibility of combination therapies (e.g., multiple siNA molecules targeted to different genes; nucleic acid molecules coupled with known small molecule modulators; or intermittent treatment with combinations of molecules, including different motifs and/or other chemical or biological molecules). The treatment of subjects with siNA molecules can also include combinations of different types of nucleic acid molecules, such as enzymatic nucleic acid molecules (ribozymes), allozymes, antisense, 2,5-A oligoadenylate, decoys, and aptamers.

In another aspect a siNA molecule of the invention comprises one or more 5' and/or a 3'-cap structure, for example on only the sense siNA strand, the antisense siNA strand, or both siNA strands.

By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples: the 5'-cap is selected from the group comprising glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In yet another embodiment, the 3'-cap is selected from a group comprising glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

An "alkyl" group refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons. The alkyl group can be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups that are unsaturated hydrocarbon groups containing at least one carbon-carbon double bond, including straight-chain, branched-chain, and cyclic groups. Preferably, the alkenyl group has 1 to 12 carbons. More preferably, it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups that have an unsaturated hydrocarbon group containing at least one carbon-carbon triple bond, including straight-chain, branched-chain, and cyclic groups. Preferably, the alkynyl group has 1 to 12 carbons. More preferably, it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups can also include aryl, alkylaryl, carbocyclic aryl, heterocyclic aryl, amide and ester groups. An "aryl" group refers to an aromatic group that has at least one ring having a conjugated pi electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al., International PCT Publication No. WO 93/15187; Uhlman & Peyman, supra, all are hereby incorporated by reference herein). There are several examples of modified nucleic acid bases known in the art as summarized by Limbach et al., 1994, Nucleic Acids Res. 22, 2183. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, Biochemistry, 35, 14090; Uhlman & Peyman, supra). By "modified bases" in this aspect is meant nucleotide bases other than adenine, guanine, cytosine and uracil at 1' position or their equivalents.

In one embodiment, the invention features modified siNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, Nucleic Acid Analogues: Synthesis and Properties, in Modern Synthetic Methods, VCH, 331-417, and Mesmaeker et al., 1994, Novel Backbone Replacements for Oligonucleotides, in Carbohydrate Modifications in Antisense Research, ACS, 24-39.

By "abasic" is meant sugar moieties lacking a base or having other chemical groups in place of a base at the 1' position, see for example Adamic et al., U.S. Pat. No. 5,998, 203.

By "unmodified nucleoside" is meant one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'—$NH_2$ or 2'-O—$NH_2$, which may be modified or unmodified. Such modified groups are described, for example, in Eckstein et al., U.S. Pat. No. 5,672,695 and Matulic-Adamic et al., U.S. Pat. No. 6,248,878, which are both incorporated by reference in their entireties.

Various modifications to nucleic acid siNA structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

F. Compositions for Administration

Suitable pharmaceutical compositions containing the present RNAi inducing oligonucleotides can be prepared in many different forms. In most cases, it is desirable to apply the active oligonucleotide topically to one or more hair producing skin areas on a subject. For these applications, a composition that flows, or is spreadable or sprayable is advantageous. Examples of such compositions include, for example, solutions, suspensions, emulsions, lotions, creams, gels, ointments, liposome preparations, and the like. Preparation of such pharmaceutical compositions is well-known in the art, and can be utilized for the present invention.

Thus, the oligonucleotide formulations useful in the present invention will generally include the oligonucleotide(s) and a pharmaceutically acceptable carrier, e.g., any liquid or nonliquid carrier, gel, cream, ointment, lotion, paste, emulsifier, solvent, liquid diluent, powder, or the like, which is stable with respect to all components of the topical pharmaceutical formulation and which is suitable for topical administration of oligonucleotides according to the method of the invention. Such carriers are well known in the art.

A topical carrier, as noted above, is one which is generally suited to topical drug administration and includes any such materials known in the art. The topical carrier is selected so as to provide the composition in the desired form, e.g., as a liquid, lotion, cream, paste, gel, or ointment, and may be comprised of a material of either naturally occurring or synthetic origin. It is essential, clearly, that the selected carrier not adversely affect the oligonucleotide or other components of the topical formulation. Examples of suitable topical carriers for use herein include water, alcohols and other nontoxic organic solvents, glycerin, mineral oil, silicone, petroleum jelly, lanolin, fatty acids, vegetable oils, waxes, and the like. Particularly preferred formulations herein are colorless, odorless ointments, lotions, creams and gels.

Ointments, which are semisolid preparations, are typically based on petrolatum or other petroleum derivatives. As will be appreciated by the ordinarily skilled artisan, the specific ointment base to be used is one that provides for optimum oligonucleotide delivery, and, preferably, provides for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to Remington: The Science and Practice of Pharmacy for further information.

Lotions, which are preparations that are to be applied to the skin surface without friction, are typically liquid or semiliquid preparations in which solid particles, including the oligonucleotide, are present in a water or alcohol base. Lotions are usually suspensions of solids, and preferably, for the present purpose, comprise a liquid oily emulsion of the oil-in-water type. Lotions are preferred formulations for oligonucleotide delivery to large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Creams containing a oligonucleotide for delivery according to the method of the invention are viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a nonionic, anionic, cationic or amphoteric surfactant.

Gel formulations can also be used in connection with the present invention. As will be appreciated by those working in the field of topical drug formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

The oligonucleotide formulations useful in the invention also encompass sprays, that generally provide the oligonucleotide in an aqueous solution which can be misted onto the skin for delivery. Such sprays include those formulated to provide for concentration of the oligonucleotide solution at the site of administration following delivery, e.g., the spray solution can be primarily composed of alcohol or other like volatile liquid in which the oligonucleotide can be dissolved. Upon delivery to the skin, the alcohol carrier evaporates, leaving concentrated oligonucleotide at the site of administration.

The oligonucleotide formulations useful in the invention can also contain other optional such as opacifiers, anti-oxidants, gelling agents, thickening agents, stabilizers, and the like. Other agents may also be added, such as antimicrobial agents, antifungal agents, antibiotics and anti-inflammatory agents such as steroids.

The oligonucleotide formulations can include other components that, while not necessary for delivery of oligonucleotides to the skin, may enhance such delivery. For example, although it is not necessary to the practice of the invention, the oligonucleotide formulations may also contain a skin permeation enhancer. Suitable enhancers are well know in the art and include, for example, dimethylsulfoxide (DMSO), dimethyl formamide (DMF), N,N-dimethylacetamide (DMA), decylmethylsulfoxide ($C_{10}$ MSO), $C_2$-$C_6$ alkanediols, and the 1-substituted azacycloheptan-2-ones, particularly 1-n-dodecylcyclazacycloheptan-2-one (available under the trademark Azone® from Whitby Research Incorporated, Richmond, Va.), alcohols, and the like. Preferably, the oligonucleotides delivered are substantially free of such permeation enhancers.

The additional components should not substantially interfere with the integrity or biological activity of the oligonucleotide or the formulation in which it is provided, i.e., the additional components do not adversely affect the uptake of the oligonucleotide by skin cells or chemically modify the oligonucleotide in an undesirable manner.

It will be recognized by those skilled in the art that the optimal quantity and spacing of individual dosages of oligonucleotides will be determined by the precise form and components of the oligonucleotide formulation to be delivered, the site of administration, the use to which the delivery device is applied (e.g., immunization, treatment of a condition, production of transgenic animals, etc.), and the particular subject to which the oligonucleotide formulation is to be delivered, and that such optimums can be determined by conventional techniques. It will also be appreciated by one skilled in the art that the optimal dosing regimen, i.e., the number of doses of oligonucleotides, can be ascertained using conventional methods, e.g., course of treatment determination tests. Generally, a dosing regimen will involve administration of the selected oligonucleotide formulation at least once daily, and may be one to four times daily or more.

The practice of the present invention will employ, unless otherwise indicated, conventional techniques of drug formulation, particularly topical drug formulation, which are within the skill of the art. Such techniques are fully explained in the literature. See Remington: The Science and Practice of Pharmacy, cited supra, as well as Goodman & Gilman's The Pharmacological Basis of Therapeutics, 9th Ed. (New York: McGraw-Hill, 1996).

Dosage Forms of the Oligonucleotide Formulations

The oligonucleotides can be prepared in unit dosage form (e.g., in ampules), or in multidose form. The oligonucleotides may be present in such forms as suspensions, solutions, gels, or creams, preferably in an aqueous vehicle (e.g., in a buffered solution). Alternatively, the oligonucleotide salt may be in lyophilized form for reconstitution, at the time of delivery, with a suitable vehicle, such as sterile pyrogen-free water or phosphate-buffered saline (PBS). Both liquid as well as lyophilized forms that are to be reconstituted preferably comprise agents, preferably buffers, in amounts necessary to suitably adjust the pH of the solution. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid, gel, cream, or solid, may contain from 0.1% to 99% of oligonucleotide material.

Delivery Devices

The oligonucleotide formulation can administered using and be provided within, a delivery device (e.g., a patch, bandage, etc.) that provides for both maintenance of contact between the skin of the subject and the oligonucleotide formulation and substantially uninhibited movement of the oligonucleotide into the skin. The delivery device generally does not in and of itself facilitate movement of the oligonucleotide contained therein into the skin, but rather primarily acts to ensure that the oligonucleotide formulation is in contact with the skin for a time sufficient to allow genetic alteration of skin cells. The delivery device comprises a delivery means, or "reservoir," which is saturated with a formulation that comprises an amount of oligonucleotide sufficient to genetic alteration of skin cells to which it is to be delivered and sufficient to elicit the desired biological effect. For example, where the delivery device is to be used to deliver a oligonucleotide for genetic immunization of a human, the delivery means of the device preferably contains an amount of oligonucleotide ranging from about 10 .mu.g to about 1,000 .mu.g, preferably from about 100 .mu.g to about 500 .mu.g.

Suitable delivery means of the delivery devices of the invention include, but are not limited to, sponges, hydrogels, and absorptive materials (e.g., gauze) that allow for retention of the oligonucleotide formulation at the site of oligonucleotide administration without substantially interfering with the delivery of oligonucleotide to the skin. It is important that, upon contact of the delivery means with the skin, the oligonucleotides contained in the delivery means diffuse or otherwise pass from the delivery means into the skin at a rate and in an amount suitable to accomplish the desired effect.

In general, the delivery means has at least two surfaces: a first surface that serves as a skin-contacting surface; and a second surface opposite the skin-contacting surface. Preferably, the second surface is in contact with a liquid-impermeable coating that substantially prevents movement of the oligonucleotide out of the delivery means through the second surface (e.g., in a direction away from the first skin-contacting surface). Preferably, the liquid-impermeable coating also decreases the rate of dehydration of the oligonucleotide formulation contained in the delivery means. In one embodiment, the first skin-contacting surface of the delivery means is associated with a liquid-impermeable, removable layer (e.g., release liner), which layer is removed just prior to placement of the first surface on the skin of a subject for administration of the oligonucleotide.

The delivery device preferably comprises an adhesive means, which can be a polymeric matrix of a pharmaceutically acceptable contact adhesive material, which serves to affix the system to the skin during drug delivery. The adhesive means facilitates retention of the delivery means on the skin at the desired site of administration. Preferably, the adhesive means comprises an adhesive substance that allows for retention of the delivery means at the desired site for a selected amount of time, but additionally allows for easy removal of the delivery means without substantially adversely affecting the skin with which the adhesive substance was in contact.

The adhesive substance used must be biocompatible with the skin of the subject, and should not substantially interfere with the delivery of oligonucleotide to the subject. Examples of suitable skin contact adhesive materials include, but are not limited to, polyethylenes, polysiloxanes, polyisobutylenes, polyacrylates, polyurethanes, and the like. The particular polymeric adhesive selected will depend on the particular oligonucleotide formulation, vehicle, etc., i.e., the adhesive must be compatible with all components of the oligonucleotide formulation.

In one embodiment, the delivery means and skin contact adhesive are present as separate and distinct layers of the delivery device, with the adhesive underlying the delivery means which, in this case, may be either a polymeric matrix as described above, or it may be a liquid or hydrogel reservoir, or may take some other form. In another embodiment, the delivery means is an adhesive bandage. Exemplary delivery devices suitable for use in the invention include, but are not limited to, those devices described in U.S. Pat. No. 5,160,328; U.S. Pat. No. 5,254,346; U.S. Pat. No. 5,714,162; U.S. Pat. No. 5,667,798; U.S. Pat. No. 5,230,896; and U.S. Pat. No. 5,260,066. Methods for preparation of suitable delivery means and other elements associated with the delivery means, such as an adhesive means are well known in the art.

In another embodiment, the oligonucleotide formulation of the invention is provided as a patch, wherein the drug composition is contained within, for example, a laminated structure that serves as a drug delivery device to be affixed to the skin. In such a structure, the oligonucleotide composition is contained within a delivery means, or "reservoir," which lies beneath an upper backing layer. The laminated structure may contain a single reservoir, or it may contain multiple reservoirs.

The backing layer in the laminates of the patch, which serves as the upper surface of the delivery device, functions as the primary structural element of the laminated structure and provides the device with much of its flexibility. The material selected for the backing material should be selected so that it is substantially impermeable to oligonucleotide and, preferably, to other components of the oligonucleotide formulation, thus preventing loss of any components through the upper surface of the device, and preferably substantially impeding dehydration of the composition in the reservoir. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the skin-contacting surface of the device, which as noted above may be either the reservoir itself or a separate contact adhesive layer, so that the system may be affixed to the skin. The release liner is preferably made of a material that is substantially impermeable to the oligonucleotide and other components in the oligonucleotide formulation.

Delivery devices suitable for use in the present invention may be fabricated using conventional techniques, known in the art, for example by casting a fluid admixture of adhesive, oligonucleotide, and carrier/vehicle onto the backing layer, followed by lamination of the release liner. Similarly, the adhesive mixture may be cast onto the release liner, followed by lamination of the backing layer. Alternatively, the oligonucleotide reservoir may be prepared in the absence of oligonucleotide formulation or excipient, and then loaded by "soaking" in a drug/vehicle mixture.

As with the topical formulations of the invention, the oligonucleotide formulation contained within the delivery means of the delivery devices may contain a number of components. Furthermore, such delivery devices can be used in connection with administration of any of the oligonucleotide formulations described herein, e.g., naked oligonucleotide formulations, or lipid- or liposome-comprising oligonucleotide formulations. Regardless of the specific basic components of the oligonucleotide formulation, the oligonucleotide formulation will generally dissolved, dispersed or suspended in a suitable pharmaceutically acceptable vehicle, typically an aqueous solution or gel. Other components that may be present include preservatives, stabilizers, and the like.

Packaging of the Oligonucleotide Formulations and Delivery Devices

The units dosage ampules, multidose containers, and/or delivery devices (e.g., patches) in which the oligonucleotides are packaged prior to use may comprise an hermetically sealed container enclosing an amount of oligonucleotide or oligonucleotide formulation containing a oligonucleotide suitable for a pharmaceutically effective dose thereof, or multiples of an effective dose. The oligonucleotide is preferably packaged as a sterile formulation, and the hermetically sealed container is designed to preserve sterility of the formulation until use. Where the oligonucleotides are provided in a patch-style delivery device, the patches may be contained in a strip of individually separable packaged patches for ease in dispensing.

The container in which the oligonucleotide formulation and/or delivery device is packaged is labeled, and the label bears a notice in the form prescribed by any appropriate governmental agency. For example, where the oligonucleotides are to be administered to humans, the package comprises a notice that reflects approval by the Food and Drug Administration under the applicable federal law, of the manufacture, use, or sale of the oligonucleotide material therein for human administration. Federal law requires that the use of pharmaceutical agents in the therapy of humans be approved by an agency of the Federal government. Responsibility for enforcement is the responsibility of the Food and Drug Administration, which issues appropriate regulations for securing such approval, detailed in 21 U.S.C. 301-392. Regulation for biologic material, comprising products made from the tissues of animals is provided under 42 U.S.C 262. Similar approval is required by most foreign countries. Regulations vary from country to country, but the individual procedures are well known to those in the art.

Introduction of Oligonucleotides into Skin Cells According to the Method of the Invention Application of the Oligonucleotide to Skin Administration of the oligonucleotide is accomplished by contacting a oligonucleotide-comprising formulation (e.g., a buffered salt solution comprising the oligonucleotide) with an area of skin for a time sufficient to allow genetic alteration of skin cells. Preferably, the oligonucleotide is applied to hirsute skin. The oligonucleotide can be applied to skin without substantial pretreatment or with pretreatment, preferably without pretreatment of the skin. "Pretreatment" can generally encompass removal of hair from the skin, increasing skin permeability by mechanical means (e.g, abrasion), increasing skin permeability by application of a chemical agent to the site either before or during oligonucleotide administration, and application of an irritant or other like chemical agent to elicit a non-specific immune response or an immune response toward the irritant (e.g., by application of a keratinolytic agent). Administration of the oligonucleotide can be accomplished according to the invention without the application of an electric field or electric pulse (e.g., as in iontophoresis), without breaking the skin (e.g., by abrasion or through use of a needle), and without application of pressure to the site of administration (e.g., via jet propulsion, pressurized air, etc.). Furthermore, oligonucleotide administration can be accomplished using a oligonucleotide formulation that is substantially free of permeabilizing agents, detergents, or other chemical agents that facilitate entry of the oligonucleotide into the skin.

Once the oligonucleotide-comprising formulation is brought into contact with skin, contact is maintained for a time sufficient to allow movement of the oligonucleotide from the formulation into skin and into skin cells. In general, the time of contact between the oligonucleotide and the skin will be at least about 1 min to about 1 hr or more, preferably at least about 30 min. Because there is substantially no toxicity associated with contacting the oligonucleotide with the skin, the time of contact maintained between the oligonucleotide and the skin to which the oligonucleotide is to be delivered is limited only by such factors as the ability to keep the oligonucleotide in a suitable delivery form (e.g., a time during which the oligonucleotide-comprising solution can be prevented from dehydrating) and the ability to physically maintain contact between the oligonucleotide and the site of delivery (e.g., maintenance of a patch comprising the oligonucleotide(s) on the skin). Therefore, the time of contact of a single dose can be as long as several hours to several days, and may be weeks or more. Furthermore, the time of delivery can be further extended by additional subsequent applications of the oligonucleotide to the same or different delivery site on the skin.

While an ethanolic/propylene glycol solution of anti-hairless oligonucleotide as found to deliver beneficial amounts of oligonucleotide to the hair follicle and result in inhibition of hairless, other formulations can also advantageously be used. In particular, liposome compositions can be advantageous. Liposomes were introduced first in about 1980 for topical drug delivery and have since attracted considerable interest due to their potential utility both as a drug carrier and a reservoir for controlled release of drugs within various layers of the skin and the hair follicle. In addition to reducing the undesirable high systemic absorption of topically applied drugs, the major advantage of liposomes compared to other formulations such as ointments or creams, is based on their ability to create a depot, from which the drug is slowly released. The delivery agents also provide advantages in that they protect oligonucleotides against degradation, increase cellular uptake, and may target the drug to specific cells or tissue compartment. Thus, a delivery system allowing the controlled and sustained release of oligonucleotides in vivo can greatly increase the efficacy of gene inhibition technology.

One of the most favored sites of liposome penetration is into the hair follicle, since the hair canal opens directly onto the surface of the skin. Liposomes applied to cultured hair follicles are easily detected in cells lining the inner root sheath. (Li et al., 1992b, *In Vitro Cell Dev Biol* 28A:679-681.) Liposomes also find their way into the pilosebaceous unit once traveling down the root sheath. (Lieb et al. 1992, *J Invest Dermatol* 99:108-113.) Liposomes have been shown to direct compounds into the sebaceous gland, when they would otherwise be trapped in the stratum corneum. (Bernard et al., 1997, *J Pharm Sci* 86:573-578.) Liposomes function both as a controlled release system and as a delivery system transporting encapsulated substances into cells. After topical application, and upon drying, the liposomes develop into a structured film that fills the follicular openings, intimately mixing with the follicular contents, and fostering drug diffusion to the depths of the follicles.

A number of different compositions of liposomes have been tested for in vivo oligonucleotide delivery. For example, three different lipids were compared: N-[1-(2,3-dioleoyloxy)propyl]-N,N,N-trimethyl ammonium chloride (DOTMA), 2,3-dioleyloxy-N-[2(sperminecarboxamido) ethyl]-N,N-dimethyl-1-propanaminium trifluoroacetate (DOSPA) and N-(1-(2,3-dimyristyloxypropyl)-N,N dimethyl-(2-hydroxyethyl) ammonium bromide (DMRIE). The macrophages incorporated tenfold more oligonucleotide when delivered in conjunction with DOSPA than with the other cationic lipids.

Liposome preparation and encapsulation of oligonucleotides are available from commercial manufacturer, e.g., Bio-Zone Laboratories, Inc. Pittsburg, Calif., which manufactures a wide range of topically applied LipoCeutical products that include cationic lipids.

In addition to cationic lipid liposomes, other types of liposomes can also be used, e.g. pH-sensitive liposomes. The cellular uptake of liposomes passes mainly through an endocytic pathway, and occasionally, liposomes and their contents inadvertently arrive in the lysosomes where they are degraded. The quantity of oligonucleotides that can avoid degradation and reach their nuclear or cytoplasmic target is probably very low. To overcome lysosomal degradation and in order to increase the efficiency of delivery, pH sensitive fusogenic liposomes have been used. These consist of a non-bilayer-forming lipid such as dioleylphosphatidylethanolamine (DOPE) and a titratable acidic amphiphile such as oleic acid (OA) or cholesterylhemisuccinate (CHEMS). (DeOliveira et al., 1998, *Biochim. Biophys. Acta Biomembr.* 1372: 301-310.) At pH 7, the amphiphile maintains the lipid mix in a bilayer (liposome) structure. However, as the complex moves through the endosomes, the pH drops and the amphiphile becomes protonated. This causes the liposome to collapse resulting in fusion with the endosomal membrane and release of the liposome contents into the cytoplasm. However, the anionic nature of pH-sensitive liposomes may lead to poor encapsulation of ODNs. (Hughes et al., 2000, *Methods Enzymol* 313:342-358.).

As one alternative to liposomes, other carriers/delivery agents can be used, such as cationic polymers. The most widely studied polymers are polylactides and co-polymers of lactic acid and glycolic acid P(LA-GA) and both of these have been evaluated for the use for delivery of oligonucleotides. (Lewis et al., 1998, *J Drug Target* 5:291-302; Hudson et al., 1999, *Int J Pharm* 182:49-58.)

In addition to the above, certain patents have described methods for delivery that can be used in the present invention. Examples include the following.

Li and Lishko, U.S. Pat. No. 5,914,126 (incorporated herein by reference in its entirety) describes methods to deliver macromolecules to hair follicles, where the method involves applying to the skin a formulation that includes a macromolecule, such as a nucleic acid, in a liposomal formulation, such that the liposomes target the macromolecule selectively into hair follicle cells by transfer into the follicle without entry into the circulation of the adjacent skin tissue.

Khavari et al., U.S. Pat. No. 6,087,341 (incorporated herein by reference in its entirety) describes methods and compositions for introduction of nucleic acid into skin cells by topical application.

Li and Baranov, U.S. Pat. No. 6,080,127 (incorporated herein by reference in its entirety) describes a skin vibration method for topical targeted delivery of beneficial agents into hair follicles. The vibration frequency can, for example, be about 1 Hz to 100 Hz.

In some applications, it may be useful to include transdermal penetration enhancers, for example, as described in Karande et al., 2004, *Nature Biotech.* 192-197. As described, two types of compositions were particularly effective. One included sodium laureth sulfate (SLA) with phenyl piperazine (PP). In a particular composition the SLA:PP was as 0.5% (w/v) with the weight ration of SLA=0.7 in the combination. The second included N-lauroyl sarcosine (NLS) with sorbitan monolaurate (S20). In a particular composition, the combination was at 1.0% (w/v) with the weight ration of NLS=0.6.

G. Administration

The present compositions can be administered in various ways, e.g., depending on the condition to be treated, and the type of composition to be used. In many cases, topical administration will be used. This mode of administration is particularly suitable for local hair removal.

In some applications, hair removal is desired in only a portion of the skin area of a subject. In those cases, the composition can be applied locally.

Exemplary Topical Application Methods

Spreading

In most cases, the composition containing the RNAi inducing oligonucleotides will be spread or wiped on the treatment area to form a thin film. Thus, for example, for any of the forms of liquid suspension or solution, cream, lotion, gel, or ointment, a quantity of the composition is spread on the treatment surface or surfaces of the subject, and left for a time to allow oligonucleotides (which may be in a carrier species such as in liposomes, to migrate to the hair follicles.

Spraying

For compositions that are sufficiently liquid, the composition can be sprayed on the treatment site, either with or without protection against overspray on surrounding areas. For spray applications, it may be desirable to protect against inhalation of sprayed material, e.g., by using masks that will filter out the relevant sized aerosol particles.

Injection

In some applications, it will be desirable to remove only specific hairs. Thus, rather than contacting a particular area, a composition will be delivered to one or more particular hair follicles. Such individual follicle delivery can be accomplished in various ways. For example, a drop of liquid containing the active oligonucleotide(s) can be deposited on the hair shaft, and allowed to migrate down the shaft to the follicle. In another approach, a needle can be inserted in the hair channel, and liquid or other composition deposited at or near the follicle.

Application Site Preparation and Hair Cycle Synchronization

In some cases, the present compositions can be applied without any special preparation of the application site. In other cases, however, it is advantageous to prepare the site, e.g., by preliminary removal of hair from the site and/or to combine the present invention with a supplementary method of hair removal. Such removal can be beneficial in several different ways. For example, such removal can reduce the amount of active agent required for the present invention because the material will not be lost by adhering to the hair, and instead will be available for absorption/migration to the hair follicles.

Such removal can also be beneficially be used to supplement the present invention by removing residual hairs. Depending on the manner and amount of RNAi inducing oligonucleotide delivered to the hair follicles, some of the follicles may not be sufficiently inhibited, such that some hairs may grow in the treated area and/or some hairs may be reduced in thickness or length but still present. In such cases, a supplementary method of hair removal can be used to produce a desired level of hair removal, e.g., shaving, chemical depilation, enzymatic hair removal; laser treatment; electrolysis. Certain embodiments of the present invention include such an supplemental method.

It can also be advantageous to synchronize hair cycles in the treatment area. Such synchronization can advantageously be done prior to application of the present compositions, or during an interval of treatment with the present compositions, or in an interval between two occasions or intervals of application of the present compositions.

Such synchronization can be accomplished, for example, by pulling hairs from the follicles (either individually or in larger numbers). Examples of methods for pulling the hairs include plucking and waxing. In some circumstances it will be necessary/desirable to induce follicle synchrony by molecular means. In these instances, skin is treated with a known follicle growth inducer such as cyclosporin A, TPA, Noggin, estrogen receptor agonist, and the like.

In general, if a hair is pulled from a follicle in anagen, that follicle goes into catagen; if a hair is pulled from a follicle in telogen, the follicle is stimulated to produce hair, and thus goes into anagen. Thus, for a more extensive effect using the present invention, a distribution of hairs in anagen, catagen, and telogen can be synchronized in catagen, with one pulling to push anagen follicles to catagen, and two pullings to stimulate telegen follicles to anagen, and then push the newly anagen follicles to catagen. Depending on the reaction of the follicles, such procedure can produce a single phase synchrony, or a two phase synchrony.

EXAMPLE 1

In Vitro siRNA Inhibition of Hairless mRNA siRNAs were commercially obtained from Ambion, Inc. for human and mouse hairless genes. These are validated, chemically synthesized siRNAs, that are HPLC purified, annealed and ready to use, and guaranteed to reduce target gene expression by 70% or more. For both human and mouse transcripts, two different siRNAs were used. The sequence of the hairless siRNAs is given in the following table. In this and the subsequent tables in this example, upper case letter are used to refer to the human homologs, and lower case letter refer to the mouse homologs of the specified genes.
List of Pre-Designed siRNAs Used for Gene Silencing Experiments.

| siRNA | Sense Sequence | Antisense Sequence |
|---|---|---|
| HR#1 | 5'-GGACAUGCUCCCACUUGUGtt-3' (SEQ ID NO: 11355) | 5'-CACAAGUGGGAGCAUGUCCtt-3' (SEQ ID NO: 11356) |
| HR#2 | 5'-GGAGGCCAUGCUUACCCAUtt-3' (SEQ ID NO: 11357) | 5'-AUGGGUAAGCAUGGCCUCCtt-3' (SEQ ID NO: 11358) |
| hr#1 | 5'-GGACACACUCUCACUGGUGtt-3' (SEQ ID NO: 11359) | 5'-CACCAGUGAGAGUGUGUCCtt-3' (SEQ ID NO: 11360) |
| hr#2 | 5'-GGGCUUUUACCACAAGGAUtt-3' (SEQ ID NO: 11361) | 5'-AUCCUUGUGGUAAAAGCCCtt-3' (SEQ ID NO: 11362) |

We also used siRNAs for the mouse glyceraldehyde-3-phosphate dehydrogenase (gapdh) gene, Silencer™ GAPDH siRNA (Cat no. 4605, Ambion, Inc. Austin, Tex.) as controls to monitor and optimize siRNA experiments.

Human HaCaT, HeLa and mouse NIH 3T3 cells were used in siRNA transfection experiments. Cells were plated on 6-well tissue culture plates in Dulbecco's Modified Eagle Media (D-MEM, Cat no. 10569-010, Invitrogen Corp., Carlsbad, Calif.) with 10% Fetal Bovine Serum (Cat no. 16000-044, Invitrogen, Corp.) so that they were 30-50% confluent at the time of transfection. Immediately before the transfection, the cells were washed in Opti-MEM I Reduced Serum Medium (Cat no. 31985-070, Invitrogen, Inc.). We used 200 μmol of short interfering RNA (siRNA) for each well and the Oligofectamine™ reagent. The transfections were performed according to the manufacturer's instructions (Cat no. 12252-011, Invitrogen, Inc).

Total RNA was isolated 24 and 48 hours post-transfection using the RNeasy Mini Kit (Cat no. 74104, QIAGEN, Inc., Valencia, Calif.) according to the manufacturer's instructions. cDNA synthesis was performed using the SuperScript First-Strand Synthesis System for RT-PCR kit (Cat no. 11904-018, Invitrogen, Corp.) and oligo (dT) primers. Gene activity was determined by the Real-Time quantitative RT-PCR (qRT-PCR) technique.

Real Time Quantitative RT-PCR (qRT-PCR)

Real-Time qRT-PCR was performed using MJ Research Opticon 2 continuous fluorescence detector. For qRT-PCR 40 ng of cDNA obtained from cultured HaCaT, HeLa, and NIH3T3 cells (siRNA treated and untreated), was amplified using the MJ Research DyNAmo Hot Start SYBR Green qPCR kit (Cat no. F-410L, MJ Research, Inc., Waltham, Mass. The DyNAmo Hot Start SYBR Green qPCR kit is a master mix of a modified hot start DNA polymerase with SYBR Green I and the appropriate buffers, all of which have been optimized for real-time quantitative analysis with the MJ Research Opticon 2. PCR amplification of cDNA samples was performed in 96 well optical plates under the following conditions:

| | |
|---|---|
| 1. | Incubate at 95.0 C. for 00:10:00 |
| 2. | Incubate at 95.0 C. for 00:00:20 |
| 3. | Incubate at 55.0 C. for 00:00:30 |
| 4. | Incubate at 72.0 C. for 00:00:40 |
| 5. | Plate Read |
| 6. | Incubate at 77.0 C. for 00:00:01 |
| 7. | Plate Read |
| 8. | Go to line 3 for 39 more times |

-continued

| | |
|---|---|
| 9. | Incubate at 72.0 C. for 00:05:00 |
| 10. | Melting Curve from 65.0 C. to 95.0 C. read every 0.2 C. hold 00:00:01 |
| 11. | Incubate at 72.0 C. for 00:05:00 |
| | END |

The list of PCR primers used for Real Time PCR amplifications is given in the following table.

PCR primers used for Real-Time RT-PCR amplifications of mouse and human hairless, mouse glyceraldehyde-3-phosphate dehydrogenase gene, and hypoxanthine guanine phosphoriboxyltransferase 1 (hprt). (HPRT was used as a normalizing internal control in mouse cells the same way GAPDH was used for the human cell lines.)

| Gene | Forward primer | Reverse primer |
|---|---|---|
| Hr | 5'-TTCTACCGCGGTCAAACTCT-3' (SEQ ID NO: 11363) | 5'-TTGGTGTCAGGGATCCAAAG-3' (SEQ ID NO: 11364) |
| GAPDH | 5'-AGCCACATCGCTCAGAACAC-3' (SEQ ID NO: 11365) | 5'-GAGGCATTGCTGATGATCTTG-3' (SEQ ID NO: 11366) |
| hr | 5'-ACATCAAAGAAGAGACCCCAG-3' (SEQ ID NO: 11367) | 5'-TTCGCACTGGTGACAATGGAA-3' (SEQ ID NO: 11368) |
| gapdh | 5'-GTGAACGGATTTGGCCGTATT-3' (SEQ ID NO: 11369) | 5'-TTTTGGCTCCACCCTTCAAGT-3' (SEQ ID NO: 11370) |
| hplt | 5'-CCCTGGTTAAGCAGTACAGC-3' (SEQ ID NO: 11371) | 5'-CAGGACTAGAACACCTGCTAA-3' (SEQ ID NO: 11372) |

Plate readings for fluorescence levels are taken at two steps, 5 and 7. These values indicate the relative amounts of amplicon per well at a particular cycle. The raw numbers obtained from these readings were used to determine the PCR amplification efficiency. This is the measurement of fold amplification per PCR cycle, and is expressed as a fraction or percentage relative to perfect doubling. A PCR resulting in perfect doubling would exhibit 100% amplification efficiency. All of the calculations are done using the LinRegPCR program by J. M. Ruijter and C. Ramakers. The crossing threshold for the experiment is determined manually and is defined at the cycle at which amplification for all samples becomes logarithmic. The relative fold for each amplicon is then determined using the amplification efficiency and crossing threshold for that particular amplicon and normalizing it against the relative starting amounts, which is determined by the GAPDH amplification efficiency and crossing threshold that corresponds to that sample. This is done using parameters and equations set by Lui and Saint (Analytical Biochemistry 302, 52-59 (2002)). The final values can then be used to compare the fold differences in gene expression of a particular gene across several different samples or conditions.

This technique and analysis can be applied to determine the levels of hairless expression, or more specifically, the efficiency of gene silencing using hairless siRNA through comparison of the treated and untreated cell populations.

The following table shows the percentage of gene silencing observed following siRNA treatment of human HeLa and HaCaT cells. Total RNA was collected 48 hours following transfection with siRNAs for hairless (Hr) gene. Gene activity was assayed by real-time quantitative RT-PCR (qRT-PCR) technique. Percent knockdown is calculated by obtaining the ratio of the normalized level of Hr expression in treated and untreated cell populations and subtracting this value from 1 (100% expression).

| siRNA | Gene Expression Tested | Cell Type | Percent Knockdown | RNA isolation time point |
|---|---|---|---|---|
| HR#1 | Hr | HeLa | 97.3% | 48 hours |
| HR#2 | Hr | HeLa | 98.7% | 48 hours |
| HR#2 | Hr | HaCaT | 95.8% | 48 hours |

The following table shows the percentage of gene silencing observed following siRNA treatment of mouse NIH3T3 cells. Total RNA was collected 48 hours following transfection with siRNAs for hairless (hr) and glyceraldehyde-3-phosphate dehydrogenase (gpdh) genes. Gene activity was assayed by real-time quantitative RT-PCR (qRT-PCR) technique. Percent knockdown is calculated by obtaining the ratio of the normalized level of hr and gapdh expression in treated and untreated cell populations and subtracting this value from 1 (100% expression).

| siRNA | Gene Expression Tested | Cell Type | Percent Knockdown | RNA isolation time point |
|---|---|---|---|---|
| hr#1 | Hr | NIH3T3 | 99.3% | 48 hours |
| hr#2 | Hr | NIH3T3 | 99.17% | 48 hours |
| Gapdh | Gapdh | NIH3T3 | 99.3% | 48 hours |

EXAMPLE 2

In Vivo Testing: A Phase 1 Clinical Trial of Anti-Hairless siRNA

The goal of this study is to establish the safety of topical application of anti-hairless siRNA (Trichozyme) in healthy human subjects at a dose of 10 µg daily, administered over a period of 3 months.

Inhibition of gene expression using or siRNA technology is a recently developing area of therapy. Several recent studies indicate the usefulness of such therapeutic strategies in a number of different conditions. Our preliminary in vivo studies demonstrated the inhibition of hairless mRNA can be used to permanently inhibit hair growth in experimental animals. Briefly, they inhibit translation from the mRNA transcript originating from the human hairless gene, the first known gene participating in the regulation of the human hair cycle as identified by our group earlier, preventing the synthesis of functional hairless protein. Presence of hairless protein is necessary for uninterrupted hair cycling, and lack of hairless gene expression due to a deleterious mutation or temporary inhibition leads to a permanent inhibition of hair growth and the involution of hair follicles as evidenced by our own in vivo trials in animal models. The successful translation of the result of animal studies to human application leads to a strategy to obtain permanent inhibition of hair growth by temporary topical treatment with Trichozyme.

Study Design

This will be an open label, uncontrolled, safety study. Monitoring for side effects, alterations in hematology, serum chemistries and urine analysis will continue during the 3 month treatment period as well as during the 6 month follow up period after the application is stopped. Subjects will be seen daily by Study personnel during the treatment period and monthly during the follow-up period. The Study will not offer treatment of any side effects that develop.

We will enlist 20 subjects, 10 of which will be treated with the siRNA in an isopropranol or liposomal based vehicle, the other 10 subject will receive treatment with vehicle only. Hair from the dorsal surface of the left forearm will be removed by waxing before applying treatment during the first 30 days of the study. Treatment will consist of topical application of an isopropranol based solution alone or containing anti-hairless siRNA over a 15 cm² area of the dorsal surface of the left forearm using a glass rod. Ample time will be left for absorption.

Subjective side effects, alterations in serum chemistry, hematology and urine analysis will be monitored as well as serum and urine isopropranol level and presence of Trichozymes in serum and urine samples. Photography of the treatment area and hair count will be performed during the initial visit and weekly afterwards during the treatment period of the study then monthly during the follow-up period of the study.

Study Procedures

Before entering in the study subjects will sign an informed consent for disclosure of medical records. A screening questionnaire will be completed as well as a review of medical records to exclude any preexisting medical conditions affecting hair growth or other preexisting diseases listed as exclusion criteria.

Laboratory evaluation—Fasting blood and urine samples will be obtained for the following tests: (a) Hematology—hemoglobin and hematocrit, CBC with differential and platelet count, (b) Serum Chemistry—sodium, total bilirubin, potassium, glucose, chloride, alkaline phosphatase, calcium, AST, ALT, inorganic phosphorus, BUN, creatinine, bicarbonate; (c) urinalysis—protein, glucose, pH, Ketones, nitrates, blood (d.) pregnancy test.

Screening/Baseline Visit—Informed consent for study participation signed. Complete history (including record of systemic and topical medication, both prescription and non-prescription). Physical exam—Comprehensive skin exam and photography of the treatment area and hair count. (e) Review criteria for inclusion/exclusion and determine eligibility.

Daily Clinic Visits for treatment—waxing of the treatment area (for first 30 days only) followed by topical application of Treatment. Blood and urine samples for Hematology, Serum chemistry, Urine analysis, Isporopranol serum/urine level and siRNA detection in serum/urine will be obtained monthly. Photography of the treatment area and hair count will be performed weekly. Subjects will be interviewed for subjective side effects weekly.

Monthly Clinic Visits for follow-up—Blood and urine samples for Hematology, Serum chemistry, Urine analysis, Isporopranol serum/urine level and siRNA detection in serum/urine will be obtained. Photography of the treatment area and hair count. Subjects will be interviewed for subjective side effects.

Study Site—Subjects will be seen at the clinical facilities for the study.

Study Drugs siRNAs for the study are are oligonucleotides with RNAi activity that is specific to mRNA sequences present in the human hairless mRNA. This study will utilize a mixture of 8-10 different siRNAs. To date there is no data available of topical cutaneous application of any deoxy-ribozymes. The siRNAs to be used in this study will be provided by a manufacturer offering custom synthesized human grade oligonucleotides.

Study Questionnaires

All subjects will complete study questionnaires at baseline.

Study Subjects

Criteria—Inclusion—(i) Study subjects must be 18 to 35 years of age, female of Hispanic ethnicity. (ii) Have no previous medical history of hair growth abnormalities or endocrine, renal, autoimmune, cardiac, pulmonary, hematological or psychiatric disorders. (iii) Other inclusion criteria: (iv) The subject has provided written informed consent prior to administration of any study-related procedures. (v) The subject has been using adequate contraception since her last menses and will use adequate contraception during the study, is not lactating, and has a documented negative serum pregnancy test within 14 days prior to the first dose of study medication. (vi) The subject is willing to abstain from any voluntary alteration of body hair of the treated area. (vii) The subject is willing to abstain from application of prescription and over the counter topical medications for the duration of the study, including moisturizers, emollients and sunscreens. (viii) The subject is willing to return for scheduled follow-up visits for the duration of the study. (ix) The subject must meet the following laboratory criteria during a time not to exceed 8 weeks prior to randomization: 1) hemoglobin level of greater than 12.0 (women) or 13.0 (men); 2) WBC count greater than 3000/mm³; 3) platelet count greater than 125,000; 4) BUN within normal limits; 5) electrolytes within normal limits; 6) creatinine≦1.5×ULN; 7) AST≦1.5×ULN; 8) ALT≦1.5×ULN; 9) total bilirubin within normal limits; and 10) creatinin clearance within normal limits.

Exclusion—(i) existence of any medical conditions listed above. (ii) any laboratory values that do not meet the criteria listed above. (iii) Pregnancy or lactation. (iv) Invasive cancer or anticipated hormonal, chemo-, or radiotherapy while participating in the study. (v) Any medical or psychosocial condition that, in the opinion of the investigator, could jeopardize subject's participation in this study.

Recruitment of Subjects

Potential subjects for this Study will be recruited from among residents in proximity to the study site because of the daily visit requirements. Subjects with Hispanic ethnicity will be recruited to avoid inter-ethnicity variations of hair density and follicle site as well as blonde hair that is less appropriate for complete hair count and photography.

EXAMPLE 3

Hair Removal Using In Vivo Knockdown of Hairless mRNA

It was demonstrated that inhibiting the expression of hairless mRNA in an animal model system created essentially a hairless condition. This exemplary test was conducted using ribozymes targeting the hairless mRNA, and is described in Cserhalmi-Friedman et al., *Exp Dermatol.*, 2004 March; 13(3):155-62, which is incorporated herein by reference in its entirety.

Short Term Results in Newborn Mice

The mice, who were gender-matched littermates, were sacrificed after four weeks of treatment that started immediately after the animals were born. All treated mice demonstrated a variable degree of visible sparseness of hair at the treated area of the back, which was not observed in the control animals treated with nonspecific deoxyribozymes. The specimens taken from the control animal show the presence of large number of hair follicles in anagen V stage, corresponding to the clinical appearance. In contrast, the samples taken from the treated mice demonstrate the presence of smaller hair follicles with morphological features similar to those observed in anagen III stage (i.e.: hair shaft did not reach the level of the sebaceous gland). A large portion of the hair follicles in the treated region showed delayed anagen development as well as significant dilatation of the hair canal, reminiscent of utricles characteristic of the hairless phenotype. In these samples, we observed several large cysts filled with keratinous material and remnants of coiled and degraded hair follicles. These dermal cysts are believed to be the result of hair follicle disintegration and abnormal hair shaft formation. Importantly, dermal cysts are hallmark features of the hairless phenotype and usually contain either keratinous mass or a degraded hair shaft, as seen in the sample taken from the skin of a hairless mouse. The inhibition of hair growth, formation of the utriculi, and appearance of dermal cysts were present in all treated mice, but were not detected in any control animals.

b. Long Term Results in Newborn Mice

Another group of littermates of identical gender was sacrificed after seven weeks of treatment that started immediately after the animals were born. A noticeable decrease in the density of hair was present in the treated animals as compared to the control mice treated with on specific deoxyribozymes. The sample from the control animals showed the presence of regularly spaced telogen hair follicles. In the treated area, we observed a significantly decreased number of follicles with large areas of the skin devoid of any hair follicles at all. In the treated area, we detected the presence of large cysts filled with amorphous keratin material, corresponding to dermal cysts, which are characteristics of the hairless phenotype. Histopathology of the treated area showed the presence of small dense groups of cells with condensed nuclei in the deep dermis. These cell groups were reminiscent of detached dermal papillae, which are typically found in hairless mice. The lack of hair follicles, the presence of dermal cysts and the detached dermal papillae were present in every treated animal, while all the control animals showed the presence of evenly spaced telogen follicles.

c. Results in Depilated Animals

This group of eight week old female littermates was wax-depilated and subsequently sacrificed after four weeks of treatment that began immediately after the depilation. Clinically, the control animals showed active hair regrowth in the depilated area.

In contrast, the hair regrowth was of lesser magnitude in the treated mice, and the hair became sparse (not shown). Histopathology of the control mouse skin shows the presence of a large number of hair follicles in advanced anagen. In the samples taken from the treated animals, the treated regions could be easily identified by the lack of depilation-induced hair regrowth. These untreated hair follicles were identical to those observed in the control animals treated with nonspecific deoxyribozymes. On histology, the treated area with small telogen hair follicles could be easily distinguished from neighboring untreated area with hair follicles at advanced anagen stages, suggesting that in the treated portion of skin the hair follicles were not able to enter depilation-induced anagen at all, or exhibited much lower growth rates compare to control skin.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to the number, length, and chemical modifications in the dsRNA. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

TABLE 1 cDNA Human Hairless 19-mer Target Sequences and Complement Referenced to NM_005144- Homo sapiens hairless homolog (mouse) (HR), transcript variant 1, complete mRNA (1-5699 bp). (SEQ ID NO: for Sense equals (2X - 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1 | TCTCCCGGGAGCCACTCCC | GGGAGTGGCTCCCGGGAGA |
| 2 | CTCCCGGGAGCCACTCCCA | TGGGAGTGGCTCCCGGGAG |
| 3 | TCCCGGGAGCCACTCCCAT | ATGGGAGTGGCTCCCGGGA |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 4 | CCCGGGAGCCACTCCCATG | CATGGGAGTGGCTCCCGGG |
| 5 | CCGGGAGCCACTCCCATGG | CCATGGGAGTGGCTCCCGG |
| 6 | CGGGAGCCACTCCCATGGG | CCCATGGGAGTGGCTCCCG |
| 7 | GGGAGCCACTCCCATGGGC | GCCCATGGGAGTGGCTCCC |
| 8 | GGAGCCACTCCCATGGGCG | CGCCCATGGGAGTGGCTCC |
| 9 | GAGCCACTCCCATGGGCGC | GCGCCCATGGGAGTGGCTC |
| 10 | AGCCACTCCCATGGGCGCC | GGCGCCCATGGGAGTGGCT |
| 11 | GCCACTCCCATGGGCGCCT | AGGCGCCCATGGGAGTGGC |
| 12 | CCACTCCCATGGGCGCCTC | GAGGCGCCCATGGGAGTGG |
| 13 | CACTCCCATGGGCGCCTCT | AGAGGCGCCCATGGGAGTG |
| 14 | ACTCCCATGGGCGCCTCTC | GAGAGGCGCCCATGGGAGT |
| 15 | CTCCCATGGGCGCCTCTCC | GGAGAGGCGCCCATGGGAG |
| 16 | TCCCATGGGCGCCTCTCCA | TGGAGAGGCGCCCATGGGA |
| 17 | CCCATGGGCGCCTCTCCAG | CTGGAGAGGCGCCCATGGG |
| 18 | CCATGGGCGCCTCTCCAGC | GCTGGAGAGGCGCCCATGG |
| 19 | CATGGGCGCCTCTCCAGCC | GGCTGGAGAGGCGCCCATG |
| 20 | ATGGGCGCCTCTCCAGCCC | GGGCTGGAGAGGCGCCGAT |
| 21 | TGGGCGCCTCTCCAGCCCC | GGGGCTGGAGAGGCGCCCA |
| 22 | GGGCGCCTCTCCAGCCCCT | AGGGGCTGGAGAGGCGCCC |
| 23 | GGCGCCTCTCCAGCCCCTG | CAGGGGCTGGAGAGGCGCC |
| 24 | GCGCCTCTCCAGCCCCTGG | CCAGGGGCTGGAGAGGCGC |
| 25 | CGCCTCTCCAGCCCCTGGC | GCCAGGGGCTGGAGAGGCG |
| 26 | GCCTCTCCAGCCCCTGGCC | GGCCAGGGGCTGGAGAGGC |
| 27 | CCTCTCCAGCCCCTGGCCT | AGGCCAGGGGCTGGAGAGG |
| 28 | CTCTCCAGCCCCTGGCCTG | CAGGCCAGGGGCTGGAGAG |
| 29 | TCTCCAGCCCCTGGCCTGG | CCAGGCCAGGGGCTGGAGA |
| 30 | CTCCAGCCCCTGGCCTGGA | TCCAGGCCAGGGGCTGGAG |
| 31 | TCCAGCCCCTGGCCTGGAA | TTCCAGGCCAGGGGCTGGA |
| 32 | CCAGCCCCTGGCCTGGAAG | CTTCCAGGCCAGGGGCTGG |
| 33 | CAGCCCCTGGCCTGGAAGC | GCTTCCAGGCCAGGGGCTG |
| 34 | AGCCCCTGGCCTGGAAGCA | TGCTTCCAGGCCAGGGGCT |
| 35 | GCCCCTGGCCTGGAAGCAC | GTGCTTCCAGGCCAGGGGC |
| 36 | CCCCTGGCCTGGAAGCACC | GGTGCTTCCAGGCCAGGGG |
| 37 | CCCTGGCCTGGAAGCACCA | TGGTGCTTCCAGGCCAGGG |
| 38 | CCTGGCCTGGAAGCACCAG | CTGGTGCTTCCAGGCCAGG |
| 39 | CTGGCCTGGAAGCACCAGG | CCTGGTGCTTCCAGGCCAG |
| 40 | TGGCCTGGAAGCACCAGGA | TCCTGGTGCTTCCAGGCCA |
| 41 | GGCCTGGAAGCACCAGGAA | TTCCTGGTGCTTCCAGGCC |
| 42 | GCCTGGAAGCACCAGGAAC | GTTCCTGGTGCTTCCAGGC |
| 43 | CCTGGAAGCACCAGGAACC | GGTTCCTGGTGCTTCCAGG |
| 44 | CTGGAAGCACCAGGAACCC | GGGTTCCTGGTGCTTCCAG |
| 45 | TGGAAGCACCAGGAACCCT | AGGGTTCCTGGTGCTTCCA |
| 46 | GGAAGCACCAGGAACCCTG | CAGGGTTCCTGGTGCTTCC |
| 47 | GAAGCACCAGGAACCCTGG | CCAGGGTTCCTGGTGCTTC |
| 48 | AAGCACCAGGAACCCTGGG | CCCAGGGTTCCTGGTGCTT |
| 49 | AGCACCAGGAACCCTGGGG | CCCCAGGGTTCCTGGTGCT |
| 50 | GCACCAGGAACCCTGGGGA | TCCCCAGGGTTCCTGGTGC |
| 51 | CACCAGGAACCCTGGGGAT | ATCCCCAGGGTTCCTGGTG |
| 52 | ACCAGGAACCCTGGGGATG | CATCCCCAGGGTTCCTGGT |
| 53 | CCAGGAACCCTGGGGATGG | CCATCCCCAGGGTTCCTGG |
| 54 | CAGGAACCCTGGGGATGGG | CCCATCCCCAGGGTTCCTG |
| 55 | AGGAACCCTGGGGATGGGG | CCCCATCCCCAGGGTTCCT |
| 56 | GGAACCCTGGGGATGGGGC | GCCCCATCCCCAGGGTTCC |
| 57 | GAACCCTGGGGATGGGGCA | TGCCCCATCCCCAGGGTTC |
| 58 | AACCCTGGGGATGGGGCAG | CTGCCCCATCCCCAGGGTT |
| 59 | ACCCTGGGGATGGGGCAGA | TCTGCCCCATCCCCAGGGT |
| 60 | CCCTGGGGATGGGGCAGAC | GTCTGCCCCATCCCCAGGG |
| 61 | CCTGGGGATGGGGCAGACC | GGTCTGCCCCATCCCCAGG |
| 62 | CTGGGGATGGGGCAGACCC | GGGTCTGCCCCATCCCCAG |
| 63 | TGGGGATGGGGCAGACCCT | AGGGTCTGCCCCATCCCCA |
| 64 | GGGGATGGGGCAGACCCTC | GAGGGTCTGCCCCATCCCC |
| 65 | GGGATGGGGCAGACCCTCA | TGAGGGTCTGCCCCATCCC |
| 66 | GGATGGGGCAGACCCTCAC | GTGAGGGTCTGCCCCATCC |
| 67 | GATGGGGCAGACCCTCACA | TGTGAGGGTCTGCCCCATC |
| 68 | ATGGGGCAGACCCTCACAG | CTGTGAGGGTCTGCCCCAT |
| 69 | TGGGGCAGACCCTCACAGC | GCTGTGAGGGTCTGCCCCA |
| 70 | GGGGCAGACCCTCACAGCC | GGCTGTGAGGGTCTGCCCC |
| 71 | GGGCAGACCCTCACAGCCC | GGGCTGTGAGGGTCTGCCC |
| 72 | GGCAGACCCTCACAGCCCG | CGGGCTGTGAGGGTCTGCC |

TABLE 1-continued cDNA Human Hairless 19-mer Target Sequences and Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 73 | GCAGACCCTCACAGCCCGG | CCGGGCTGTGAGGGTCTGC |
| 74 | CAGACCCTCACAGCCCGGG | CCCGGGCTGTGAGGGTCTG |
| 75 | AGACCCTCACAGCCCGGGG | CCCCGGGCTGTGAGGGTCT |
| 76 | GACCCTCACAGCCCGGGGT | ACCCCGGGCTGTGAGGGTC |
| 77 | ACCCTCACAGCCCGGGGTC | GACCCCGGGCTGTGAGGGT |
| 78 | CCCTCACAGCCCGGGGTCT | AGACCCCGGGCTGTGAGGG |
| 79 | CCTCACAGCCCGGGGTCTG | CAGACCCCGGGCTGTGAGG |
| 80 | CTCACAGCCCGGGGTCTGG | CCAGACCCCGGGCTGTGAG |
| 81 | TCACAGCCCGGGGTCTGGA | TCCAGACCCCGGGCTGTGA |
| 82 | CACAGCCCGGGGTCTGGAG | CTCCAGACCCCGGGCTGTG |
| 83 | ACAGCCCGGGGTCTGGAGC | GCTCCAGACCCCGGGCTGT |
| 84 | CAGCCCGGGGTCTGGAGCC | GGCTCCAGACCCCGGGCTG |
| 85 | AGCCCGGGGTCTGGAGCCG | CGGCTCCAGACCCCGGGCT |
| 86 | GCCCGGGGTCTGGAGCCGG | CCGGCTCCAGACCCCGGGC |
| 87 | CCCGGGGTCTGGAGCCGGT | ACCGGCTCCAGACCCCGGG |
| 88 | CCGGGGTCTGGAGCCGGTG | CACCGGCTCCAGACCCCGG |
| 89 | CGGGGTCTGGAGCCGGTGT | ACACCGGCTCCAGACCCCG |
| 90 | GGGGTCTGGAGCCGGTGTC | GACACCGGCTCCAGACCCC |
| 91 | GGGTCTGGAGCCGGTGTCG | CGACACCGGCTCCAGACCC |
| 92 | GGTCTGGAGCCGGTGTCGG | CCGACACCGGCTCCAGACC |
| 93 | GTCTGGAGCCGGTGTCGGA | TCCGACACCGGCTCCAGAC |
| 94 | TCTGGAGCCGGTGTCGGAG | CTCCGACACCGGCTCCAGA |
| 95 | CTGGAGCCGGTGTCGGAGC | GCTCCGACACCGGCTCCAG |
| 96 | TGGAGCCGGTGTCGGAGCT | AGCTCCGACACCGGCTCCA |
| 97 | GGAGCCGGTGTCGGAGCTC | GAGCTCCGACACCGGCTCC |
| 98 | GAGCCGGTGTCGGAGCTCA | TGAGCTCCGACACCGGCTC |
| 99 | AGCCGGTGTCGGAGCTCAT | ATGAGCTCCGACACCGGCT |
| 100 | GCCGGTGTCGGAGCTCATC | GATGAGCTCCGACACCGGC |
| 101 | CCGGTGTCGGAGCTCATCT | AGATGAGCTCCGACACCGG |
| 102 | CGGTGTCGGAGCTCATCTG | CAGATGAGCTCCGACACCG |
| 103 | GGTGTCGGAGCTCATCTGG | CCAGATGAGCTCCGACACC |
| 104 | GTGTCGGAGCTCATCTGGG | CCCAGATGAGCTCCGACAC |
| 105 | TGTCGGAGCTCATCTGGGC | GCCCAGATGAGCTCCGACA |
| 106 | GTCGGAGCTCATCTGGGCC | GGCCCAGATGAGCTCCGAC |
| 107 | TCGGAGCTCATCTGGGCCC | GGGCCCAGATGAGCTCCGA |
| 108 | CGGAGCTCATCTGGGCCCA | TGGGCCCAGATGAGCTCCG |
| 109 | GGAGCTCATCTGGGCCCAT | ATGGGCCCAGATGAGCTCC |
| 110 | GAGCTCATCTGGGCCCATG | CATGGGCCCAGATGAGCTC |
| 111 | AGCTCATCTGGGCCCATGA | TCATGGGCCCAGATGAGCT |
| 112 | GCTCATCTGGGCCCATGAC | GTCATGGGCCCAGATGAGC |
| 113 | CTCATCTGGGCCCATGACC | GGTCATGGGCCCAGATGAG |
| 114 | TCATCTGGGCCCATGACCT | AGGTCATGGGCCCAGATGA |
| 115 | CATCTGGGCCCATGACCTC | GAGGTCATGGGCCCAGATG |
| 116 | ATCTGGGCCCATGACCTCT | AGAGGTCATGGGCCCAGAT |
| 117 | TCTGGGCCCATGACCTCTC | GAGAGGTCATGGGCCCAGA |
| 118 | CTGGGCCCATGACCTCTCC | GGAGAGGTCATGGGCCCAG |
| 119 | TGGGCCCATGACCTCTCCA | TGGAGAGGTCATGGGCCCA |
| 120 | GGGCCCATGACCTCTCCAG | CTGGAGAGGTCATGGGCCC |
| 121 | GGCCCATGACCTCTCCAGA | TCTGGAGAGGTCATGGGCC |
| 122 | GCCCATGACCTCTCCAGAC | GTCTGGAGAGGTCATGGGC |
| 123 | CCCATGACCTCTCCAGACA | TGTCTGGAGAGGTCATGGG |
| 124 | CCATGACCTCTCCAGACAT | ATGTCTGGAGAGGTCATGG |
| 125 | CATGACCTCTCCAGACATT | AATGTCTGGAGAGGTCATG |
| 126 | ATGACCTCTCCAGACATTT | AAATGTCTGGAGAGGTCAT |
| 127 | TGACCTCTCCAGACATTTG | CAAATGTCTGGAGAGGTCA |
| 128 | GACCTCTCCAGACATTTGG | CCAAATGTCTGGAGAGGTC |
| 129 | ACCTCTCCAGACATTTGGC | GCCAAATGTCTGGAGAGGT |
| 130 | CCTCTCCAGACATTTGGCA | TGCCAAATGTCTGGAGAGG |
| 131 | CTCTCCAGACATTTGGCAA | TTGCCAAATGTCTGGAGAG |
| 132 | TCTCCAGACATTTGGCAAA | TTTGCCAAATGTCTGGAGA |
| 133 | CTCCAGACATTTGGCAAAA | TTTTGCCAAATGTCTGGAG |
| 134 | TCCAGACATTTGGCAAAAT | ATTTTGCCAAATGTCTGGA |
| 135 | CCAGACATTTGGCAAAATC | GATTTTGCCAAATGTCTGG |
| 136 | CAGACATTTGGCAAAATCA | TGATTTTGCCAAATGTCTG |
| 137 | AGACATTTGGCAAAATCAA | TTGATTTTGCCAAATGTCT |
| 138 | GACATTTGGCAAAATCAAG | CTTGATTTTGCCAAATGTC |
| 139 | ACATTTGGCAAAATCAAGG | CCTTGATTTTGCCAAATGT |
| 140 | CATTTGGCAAAATCAAGGC | GCCTTGATTTTGCCAAATG |
| 141 | ATTTGGCAAAATCAAGGCC | GGCCTTGATTTTGCCAAAT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 142 | TTTGGCAAAATCAAGGCCC | GGGCCTTGATTTTGCCAAA |
| 143 | TTGGCAAAATCAAGGCCCT | AGGGCCTTGATTTTGCCAA |
| 144 | TGGCAAAATCAAGGCCCTT | AAGGGCCTTGATTTTGCCA |
| 145 | GGCAAAATCAAGGCCCTTA | TAAGGGCCTTGATTTTGCC |
| 146 | GCAAAATCAAGGCCCTTAG | CTAAGGGCCTTGATTTTGC |
| 147 | CAAAATCAAGGCCCTTAGA | TCTAAGGGCCTTGATTTTG |
| 148 | AAAATCAAGGCCCTTAGAC | GTCTAAGGGCCTTGATTTT |
| 149 | AAATCAAGGCCCTTAGACC | GGTCTAAGGGCCTTGATTT |
| 150 | AATCAAGGCCCTTAGACCA | TGGTCTAAGGGCCTTGATT |
| 151 | ATCAAGGCCCTTAGACCAG | CTGGTCTAAGGGCCTTGAT |
| 152 | TCAAGGCCCTTAGACCAGG | CCTGGTCTAAGGGCCTTGA |
| 153 | CAAGGCCCTTAGACCAGGG | CCCTGGTCTAAGGGCCTTG |
| 154 | AAGGCCCTTAGACCAGGGA | TCCCTGGTCTAAGGGCCTT |
| 155 | AGGCCCTTAGACCAGGGAC | GTCCCTGGTCTAAGGGCCT |
| 156 | GGCCCTTAGACCAGGGACA | TGTCCCTGGTCTAAGGGCC |
| 157 | GCCCTTAGACCAGGGACAG | CTGTCCCTGGTCTAAGGGC |
| 158 | CCCTTAGACCAGGGACAGA | TCTGTCCCTGGTCTAAGGG |
| 159 | CCTTAGACCAGGGACAGAC | GTCTGTCCCTGGTCTAAGG |
| 160 | CTTAGACCAGGGACAGACC | GGTCTGTCCCTGGTCTAAG |
| 161 | TTAGACCAGGGACAGACCC | GGGTCTGTCCCTGGTCTAA |
| 162 | TAGACCAGGGACAGACCCA | TGGGTCTGTCCCTGGTCTA |
| 163 | AGACCAGGGACAGACCCAA | TTGGGTCTGTCCCTGGTCT |
| 164 | GACCAGGGACAGACCCAAG | CTTGGGTCTGTCCCTGGTC |
| 165 | ACCAGGGACAGACCCAAGC | GCTTGGGTCTGTCCCTGGT |
| 166 | CCAGGGACAGACCCAAGCC | GGCTTGGGTCTGTCCCTGG |
| 167 | CAGGGACAGACCCAAGCCC | GGGCTTGGGTCTGTCCCTG |
| 168 | AGGGACAGACCCAAGCCCA | TGGGCTTGGGTCTGTCCCT |
| 169 | GGGACAGACCCAAGCCCAG | CTGGGCTTGGGTCTGTCCC |
| 170 | GGACAGACCCAAGCCCAGG | CCTGGGCTTGGGTCTGTCC |
| 171 | GACAGACCCAAGCCCAGGC | GCCTGGGCTTGGGTCTGTC |
| 172 | ACAGACCCAAGCCCAGGCC | GGCCTGGGCTTGGGTCTGT |
| 173 | CAGACCCAAGCCCAGGCCC | GGGCCTGGGCTTGGGTCTG |
| 174 | AGACCCAAGCCCAGGCCCT | AGGGCCTGGGCTTGGGTCT |
| 175 | GACCCAAGCCCAGGCCCTC | GAGGGCCTGGGCTTGGGTC |
| 176 | ACCCAAGCCCAGGCCCTCC | GGAGGGCCTGGGCTTGGGT |
| 177 | CCCAAGCCCAGGCCCTCCC | GGGAGGGCCTGGGCTTGGG |
| 178 | CCAAGCCCAGGCCCTCCCA | TGGGAGGGCCTGGGCTTGG |
| 179 | CAAGCCCAGGCCCTCCCAG | CTGGGAGGGCCTGGGCTTG |
| 180 | AAGCCCAGGCCCTCCCAGA | TCTGGGAGGGCCTGGGCTT |
| 181 | AGCCCAGGCCCTCCCAGAG | CTCTGGGAGGGCCTGGGCT |
| 182 | GCCCAGGCCCTCCCAGAGG | CCTCTGGGAGGGCCTGGGC |
| 183 | CCCAGGCCCTCCCAGAGGT | ACCTCTGGGAGGGCCTGGG |
| 184 | CCAGGCCCTCCCAGAGGTC | GACCTCTGGGAGGGCCTGG |
| 185 | CAGGCCCTCCCAGAGGTCC | GGACCTCTGGGAGGGCCTG |
| 186 | AGGCCCTCCCAGAGGTCCT | AGGACCTCTGGGAGGGCCT |
| 187 | GGCCCTCCCAGAGGTCCTA | TAGGACCTCTGGGAGGGCC |
| 188 | GCCCTCCCAGAGGTCCTAG | CTAGGACCTCTGGGAGGGC |
| 189 | CCCTCCCAGAGGTCCTAGG | CCTAGGACCTCTGGGAGGG |
| 190 | CCTCCCAGAGGTCCTAGGA | TCCTAGGACCTCTGGGAGG |
| 191 | CTCCCAGAGGTCCTAGGAC | GTCCTAGGACCTCTGGGAG |
| 192 | TCCCAGAGGTCCTAGGACG | CGTCCTAGGACCTCTGGGA |
| 193 | CCCAGAGGTCCTAGGACGC | GCGTCCTAGGACCTCTGGG |
| 194 | CCAGAGGTCCTAGGACGCA | TGCGTCCTAGGACCTCTGG |
| 195 | CAGAGGTCCTAGGACGCAA | TTGCGTCCTAGGACCTCTG |
| 196 | AGAGGTCCTAGGACGCAAC | GTTGCGTCCTAGGACCTCT |
| 197 | GAGGTCCTAGGACGCAACC | GGTTGCGTCCTAGGACCTC |
| 198 | AGGTCCTAGGACGCAACCC | GGGTTGCGTCCTAGGACCT |
| 199 | GGTCCTAGGACGCAACCCT | AGGGTTGCGTCCTAGGACC |
| 200 | GTCCTAGGACGCAACCCTT | AAGGGTTGCGTCCTAGGAC |
| 201 | TCCTAGGACGCAACCCTTT | AAAGGGTTGCGTCCTAGGA |
| 202 | CCTAGGACGCAACCCTTTG | CAAAGGGTTGCGTCCTAGG |
| 203 | CTAGGACGCAACCCTTTGT | ACAAAGGGTTGCGTCCTAG |
| 204 | TAGGACGCAACCCTTTGTG | CACAAAGGGTTGCGTCCTA |
| 205 | AGGACGCAACCCTTTGTGC | GCACAAAGGGTTGCGTCCT |
| 206 | GGACGCAACCCTTTGTGCC | GGCACAAAGGGTTGCGTCC |
| 207 | GACGCAACCCTTTGTGCCC | GGGCACAAAGGGTTGCGTC |
| 208 | ACGCAACCCTTTGTGCCCT | AGGGCACAAAGGGTTGCGT |
| 209 | CGCAACCCTTTGTGCCCTT | AAGGGCACAAAGGGTTGCG |
| 210 | GCAACCCTTTGTGCCCTTG | CAAGGGCACAAAGGGTTGC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 211 | CAACCCTTTGTGCCCTTGG | CCAAGGGCACAAAGGGTTG |
| 212 | AACCCTTTGTGCCCTTGGG | CCCAAGGGCACAAAGGGTT |
| 213 | ACCCTTTGTGCCCTTGGGC | GCCCAAGGGCACAAAGGGT |
| 214 | CCCTTTGTGCCCTTGGGCT | AGCCCAAGGGCACAAAGGG |
| 215 | CCTTTGTGCCCTTGGGCTC | GAGCCCAAGGGCACAAAGG |
| 216 | CTTTGTGCCCTTGGGCTCT | AGAGCCCAAGGGCACAAAG |
| 217 | TTTGTGCCCTTGGGCTCTG | CAGAGCCCAAGGGCACAAA |
| 218 | TTGTGCCCTTGGGCTCTGG | CCAGAGCCCAAGGGCACAA |
| 219 | TGTGCCCTTGGGCTCTGGA | TCCAGAGCCCAAGGGCACA |
| 220 | GTGCCCTTGGGCTCTGGAA | TTCCAGAGCCCAAGGGCAC |
| 221 | TGCCCTTGGGCTCTGGAAG | CTTCCAGAGCCCAAGGGCA |
| 222 | GCCCTTGGGCTCTGGAAGA | TCTTCCAGAGCCCAAGGGC |
| 223 | CCCTTGGGCTCTGGAAGAG | CTCTTCCAGAGCCCAAGGG |
| 224 | CCTTGGGCTCTGGAAGAGG | CCTCTTCCAGAGCCCAAGG |
| 225 | CTTGGGCTCTGGAAGAGGT | ACCTCTTCCAGAGCCCAAG |
| 226 | TTGGGCTCTGGAAGAGGTT | AACCTCTTCCAGAGCCCAA |
| 227 | TGGGCTCTGGAAGAGGTTT | AAACCTCTTCCAGAGCCCA |
| 228 | GGGCTCTGGAAGAGGTTTG | CAAACCTCTTCCAGAGCCC |
| 229 | GGCTCTGGAAGAGGTTTGG | CCAAACCTCTTCCAGAGCC |
| 230 | GCTCTGGAAGAGGTTTGGG | CCCAAACCTCTTCCAGAGC |
| 231 | CTCTGGAAGAGGTTTGGGA | TCCCAAACCTCTTCCAGAG |
| 232 | TCTGGAAGAGGTTTGGGAA | TTCCCAAACCTCTTCCAGA |
| 233 | CTGGAAGAGGTTTGGGAAG | CTTCCCAAACCTCTTCCAG |
| 234 | TGGAAGAGGTTTGGGAAGG | CCTTCCCAAACCTCTTCCA |
| 235 | GGAAGAGGTTTGGGAAGGG | CCCTTCCCAAACCTCTTCC |
| 236 | GAAGAGGTTTGGGAAGGGT | ACCCTTCCCAAACCTCTTC |
| 237 | AAGAGGTTTGGGAAGGGTT | AACCCTTCCCAAACCTCTT |
| 238 | AGAGGTTTGGGAAGGGTTT | AAACCCTTCCCAAACCTCT |
| 239 | GAGGTTTGGGAAGGGTTTG | CAAACCCTTCCCAAACCTC |
| 240 | AGGTTTGGGAAGGGTTTGG | CCAAACCCTTCCCAAACCT |
| 241 | GGTTTGGGAAGGGTTTGGG | CCCAAACCCTTCCCAAACC |
| 242 | GTTTGGGAAGGGTTTGGGG | CCCCAAACCCTTCCCAAAC |
| 243 | TTTGGGAAGGGTTTGGGGT | ACCCCAAACCCTTCCCAAA |
| 244 | TTGGGAAGGGTTTGGGGTG | CACCCCAAACCCTTCCCAA |
| 245 | TGGGAAGGGTTTGGGGTGG | CCACCCCAAACCCTTCCCA |
| 246 | GGGAAGGGTTTGGGGTGGA | TCCACCCCAAACCCTTCCC |
| 247 | GGAAGGGTTTGGGGTGGAA | TTCCACCCCAAACCCTTCC |
| 248 | GAAGGGTTTGGGGTGGAAG | CTTCCACCCCAAACCCTTC |
| 249 | AAGGGTTTGGGGTGGAAGA | TCTTCCACCCCAAACCCTT |
| 250 | AGGGTTTGGGGTGGAAGAT | ATCTTCCACCCCAAACCCT |
| 251 | GGGTTTGGGGTGGAAGATG | CATCTTCCACCCCAAACCC |
| 252 | GGTTTGGGGTGGAAGATGG | CCATCTTCCACCCCAAACC |
| 253 | GTTTGGGGTGGAAGATGGC | GCCATCTTCCACCCCAAAC |
| 254 | TTTGGGGTGGAAGATGGCA | TGCCATCTTCCACCCCAAA |
| 255 | TTGGGGTGGAAGATGGCAA | TTGCCATCTTCCACCCCAA |
| 256 | TGGGGTGGAAGATGGCAAA | TTTGCCATCTTCCACCCCA |
| 257 | GGGGTGGAAGATGGCAAAG | CTTTGCCATCTTCCACCCC |
| 258 | GGGTGGAAGATGGCAAAGA | TCTTTGCCATCTTCCACCC |
| 259 | GGTGGAAGATGGCAAAGAG | CCTCTTTGCCATCTTCCACC |
| 260 | GTGGAAGATGGCAAAGAGC | GCTCTTTGCCATCTTCCAC |
| 261 | TGGAAGATGGCAAAGAGCA | TGCTCTTTGCCATCTTCCA |
| 262 | GGAAGATGGCAAAGAGCAG | CTGCTCTTTGCCATCTTCC |
| 263 | GAAGATGGCAAAGAGCAGC | GCTGCTCTTTGCCATCTTC |
| 264 | AAGATGGCAAAGAGCAGCT | AGCTGCTCTTTGCCATCTT |
| 265 | AGATGGCAAAGAGCAGCTT | AAGCTGCTCTTTGCCATCT |
| 266 | GATGGCAAAGAGCAGCTTG | CAAGCTGCTCTTTGCCATC |
| 267 | ATGGCAAAGAGCAGCTTGG | CCAAGCTGCTCTTTGCCAT |
| 268 | TGGCAAAGAGCAGCTTGGC | GCCAAGCTGCTCTTTGCCA |
| 269 | GGCAAAGAGCAGCTTGGCC | GGCCAAGCTGCTCTTTGCC |
| 270 | GCAAAGAGCAGCTTGGCCA | TGGCCAAGCTGCTCTTTGC |
| 271 | CAAAGAGCAGCTTGGCCAG | CTGGCCAAGCTGCTCTTTG |
| 272 | AAAGAGCAGCTTGGCCAGG | CCTGGCCAAGCTGCTCTTT |
| 273 | AAGAGCAGCTTGGCCAGGT | ACCTGGCCAAGCTGCTCTT |
| 274 | AGAGCAGCTTGGCCAGGTG | CACCTGGCCAAGCTGCTCT |
| 275 | GAGCAGCTTGGCCAGGTGA | TCACCTGGCCAAGCTGCTC |
| 276 | AGCAGCTTGGCCAGGTGAG | CTCACCTGGCCAAGCTGCT |
| 277 | GCAGCTTGGCCAGGTGAGG | CCTCACCTGGCCAAGCTGC |
| 278 | CAGCTTGGCCAGGTGAGGA | TCCTCACCTGGCCAAGCTG |
| 279 | AGCTTGGCCAGGTGAGGAT | ATCCTCACCTGGCCAAGCT |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 280 | GCTTGGCCAGGTGAGGATG | CATCCTCACCTGGCCAAGC |
| 281 | CTTGGCCAGGTGAGGATGA | TCATCCTCACCTGGCCAAG |
| 282 | TTGGCCAGGTGAGGATGAG | CTCATCCTCACCTGGCCAA |
| 283 | TGGCCAGGTGAGGATGAGG | CCTCATCCTCACCTGGCCA |
| 284 | GGCCAGGTGAGGATGAGGC | GCCTCATCCTCACCTGGCC |
| 285 | GCCAGGTGAGGATGAGGCA | TGCCTCATCCTCACCTGGC |
| 286 | CCAGGTGAGGATGAGGCAG | CTGCCTCATCCTCACCTGG |
| 287 | CAGGTGAGGATGAGGCAGG | CCTGCCTCATCCTCACCTG |
| 288 | AGGTGAGGATGAGGCAGGG | CCCTGCCTCATCCTCACCT |
| 289 | GGTGAGGATGAGGCAGGGC | GCCCTGCCTCATCCTCACC |
| 290 | GTGAGGATGAGGCAGGGCA | TGCCCTGCCTCATCCTCAC |
| 291 | TGAGGATGAGGCAGGGCAG | CTGCCCTGCCTCATCCTCA |
| 292 | GAGGATGAGGCAGGGCAGA | TCTGCCCTGCCTCATCCTC |
| 293 | AGGATGAGGCAGGGCAGAC | GTCTGCCCTGCCTCATCCT |
| 294 | GGATGAGGCAGGGCAGACA | TGTCTGCCCTGCCTCATCC |
| 295 | GATGAGGCAGGGCAGACAC | GTGTCTGCCCTGCCTCATC |
| 296 | ATGAGGCAGGGCAGACACA | TGTGTCTGCCCTGCCTCAT |
| 297 | TGAGGCAGGGCAGACACAG | CTGTGTCTGCCCTGCCTCA |
| 298 | GAGGCAGGGCAGACACAGG | CCTGTGTCTGCCCTGCCTC |
| 299 | AGGCAGGGCAGACACAGGC | GCCTGTGTCTGCCCTGCCT |
| 300 | GGCAGGGCAGACACAGGCC | GGCCTGTGTCTGCCCTGCC |
| 301 | GCAGGGCAGACACAGGCCA | TGGCCTGTGTCTGCCCTGC |
| 302 | CAGGGCAGACACAGGCCAG | CTGGCCTGTGTCTGCCCTG |
| 303 | AGGGCAGACACAGGCCAGT | ACTGGCCTGTGTCTGCCCT |
| 304 | GGGCAGACACAGGCCAGTG | CACTGGCCTGTGTCTGCCC |
| 305 | GGCAGACAGAGGCCAGTGG | CCACTGGCCTGTGTCTGCC |
| 306 | GCAGACACAGGCCAGTGGG | CCCACTGGCCTGTGTCTGC |
| 307 | CAGACACAGGCCAGTGGGG | CCCCACTGGCCTGTGTCTG |
| 308 | AGACACAGGCCAGTGGGGC | GCCCCACTGGCCTGTGTCT |
| 309 | GACACAGGCCAGTGGGGCG | CGCCCCACTGGCCTGTGTC |
| 310 | ACACAGGCCAGTGGGGCGT | ACGCCCCACTGGCCTGTGT |
| 311 | CACAGGCCAGTGGGGCGTG | CACGCCCCACTGGCCTGTG |
| 312 | ACAGGCCAGTGGGGCGTGC | GCACGCCCCACTGGCCTGT |
| 313 | CAGGCCAGTGGGGCGTGCC | GGCACGCCCCACTGGCCTG |
| 314 | AGGCCAGTGGGGCGTGCCA | TGGCACGCCCCACTGGCCT |
| 315 | GGCCAGTGGGGCGTGCCAT | ATGGCACGCCCCACTGGCC |
| 316 | GCCAGTGGGGCGTGCCATG | CATGGCACGCCCCACTGGC |
| 317 | CCAGTGGGGCGTGCCATGT | ACATGGCACGCCCCACTGG |
| 318 | CAGTGGGGCGTGCCATGTG | CACATGGCACGCCCCACTG |
| 319 | AGTGGGGCGTGCCATGTGC | GCACATGGCACGCCCCACT |
| 320 | GTGGGGCGTGCCATGTGCC | GGCACATGGCACGCCCCAC |
| 321 | TGGGGCGTGCCATGTGCCA | TGGCACATGGCACGCCCCA |
| 322 | GGGGCGTGCCATGTGCCAC | GTGGCACATGGCACGCCCC |
| 323 | GGGCGTGCCATGTGCCACA | TGTGGCACATGGCACGCCC |
| 324 | GGCGTGCCATGTGCCACAG | CTGTGGCACATGGCACGCC |
| 325 | GCGTGCCATGTGCCACAGA | TCTGTGGCACATGGCACGC |
| 326 | CGTGCCATGTGCCACAGAT | ATCTGTGGCACATGGCACG |
| 327 | GTGCCATGTGCCACAGATG | CATCTGTGGCACATGGCAC |
| 328 | TGCCATGTGCCACAGATGG | CCATCTGTGGCACATGGCA |
| 329 | GCCATGTGCCACAGATGGA | TCCATCTGTGGCACATGGC |
| 330 | CCATGTGCCACAGATGGAG | CTCCATCTGTGGCACATGG |
| 331 | CATGTGCCACAGATGGAGA | TCTCCATCTGTGGCACATG |
| 332 | ATGTGCCACAGATGGAGAG | CTCTCCATCTGTGGCACAT |
| 333 | TGTGCCACAGATGGAGAGG | CCTCTCCATCTGTGGCACA |
| 334 | GTGCCACAGATGGAGAGGA | TCCTCTCCATCTGTGGCAC |
| 335 | TGCCACAGATGGAGAGGAC | GTCCTCTCCATCTGTGGCA |
| 336 | GCCACAGATGGAGAGGACC | GGTCCTCTCCATCTGTGGC |
| 337 | CCACAGATGGAGAGGACCA | TGGTCCTCTCCATCTGTGG |
| 338 | CACAGATGGAGAGGACCAG | CTGGTCCTCTCCATCTGTG |
| 339 | ACAGATGGAGAGGACCAGG | CCTGGTCCTCTCCATCTGT |
| 340 | CAGATGGAGAGGACCAGGA | TCCTGGTCCTCTCCATCTG |
| 341 | AGATGGAGAGGACCAGGAG | CTCCTGGTCCTCTCCATCT |
| 342 | GATGGAGAGGACCAGGAGC | GCTCCTGGTCCTCTCCATC |
| 343 | ATGGAGAGGACCAGGAGCC | GGCTCCTGGTCCTCTCCAT |
| 344 | TGGAGAGGACCAGGAGCCA | TGGCTCCTGGTCCTCTCCA |
| 345 | GGAGAGGACCAGGAGCCAG | CTGGCTCCTGGTCCTCTCC |
| 346 | GAGAGGACCAGGAGCCAGT | ACTGGCTCCTGGTCCTCTC |
| 347 | AGAGGACCAGGAGCCAGTG | CACTGGCTCCTGGTCCTCT |
| 348 | GAGGACCAGGAGCCAGTGG | CCACTGGCTCCTGGTCCTC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 349 | AGGACCAGGAGCCAGTGGC | GCCACTGGCTCCTGGTCCT |
| 350 | GGACCAGGAGCCAGTGGCC | GGCCACTGGCTCCTGGTCC |
| 351 | GACCAGGAGCCAGTGGCCC | GGGCCACTGGCTCCTGGTC |
| 352 | ACCAGGAGCCAGTGGCCCG | CGGGCCACTGGCTCCTGGT |
| 353 | CCAGGAGCCAGTGGCCCGG | CCGGGCCACTGGCTCCTGG |
| 354 | CAGGAGCCAGTGGCCCGGC | GCCGGGCCACTGGCTCCTG |
| 355 | AGGAGCCAGTGGCCCGGCA | TGCCGGGCCACTGGCTCCT |
| 356 | GGAGCCAGTGGCCCGGCAG | CTGCCGGGCCACTGGCTCC |
| 357 | GAGCCAGTGGCCCGGCAGG | CCTGCCGGGCCACTGGCTC |
| 358 | AGCCAGTGGCCCGGCAGGC | GCCTGCCGGGCCACTGGCT |
| 359 | GCCAGTGGCCCGGCAGGCA | TGCCTGCCGGGCCACTGGC |
| 360 | CCAGTGGCCCGGCAGGCAC | GTGCCTGCCGGGCCACTGG |
| 361 | CAGTGGCCCGGCAGGCACA | TGTGCCTGCCGGGCCACTG |
| 362 | AGTGGCCCGGCAGGCACAG | CTGTGCCTGCCGGGCCACT |
| 363 | GTGGCCCGGCAGGCACAGC | GCTGTGCCTGCCGGGCCAC |
| 364 | TGGCCCGGCAGGCACAGCC | GGCTGTGCCTGCCGGGCCA |
| 365 | GGCCCGGCAGGCACAGCCC | GGGCTGTGCCTGCCGGGCC |
| 366 | GCCCGGCAGGCACAGCCCG | CGGGCTGTGCCTGCCGGGC |
| 367 | CCCGGCAGGCACAGCCCGG | CCGGGCTGTGCCTGCCGGG |
| 368 | CCGGCAGGCACAGCCCGGT | ACCGGGCTGTGCCTGCCGG |
| 369 | CGGCAGGCACAGCCCGGTT | AACCGGGCTGTGCCTGCCG |
| 370 | GGCAGGCACAGCCCGGTTG | CAACCGGGCTGTGCCTGCC |
| 371 | GCAGGCACAGCCCGGTTGG | CCAACCGGGCTGTGCCTGC |
| 372 | CAGGCACAGCCCGGTTGGC | GCCAACCGGGCTGTGCCTG |
| 373 | AGGCACAGCCCGGTTGGCG | CGCCAACCGGGCTGTGCCT |
| 374 | GGCACAGCCCGGTTGGCGT | ACGCCAACCGGGCTGTGCC |
| 375 | GCACAGCCCGGTTGGCGTG | CACGCCAACCGGGCTGTGC |
| 376 | CACAGCCCGGTTGGCGTGG | CCACGCCAACCGGGCTGTG |
| 377 | ACAGCCCGGTTGGCGTGGG | CCCACGCCAACCGGGCTGT |
| 378 | CAGCCCGGTTGGCGTGGGC | GCCCACGCCAACCGGGCTG |
| 379 | AGCCCGGTTGGCGTGGGCC | GGCCCACGCCAACCGGGCT |
| 380 | GCCCGGTTGGCGTGGGCCA | TGGCCCACGCCAACCGGGC |
| 381 | CCCGGTTGGCGTGGGCCAG | CTGGCCCACGCCAACCGGG |
| 382 | CCGGTTGGCGTGGGCCAGA | TCTGGCCCACGCCAACCGG |
| 383 | CGGTTGGCGTGGGCCAGAG | CTCTGGCCCACGCCAACCG |
| 384 | GGTTGGCGTGGGCCAGAGC | GCTCTGGCCCACGCCAACC |
| 385 | GTTGGCGTGGGCCAGAGCG | CGCTCTGGCCCACGCCAAC |
| 386 | TTGGCGTGGGCCAGAGCGC | GCGCTCTGGCCCACGCCAA |
| 387 | TGGCGTGGGCCAGAGCGCC | GGCGCTCTGGCCCACGCCA |
| 388 | GGCGTGGGCCAGAGCGCCC | GGGCGCTCTGGCCCACGCC |
| 389 | GCGTGGGCCAGAGCGCCCA | TGGGCGCTCTGGCCCACGC |
| 390 | CGTGGGCCAGAGCGCCCAT | ATGGGCGCTCTGGCCCACG |
| 391 | GTGGGCCAGAGCGCCCATC | GATGGGCGCTCTGGCCCAC |
| 392 | TGGGCCAGAGCGCCCATCA | TGATGGGCGCTCTGGCCCA |
| 393 | GGGCCAGAGCGCCCATCAC | GTGATGGGCGCTCTGGCCC |
| 394 | GGCCAGAGCGCCCATCACT | AGTGATGGGCGCTCTGGCC |
| 395 | GCCAGAGCGCCCATCACTG | CAGTGATGGGCGCTCTGGC |
| 396 | CCAGAGCGCCCATCACTGA | TCAGTGATGGGCGCTCTGG |
| 397 | CAGAGCGCCCATCACTGAC | GTCAGTGATGGGCGCTCTG |
| 398 | AGAGCGCCCATCACTGACC | GGTCAGTGATGGGCGCTCT |
| 399 | GAGCGCCCATCACTGACCC | GGGTCAGTGATGGGCGCTC |
| 400 | AGCGCCCATCACTGACCCG | CGGGTCAGTGATGGGCGCT |
| 401 | GCGCCCATCACTGACCCGT | ACGGGTCAGTGATGGGCGC |
| 402 | CGCCCATCACTGACCCGTG | CACGGGTCAGTGATGGGCG |
| 403 | GCCCATCACTGACCCGTGA | TCACGGGTCAGTGATGGGC |
| 404 | CCCATCACTGACCCGTGAG | CTCACGGGTCAGTGATGGG |
| 405 | CCATCACTGACCCGTGAGA | TCTCACGGGTCAGTGATGG |
| 406 | CATCACTGACCCGTGAGAA | TTCTCACGGGTCAGTGATG |
| 407 | ATCACTGACCCGTGAGAAC | GTTCTCACGGGTCAGTGAT |
| 408 | TCACTGACCCGTGAGAACT | AGTTCTCACGGGTCAGTGA |
| 409 | CACTGACCCGTGAGAACTC | GAGTTCTCACGGGTCAGTG |
| 410 | ACTGACCCGTGAGAACTCG | CGAGTTCTCACGGGTCAGT |
| 411 | CTGACCCGTGAGAACTCGA | TCGAGTTCTCACGGGTCAG |
| 412 | TGACCCGTGAGAACTCGAC | GTCGAGTTCTCACGGGTCA |
| 413 | GACCCGTGAGAACTCGACT | AGTCGAGTTCTCACGGGTC |
| 414 | ACCCGTGAGAACTCGACTG | CAGTCGAGTTCTCACGGGT |
| 415 | CCCGTGAGAACTCGACTGC | GCAGTCGAGTTCTCACGGG |
| 416 | CCGTGAGAACTCGACTGCC | GGCAGTCGAGTTCTCACGG |
| 417 | CGTGAGAACTCGACTGCCC | GGGCAGTCGAGTTCTCACG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 418 | GTGAGAACTCGACTGCCCC | GGGGCAGTCGAGTTCTCAC |
| 419 | TGAGAACTCGACTGCCCCT | AGGGGCAGTCGAGTTCTCA |
| 420 | GAGAACTCGACTGCCCCTG | CAGGGGCAGTCGAGTTCTC |
| 421 | AGAACTCGACTGCCCCTGC | GCAGGGGCAGTCGAGTTCT |
| 422 | GAACTCGACTGCCCCTGCC | GGCAGGGGCAGTCGAGTTC |
| 423 | AACTCGACTGCCCCTGCCA | TGGCAGGGGCAGTCGAGTT |
| 424 | ACTCGACTGCCCCTGCCAG | CTGGCAGGGGCAGTCGAGT |
| 425 | CTCGACTGCCCCTGCCAGC | GCTGGCAGGGGCAGTCGAG |
| 426 | TCGACTGCCCCTGCCAGCT | AGCTGGCAGGGGCAGTCGA |
| 427 | CGACTGCCCCTGCCAGCTC | GAGCTGGCAGGGGCAGTCG |
| 428 | GACTGCCCCTGCCAGCTCT | AGAGCTGGCAGGGGCAGTC |
| 429 | ACTGCCCCTGCCAGCTCTG | CAGAGCTGGCAGGGGCAGT |
| 430 | CTGCCCCTGCCAGCTCTGG | CCAGAGCTGGCAGGGGCAG |
| 431 | TGCCCCTGCCAGCTCTGGC | GCCAGAGCTGGCAGGGGCA |
| 432 | GCCCCTGCCAGCTCTGGCA | TGCCAGAGCTGGCAGGGGC |
| 433 | CCCCTGCCAGCTCTGGCAC | GTGCCAGAGCTGGCAGGGG |
| 434 | CCCTGCCAGCTCTGGCACT | AGTGCCAGAGCTGGCAGGG |
| 435 | CCTGCCAGCTCTGGCACTG | CAGTGCCAGAGCTGGCAGG |
| 436 | CTGCCAGCTCTGGCACTGC | GCAGTGCCAGAGCTGGCAG |
| 437 | TGCCAGCTCTGGCACTGCC | GGCAGTGCCAGAGCTGGCA |
| 438 | GCCAGCTCTGGCACTGCCC | GGGCAGTGCCAGAGCTGGC |
| 439 | CCAGCTCTGGCACTGCCCC | GGGGCAGTGCCAGAGCTGG |
| 440 | CAGCTCTGGCACTGCCCCC | GGGGGCAGTGCCAGAGCTG |
| 441 | AGCTCTGGCACTGCCCCCT | AGGGGGCAGTGCCAGAGCT |
| 442 | GCTCTGGCACTGCCCCCTC | GAGGGGGCAGTGCCAGAGC |
| 443 | CTCTGGCACTGCCCCCTCC | GGAGGGGGCAGTGCCAGAG |
| 444 | TCTGGCACTGCCCCCTCCC | GGGAGGGGGCAGTGCCAGA |
| 445 | CTGGCACTGCCCCCTCCCA | TGGGAGGGGGCAGTGCCAG |
| 446 | TGGCACTGCCCCCTCCCAG | CTGGGAGGGGGCAGTGCCA |
| 447 | GGCACTGCCCCCTCCCAGC | GCTGGGAGGGGGCAGTGCC |
| 448 | GCACTGCCCCCTCCCAGCC | GGCTGGGAGGGGGCAGTGC |
| 449 | CACTGCCCCCTCCCAGCCG | CGGCTGGGAGGGGGCAGTG |
| 450 | ACTGCCCCCTCCCAGCCGC | GCGGCTGGGAGGGGGCAGT |
| 451 | CTGCCCCCTCCCAGCCGCC | GGCGGCTGGGAGGGGGCAG |
| 452 | TGCCCCCTCCCAGCCGCCC | GGGCGGCTGGGAGGGGGCA |
| 453 | GCCCCCTCCCAGCCGCCCC | GGGGCGGCTGGGAGGGGGC |
| 454 | CCCCCTCCCAGCCGCCCCG | CGGGGCGGCTGGGAGGGGG |
| 455 | CCCCTCCCAGCCGCCCCGC | GCGGGGCGGCTGGGAGGGG |
| 456 | CCCTCCCAGCCGCCCCGCC | GGCGGGGCGGCTGGGAGGG |
| 457 | CCTCCCAGCCGCCCCGCCC | GGGCGGGGCGGCTGGGAGG |
| 458 | CTCCCAGCCGCCCCGCCCT | AGGGCGGGGCGGCTGGGAG |
| 459 | TCCCAGCCGCCCCGCCCTA | TAGGGCGGGGCGGCTGGGA |
| 460 | CCCAGCCGCCCCGCCCTAG | CTAGGGCGGGGCGGCTGGG |
| 461 | CCAGCCGCCCCGCCCTAGC | GCTAGGGCGGGGCGGCTGG |
| 462 | CAGCCGCCCCGCCCTAGCA | TGCTAGGGCGGGGCGGCTG |
| 463 | AGCCGCCCCGCCCTAGCAC | GTGCTAGGGCGGGGCGGCT |
| 464 | GCCGCCCCGCCCTAGCACC | GGTGCTAGGGCGGGGCGGC |
| 465 | CCGCCCCGCCCTAGCACCC | GGGTGCTAGGGCGGGGCGG |
| 466 | CGCCCCGCCCTAGCACCCT | AGGGTGCTAGGGCGGGGCG |
| 467 | GCCCCGCCCTAGCACCCTG | CAGGGTGCTAGGGCGGGGC |
| 468 | CCCCGCCCTAGCACCCTGG | CCAGGGTGCTAGGGCGGGG |
| 469 | CCCGCCCTAGCACCCTGGG | CCCAGGGTGCTAGGGCGGG |
| 470 | CCGCCCTAGCACCCTGGGG | CCCCAGGGTGCTAGGGCGG |
| 471 | CGCCCTAGCACCCTGGGGG | CCCCCAGGGTGCTAGGGCG |
| 472 | GCCCTAGCACCCTGGGGGG | CCCCCCAGGGTGCTAGGGC |
| 473 | CCCTAGCACCCTGGGGGGC | GCCCCCCAGGGTGCTAGGG |
| 474 | CCTAGCACCCTGGGGGGCA | TGCCCCCCAGGGTGCTAGG |
| 475 | CTAGCACCCTGGGGGGCAC | GTGCCCCCCAGGGTGCTAG |
| 476 | TAGCACCCTGGGGGGCACC | GGTGCCCCCCAGGGTGCTA |
| 477 | AGCACCCTGGGGGGCACCC | GGGTGCCCCCCAGGGTGCT |
| 478 | GCACCCTGGGGGGCACCCC | GGGGTGCCCCCCAGGGTGC |
| 479 | CACCCTGGGGGGCACCCCG | CGGGGTGCCCCCCAGGGTG |
| 480 | ACCCTGGGGGGCACCCCGC | GCGGGGTGCCCCCCAGGGT |
| 481 | CCCTGGGGGGCACCCCGCC | GGCGGGGTGCCCCCCAGGG |
| 482 | CCTGGGGGGCACCCCGCCC | GGGCGGGGTGCCCCCCAGG |
| 483 | CTGGGGGGCACCCCGCCCA | TGGGCGGGGTGCCCCCCAG |
| 484 | TGGGGGGCACCCCGCCCAA | TTGGGCGGGGTGCCCCCCA |
| 485 | GGGGGGCACCCCGCCCAAC | GTTGGGCGGGGTGCCCCCC |
| 486 | GGGGGCACCCCGCCCAACC | GGTTGGGCGGGGTGCCCCC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 487 | GGGGCACCCCGCCCAACCG | CGGTTGGGCGGGGTGCCCC |
| 488 | GGGCACCCCGCCCAACCGT | ACGGTTGGGCGGGGTGCCC |
| 489 | GGCACCCCGCCCAACCGTG | CACGGTTGGGCGGGGTGCC |
| 490 | GCACCCCGCCCAACCGTGG | CCACGGTTGGGCGGGGTGC |
| 491 | CACCCCGCCCAACCGTGGC | GCCACGGTTGGGCGGGGTG |
| 492 | ACCCCGCCCAACCGTGGCC | GGCCACGGTTGGGCGGGGT |
| 493 | CCCCGCCCAACCGTGGCCT | AGGCCACGGTTGGGCGGGG |
| 494 | CCCGCCCAACCGTGGCCTG | CAGGCCACGGTTGGGCGGG |
| 495 | CCGCCCAACCGTGGCCTGG | CCAGGCCACGGTTGGGCGG |
| 496 | CGCCCAACCGTGGCCTGGT | ACCAGGCCACGGTTGGGCG |
| 497 | GCCCAACCGTGGCCTGGTC | GACCAGGCCACGGTTGGGC |
| 498 | CCCAACCGTGGCCTGGTCC | GGACCAGGCCACGGTTGGG |
| 499 | CCAACCGTGGCCTGGTCCG | CGGACCAGGCCACGGTTGG |
| 500 | CAACCGTGGCCTGGTCCGG | CCGGACCAGGCCACGGTTG |
| 501 | AACCGTGGCCTGGTCCGGC | GCCGGACCAGGCCACGGTT |
| 502 | ACCGTGGCCTGGTCCGGCC | GGCCGGACCAGGCCACGGT |
| 503 | CCGTGGCCTGGTCCGGCCC | GGGCCGGACCAGGCCACGG |
| 504 | CGTGGCCTGGTCCGGCCCC | GGGGCCGGACCAGGCCACG |
| 505 | GTGGCCTGGTCCGGCCCCT | AGGGGCCGGACCAGGCCAC |
| 506 | TGGCCTGGTCCGGCCCCTC | GAGGGGCCGGACCAGGCCA |
| 507 | GGCCTGGTCCGGCCCCTCC | GGAGGGGCCGGACCAGGCC |
| 508 | GCCTGGTCCGGCCCCTCCC | GGGAGGGGCCGGACCAGGC |
| 509 | CCTGGTCCGGCCCCTCCCG | CGGGAGGGGCCGGACCAGG |
| 510 | CTGGTCCGGCCCCTCCCGC | GCGGGAGGGGCCGGACCAG |
| 511 | TGGTCCGGCCCCTCCCGCC | GGCGGGAGGGGCCGGACCA |
| 512 | GGTCCGGCCCCTCCCGCCC | GGGCGGGAGGGGCCGGACC |
| 513 | GTCCGGCCCCTCCCGCCCT | AGGGCGGGAGGGGCCGGAC |
| 514 | TCCGGCCCCTCCCGCCCTT | AAGGGCGGGAGGGGCCGGA |
| 515 | CCGGCCCCTCCCGCCCTTT | AAAGGGCGGGAGGGGCCGG |
| 516 | CGGCCCCTCCCGCCCTTTG | CAAAGGGCGGGAGGGGCCG |
| 517 | GGCCCCTCCCGCCCTTTGC | GCAAAGGGCGGGAGGGGCC |
| 518 | GCCCCTCCCGCCCTTTGCT | AGCAAAGGGCGGGAGGGGC |
| 519 | CCCCTCCCGCCCTTTGCTC | GAGCAAAGGGCGGGAGGGG |
| 520 | CCCTCCCGCCCTTTGCTCC | GGAGCAAAGGGCGGGAGGG |
| 521 | CCTCCCGCCCTTTGCTCCA | TGGAGCAAAGGGCGGGAGG |
| 522 | CTCCCGCCCTTTGCTCCAG | CTGGAGCAAAGGGCGGGAG |
| 523 | TCCCGCCCTTTGCTCCAGT | ACTGGAGCAAAGGGCGGGA |
| 524 | CCCGCCCTTTGCTCCAGTT | AACTGGAGCAAAGGGCGGG |
| 525 | CCGCCCTTTGCTCCAGTTC | GAACTGGAGCAAAGGGCGG |
| 526 | CGCCCTTTGCTCCAGTTCC | GGAACTGGAGCAAAGGGCG |
| 527 | GCCCTTTGCTCCAGTTCCC | GGGAACTGGAGCAAAGGGC |
| 528 | CCCTTTGCTCCAGTTCCCG | CGGGAACTGGAGCAAAGGG |
| 529 | CCTTTGCTCCAGTTCCCGG | CCGGGAACTGGAGCAAAGG |
| 530 | CTTTGCTCCAGTTCCCGGG | CCCGGGAACTGGAGCAAAG |
| 531 | TTTGCTCCAGTTCCCGGGC | GCCCGGGAACTGGAGCAAA |
| 532 | TTGCTCCAGTTCCCGGGCT | AGCCCGGGAACTGGAGCAA |
| 533 | TGCTCCAGTTCCCGGGCTT | AAGCCCGGGAACTGGAGCA |
| 534 | GCTCCAGTTCCCGGGCTTG | CAAGCCCGGGAACTGGAGC |
| 535 | CTCCAGTTCCCGGGCTTGG | CCAAGCCCGGGAACTGGAG |
| 536 | TCCAGTTCCCGGGCTTGGC | GCCAAGCCCGGGAACTGGA |
| 537 | CCAGTTCCCGGGCTTGGCA | TGCCAAGCCCGGGAACTGG |
| 538 | CAGTTCCCGGGCTTGGCAC | GTGCCAAGCCCGGGAACTG |
| 539 | AGTTCCCGGGCTTGGCACC | GGTGCCAAGCCCGGGAACT |
| 540 | GTTCCCGGGCTTGGCACCT | AGGTGCCAAGCCCGGGAAC |
| 541 | TTCCCGGGCTTGGCACCTA | TAGGTGCCAAGCCCGGGAA |
| 542 | TCCCGGGCTTGGCACCTAT | ATAGGTGCCAAGCCCGGGA |
| 543 | CCCGGGCTTGGCACCTATA | TATAGGTGCCAAGCCCGGG |
| 544 | CCGGGCTTGGCACCTATAG | CTATAGGTGCCAAGCCCGG |
| 545 | CGGGCTTGGCACCTATAGT | ACTATAGGTGCCAAGCCCG |
| 546 | GGGCTTGGCACCTATAGTG | CACTATAGGTGCCAAGCCC |
| 547 | GGCTTGGCACCTATAGTGG | CCACTATAGGTGCCAAGCC |
| 548 | GCTTGGCACCTATAGTGGG | CCCACTATAGGTGCCAAGC |
| 549 | CTTGGCACCTATAGTGGGG | CCCCACTATAGGTGCCAAG |
| 550 | TTGGCACCTATAGTGGGGG | CCCCCACTATAGGTGCCAA |
| 551 | TGGCACCTATAGTGGGGGT | ACCCCCACTATAGGTGCCA |
| 552 | GGCACCTATAGTGGGGGTG | CACCCCCACTATAGGTGCC |
| 553 | GCACCTATAGTGGGGGTGC | GCACCCCCACTATAGGTGC |
| 554 | CACCTATAGTGGGGGTGCC | GGCACCCCCACTATAGGTG |
| 555 | ACCTATAGTGGGGGTGCCG | CGGCACCCCCACTATAGGT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 556 | CCTATAGTGGGGGTGCCGC | GCGGCACCCCCACTATAGG |
| 557 | CTATAGTGGGGGTGCCGCC | GGCGGCACCCCCACTATAG |
| 558 | TATAGTGGGGGTGCCGCCC | GGGCGGCACCCCCACTATA |
| 559 | ATAGTGGGGGTGCCGCCCG | CGGGCGGCACCCCCACTAT |
| 560 | TAGTGGGGGTGCCGCCCGC | GCGGGCGGCACCCCCACTA |
| 561 | AGTGGGGGTGCCGCCCGCC | GGCGGGCGGCACCCCCACT |
| 562 | GTGGGGGTGCCGCCCGCCT | AGGCGGGCGGCACCCCCAC |
| 563 | TGGGGGTGCCGCCCGCCTG | CAGGCGGGCGGCACCCCCA |
| 564 | GGGGGTGCCGCCCGCCTGC | GCAGGCGGGCGGCACCCCC |
| 565 | GGGGTGCCGCCCGCCTGCC | GGCAGGCGGGCGGCACCCC |
| 566 | GGGTGCCGCCCGCCTGCCA | TGGCAGGCGGGCGGCACCC |
| 567 | GGTGCCGCCCGCCTGCCAG | CTGGCAGGCGGGCGGCACC |
| 568 | GTGCCGCCCGCCTGCCAGG | CCTGGCAGGCGGGCGGCAC |
| 569 | TGCCGCCCGCCTGCCAGGC | GCCTGGCAGGCGGGCGGCA |
| 570 | GCCGCCCGCCTGCCAGGCT | AGCCTGGCAGGCGGGCGGC |
| 571 | CCGCCCGCCTGCCAGGCTC | GAGCCTGGCAGGCGGGCGG |
| 572 | CGCCCGCCTGCCAGGCTCC | GGAGCCTGGCAGGCGGGCG |
| 573 | GCCCGCCTGCCAGGCTCCG | CGGAGCCTGGCAGGCGGGC |
| 574 | CCCGCCTGCCAGGCTCCGG | CCGGAGCCTGGCAGGCGGG |
| 575 | CCGCCTGCCAGGCTCCGGG | CCCGGAGCCTGGCAGGCGG |
| 576 | CGCCTGCCAGGCTCCGGGG | CCCCGGAGCCTGGCAGGCG |
| 577 | GCCTGCCAGGCTCCGGGGC | GCCCCGGAGCCTGGCAGGC |
| 578 | CCTGCCAGGCTCCGGGGCC | GGCCCCGGAGCCTGGCAGG |
| 579 | CTGCCAGGCTCCGGGGCCG | CGGCCCCGGAGCCTGGCAG |
| 580 | TGCCAGGCTCCGGGGCCGG | CCGGCCCCGGAGCCTGGCA |
| 581 | GCCAGGCTCCGGGGCCGGG | CCCGGCCCCGGAGCCTGGC |
| 582 | CCAGGCTCCGGGGCCGGGC | GCCCGGCCCCGGAGCCTGG |
| 583 | CAGGCTCCGGGGCCGGGCC | GGCCCGGCCCCGGAGCCTG |
| 584 | AGGCTCCGGGGCCGGGCCC | GGGCCCGGCCCCGGAGCCT |
| 585 | GGCTCCGGGGCCGGGCCCA | TGGGCCCGGCCCCGGAGCC |
| 586 | GCTCCGGGGCCGGGCCCAC | GTGGGCCCGGCCCCGGAGC |
| 587 | CTCCGGGGCCGGGCCCACG | CGTGGGCCCGGCCCCGGAG |
| 588 | TCCGGGGCCGGGCCCACGG | CCGTGGGCCCGGCCCCGGA |
| 589 | CCGGGGCCGGGCCCACGGG | CCCGTGGGCCCGGCCCCGG |
| 590 | CGGGGCCGGGCCCACGGGA | TCCCGTGGGCCCGGCCCCG |
| 591 | GGGGCCGGGCCCACGGGAG | CTCCCGTGGGCCCGGCCCC |
| 592 | GGGCCGGGCCCACGGGAGG | CCTCCCGTGGGCCCGGCCC |
| 593 | GGCCGGGCCCACGGGAGGG | CCCTCCCGTGGGCCCGGCC |
| 594 | GCCGGGCCCACGGGAGGGT | ACCCTCCCGTGGGCCCGGC |
| 595 | CCGGGCCCACGGGAGGGTG | CACCCTCCCGTGGGCCCGG |
| 596 | CGGGCCCACGGGAGGGTGG | CCACCCTCCCGTGGGCCCG |
| 597 | GGGCCCACGGGAGGGTGGG | CCCACCCTCCCGTGGGCCC |
| 598 | GGCCCACGGGAGGGTGGGG | CCCCACCCTCCCGTGGGCC |
| 599 | GCCCACGGGAGGGTGGGGC | GCCCCACCCTCCCGTGGGC |
| 600 | CCCACGGGAGGGTGGGGCG | CGCCCCACCCTCCCGTGGG |
| 601 | CCACGGGAGGGTGGGGCGG | CCGCCCCACCCTCCCGTGG |
| 602 | CACGGGAGGGTGGGGCGGC | GCCGCCCCACCCTCCCGTG |
| 603 | ACGGGAGGGTGGGGCGGCT | AGCCGCCCCACCCTCCCGT |
| 604 | CGGGAGGGTGGGGCGGCTG | CAGCCGCCCCACCCTCCCG |
| 605 | GGGAGGGTGGGGCGGCTGG | CCAGCCGCCCCACCCTCCC |
| 606 | GGAGGGTGGGGCGGCTGGG | CCCAGCCGCCCCACCCTCC |
| 607 | GAGGGTGGGGCGGCTGGGA | TCCCAGCCGCCCCACCCTC |
| 608 | AGGGTGGGGCGGCTGGGAA | TTCCCAGCCGCCCCACCCT |
| 609 | GGGTGGGGCGGCTGGGAAG | CTTCCCAGCCGCCCCACCC |
| 610 | GGTGGGGCGGCTGGGAAGC | GCTTCCCAGCCGCCCCACC |
| 611 | GTGGGGCGGCTGGGAAGCT | AGCTTCCCAGCCGCCCCAC |
| 612 | TGGGGCGGCTGGGAAGCTG | CAGCTTCCCAGCCGCCCCA |
| 613 | GGGGCGGCTGGGAAGCTGG | CCAGCTTCCCAGCCGCCCC |
| 614 | GGGCGGCTGGGAAGCTGGC | GCCAGCTTCCCAGCCGCCC |
| 615 | GGCGGCTGGGAAGCTGGCA | TGCCAGCTTCCCAGCCGCC |
| 616 | GCGGCTGGGAAGCTGGCAC | GTGCCAGCTTCCCAGCCGC |
| 617 | CGGCTGGGAAGCTGGCACG | CGTGCCAGCTTCCCAGCCG |
| 618 | GGCTGGGAAGCTGGCACGC | GCGTGCCAGCTTCCCAGCC |
| 619 | GCTGGGAAGCTGGCACGCT | AGCGTGCCAGCTTCCCAGC |
| 620 | CTGGGAAGCTGGCACGCTG | CAGCGTGCCAGCTTCCCAG |
| 621 | TGGGAAGCTGGCACGCTGC | GCAGCGTGCCAGCTTCCCA |
| 622 | GGGAAGCTGGCACGCTGCC | GGCAGCGTGCCAGCTTCCC |
| 623 | GGAAGCTGGCACGCTGCCC | GGGCAGCGTGCCAGCTTCC |
| 624 | GAAGCTGGCACGCTGCCCC | GGGGCAGCGTGCCAGCTTC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 625 | AAGCTGGCACGCTGCCCCG | CGGGGCAGCGTGCCAGCTT |
| 626 | AGCTGGCACGCTGCCCCGG | CCGGGGCAGCGTGCCAGCT |
| 627 | GCTGGCACGCTGCCCCGGG | CCCGGGGCAGCGTGCCAGC |
| 628 | CTGGCACGCTGCCCCGGGG | CCCCGGGGCAGCGTGCCAG |
| 629 | TGGCACGCTGCCCCGGGGG | CCCCCGGGGCAGCGTGCCA |
| 630 | GGCACGCTGCCCCGGGGGA | TCCCCCGGGGCAGCGTGCC |
| 631 | GCACGCTGCCCCGGGGGAG | CTCCCCCGGGGCAGCGTGC |
| 632 | CACGCTGCCCCGGGGGAGC | GCTCCCCCGGGGCAGCGTG |
| 633 | ACGCTGCCCCGGGGGAGCC | GGCTCCCCCGGGGCAGCGT |
| 634 | CGCTGCCCCGGGGGAGCCT | AGGCTCCCCCGGGGCAGCG |
| 635 | GCTGCCCCGGGGGAGCCTC | GAGGCTCCCCCGGGGCAGC |
| 636 | CTGCCCCGGGGGAGCCTCT | AGAGGCTCCCCCGGGGCAG |
| 637 | TGCCCCGGGGGAGCCTCTC | GAGAGGCTCCCCCGGGGCA |
| 638 | GCCCCGGGGGAGCCTCTCT | AGAGAGGCTCCCCCGGGGC |
| 639 | CCCCGGGGGAGCCTCTCTC | GAGAGAGGCTCCCCCGGGG |
| 640 | CCCGGGGGAGCCTCTCTCG | CGAGAGAGGCTCCCCCGGG |
| 641 | CCGGGGGAGCCTCTCTCGG | CCGAGAGAGGCTCCCCCGG |
| 642 | CGGGGGAGCCTCTCTCGGC | GCCGAGAGAGGCTCCCCCG |
| 643 | GGGGGAGCCTCTCTCGGCA | TGCCGAGAGAGGCTCCCCC |
| 644 | GGGGAGCCTCTCTCGGCAG | CTGCCGAGAGAGGCTCCCC |
| 645 | GGGAGCCTCTCTCGGCAGG | CCTGCCGAGAGAGGCTCCC |
| 646 | GGAGCCTCTCTCGGCAGGC | GCCTGCCGAGAGAGGCTCC |
| 647 | GAGCCTCTCTCGGCAGGCG | CGCCTGCCGAGAGAGGCTC |
| 648 | AGCCTCTCTCGGCAGGCGC | GCGCCTGCCGAGAGAGGCT |
| 649 | GCCTCTCTCGGCAGGCGCC | GGCGCCTGCCGAGAGAGGC |
| 650 | CCTCTCTCGGCAGGCGCCC | GGGCGCCTGCCGAGAGAGG |
| 651 | CTCTCTCGGCAGGCGCCCG | CGGGCGCCTGCCGAGAGAG |
| 652 | TCTCTCGGCAGGCGCCCGG | CCGGGCGCCTGCCGAGAGA |
| 653 | CTCTCGGCAGGCGCCCGGG | CCCGGGCGCCTGCCGAGAG |
| 654 | TCTCGGCAGGCGCCCGGGT | ACCCGGGCGCCTGCCGAGA |
| 655 | CTCGGCAGGCGCCCGGGTG | CACCCGGGCGCCTGCCGAG |
| 656 | TCGGCAGGCGCCCGGGTGC | GCACCCGGGCGCCTGCCGA |
| 657 | CGGCAGGCGCCCGGGTGCC | GGCACCCGGGCGCCTGCCG |
| 658 | GGCAGGCGCCCGGGTGCCG | CGGCACCCGGGCGCCTGCC |
| 659 | GCAGGCGCCCGGGTGCCGC | GCGGCACCCGGGCGCCTGC |
| 660 | CAGGCGCCCGGGTGCCGCG | CGCGGCACCCGGGCGCCTG |
| 661 | AGGCGCCCGGGTGCCGCGG | CCGCGGCACCCGGGCGCCT |
| 662 | GGCGCCCGGGTGCCGCGGG | CCCGCGGCACCCGGGCGCC |
| 663 | GCGCCCGGGTGCCGCGGGG | CCCCGCGGCACCCGGGCGC |
| 664 | CGCCCGGGTGCCGCGGGGG | CCCCCGCGGCACCCGGGCG |
| 665 | GCCCGGGTGCCGCGGGGGG | CCCCCCGCGGCACCCGGGC |
| 666 | CCCGGGTGCCGCGGGGGGG | CCCCCCCGCGGCACCCGGG |
| 667 | CCGGGTGCCGCGGGGGGGA | TCCCCCCCGCGGCACCCGG |
| 668 | CGGGTGCCGCGGGGGGGAG | CTCCCCCCCGCGGCACCCG |
| 669 | GGGTGCCGCGGGGGGGAGG | CCTCCCCCCCGCGGCACCC |
| 670 | GGTGCCGCGGGGGGGAGGG | CCCTCCCCCCCGCGGCACC |
| 671 | GTGCCGCGGGGGGGAGGGG | CCCCTCCCCCCCGCGGCAC |
| 672 | TGCCGCGGGGGGGAGGGGG | CCCCCTCCCCCCCGCGGCA |
| 673 | GCCGCGGGGGGGAGGGGGA | TCCCCCTCCCCCCCGCGGC |
| 674 | CCGCGGGGGGGAGGGGGAA | TTCCCCCTCCCCCCCGCGG |
| 675 | CGCGGGGGGGAGGGGGAAC | GTTCCCCCTCCCCCCCGCG |
| 676 | GCGGGGGGGAGGGGGAACA | TGTTCCCCCTCCCCCCCGC |
| 677 | CGGGGGGGAGGGGGAACAA | TTGTTCCCCCTCCCCCCCG |
| 678 | GGGGGGGAGGGGGAACAAA | TTTGTTCCCCCTCCCCCCC |
| 679 | GGGGGGAGGGGGAACAAAG | CTTTGTTCCCCCTCCCCCC |
| 680 | GGGGGAGGGGGAACAAAGG | CCTTTGTTCCCCCTCCCCC |
| 681 | GGGGAGGGGGAACAAAGGG | CCCTTTGTTCCCCCTCCCC |
| 682 | GGGAGGGGGAACAAAGGGC | GCCCTTTGTTCCCCCTCCC |
| 683 | GGAGGGGGAACAAAGGGCT | AGCCCTTTGTTCCCCCTCC |
| 684 | GAGGGGGAACAAAGGGCTC | GAGCCCTTTGTTCCCCCTC |
| 685 | AGGGGGAACAAAGGGCTCA | TGAGCCCTTTGTTCCCCCT |
| 686 | GGGGGAACAAAGGGCTCAT | ATGAGCCCTTTGTTCCCCC |
| 687 | GGGGAACAAAGGGCTCATT | AATGAGCCCTTTGTTCCCC |
| 688 | GGGAACAAAGGGCTCATTC | GAATGAGCCCTTTGTTCCC |
| 689 | GGAACAAAGGGCTCATTCT | AGAATGAGCCCTTTGTTCC |
| 690 | GAACAAAGGGCTCATTCTC | GAGAATGAGCCCTTTGTTC |
| 691 | AACAAAGGGCTCATTCTCC | GGAGAATGAGCCCTTTGTT |
| 692 | ACAAAGGGCTCATTCTCCC | GGGAGAATGAGCCCTTTGT |
| 693 | CAAAGGGCTCATTCTCCCC | GGGGAGAATGAGCCCTTTG |

TABLE 1-continued cDNA Human Hairless 19-mer Target Sequences and Complement Referenced to NM_005144-
*Homo sapiens* hairless homolog (mouse) (HR), transcript variant 1, complete mRNA (1-5699 bp).
(SEQ ID NO: for Sense equals (2X - 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 694 | AAAGGGCTCATTCTCCCCG | CGGGGAGAATGAGCCCTTT |
| 695 | AAGGGCTCATTCTCCCCGT | ACGGGGAGAATGAGCCCTT |
| 696 | AGGGCTCATTCTCCCCGTG | CACGGGGAGAATGAGCCCT |
| 697 | GGGCTCATTCTCCCCGTGC | GCACGGGGAGAATGAGCCC |
| 698 | GGCTCATTCTCCCCGTGCG | CGCACGGGGAGAATGAGCC |
| 699 | GCTCATTCTCCCCGTGCGC | GCGCACGGGGAGAATGAGC |
| 700 | CTCATTCTCCCCGTGCGCA | TGCGCACGGGGAGAATGAG |
| 701 | TCATTCTCCCCGTGCGCAG | CTGCGCACGGGGAGAATGA |
| 702 | CATTCTCCCCGTGCGCAGC | GCTGCGCACGGGGAGAATG |
| 703 | ATTCTCCCCGTGCGCAGCC | GGCTGCGCACGGGGAGAAT |
| 704 | TTCTCCCCGTGCGCAGCCG | CGGCTGCGCACGGGGAGAA |
| 705 | TCTCCCCGTGCGCAGCCGG | CCGGCTGCGCACGGGGAGA |
| 706 | CTCCCCGTGCGCAGCCGGT | ACCGGCTGCGCACGGGGAG |
| 707 | TCCCCGTGCGCAGCCGGTG | CACCGGCTGCGCACGGGGA |
| 708 | CCCCGTGCGCAGCCGGTGG | CCACCGGCTGCGCACGGGG |
| 709 | CCCGTGCGCAGCCGGTGGC | GCCACCGGCTGCGCACGGG |
| 710 | CCGTGCGCAGCCGGTGGCA | TGCCACCGGCTGCGCACGG |
| 711 | CGTGCGCAGCCGGTGGCAT | ATGCCACCGGCTGCGCACG |
| 712 | GTGCGCAGCCGGTGGCATC | GATGCCACCGGCTGCGCAC |
| 713 | TGCGCAGCCGGTGGCATCG | CGATGCCACCGGCTGCGCA |
| 714 | GCGCAGCCGGTGGCATCGC | GCGATGCCACCGGCTGCGC |
| 715 | CGCAGCCGGTGGCATCGCC | GGCGATGCCACCGGCTGCG |
| 716 | GCAGCCGGTGGCATCGCCG | CGGCGATGCCACCGGCTGC |
| 717 | CAGCCGGTGGCATCGCCGG | CCGGCGATGCCACCGGCTG |
| 718 | AGCCGGTGGCATCGCCGGG | CCCGGCGATGCCACCGGCT |
| 719 | GCCGGTGGCATCGCCGGGG | CCCCGGCGATGCCACCGGC |
| 720 | CCGGTGGCATCGCCGGGGC | GCCCCGGCGATGCCACCGG |
| 721 | CGGTGGCATCGCCGGGGCG | CGCCCCGGCGATGCCACCG |
| 722 | GGTGGCATCGCCGGGGCGT | ACGCCCCGGCGATGCCACC |
| 723 | GTGGCATCGCCGGGGCGTT | AACGCCCCGGCGATGCCAC |
| 724 | TGGCATCGCCGGGGCGTTG | CAACGCCCCGGCGATGCCA |
| 725 | GGCATCGCCGGGGCGTTGG | CCAACGCCCCGGCGATGCC |
| 726 | GCATCGCCGGGGCGTTGGC | GCCAACGCCCCGGCGATGC |
| 727 | CATCGCCGGGGCGTTGGCG | CGCCAACGCCCCGGCGATG |
| 728 | ATCGCCGGGGCGTTGGCGG | CCGCCAACGCCCCGGCGAT |
| 729 | TCGCCGGGGCGTTGGCGGA | TCCGCCAACGCCCCGGCGA |
| 730 | CGCCGGGGCGTTGGCGGAA | TTCCGCCAACGCCCCGGCG |
| 731 | GCCGGGGCGTTGGCGGAAG | CTTCCGCCAACGCCCCGGC |
| 732 | CCGGGGCGTTGGCGGAAGC | GCTTCCGCCAACGCCCCGG |
| 733 | CGGGGCGTTGGCGGAAGCC | GGCTTCCGCCAACGCCCCG |
| 734 | GGGGCGTTGGCGGAAGCCC | GGGCTTCCGCCAACGCCCC |
| 735 | GGGCGTTGGCGGAAGCCCC | GGGGCTTCCGCCAACGCCC |
| 736 | GGCGTTGGCGGAAGCCCCC | GGGGGCTTCCGCCAACGCC |
| 737 | GCGTTGGCGGAAGCCCCCG | CGGGGGCTTCCGCCAACGC |
| 738 | CGTTGGCGGAAGCCCCCGG | CCGGGGGCTTCCGCCAACG |
| 739 | GTTGGCGGAAGCCCCCGGG | CCCGGGGGCTTCCGCCAAC |
| 740 | TTGGCGGAAGCCCCCGGGG | CCCCGGGGGCTTCCGCCAA |
| 741 | TGGCGGAAGCCCCCGGGGC | GCCCCGGGGGCTTCCGCCA |
| 742 | GGCGGAAGCCCCCGGGGCC | GGCCCCGGGGGCTTCCGCC |
| 743 | GCGGAAGCCCCCGGGGCCC | GGGCCCCGGGGGCTTCCGC |
| 744 | CGGAAGCCCCCGGGGCCCG | CGGGCCCCGGGGGCTTCCG |
| 745 | GGAAGCCCCCGGGGCCCGG | CCGGGCCCCGGGGGCTTCC |
| 746 | GAAGCCCCCGGGGCCCGGG | CCCGGGCCCCGGGGGCTTC |
| 747 | AAGCCCCCGGGGCCCGGGA | TCCCGGGCCCCGGGGGCTT |
| 748 | AGCCCCCGGGGCCCGGGAG | CTCCCGGGCCCCGGGGGCT |
| 749 | GCCCCCGGGGCCCGGGAGG | CCTCCCGGGCCCCGGGGGC |
| 750 | CCCCCGGGGCCCGGGAGGG | CCCTCCCGGGCCCCGGGGG |
| 751 | CCCCGGGGCCCGGGAGGGG | CCCCTCCCGGGCCCCGGGG |
| 752 | CCCGGGGCCCGGGAGGGGG | CCCCCTCCCGGGCCCCGGG |
| 753 | CCGGGGCCCGGGAGGGGGC | GCCCCCTCCCGGGCCCCGG |
| 754 | CGGGGCCCGGGAGGGGGCA | TGCCCCCTCCCGGGCCCCG |
| 755 | GGGGCCCGGGAGGGGGCAG | CTGCCCCCTCCCGGGCCCC |
| 756 | GGGCCCGGGAGGGGGCAGG | CCTGCCCCCTCCCGGGCCC |
| 757 | GGCCCGGGAGGGGGCAGGC | GCCTGCCCCCTCCCGGGCC |
| 758 | GCCCGGGAGGGGGCAGGCC | GGCCTGCCCCCTCCCGGGC |
| 759 | CCCGGGAGGGGGCAGGCCC | GGGCCTGCCCCCTCCCGGG |
| 760 | CCGGGAGGGGGCAGGCCCA | TGGGCCTGCCCCCTCCCGG |
| 761 | CGGGAGGGGGCAGGCCCAG | CTGGGCCTGCCCCCTCCCG |
| 762 | GGGAGGGGGCAGGCCCAGG | CCTGGGCCTGCCCCCTCCC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 763 | GGAGGGGGCAGGCCCAGGC | GCCTGGGCCTGCCCCCTCC |
| 764 | GAGGGGGCAGGCCCAGGCG | CGCCTGGGCCTGCCCCCTC |
| 765 | AGGGGGCAGGCCCAGGCGC | GCGCCTGGGCCTGCCCCCT |
| 766 | GGGGGCAGGCCCAGGCGCG | CGCGCCTGGGCCTGCCCCC |
| 767 | GGGGCAGGCCCAGGCGCGG | CCGCGCCTGGGCCTGCCCC |
| 768 | GGGCAGGCCCAGGCGCGGC | GCCGCGCCTGGGCCTGCCC |
| 769 | GGCAGGCCCAGGCGCGGCC | GGCCGCGCCTGGGCCTGCC |
| 770 | GCAGGCCCAGGCGCGGCCG | CGGCCGCGCCTGGGCCTGC |
| 771 | CAGGCCCAGGCGCGGCCGC | GCGGCCGCGCCTGGGCCTG |
| 772 | AGGCCCAGGCGCGGCCGCC | GGCGGCCGCGCCTGGGCCT |
| 773 | GGCCCAGGCGCGGCCGCCG | CGGCGGCCGCGCCTGGGCC |
| 774 | GCCCAGGCGCGGCCGCCGA | TCGGCGGCCGCGCCTGGGC |
| 775 | CCCAGGCGCGGCCGCCGAA | TTCGGCGGCCGCGCCTGGG |
| 776 | CCAGGCGCGGCCGCCGAAT | ATTCGGCGGCCGCGCCTGG |
| 777 | CAGGCGCGGCCGCCGAATC | GATTCGGCGGCCGCGCCTG |
| 778 | AGGCGCGGCCGCCGAATCA | TGATTCGGCGGCCGCGCCT |
| 779 | GGCGCGGCCGCCGAATCAC | GTGATTCGGCGGCCGCGCC |
| 780 | GCGCGGCCGCCGAATCACG | CGTGATTCGGCGGCCGCGC |
| 781 | CGCGGCCGCCGAATCACGG | CCGTGATTCGGCGGCCGCG |
| 782 | GCGGCCGCCGAATCACGGG | CCCGTGATTCGGCGGCCGC |
| 783 | CGGCCGCCGAATCACGGGC | GCCCGTGATTCGGCGGCCG |
| 784 | GGCCGCCGAATCACGGGCT | AGCCCGTGATTCGGCGGCC |
| 785 | GCCGCCGAATCACGGGCTC | GAGCCCGTGATTCGGCGG |
| 786 | CCGCCGAATCACGGGCTCC | GGAGCCCGTGATTCGGCGG |
| 787 | CGCCGAATCACGGGCTCCT | AGGAGCCCGTGATTCGGCG |
| 788 | GCCGAATCACGGGCTCCTG | CAGGAGCCCGTGATTCGGC |
| 789 | CCGAATCACGGGCTCCTGT | ACAGGAGCCCGTGATTCGG |
| 790 | CGAATCACGGGCTCCTGTT | AACAGGAGCCCGTGATTCG |
| 791 | GAATCACGGGCTCCTGTTT | AAACAGGAGCCCGTGATTC |
| 792 | AATCACGGGCTCCTGTTTC | GAAACAGGAGCCCGTGATT |
| 793 | ATCACGGGCTCCTGTTTCC | GGAAACAGGAGCCCGTGAT |
| 794 | TCACGGGCTCCTGTTTCCC | GGGAAACAGGAGCCCGTGA |
| 795 | CACGGGCTCCTGTTTCCCG | CGGGAAACAGGAGCCCGTG |
| 796 | ACGGGCTCCTGTTTCCCGC | GCGGGAAACAGGAGCCCGT |
| 797 | CGGGCTCCTGTTTCCCGCA | TGCGGGAAACAGGAGCCCG |
| 798 | GGGCTCCTGTTTCCCGCAG | CTGCGGGAAACAGGAGCCC |
| 799 | GGCTCCTGTTTCCCGCAGG | CCTGCGGGAAACAGGAGCC |
| 800 | GCTCCTGTTTCCCGCAGGG | CCCTGCGGGAAACAGGAGC |
| 801 | CTCCTGTTTCCCGCAGGGT | ACCCTGCGGGAAACAGGAG |
| 802 | TCCTGTTTCCCGCAGGGTG | CACCCTGCGGGAAACAGGA |
| 803 | CCTGTTTCCCGCAGGGTGC | GCACCCTGCGGGAAACAGG |
| 804 | CTGTTTCCCGCAGGGTGCT | AGCACCCTGCGGGAAACAG |
| 805 | TGTTTCCCGCAGGGTGCTG | CAGCACCCTGCGGGAAACA |
| 806 | GTTTCCCGCAGGGTGCTGG | CCAGCACCCTGCGGGAAAC |
| 807 | TTTCCCGCAGGGTGCTGGA | TCCAGCACCCTGCGGGAAA |
| 808 | TTCCCGCAGGGTGCTGGAG | CTCCAGCACCCTGCGGGAA |
| 809 | TCCCGCAGGGTGCTGGAGG | CCTCCAGCACCCTGCGGGA |
| 810 | CCCGCAGGGTGCTGGAGGA | TCCTCCAGCACCCTGCGGG |
| 811 | CCGCAGGGTGCTGGAGGAG | CTCCTCCAGCACCCTGCGG |
| 812 | CGCAGGGTGCTGGAGGAGG | CCTCCTCCAGCACCCTGCG |
| 813 | GCAGGGTGCTGGAGGAGGA | TCCTCCTCCAGCACCCTGC |
| 814 | CAGGGTGCTGGAGGAGGAA | TTCCTCCTCCAGCACCCTG |
| 815 | AGGGTGCTGGAGGAGGAAA | TTTCCTCCTCCAGCACCCT |
| 816 | GGGTGCTGGAGGAGGAAAC | GTTTCCTCCTCCAGCACCC |
| 817 | GGTGCTGGAGGAGGAAACC | GGTTTCCTCCTCCAGCACC |
| 818 | GTGCTGGAGGAGGAAACCG | CGGTTTCCTCCTCCAGCAC |
| 819 | TGCTGGAGGAGGAAACCGG | CCGGTTTCCTCCTCCAGCA |
| 820 | GCTGGAGGAGGAAACCGGC | GCCGGTTTCCTCCTCCAGC |
| 821 | CTGGAGGAGGAAACCGGCG | CGCCGGTTTCCTCCTCCAG |
| 822 | TGGAGGAGGAAACCGGCGG | CCGCCGGTTTCCTCCTCCA |
| 823 | GGAGGAGGAAACCGGCGGA | TCCGCCGGTTTCCTCCTCC |
| 824 | GAGGAGGAAACCGGCGGAG | CTCCGCCGGTTTCCTCCTC |
| 825 | AGGAGGAAACCGGCGGAGC | GCTCCGCCGGTTTCCTCCT |
| 826 | GGAGGAAACCGGCGGAGCA | TGCTCCGCCGGTTTCCTCC |
| 827 | GAGGAAACCGGCGGAGCAG | CTGCTCCGCCGGTTTCCTC |
| 828 | AGGAAACCGGCGGAGCAGC | GCTGCTCCGCCGGTTTCCT |
| 829 | GGAAACCGGCGGAGCAGCT | AGCTGCTCCGCCGGTTTCC |
| 830 | GAAACCGGCGGAGCAGCTT | AAGCTGCTCCGCCGGTTTC |
| 831 | AAACCGGCGGAGCAGCTTC | GAAGCTGCTCCGCCGGTTT |

TABLE 1-continued cDNA Human Hairless 19-mer Target Sequences and Complement Referenced to NM_005144-
*Homo sapiens* hairless homolog (mouse) (HR),
transcript variant 1, complete mRNA (1-5699 bp).
(SEQ ID NO: for Sense equals (2X – 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 832 | AACCGGCGGAGCAGCTTCC | GGAAGCTGCTCCGCCGGTT |
| 833 | ACCGGCGGAGCAGCTTCCC | GGGAAGCTGCTCCGCCGGT |
| 834 | CCGGCGGAGCAGCTTCCCC | GGGGAAGCTGCTCCGCCGG |
| 835 | CGGCGGAGCAGCTTCCCCA | TGGGGAAGCTGCTCCGCCG |
| 836 | GGCGGAGCAGCTTCCCCAC | GTGGGGAAGCTGCTCCGCC |
| 837 | GCGGAGCAGCTTCCCCACT | AGTGGGGAAGCTGCTCCGC |
| 838 | CGGAGCAGCTTCCCCACTC | GAGTGGGGAAGCTGCTCCG |
| 839 | GGAGCAGCTTCCCCACTCT | AGAGTGGGGAAGCTGCTCC |
| 840 | GAGCAGCTTCCCCACTCTC | GAGAGTGGGGAAGCTGCTC |
| 841 | AGCAGCTTCCCCACTCTCA | TGAGAGTGGGGAAGCTGCT |
| 842 | GCAGCTTCCCCACTCTCAG | CTGAGAGTGGGGAAGCTGC |
| 843 | CAGCTTCCCCACTCTCAGT | ACTGAGAGTGGGGAAGCTG |
| 844 | AGCTTCCCCACTCTCAGTT | AACTGAGAGTGGGGAAGCT |
| 845 | GCTTCCCCACTCTCAGTTG | CAACTGAGAGTGGGGAAGC |
| 846 | CTTCCCCACTCTCAGTTGC | GCAACTGAGAGTGGGGAAG |
| 847 | TTCCCCACTCTCAGTTGCG | CGCAACTGAGAGTGGGGAA |
| 848 | TCCCCACTCTCAGTTGCGC | GCGCAACTGAGAGTGGGGA |
| 849 | CCCCACTCTCAGTTGCGCT | AGCGCAACTGAGAGTGGGG |
| 850 | CCCACTCTCAGTTGCGCTT | AAGCGCAACTGAGAGTGGG |
| 851 | CCACTCTCAGTTGCGCTTC | GAAGCGCAACTGAGAGTGG |
| 852 | CACTCTCAGTTGCGCTTCT | AGAAGCGCAACTGAGAGTG |
| 853 | ACTCTCAGTTGCGCTTCTG | CAGAAGCGCAACTGAGAGT |
| 854 | CTCTCAGTTGCGCTTCTGG | CCAGAAGCGCAACTGAGAG |
| 855 | TCTCAGTTGCGCTTCTGGC | GCCAGAAGCGCAACTGAGA |
| 856 | CTCAGTTGCGCTTCTGGCG | CGCCAGAAGCGCAACTGAG |
| 857 | TCAGTTGCGCTTCTGGCGA | TCGCCAGAAGCGCAACTGA |
| 858 | CAGTTGCGCTTCTGGCGAT | ATCGCCAGAAGCGCAACTG |
| 859 | AGTTGCGCTTCTGGCGATG | CATCGCCAGAAGCGCAACT |
| 860 | GTTGCGCTTCTGGCGATGG | CCATCGCCAGAAGCGCAAC |
| 861 | TTGCGCTTCTGGCGATGGC | GCCATCGCCAGAAGCGCAA |
| 862 | TGCGCTTCTGGCGATGGCG | CGCCATCGCCAGAAGCGCA |
| 863 | GCGCTTCTGGCGATGGCGA | TCGCCATCGCCAGAAGCGC |
| 864 | CGCTTCTGGCGATGGCGAT | ATCGCCATCGCCAGAAGCG |
| 865 | GCTTCTGGCGATGGCGATC | GATCGCCATCGCCAGAAGC |
| 866 | CTTCTGGCGATGGCGATCA | TGATCGCCATCGCCAGAAG |
| 867 | TTCTGGCGATGGCGATCAG | CTGATCGCCATCGCCAGAA |
| 868 | TCTGGCGATGGCGATCAGA | TCTGATCGCCATCGCCAGA |
| 869 | CTGGCGATGGCGATCAGAG | CTCTGATCGCCATCGCCAG |
| 870 | TGGCGATGGCGATCAGAGG | CCTCTGATCGCCATCGCCA |
| 871 | GGCGATGGCGATCAGAGGT | ACCTCTGATCGCCATCGCC |
| 872 | GCGATGGCGATCAGAGGTC | GACCTCTGATCGCCATCGC |
| 873 | CGATGGCGATCAGAGGTCC | GGACCTCTGATCGCCATCG |
| 874 | GATGGCGATCAGAGGTCCT | AGGACCTCTGATCGCCATC |
| 875 | ATGGCGATCAGAGGTCCTG | CAGGACCTCTGATCGCCAT |
| 876 | TGGCGATCAGAGGTCCTGC | GCAGGACCTCTGATCGCCA |
| 877 | GGCGATCAGAGGTCCTGCT | AGCAGGACCTCTGATCGCC |
| 878 | GCGATCAGAGGTCCTGCTG | CAGCAGGACCTCTGATCGC |
| 879 | CGATCAGAGGTCCTGCTGC | GCAGCAGGACCTCTGATCG |
| 880 | GATCAGAGGTCCTGCTGCG | CGCAGCAGGACCTCTGATC |
| 881 | ATCAGAGGTCCTGCTGCGC | GCGCAGCAGGACCTCTGAT |
| 882 | TCAGAGGTCCTGCTGCGCT | AGCGCAGCAGGACCTCTGA |
| 883 | CAGAGGTCCTGCTGCGCTC | GAGCGCAGCAGGACCTCTG |
| 884 | AGAGGTCCTGCTGCGCTCT | AGAGCGCAGCAGGACCTCT |
| 885 | GAGGTCCTGCTGCGCTCTC | GAGAGCGCAGCAGGACCTC |
| 886 | AGGTCCTGCTGCGCTCTCC | GGAGAGCGCAGCAGGACCT |
| 887 | GGTCCTGCTGCGCTCTCCG | CGGAGAGCGCAGCAGGACC |
| 888 | GTCCTGCTGCGCTCTCCGC | GCGGAGAGCGCAGCAGGAC |
| 889 | TCCTGCTGCGCTCTCCGCC | GGCGGAGAGCGCAGCAGGA |
| 890 | CCTGCTGCGCTCTCCGCCG | CGGCGGAGAGCGCAGCAGG |
| 891 | CTGCTGCGCTCTCCGCCGC | GCGGCGGAGAGCGCAGCAG |
| 892 | TGCTGCGCTCTCCGCCGCG | CGCGGCGGAGAGCGCAGCA |
| 893 | GCTGCGCTCTCCGCCGCGC | GCGCGGCGGAGAGCGCAGC |
| 894 | CTGCGCTCTCCGCCGCGCT | AGCGCGGCGGAGAGCGCAG |
| 895 | TGCGCTCTCCGCCGCGCTC | GAGCGCGGCGGAGAGCGCA |
| 896 | GCGCTCTCCGCCGCGCTCT | AGAGCGCGGCGGAGAGCGC |
| 897 | CGCTCTCCGCCGCGCTCTA | TAGAGCGCGGCGGAGAGCG |
| 898 | GCTCTCCGCCGCGCTCTAC | GTAGAGCGCGGCGGAGAGC |
| 899 | CTCTCCGCCGCGCTCTACC | GGTAGAGCGCGGCGGAGAG |
| 900 | TCTCCGCCGCGCTCTACCT | AGGTAGAGCGCGGCGGAGA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 901 | CTCCGCCGCGCTCTACCTC | GAGGTAGAGCGCGGCGGAG |
| 902 | TCCGCCGCGCTCTACCTCC | GGAGGTAGAGCGCGGCGGA |
| 903 | CCGCCGCGCTCTACCTCCA | TGGAGGTAGAGCGCGGCGG |
| 904 | CGCCGCGCTCTACCTCCAT | ATGGAGGTAGAGCGCGGCG |
| 905 | GCCGCGCTCTACCTCCATT | AATGGAGGTAGAGCGCGGC |
| 906 | CCGCGCTCTACCTCCATTA | TAATGGAGGTAGAGCGCGG |
| 907 | CGCGCTCTACCTCCATTAG | CTAATGGAGGTAGAGCGCG |
| 908 | GCGCTCTACCTCCATTAGC | GCTAATGGAGGTAGAGCGC |
| 909 | CGCTCTACCTCCATTAGCC | GGCTAATGGAGGTAGAGCG |
| 910 | GCTCTACCTCCATTAGCCG | CGGCTAATGGAGGTAGAGC |
| 911 | CTCTACCTCCATTAGCCGC | GCGGCTAATGGAGGTAGAG |
| 912 | TCTACCTCCATTAGCCGCG | CGCGGCTAATGGAGGTAGA |
| 913 | CTACCTCCATTAGCCGCGC | GCGCGGCTAATGGAGGTAG |
| 914 | TACCTCCATTAGCCGCGCT | AGCGCGGCTAATGGAGGTA |
| 915 | ACCTCCATTAGCCGCGCTG | CAGCGCGGCTAATGGAGGT |
| 916 | CCTCCATTAGCCGCGCTGC | GCAGCGCGGCTAATGGAGG |
| 917 | CTCCATTAGCCGCGCTGCG | CGCAGCGCGGCTAATGGAG |
| 918 | TCCATTAGCCGCGCTGCGC | GCGCAGCGCGGCTAATGGA |
| 919 | CCATTAGCCGCGCTGCGCG | CGCGCAGCGCGGCTAATGG |
| 920 | CATTAGCCGCGCTGCGCGG | CCGCGCAGCGCGGCTAATG |
| 921 | ATTAGCCGCGCTGCGCGGT | ACCGCGCAGCGCGGCTAAT |
| 922 | TTAGCCGCGCTGCGCGGTG | CACCGCGCAGCGCGGCTAA |
| 923 | TAGCCGCGCTGCGCGGTGC | GCACCGCGCAGCGCGGCTA |
| 924 | AGCCGCGCTGCGCGGTGCT | AGCACCGCGCAGCGCGGCT |
| 925 | GCCGCGCTGCGCGGTGCTG | CAGCACCGCGCAGCGCGGC |
| 926 | CCGCGCTGCGCGGTGCTGC | GCAGCACCGCGCAGCGCGG |
| 927 | CGCGCTGCGCGGTGCTGCG | CGCAGCACCGCGCAGCGCG |
| 928 | GCGCTGCGCGGTGCTGCGC | GCGCAGCACCGCGCAGCGC |
| 929 | CGCTGCGCGGTGCTGCGCC | GGCGCAGCACCGCGCAGCG |
| 930 | GCTGCGCGGTGCTGCGCCC | GGGCGCAGCACCGCGCAGC |
| 931 | CTGCGCGGTGCTGCGCCCT | AGGGCGCAGCACCGCGCAG |
| 932 | TGCGCGGTGCTGCGCCCTC | GAGGGCGCAGCACCGCGCA |
| 933 | GCGCGGTGCTGCGCCCTCG | CGAGGGCGCAGCACCGCGC |
| 934 | CGCGGTGCTGCGCCCTCGC | GCGAGGGCGCAGCACCGCG |
| 935 | GCGGTGCTGCGCCCTCGCC | GGCGAGGGCGCAGCACCGC |
| 936 | CGGTGCTGCGCCCTCGCCG | CGGCGAGGGCGCAGCACCG |
| 937 | GGTGCTGCGCCCTCGCCGG | CCGGCGAGGGCGCAGCACC |
| 938 | GTGCTGCGCCCTCGCCGGT | ACCGGCGAGGGCGCAGCAC |
| 939 | TGCTGCGCCCTCGCCGGTG | CACCGGCGAGGGCGCAGCA |
| 940 | GCTGCGCCCTCGCCGGTGC | GCACCGGCGAGGGCGCAGC |
| 941 | CTGCGCCCTCGCCGGTGCC | GGCACCGGCGAGGGCGCAG |
| 942 | TGCGCCCTCGCCGGTGCCT | AGGCACCGGCGAGGGCGCA |
| 943 | GCGCCCTCGCCGGTGCCTC | GAGGCACCGGCGAGGGCGC |
| 944 | CGCCCTCGCCGGTGCCTCT | AGAGGCACCGGCGAGGGCG |
| 945 | GCCCTCGCCGGTGCCTCTC | GAGAGGCACCGGCGAGGGC |
| 946 | CCCTCGCCGGTGCCTCTCT | AGAGAGGCACCGGCGAGGG |
| 947 | CCTCGCCGGTGCCTCTCTC | GAGAGAGGCACCGGCGAGG |
| 948 | CTCGCCGGTGCCTCTCTCC | GGAGAGAGGCACCGGCGAG |
| 949 | TCGCCGGTGCCTCTCTCCT | AGGAGAGAGGCACCGGCGA |
| 950 | CGCCGGTGCCTCTCTCCTG | CAGGAGAGAGGCACCGGCG |
| 951 | GCCGGTGCCTCTCTCCTGG | CCAGGAGAGAGGCACCGGC |
| 952 | CCGGTGCCTCTCTCCTGGG | CCCAGGAGAGAGGCACCGG |
| 953 | CGGTGCCTCTCTCCTGGGT | ACCCAGGAGAGAGGCACCG |
| 954 | GGTGCCTCTCTCCTGGGTC | GACCCAGGAGAGAGGCACC |
| 955 | GTGCCTCTCTCCTGGGTCC | GGACCCAGGAGAGAGGCAC |
| 956 | TGCCTCTCTCCTGGGTCCC | GGGACCCAGGAGAGAGGCA |
| 957 | GCCTCTCTCCTGGGTCCCA | TGGGACCCAGGAGAGAGGC |
| 958 | CCTCTCTCCTGGGTCCCAG | CTGGGACCCAGGAGAGAGG |
| 959 | CTCTCTCCTGGGTCCCAGG | CCTGGGACCCAGGAGAGAG |
| 960 | TCTCTCCTGGGTCCCAGGA | TCCTGGGACCCAGGAGAGA |
| 961 | CTCTCCTGGGTCCCAGGAT | ATCCTGGGACCCAGGAGAG |
| 962 | TCTCCTGGGTCCCAGGATC | GATCCTGGGACCCAGGAGA |
| 963 | CTCCTGGGTCCCAGGATCG | CGATCCTGGGACCCAGGAG |
| 964 | TCCTGGGTCCCAGGATCGG | CCGATCCTGGGACCCAGGA |
| 965 | CCTGGGTCCCAGGATCGGC | GCCGATCCTGGGACCCAGG |
| 966 | CTGGGTCCCAGGATCGGCC | GGCCGATCCTGGGACCCAG |
| 967 | TGGGTCCCAGGATCGGCCC | GGGCCGATCCTGGGACCCA |
| 968 | GGGTCCCAGGATCGGCCCC | GGGGCCGATCCTGGGACCC |
| 969 | GGTCCCAGGATCGGCCCCC | GGGGGCCGATCCTGGGACC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X – 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 970 | GTCCCAGGATCGGCCCCCA | TGGGGGCCGATCCTGGGAC |
| 971 | TCCCAGGATCGGCCCCCAC | GTGGGGGCCGATCCTGGGA |
| 972 | CCCAGGATCGGCCCCCACC | GGTGGGGGCCGATCCTGGG |
| 973 | CCAGGATCGGCCCCCACCA | TGGTGGGGGCCGATCCTGG |
| 974 | CAGGATCGGCCCCCACCAT | ATGGTGGGGGCCGATCCTG |
| 975 | AGGATCGGCCCCCACCATC | GATGGTGGGGGCCGATCCT |
| 976 | GGATCGGCCCCCACCATCC | GGATGGTGGGGGCCGATCC |
| 977 | GATCGGCCCCCACCATCCA | TGGATGGTGGGGGCCGATC |
| 978 | ATCGGCCCCCACCATCCAG | CTGGATGGTGGGGGCCGAT |
| 979 | TCGGCCCCCACCATCCAGG | CCTGGATGGTGGGGGCCGA |
| 980 | CGGCCCCCACCATCCAGGC | GCCTGGATGGTGGGGGCCG |
| 981 | GGCCCCCACCATCCAGGCA | TGCCTGGATGGTGGGGGCC |
| 982 | GCCCCCACCATCCAGGCAC | GTGCCTGGATGGTGGGGGC |
| 983 | CCCCCACCATCCAGGCACG | CGTGCCTGGATGGTGGGGG |
| 984 | CCCCACCATCCAGGCACGA | TCGTGCCTGGATGGTGGGG |
| 985 | CCCACCATCCAGGCACGAC | GTCGTGCCTGGATGGTGGG |
| 986 | CCACCATCCAGGCACGACC | GGTCGTGCCTGGATGGTGG |
| 987 | CACCATCCAGGCACGACCC | GGGTCGTGCCTGGATGGTG |
| 988 | ACCATCCAGGCACGACCCC | GGGGTCGTGCCTGGATGGT |
| 989 | CCATCCAGGCACGACCCCC | GGGGGTCGTGCCTGGATGG |
| 990 | CATCCAGGCACGACCCCCT | AGGGGGTCGTGCCTGGATG |
| 991 | ATCCAGGCACGACCCCCTT | AAGGGGGTCGTGCCTGGAT |
| 992 | TCCAGGCACGACCCCCTTC | GAAGGGGGTCGTGCCTGGA |
| 993 | CCAGGCACGACCCCCTTCC | GGAAGGGGGTCGTGCCTGG |
| 994 | CAGGCACGACCCCCTTCCC | GGGAAGGGGGTCGTGCCTG |
| 995 | AGGCACGACCCCCTTCCCC | GGGGAAGGGGGTCGTGCCT |
| 996 | GGCACGACCCCCTTCCCCG | CGGGGAAGGGGGTCGTGCC |
| 997 | GCACGACCCCCTTCCCCGG | CCGGGGAAGGGGGTCGTGC |
| 998 | CACGACCCCCTTCCCCGGC | GCCGGGGAAGGGGGTCGTG |
| 999 | ACGACCCCCTTCCCCGGCC | GGCCGGGGAAGGGGGTCGT |
| 1000 | CGACCCCCTTCCCCGGCCC | GGGCCGGGGAAGGGGGTCG |
| 1001 | GACCCCCTTCCCCGGCCCC | GGGGCCGGGGAAGGGGGTC |
| 1002 | ACCCCCTTCCCCGGCCCCT | AGGGGCCGGGGAAGGGGGT |
| 1003 | CCCCCTTCCCCGGCCCCTC | GAGGGGCCGGGGAAGGGGG |
| 1004 | CCCCTTCCCCGGCCCCTCG | CGAGGGGCCGGGGAAGGGG |
| 1005 | CCCTTCCCCGGCCCCTCGG | CCGAGGGGCCGGGGAAGGG |
| 1006 | CCTTCCCCGGCCCCTCGGC | GCCGAGGGGCCGGGGAAGG |
| 1007 | CTTCCCCGGCCCCTCGGCC | GGCCGAGGGGCCGGGGAAG |
| 1008 | TTCCCCGGCCCCTCGGCCT | AGGCCGAGGGGCCGGGGAA |
| 1009 | TCCCCGGCCCCTCGGCCTT | AAGGCCGAGGGGCCGGGGA |
| 1010 | CCCCGGCCCCTCGGCCTTT | AAAGGCCGAGGGGCCGGGG |
| 1011 | CCCGGCCCCTCGGCCTTTC | GAAAGGCCGAGGGGCCGGG |
| 1012 | CCGGCCCCTCGGCCTTTCC | GGAAAGGCCGAGGGGCCGG |
| 1013 | CGGCCCCTCGGCCTTTCCC | GGGAAAGGCCGAGGGGCCG |
| 1014 | GGCCCCTCGGCCTTTCCCC | GGGGAAAGGCCGAGGGGCC |
| 1015 | GCCCCTCGGCCTTTCCCCC | GGGGGAAAGGCCGAGGGGC |
| 1016 | CCCCTCGGCCTTTCCCCCA | TGGGGGAAAGGCCGAGGGG |
| 1017 | CCCTCGGCCTTTCCCCCAA | TTGGGGGAAAGGCCGAGGG |
| 1018 | CCTCGGCCTTTCCCCCAAC | GTTGGGGGAAAGGCCGAGG |
| 1019 | CTCGGCCTTTCCCCCAACT | AGTTGGGGGAAAGGCCGAG |
| 1020 | TCGGCCTTTCCCCCAACTC | GAGTTGGGGGAAAGGCCGA |
| 1021 | CGGCCTTTCCCCCAACTCG | CGAGTTGGGGGAAAGGCCG |
| 1022 | GGCCTTTCCCCCAACTCGG | CCGAGTTGGGGGAAAGGCC |
| 1023 | GCCTTTCCCCCAACTCGGC | GCCGAGTTGGGGGAAAGGC |
| 1024 | CCTTTCCCCCAACTCGGCC | GGCCGAGTTGGGGGAAAGG |
| 1025 | CTTTCCCCCAACTCGGCCA | TGGCCGAGTTGGGGGAAAG |
| 1026 | TTTCCCCCAACTCGGCCAT | ATGGCCGAGTTGGGGGAAA |
| 1027 | TTCCCCCAACTCGGCCATC | GATGGCCGAGTTGGGGGAA |
| 1028 | TCCCCCAACTCGGCCATCT | AGATGGCCGAGTTGGGGGA |
| 1029 | CCCCCAACTCGGCCATCTC | GAGATGGCCGAGTTGGGGG |
| 1030 | CCCCAACTCGGCCATCTCC | GGAGATGGCCGAGTTGGGG |
| 1031 | CCCAACTCGGCCATCTCCG | CGGAGATGGCCGAGTTGGG |
| 1032 | CCAACTCGGCCATCTCCGA | TCGGAGATGGCCGAGTTGG |
| 1033 | CAACTCGGCCATCTCCGAC | GTCGGAGATGGCCGAGTTG |
| 1034 | AACTCGGCCATCTCCGACC | GGTCGGAGATGGCCGAGTT |
| 1035 | ACTCGGCCATCTCCGACCC | GGGTCGGAGATGGCCGAGT |
| 1036 | CTCGGCCATCTCCGACCCG | CGGGTCGGAGATGGCCGAG |
| 1037 | TCGGCCATCTCCGACCCGG | CCGGGTCGGAGATGGCCGA |
| 1038 | CGGCCATCTCCGACCCGGG | CCCGGGTCGGAGATGGCCG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 1039 | GGCCATCTCCGACCCGGGG | CCCCGGGTCGGAGATGGCC |
| 1040 | GCCATCTCCGACCCGGGGC | GCCCCGGGTCGGAGATGGC |
| 1041 | CCATCTCCGACCCGGGGCG | CGCCCCGGGTCGGAGATGG |
| 1042 | CATCTCCGACCCGGGGCGC | GCGCCCCGGGTCGGAGATG |
| 1043 | ATCTCCGACCCGGGGCGCG | CGCGCCCCGGGTCGGAGAT |
| 1044 | TCTCCGACCCGGGGCGCGT | ACGCGCCCCGGGTCGGAGA |
| 1045 | CTCCGACCCGGGGCGCGTG | CACGCGCCCCGGGTCGGAG |
| 1046 | TCCGACCCGGGGCGCGTGT | ACACGCGCCCCGGGTCGGA |
| 1047 | CCGACCCGGGGCGCGTGTT | AACACGCGCCCCGGGTCGG |
| 1048 | CGACCCGGGGCGCGTGTTC | GAACACGCGCCCCGGGTCG |
| 1049 | GACCCGGGGCGCGTGTTCC | GGAACACGCGCCCCGGGTC |
| 1050 | ACCCGGGGCGCGTGTTCCC | GGGAACACGCGCCCCGGGT |
| 1051 | CCCGGGGCGCGTGTTCCCC | GGGGAACACGCGCCCCGGG |
| 1052 | CCGGGGCGCGTGTTCCCCC | GGGGGAACACGCGCCCCGG |
| 1053 | CGGGGCGCGTGTTCCCCCC | GGGGGGAACACGCGCCCCG |
| 1054 | GGGGCGCGTGTTCCCCCCG | CGGGGGGAACACGCGCCCC |
| 1055 | GGGCGCGTGTTCCCCCCGG | CCGGGGGGAACACGCGCCC |
| 1056 | GGCGCGTGTTCCCCCCGGC | GCCGGGGGGAACACGCGCC |
| 1057 | GCGCGTGTTCCCCCCGGCC | GGCCGGGGGGAACACGCGC |
| 1058 | CGCGTGTTCCCCCCGGCCC | GGGCCGGGGGGAACACGCG |
| 1059 | GCGTGTTCCCCCCGGCCCG | CGGGCCGGGGGGAACACGC |
| 1060 | CGTGTTCCCCCCGGCCCGG | CCGGGCCGGGGGGAACACG |
| 1061 | GTGTTCCCCCCGGCCCGGC | GCCGGGCCGGGGGGAACAC |
| 1062 | TGTTCCCCCCGGCCCGGCG | CGCCGGGCCGGGGGGAACA |
| 1063 | GTTCCCCCCGGCCCGGCGC | GCGCCGGGCCGGGGGGAAC |
| 1064 | TTCCCCCCGGCCCGGCGCC | GGCGCCGGGCCGGGGGGAA |
| 1065 | TCCCCCCGGCCCGGCGCCT | AGGCGCCGGGCCGGGGGGA |
| 1066 | CCCCCCGGCCCGGCGCCTT | AAGGCGCCGGGCCGGGGGG |
| 1067 | CCCCCGGCCCGGCGCCTTC | GAAGGCGCCGGGCCGGGGG |
| 1068 | CCCCGGCCCGGCGCCTTCT | AGAAGGCGCCGGGCCGGGG |
| 1069 | CCCGGCCCGGCGCCTTCTC | GAGAAGGCGCCGGGCCGGG |
| 1070 | CCGGCCCGGCGCCTTCTCT | AGAGAAGGCGCCGGGCCGG |
| 1071 | CGGCCCGGCGCCTTCTCTC | GAGAGAAGGCGCCGGGCCG |
| 1072 | GGCCCGGCGCCTTCTCTCC | GGAGAGAAGGCGCCGGGCC |
| 1073 | GCCCGGCGCCTTCTCTCCC | GGGAGAGAAGGCGCCGGGC |
| 1074 | CCCGGCGCCTTCTCTCCCT | AGGGAGAGAAGGCGCCGGG |
| 1075 | CCGGCGCCTTCTCTCCCTC | GAGGGAGAGAAGGCGCCGG |
| 1076 | CGGCGCCTTCTCTCCCTCC | GGAGGGAGAGAAGGCGCCG |
| 1077 | GGCGCCTTCTCTCCCTCCG | CGGAGGGAGAGAAGGCGCC |
| 1078 | GCGCCTTCTCTCCCTCCGG | CCGGAGGGAGAGAAGGCGC |
| 1079 | CGCCTTCTCTCCCTCCGGG | CCCGGAGGGAGAGAAGGCG |
| 1080 | GCCTTCTCTCCCTCCGGGG | CCCCGGAGGGAGAGAAGGC |
| 1081 | CCTTCTCTCCCTCCGGGGG | CCCCCGGAGGGAGAGAAGG |
| 1082 | CTTCTCTCCCTCCGGGGGC | GCCCCCGGAGGGAGAGAAG |
| 1083 | TTCTCTCCCTCCGGGGGCA | TGCCCCCGGAGGGAGAGAA |
| 1084 | TCTCTCCCTCCGGGGGCAC | GTGCCCCCGGAGGGAGAGA |
| 1085 | CTCTCCCTCCGGGGGCACC | GGTGCCCCCGGAGGGAGAG |
| 1086 | TCTCCCTCCGGGGGCACCC | GGGTGCCCCCGGAGGGAGA |
| 1087 | CTCCCTCCGGGGGCACCCG | CGGGTGCCCCCGGAGGGAG |
| 1088 | TCCCTCCGGGGGCACCCGC | GCGGGTGCCCCCGGAGGGA |
| 1089 | CCCTCCGGGGGCACCCGCT | AGCGGGTGCCCCCGGAGGG |
| 1090 | CCTCCGGGGGCACCCGCTC | GAGCGGGTGCCCCCGGAGG |
| 1091 | CTCCGGGGGCACCCGCTCC | GGAGCGGGTGCCCCCGGAG |
| 1092 | TCCGGGGGCACCCGCTCCC | GGGAGCGGGTGCCCCCGGA |
| 1093 | CCGGGGGCACCCGCTCCCT | AGGGAGCGGGTGCCCCCGG |
| 1094 | CGGGGGCACCCGCTCCCTA | TAGGGAGCGGGTGCCCCCG |
| 1095 | GGGGGCACCCGCTCCCTAG | CTAGGGAGCGGGTGCCCCC |
| 1096 | GGGGCACCCGCTCCCTAGC | GCTAGGGAGCGGGTGCCCC |
| 1097 | GGGCACCCGCTCCCTAGCC | GGCTAGGGAGCGGGTGCCC |
| 1098 | GGCACCCGCTCCCTAGCCC | GGGCTAGGGAGCGGGTGCC |
| 1099 | GCACCCGCTCCCTAGCCCC | GGGGCTAGGGAGCGGGTGC |
| 1100 | CACCCGCTCCCTAGCCCCG | CGGGGCTAGGGAGCGGGTG |
| 1101 | ACCCGCTCCCTAGCCCCGG | CCGGGGCTAGGGAGCGGGT |
| 1102 | CCCGCTCCCTAGCCCCGGC | GCCGGGGCTAGGGAGCGGG |
| 1103 | CCGCTCCCTAGCCCCGGCC | GGCCGGGGCTAGGGAGCGG |
| 1104 | CGCTCCCTAGCCCCGGCCC | GGGCCGGGGCTAGGGAGCG |
| 1105 | GCTCCCTAGCCCCGGCCCG | CGGGCCGGGGCTAGGGAGC |
| 1106 | CTCCCTAGCCCCGGCCCGG | CCGGGCCGGGGCTAGGGAG |
| 1107 | TCCCTAGCCCCGGCCCGGC | GCCGGGCCGGGGCTAGGGA |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X – 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1108 | CCCTAGCCCCGGCCCGGCC | GGCCGGGCCGGGGCTAGGG |
| 1109 | CCTAGCCCCGGCCCGGCCC | GGGCCGGGCCGGGGCTAGG |
| 1110 | CTAGCCCCGGCCCGGCCCT | AGGGCCGGGCCGGGGCTAG |
| 1111 | TAGCCCCGGCCCGGCCCTC | GAGGGCCGGGCCGGGGCTA |
| 1112 | AGCCCCGGCCCGGCCCTCC | GGAGGGCCGGGCCGGGGCT |
| 1113 | GCCCCGGCCCGGCCCTCCC | GGGAGGGCCGGGCCGGGGC |
| 1114 | CCCCGGCCCGGCCCTCCCC | GGGGAGGGCCGGGCCGGGG |
| 1115 | CCCGGCCCGGCCCTCCCCG | CGGGGAGGGCCGGGCCGGG |
| 1116 | CCGGCCCGGCCCTCCCCGC | GCGGGGAGGGCCGGGCCGG |
| 1117 | CGGCCCGGCCCTCCCCGCG | CGCGGGGAGGGCCGGGCCG |
| 1118 | GGCCCGGCCCTCCCCGCGG | CCGCGGGGAGGGCCGGGCC |
| 1119 | GCCCGGCCCTCCCCGCGGC | GCCGCGGGGAGGGCCGGGC |
| 1120 | CCCGGCCCTCCCCGCGGCG | CGCCGCGGGGAGGGCCGGG |
| 1121 | CCGGCCCTCCCCGCGGCGC | GCGCCGCGGGGAGGGCCGG |
| 1122 | CGGCCCTCCCCGCGGCGCA | TGCGCCGCGGGGAGGGCCG |
| 1123 | GGCCCTCCCCGCGGCGCAG | CTGCGCCGCGGGGAGGGCC |
| 1124 | GCCCTCCCCGCGGCGCAGC | GCTGCGCCGCGGGGAGGGC |
| 1125 | CCCTCCCCGCGGCGCAGCA | TGCTGCGCCGCGGGGAGGG |
| 1126 | CCTCCCCGCGGCGCAGCAC | GTGCTGCGCCGCGGGGAGG |
| 1127 | CTCCCCGCGGCGCAGCACG | CGTGCTGCGCCGCGGGGAG |
| 1128 | TCCCCGCGGCGCAGCACGG | CCGTGCTGCGCCGCGGGGA |
| 1129 | CCCCGCGGCGCAGCACGGA | TCCGTGCTGCGCCGCGGGG |
| 1130 | CCCGCGGCGCAGCACGGAG | CTCCGTGCTGCGCCGCGGG |
| 1131 | CCGCGGCGCAGCACGGAGT | ACTCCGTGCTGCGCCGCGG |
| 1132 | CGCGGCGCAGCACGGAGTC | GACTCCGTGCTGCGCCGCG |
| 1133 | GCGGCGCAGCACGGAGTCT | AGACTCCGTGCTGCGCCGC |
| 1134 | CGGCGCAGCACGGAGTCTC | GAGACTCCGTGCTGCGCCG |
| 1135 | GGCGCAGCACGGAGTCTCG | CGAGACTCCGTGCTGCGCC |
| 1136 | GCGCAGCACGGAGTCTCGG | CCGAGACTCCGTGCTGCGC |
| 1137 | CGCAGCACGGAGTCTCGGC | GCCGAGACTCCGTGCTGCG |
| 1138 | GCAGCACGGAGTCTCGGCG | CGCCGAGACTCCGTGCTGC |
| 1139 | CAGCACGGAGTCTCGGCGT | ACGCCGAGACTCCGTGCTG |
| 1140 | AGCACGGAGTCTCGGCGTC | GACGCCGAGACTCCGTGCT |
| 1141 | GCACGGAGTCTCGGCGTCC | GGACGCCGAGACTCCGTGC |
| 1142 | CACGGAGTCTCGGCGTCCC | GGGACGCCGAGACTCCGTG |
| 1143 | ACGGAGTCTCGGCGTCCCA | TGGGACGCCGAGACTCCGT |
| 1144 | CGGAGTCTCGGCGTCCCAT | ATGGGACGCCGAGACTCCG |
| 1145 | GGAGTCTCGGCGTCCCATG | CATGGGACGCCGAGACTCC |
| 1146 | GAGTCTCGGCGTCCCATGG | CCATGGGACGCCGAGACTC |
| 1147 | AGTCTCGGCGTCCCATGGC | GCCATGGGACGCCGAGACT |
| 1148 | GTCTCGGCGTCCCATGGCG | CGCCATGGGACGCCGAGAC |
| 1149 | TCTCGGCGTCCCATGGCGC | GCGCCATGGGACGCCGAGA |
| 1150 | CTCGGCGTCCCATGGCGCA | TGCGCCATGGGACGCCGAG |
| 1151 | TCGGCGTCCCATGGCGCAA | TTGCGCCATGGGACGCCGA |
| 1152 | CGGCGTCCCATGGCGCAAC | GTTGCGCCATGGGACGCCG |
| 1153 | GGCGTCCCATGGCGCAACC | GGTTGCGCCATGGGACGCC |
| 1154 | GCGTCCCATGGCGCAACCT | AGGTTGCGCCATGGGACGC |
| 1155 | CGTCCCATGGCGCAACCTA | TAGGTTGCGCCATGGGACG |
| 1156 | GTCCCATGGCGCAACCTAC | GTAGGTTGCGCCATGGGAC |
| 1157 | TCCCATGGCGCAACCTACG | CGTAGGTTGCGCCATGGGA |
| 1158 | CCCATGGCGCAACCTACGG | CCGTAGGTTGCGCCATGGG |
| 1159 | CCATGGCGCAACCTACGGC | GCCGTAGGTTGCGCCATGG |
| 1160 | CATGGCGCAACCTACGGCC | GGCCGTAGGTTGCGCCATG |
| 1161 | ATGGCGCAACCTACGGCCT | AGGCCGTAGGTTGCGCCAT |
| 1162 | TGGCGCAACCTACGGCCTC | GAGGCCGTAGGTTGCGCCA |
| 1163 | GGCGCAACCTACGGCCTCG | CGAGGCCGTAGGTTGCGCC |
| 1164 | GCGCAACCTACGGCCTCGG | CCGAGGCCGTAGGTTGCGC |
| 1165 | CGCAACCTACGGCCTCGGC | GCCGAGGCCGTAGGTTGCG |
| 1166 | GCAACCTACGGCCTCGGCC | GGCCGAGGCCGTAGGTTGC |
| 1167 | CAACCTACGGCCTCGGCCC | GGGCCGAGGCCGTAGGTTG |
| 1168 | AACCTACGGCCTCGGCCCA | TGGGCCGAGGCCGTAGGTT |
| 1169 | ACCTACGGCCTCGGCCCAG | CTGGGCCGAGGCCGTAGGT |
| 1170 | CCTACGGCCTCGGCCCAGA | TCTGGGCCGAGGCCGTAGG |
| 1171 | CTACGGCCTCGGCCCAGAA | TTCTGGGCCGAGGCCGTAG |
| 1172 | TACGGCCTCGGCCCAGAAG | CTTCTGGGCCGAGGCCGTA |
| 1173 | ACGGCCTCGGCCCAGAAGC | GCTTCTGGGCCGAGGCCGT |
| 1174 | CGGCCTCGGCCCAGAAGCT | AGCTTCTGGGCCGAGGCCG |
| 1175 | GGCCTCGGCCCAGAAGCTG | CAGCTTCTGGGCCGAGGCC |
| 1176 | GCCTCGGCCCAGAAGCTGG | CCAGCTTCTGGGCCGAGGC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X - 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1177 | CCTCGGCCCAGAAGCTGGT | ACCAGCTTCTGGGCCGAGG |
| 1178 | CTCGGCCCAGAAGCTGGTG | CACCAGCTTCTGGGCCGAG |
| 1179 | TCGGCCCAGAAGCTGGTGC | GCACCAGCTTCTGGGCCGA |
| 1180 | CGGCCCAGAAGCTGGTGCG | CGCACCAGCTTCTGGGCCG |
| 1181 | GGCCCAGAAGCTGGTGCGG | CCGCACCAGCTTCTGGGCC |
| 1182 | GCCCAGAAGCTGGTGCGGC | GCCGCACCAGCTTCTGGGC |
| 1183 | CCCAGAAGCTGGTGCGGCC | GGCCGCACCAGCTTCTGGG |
| 1184 | CCAGAAGCTGGTGCGGCCG | CGGCCGCACCAGCTTCTGG |
| 1185 | CAGAAGCTGGTGCGGCCGA | TCGGCCGCACCAGCTTCTG |
| 1186 | AGAAGCTGGTGCGGCCGAT | ATCGGCCGCACCAGCTTCT |
| 1187 | GAAGCTGGTGCGGCCGATC | GATCGGCCGCACCAGCTTC |
| 1188 | AAGCTGGTGCGGCCGATCC | GGATCGGCCGCACCAGCTT |
| 1189 | AGCTGGTGCGGCCGATCCG | CGGATCGGCCGCACCAGCT |
| 1190 | GCTGGTGCGGCCGATCCGC | GCGGATCGGCCGCACCAGC |
| 1191 | CTGGTGCGGCCGATCCGCG | CGCGGATCGGCCGCACCAG |
| 1192 | TGGTGCGGCCGATCCGCGC | GCGCGGATCGGCCGCACCA |
| 1193 | GGTGCGGCCGATCCGCGCC | GGCGCGGATCGGCCGCACC |
| 1194 | GTGCGGCCGATCCGCGCCG | CGGCGCGGATCGGCCGCAC |
| 1195 | TGCGGCCGATCCGCGCCGT | ACGGCGCGGATCGGCCGCA |
| 1196 | GCGGCCGATCCGCGCCGTG | CACGGCGCGGATCGGCCGC |
| 1197 | CGGCCGATCCGCGCCGTGT | ACACGGCGCGGATCGGCCG |
| 1198 | GGCCGATCCGCGCCGTGTG | CACACGGCGCGGATCGGCC |
| 1199 | GCCGATCCGCGCCGTGTGC | GCACACGGCGCGGATCGGC |
| 1200 | CCGATCCGCGCCGTGTGCC | GGCACACGGCGCGGATCGG |
| 1201 | CGATCCGCGCCGTGTGCCG | CGGCACACGGCGCGGATCG |
| 1202 | GATCCGCGCCGTGTGCCGC | GCGGCACACGGCGCGGATC |
| 1203 | ATCCGCGCCGTGTGCCGCA | TGCGGCACACGGCGCGGAT |
| 1204 | TCCGCGCCGTGTGCCGCAT | ATGCGGCACACGGCGCGGA |
| 1205 | CCGCGCCGTGTGCCGCATC | GATGCGGCACACGGCGCGG |
| 1206 | CGCGCCGTGTGCCGCATCC | GGATGCGGCACACGGCGCG |
| 1207 | GCGCCGTGTGCCGCATCCT | AGGATGCGGCACACGGCGC |
| 1208 | CGCCGTGTGCCGCATCCTG | CAGGATGCGGCACACGGCG |
| 1209 | GCCGTGTGCCGCATCCTGC | GCAGGATGCGGCACACGGC |
| 1210 | CCGTGTGCCGCATCCTGCA | TGCAGGATGCGGCACACGG |
| 1211 | CGTGTGCCGCATCCTGCAG | CTGCAGGATGCGGCACACG |
| 1212 | GTGTGCCGCATCCTGCAGA | TCTGCAGGATGCGGCACAC |
| 1213 | TGTGCCGCATCCTGCAGAT | ATCTGCAGGATGCGGCACA |
| 1214 | GTGCCGCATCCTGCAGATC | GATCTGCAGGATGCGGCAC |
| 1215 | TGCCGCATCCTGCAGATCC | GGATCTGCAGGATGCGGCA |
| 1216 | GCCGCATCCTGCAGATCCC | GGGATCTGCAGGATGCGGC |
| 1217 | CCGCATCCTGCAGATCCCG | CGGGATCTGCAGGATGCGG |
| 1218 | CGCATCCTGCAGATCCCGG | CCGGGATCTGCAGGATGCG |
| 1219 | GCATCCTGCAGATCCCGGA | TCCGGGATCTGCAGGATGC |
| 1220 | CATCCTGCAGATCCCGGAG | CTCCGGGATCTGCAGGATG |
| 1221 | ATCCTGCAGATCCCGGAGT | ACTCCGGGATCTGCAGGAT |
| 1222 | TCCTGCAGATCCCGGAGTC | GACTCCGGGATCTGCAGGA |
| 1223 | CCTGCAGATCCCGGAGTCC | GGACTCCGGGATCTGCAGG |
| 1224 | CTGCAGATCCCGGAGTCCG | CGGACTCCGGGATCTGCAG |
| 1225 | TGCAGATCCCGGAGTCCGA | TCGGACTCCGGGATCTGCA |
| 1226 | GCAGATCCCGGAGTCCGAC | GTCGGACTCCGGGATCTGC |
| 1227 | CAGATCCCGGAGTCCGACC | GGTCGGACTCCGGGATCTG |
| 1228 | AGATCCCGGAGTCCGACCC | GGGTCGGACTCCGGGATCT |
| 1229 | GATCCCGGAGTCCGACCCC | GGGGTCGGACTCCGGGATC |
| 1230 | ATCCCGGAGTCCGACCCCT | AGGGGTCGGACTCCGGGAT |
| 1231 | TCCCGGAGTCCGACCCCTC | GAGGGGTCGGACTCCGGGA |
| 1232 | CCCGGAGTCCGACCCCTCC | GGAGGGGTCGGACTCCGGG |
| 1233 | CCGGAGTCCGACCCCTCCA | TGGAGGGGTCGGACTCCGG |
| 1234 | CGGAGTCCGACCCCTCCAA | TTGGAGGGGTCGGACTCCG |
| 1235 | GGAGTCCGACCCCTCCAAC | GTTGGAGGGGTCGGACTCC |
| 1236 | GAGTCCGACCCCTCCAACC | GGTTGGAGGGGTCGGACTC |
| 1237 | AGTCCGACCCCTCCAACCT | AGGTTGGAGGGGTCGGACT |
| 1238 | GTCCGACCCCTCCAACCTG | CAGGTTGGAGGGGTCGGAC |
| 1239 | TCCGACCCCTCCAACCTGC | GCAGGTTGGAGGGGTCGGA |
| 1240 | CCGACCCCTCCAACCTGCG | CGCAGGTTGGAGGGGTCGG |
| 1241 | CGACCCCTCCAACCTGCGG | CCGCAGGTTGGAGGGGTCG |
| 1242 | GACCCCTCCAACCTGCGGC | GCCGCAGGTTGGAGGGGTC |
| 1243 | ACCCCTCCAACCTGCGGCC | GGCCGCAGGTTGGAGGGGT |
| 1244 | CCCCTCCAACCTGCGGCCC | GGGCCGCAGGTTGGAGGGG |
| 1245 | CCCTCCAACCTGCGGCCCT | AGGGCCGCAGGTTGGAGGG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1246 | CCTCCAACCTGCGGCCCTA | TAGGGCCGCAGGTTGGAGG |
| 1247 | CTCCAACCTGCGGCCCTAG | CTAGGGCCGCAGGTTGGAG |
| 1248 | TCCAACCTGCGGCCCTAGA | TCTAGGGCCGCAGGTTGGA |
| 1249 | CCAACCTGCGGCCCTAGAG | CTCTAGGGCCGCAGGTTGG |
| 1250 | CAACCTGCGGCCCTAGAGC | GCTCTAGGGCCGCAGGTTG |
| 1251 | AACCTGCGGCCCTAGAGCG | CGCTCTAGGGCCGCAGGTT |
| 1252 | ACCTGCGGCCCTAGAGCGC | GCGCTCTAGGGCCGCAGGT |
| 1253 | CCTGCGGCCCTAGAGCGCC | GGCGCTCTAGGGCCGCAGG |
| 1254 | CTGCGGCCCTAGAGCGCCC | GGGCGCTCTAGGGCCGCAG |
| 1255 | TGCGGCCCTAGAGCGCCCC | GGGGCGCTCTAGGGCCGCA |
| 1256 | GCGGCCCTAGAGCGCCCCC | GGGGGCGCTCTAGGGCCGC |
| 1257 | CGGCCCTAGAGCGCCCCCG | CGGGGGCGCTCTAGGGCCG |
| 1258 | GGCCCTAGAGCGCCCCCGC | GCGGGGGCGCTCTAGGGCC |
| 1259 | GCCCTAGAGCGCCCCCGCC | GGCGGGGGCGCTCTAGGGC |
| 1260 | CCCTAGAGCGCCCCCGCCG | CGGCGGGGGCGCTCTAGGG |
| 1261 | CCTAGAGCGCCCCCGCCGC | GCGGCGGGGGCGCTCTAGG |
| 1262 | CTAGAGCGCCCCCGCCGCC | GGCGGCGGGGGCGCTCTAG |
| 1263 | TAGAGCGCCCCCGCCGCCC | GGGCGGCGGGGGCGCTCTA |
| 1264 | AGAGCGCCCCCGCCGCCCC | GGGGCGGCGGGGGCGCTCT |
| 1265 | GAGCGCCCCCGCCGCCCCG | CGGGGCGGCGGGGGCGCTC |
| 1266 | AGCGCCCCCGCCGCCCCGG | CCGGGGCGGCGGGGGCGCT |
| 1267 | GCGCCCCCGCCGCCCCGGG | CCCGGGGCGGCGGGGGCGC |
| 1268 | CGCCCCCGCCGCCCCGGGG | CCCCGGGGCGGCGGGGGCG |
| 1269 | GCCCCCGCCGCCCCGGGGG | CCCCCGGGGCGGCGGGGGC |
| 1270 | CCCCCGCCGCCCCGGGGGA | TCCCCCGGGGCGGCGGGGG |
| 1271 | CCCCGCCGCCCCGGGGGAA | TTCCCCCGGGGCGGCGGGG |
| 1272 | CCCGCCGCCCCGGGGGAAG | CTTCCCCCGGGGCGGCGGG |
| 1273 | CCGCCGCCCCGGGGGAAGG | CCTTCCCCCGGGGCGGCGG |
| 1274 | CGCCGCCCCGGGGGAAGGA | TCCTTCCCCCGGGGCGGCG |
| 1275 | GCCGCCCCGGGGGAAGGAG | CTCCTTCCCCCGGGGCGGC |
| 1276 | CCGCCCCGGGGGAAGGAGA | TCTCCTTCCCCCGGGGCGG |
| 1277 | CGCCCCGGGGGAAGGAGAG | CTCTCCTTCCCCCGGGGCG |
| 1278 | GCCCCGGGGGAAGGAGAGC | GCTCTCCTTCCCCCGGGGC |
| 1279 | CCCCGGGGGAAGGAGAGCG | CGCTCTCCTTCCCCCGGGG |
| 1280 | CCCGGGGGAAGGAGAGCGC | GCGCTCTCCTTCCCCCGGG |
| 1281 | CCGGGGGAAGGAGAGCGCG | CGCGCTCTCCTTCCCCCGG |
| 1282 | CGGGGGAAGGAGAGCGCGA | TCGCGCTCTCCTTCCCCCG |
| 1283 | GGGGGAAGGAGAGCGCGAG | CTCGCGCTCTCCTTCCCCC |
| 1284 | GGGGAAGGAGAGCGCGAGC | GCTCGCGCTCTCCTTCCCC |
| 1285 | GGGAAGGAGAGCGCGAGCG | CGCTCGCGCTCTCCTTCCC |
| 1286 | GGAAGGAGAGCGCGAGCGC | GCGCTCGCGCTCTCCTTCC |
| 1287 | GAAGGAGAGCGCGAGCGCG | CGCGCTCGCGCTCTCCTTC |
| 1288 | AAGGAGAGCGCGAGCGCGC | GCGCGCTCGCGCTCTCCTT |
| 1289 | AGGAGAGCGCGAGCGCGCT | AGCGCGCTCGCGCTCTCCT |
| 1290 | GGAGAGCGCGAGCGCGCTG | CAGCGCGCTCGCGCTCTCC |
| 1291 | GAGAGCGCGAGCGCGCTGA | TCAGCGCGCTCGCGCTCTC |
| 1292 | AGAGCGCGAGCGCGCTGAG | CTCAGCGCGCTCGCGCTCT |
| 1293 | GAGCGCGAGCGCGCTGAGC | GCTCAGCGCGCTCGCGCTC |
| 1294 | AGCGCGAGCGCGCTGAGCA | TGCTCAGCGCGCTCGCGCT |
| 1295 | GCGCGAGCGCGCTGAGCAG | CTGCTCAGCGCGCTCGCGC |
| 1296 | CGCGAGCGCGCTGAGCAGA | TCTGCTCAGCGCGCTCGCG |
| 1297 | GCGAGCGCGCTGAGCAGAC | GTCTGCTCAGCGCGCTCGC |
| 1298 | CGAGCGCGCTGAGCAGACA | TGTCTGCTCAGCGCGCTCG |
| 1299 | GAGCGCGCTGAGCAGACAG | CTGTCTGCTCAGCGCGCTC |
| 1300 | AGCGCGCTGAGCAGACAGA | TCTGTCTGCTCAGCGCGCT |
| 1301 | GCGCGCTGAGCAGACAGAG | CTCTGTCTGCTCAGCGCGC |
| 1302 | CGCGCTGAGCAGACAGAGC | GCTCTGTCTGCTCAGCGCG |
| 1303 | GCGCTGAGCAGACAGAGCG | CGCTCTGTCTGCTCAGCGC |
| 1304 | CGCTGAGCAGACAGAGCGG | CCGCTCTGTCTGCTCAGCG |
| 1305 | GCTGAGCAGACAGAGCGGG | CCCGCTCTGTCTGCTCAGC |
| 1306 | CTGAGCAGACAGAGCGGGA | TCCCGCTCTGTCTGCTCAG |
| 1307 | TGAGCAGACAGAGCGGGAG | CTCCCGCTCTGTCTGCTCA |
| 1308 | GAGCAGACAGAGCGGGAGA | TCTCCCGCTCTGTCTGCTC |
| 1309 | AGCAGACAGAGCGGGAGAA | TTCTCCCGCTCTGTCTGCT |
| 1310 | GCAGACAGAGCGGGAGAAC | GTTCTCCCGCTCTGTCTGC |
| 1311 | CAGACAGAGCGGGAGAACG | CGTTCTCCCGCTCTGTCTG |
| 1312 | AGACAGAGCGGGAGAACGC | GCGTTCTCCCGCTCTGTCT |
| 1313 | GACAGAGCGGGAGAACGCG | CGCGTTCTCCCGCTCTGTC |
| 1314 | ACAGAGCGGGAGAACGCGT | ACGCGTTCTCCCGCTCTGT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 1315 | CAGAGCGGGAGAACGCGTC | GACGCGTTCTCCCGCTCTG |
| 1316 | AGAGCGGGAGAACGCGTCC | GGACGCGTTCTCCCGCTCT |
| 1317 | GAGCGGGAGAACGCGTCCT | AGGACGCGTTCTCCCGCTC |
| 1318 | AGCGGGAGAACGCGTCCTC | GAGGACGCGTTCTCCCGCT |
| 1319 | GCGGGAGAACGCGTCCTCG | CGAGGACGCGTTCTCCCGC |
| 1320 | CGGGAGAACGCGTCCTCGC | GCGAGGACGCGTTCTCCCG |
| 1321 | GGGAGAACGCGTCCTCGCC | GGCGAGGACGCGTTCTCCC |
| 1322 | GGAGAACGCGTCCTCGCCC | GGGCGAGGACGCGTTCTCC |
| 1323 | GAGAACGCGTCCTCGCCCG | CGGGCGAGGACGCGTTCTC |
| 1324 | AGAACGCGTCCTCGCCCGC | GCGGGCGAGGACGCGTTCT |
| 1325 | GAACGCGTCCTCGCCCGCC | GGCGGGCGAGGACGCGTTC |
| 1326 | AACGCGTCCTCGCCCGCCG | CGGCGGGCGAGGACGCGTT |
| 1327 | ACGCGTCCTCGCCCGCCGG | CCGGCGGGCGAGGACGCGT |
| 1328 | CGCGTCCTCGCCCGCCGGC | GCCGGCGGGCGAGGACGCG |
| 1329 | GCGTCCTCGCCCGCCGGCC | GGCCGGCGGGCGAGGACGC |
| 1330 | CGTCCTCGCCCGCCGGCCG | CGGCCGGCGGGCGAGGACG |
| 1331 | GTCCTCGCCCGCCGGCCGG | CCGGCCGGCGGGCGAGGAC |
| 1332 | TCCTCGCCCGCCGGCCGGG | CCCGGCCGGCGGGCGAGGA |
| 1333 | CCTCGCCCGCCGGCCGGGA | TCCCGGCCGGCGGGCGAGG |
| 1334 | CTCGCCCGCCGGCCGGGAG | CTCCCGGCCGGCGGGCGAG |
| 1335 | TCGCCCGCCGGCCGGGAGG | CCTCCCGGCCGGCGGGCGA |
| 1336 | CGCCCGCCGGCCGGGAGGC | GCCTCCCGGCCGGCGGGCG |
| 1337 | GCCCGCCGGCCGGGAGGCC | GGCCTCCCGGCCGGCGGGC |
| 1338 | CCCGCCGGCCGGGAGGCCC | GGGCCTCCCGGCCGGCGGG |
| 1339 | CCGCCGGCCGGGAGGCCCC | GGGGCCTCCCGGCCGGCGG |
| 1340 | CGCCGGCCGGGAGGCCCCG | CGGGGCCTCCCGGCCGGCG |
| 1341 | GCCGGCCGGGAGGCCCCGG | CCGGGGCCTCCCGGCCGGC |
| 1342 | CCGGCCGGGAGGCCCCGGA | TCCGGGGCCTCCCGGCCGG |
| 1343 | CGGCCGGGAGGCCCCGGAG | CTCCGGGGCCTCCCGGCCG |
| 1344 | GGCCGGGAGGCCCCGGAGC | GCTCCGGGGCCTCCCGGCC |
| 1345 | GCCGGGAGGCCCCGGAGCT | AGCTCCGGGGCCTCCCGGC |
| 1346 | CCGGGAGGCCCCGGAGCTG | CAGCTCCGGGGCCTCCCGG |
| 1347 | CGGGAGGCCCCGGAGCTGG | CCAGCTCCGGGGCCTCCCG |
| 1348 | GGGAGGCCCCGGAGCTGGC | GCCAGCTCCGGGGCCTCCC |
| 1349 | GGAGGCCCCGGAGCTGGCC | GGCCAGCTCCGGGGCCTCC |
| 1350 | GAGGCCCCGGAGCTGGCCC | GGGCCAGCTCCGGGGCCTC |
| 1351 | AGGCCCCGGAGCTGGCCCA | TGGGCCAGCTCCGGGGCCT |
| 1352 | GGCCCCGGAGCTGGCCCAT | ATGGGCCAGCTCCGGGGCC |
| 1353 | GCCCCGGAGCTGGCCCATG | CATGGGCCAGCTCCGGGGC |
| 1354 | CCCCGGAGCTGGCCCATGG | CCATGGGCCAGCTCCGGGG |
| 1355 | CCCGGAGCTGGCCCATGGG | CCCATGGGCCAGCTCCGGG |
| 1356 | CCGGAGCTGGCCCATGGGG | CCCCATGGGCCAGCTCCGG |
| 1357 | CGGAGCTGGCCCATGGGGA | TCCCCATGGGCCAGCTCCG |
| 1358 | GGAGCTGGCCCATGGGGAG | CTCCCCATGGGCCAGCTCC |
| 1359 | GAGCTGGCCCATGGGGAGC | GCTCCCCATGGGCCAGCTC |
| 1360 | AGCTGGCCCATGGGGAGCA | TGCTCCCCATGGGCCAGCT |
| 1361 | GCTGGCCCATGGGGAGCAG | CTGCTCCCCATGGGCCAGC |
| 1362 | CTGGCCCATGGGGAGCAGG | CCTGCTCCCCATGGGCCAG |
| 1363 | TGGCCCATGGGGAGCAGGC | GCCTGCTCCCCATGGGCCA |
| 1364 | GGCCCATGGGGAGCAGGCG | CGCCTGCTCCCCATGGGCC |
| 1365 | GCCCATGGGGAGCAGGCGC | GCGCCTGCTCCCCATGGGC |
| 1366 | CCCATGGGGAGCAGGCGCC | GGCGCCTGCTCCCCATGGG |
| 1367 | CCATGGGGAGCAGGCGCCC | GGGCGCCTGCTCCCCATGG |
| 1368 | CATGGGGAGCAGGCGCCCG | CGGGCGCCTGCTCCCCATG |
| 1369 | ATGGGGAGCAGGCGCCCGG | CCGGGCGCCTGCTCCCCAT |
| 1370 | TGGGGAGCAGGCGCCCGGT | ACCGGGCGCCTGCTCCCCA |
| 1371 | GGGGAGCAGGCGCCCGGTG | CACCGGGCGCCTGCTCCCC |
| 1372 | GGGAGCAGGCGCCCGGTGC | GCACCGGGCGCCTGCTCCC |
| 1373 | GGAGCAGGCGCCCGGTGCC | GGCACCGGGCGCCTGCTCC |
| 1374 | GAGCAGGCGCCCGGTGCCG | CGGCACCGGGCGCCTGCTC |
| 1375 | AGCAGGCGCCCGGTGCCGG | CCGGCACCGGGCGCCTGCT |
| 1376 | GCAGGCGCCCGGTGCCGGC | GCCGGCACCGGGCGCCTGC |
| 1377 | CAGGCGCCCGGTGCCGGCC | GGCCGGCACCGGGCGCCTG |
| 1378 | AGGCGCCCGGTGCCGGCCA | TGGCCGGCACCGGGCGCCT |
| 1379 | GGCGCCCGGTGCCGGCCAC | GTGGCCGGCACCGGGCGCC |
| 1380 | GCGCCCGGTGCCGGCCACG | CGTGGCCGGCACCGGGCGC |
| 1381 | CGCCCGGTGCCGGCCACGA | TCGTGGCCGGCACCGGGCG |
| 1382 | GCCCGGTGCCGGCCACGAC | GTCGTGGCCGGCACCGGGC |
| 1383 | CCCGGTGCCGGCCACGACG | CGTCGTGGCCGGCACCGGG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 1384 | CCGGTGCCGGCCACGACGA | TCGTCGTGGCCGGCACCGG |
| 1385 | CGGTGCCGGCCACGACGAC | GTCGTCGTGGCCGGCACCG |
| 1386 | GGTGCCGGCCACGACGACC | GGTCGTCGTGGCCGGCACC |
| 1387 | GTGCCGGCCACGACGACCG | CGGTCGTCGTGGCCGGCAC |
| 1388 | TGCCGGCCACGACGACCGC | GCGGTCGTCGTGGCCGGCA |
| 1389 | GCCGGCCACGACGACCGCC | GGCGGTCGTCGTGGCCGGC |
| 1390 | CCGGCCACGACGACCGCCA | TGGCGGTCGTCGTGGCCGG |
| 1391 | CGGCCACGACGACCGCCAC | GTGGCGGTCGTCGTGGCCG |
| 1392 | GGCCACGACGACCGCCACC | GGTGGCGGTCGTCGTGGCC |
| 1393 | GCCACGACGACCGCCACCG | CGGTGGCGGTCGTCGTGGC |
| 1394 | CCACGACGACCGCCACCGC | GCGGTGGCGGTCGTCGTGG |
| 1395 | CACGACGACCGCCACCGCC | GGCGGTGGCGGTCGTCGTG |
| 1396 | ACGACGACCGCCACCGCCC | GGGCGGTGGCGGTCGTCGT |
| 1397 | CGACGACCGCCACCGCCCG | CGGGCGGTGGCGGTCGTCG |
| 1398 | GACGACCGCCACCGCCCGC | GCGGGCGGTGGCGGTCGTC |
| 1399 | ACGACCGCCACCGCCCGCG | CGCGGGCGGTGGCGGTCGT |
| 1400 | CGACCGCCACCGCCCGCGC | GCGCGGGCGGTGGCGGTCG |
| 1401 | GACCGCCACCGCCCGCGCC | GGCGCGGGCGGTGGCGGTC |
| 1402 | ACCGCCACCGCCCGCGCCG | CGGCGCGGGCGGTGGCGGT |
| 1403 | CCGCCACCGCCCGCGCCGC | GCGGCGCGGGCGGTGGCGG |
| 1404 | CGCCACCGCCCGCGCCGCG | CGCGGCGCGGGCGGTGGCG |
| 1405 | GCCACCGCCCGCGCCGCGA | TCGCGGCGCGGGCGGTGGC |
| 1406 | CCACCGCCCGCGCCGCGAC | GTCGCGGCGCGGGCGGTGG |
| 1407 | CACCGCCCGCGCCGCGACC | GGTCGCGGCGCGGGCGGTG |
| 1408 | ACCGCCCGCGCCGCGACCG | CGGTCGCGGCGCGGGCGGT |
| 1409 | CCGCCCGCGCCGCGACCGG | CCGGTCGCGGCGCGGGCGG |
| 1410 | CGCCCGCGCCGCGACCGGC | GCCGGTCGCGGCGCGGGCG |
| 1411 | GCCCGCGCCGCGACCGGCC | GGCCGGTCGCGGCGCGGGC |
| 1412 | CCCGCGCCGCGACCGGCCG | CGGCCGGTCGCGGCGCGGG |
| 1413 | CCGCGCCGCGACCGGCCGG | CCGGCCGGTCGCGGCGCGG |
| 1414 | CGCGCCGCGACCGGCCGGT | ACCGGCCGGTCGCGGCGCG |
| 1415 | GCGCCGCGACCGGCCGGTG | CACCGGCCGGTCGCGGCGC |
| 1416 | CGCCGCGACCGGCCGGTGA | TCACCGGCCGGTCGCGGCG |
| 1417 | GCCGCGACCGGCCGGTGAA | TTCACCGGCCGGTCGCGGC |
| 1418 | CCGCGACCGGCCGGTGAAG | CTTCACCGGCCGGTCGCGG |
| 1419 | CGCGACCGGCCGGTGAAGC | GCTTCACCGGCCGGTCGCG |
| 1420 | GCGACCGGCCGGTGAAGCC | GGCTTCACCGGCCGGTCGC |
| 1421 | CGACCGGCCGGTGAAGCCC | GGGCTTCACCGGCCGGTCG |
| 1422 | GACCGGCCGGTGAAGCCCA | TGGGCTTCACCGGCCGGTC |
| 1423 | ACCGGCCGGTGAAGCCCAG | CTGGGCTTCACCGGCCGGT |
| 1424 | CCGGCCGGTGAAGCCCAGG | CCTGGGCTTCACCGGCCGG |
| 1425 | CGGCCGGTGAAGCCCAGGG | CCCTGGGCTTCACCGGCCG |
| 1426 | GGCCGGTGAAGCCCAGGGA | TCCCTGGGCTTCACCGGCC |
| 1427 | GCCGGTGAAGCCCAGGGAC | GTCCCTGGGCTTCACCGGC |
| 1428 | CCGGTGAAGCCCAGGGACC | GGTCCCTGGGCTTCACCGG |
| 1429 | CGGTGAAGCCCAGGGACCC | GGGTCCCTGGGCTTCACCG |
| 1430 | GGTGAAGCCCAGGGACCCC | GGGGTCCCTGGGCTTCACC |
| 1431 | GTGAAGCCCAGGGACCCCC | GGGGGTCCCTGGGCTTCAC |
| 1432 | TGAAGCCCAGGGACCCCCC | GGGGGGTCCCTGGGCTTCA |
| 1433 | GAAGCCCAGGGACCCCCCT | AGGGGGGTCCCTGGGCTTC |
| 1434 | AAGCCCAGGGACCCCCCTC | GAGGGGGGTCCCTGGGCTT |
| 1435 | AGCCCAGGGACCCCCCTCT | AGAGGGGGGTCCCTGGGCT |
| 1436 | GCCCAGGGACCCCCCTCTG | CAGAGGGGGGTCCCTGGGC |
| 1437 | CCCAGGGACCCCCCTCTGG | CCAGAGGGGGGTCCCTGGG |
| 1438 | CCAGGGACCCCCCTCTGGG | CCCAGAGGGGGGTCCCTGG |
| 1439 | CAGGGACCCCCCTCTGGGA | TCCCAGAGGGGGGTCCCTG |
| 1440 | AGGGACCCCCCTCTGGGAG | CTCCCAGAGGGGGGTCCCT |
| 1441 | GGGACCCCCCTCTGGGAGA | TCTCCCAGAGGGGGGTCCC |
| 1442 | GGACCCCCCTCTGGGAGAG | CTCTCCCAGAGGGGGGTCC |
| 1443 | GACCCCCCTCTGGGAGAGC | GCTCTCCCAGAGGGGGGTC |
| 1444 | ACCCCCCTCTGGGAGAGCC | GGCTCTCCCAGAGGGGGGT |
| 1445 | CCCCCCTCTGGGAGAGCCC | GGGCTCTCCCAGAGGGGGG |
| 1446 | CCCCCTCTGGGAGAGCCCC | GGGGCTCTCCCAGAGGGGG |
| 1447 | CCCCTCTGGGAGAGCCCCA | TGGGGCTCTCCCAGAGGGG |
| 1448 | CCCTCTGGGAGAGCCCCAT | ATGGGGCTCTCCCAGAGGG |
| 1449 | CCTCTGGGAGAGCCCCATG | CATGGGGCTCTCCCAGAGG |
| 1450 | CTCTGGGAGAGCCCCATGA | TCATGGGGCTCTCCCAGAG |
| 1451 | TCTGGGAGAGCCCCATGAG | CTCATGGGGCTCTCCCAGA |
| 1452 | CTGGGAGAGCCCCATGAGG | CCTCATGGGGCTCTCCCAG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 1453 | TGGGAGAGCCCCATGAGGG | CCCTCATGGGGCTCTCCCA |
| 1454 | GGGAGAGCCCCATGAGGGC | GCCCTCATGGGGCTCTCCC |
| 1455 | GGAGAGCCCCATGAGGGCA | TGCCCTCATGGGGCTCTCC |
| 1456 | GAGAGCCCCATGAGGGCAG | CTGCCCTCATGGGGCTCTC |
| 1457 | AGAGCCCCATGAGGGCAGG | CCTGCCCTCATGGGGCTCT |
| 1458 | GAGCCCCATGAGGGCAGGA | TCCTGCCCTCATGGGGCTC |
| 1459 | AGCCCCATGAGGGCAGGAG | CTCCTGCCCTCATGGGGCT |
| 1460 | GCCCCATGAGGGCAGGAGA | TCTCCTGCCCTCATGGGGC |
| 1461 | CCCCATGAGGGCAGGAGAG | CTCTCCTGCCCTCATGGGG |
| 1462 | CCCATGAGGGCAGGAGAGT | ACTCTCCTGCCCTCATGGG |
| 1463 | CCATGAGGGCAGGAGAGTG | CACTCTCCTGCCCTCATGG |
| 1464 | CATGAGGGCAGGAGAGTGA | TCACTCTCCTGCCCTCATG |
| 1465 | ATGAGGGCAGGAGAGTGAT | ATCACTCTCCTGCCCTCAT |
| 1466 | TGAGGGCAGGAGAGTGATG | CATCACTCTCCTGCCCTCA |
| 1467 | GAGGGCAGGAGAGTGATGG | CCATCACTCTCCTGCCCTC |
| 1468 | AGGGCAGGAGAGTGATGGA | TCCATCACTCTCCTGCCCT |
| 1469 | GGGCAGGAGAGTGATGGAG | CTCCATCACTCTCCTGCCC |
| 1470 | GGCAGGAGAGTGATGGAGA | TCTCCATCACTCTCCTGCC |
| 1471 | GCAGGAGAGTGATGGAGAG | CTCTCCATCACTCTCCTGC |
| 1472 | CAGGAGAGTGATGGAGAGT | ACTCTCCATCACTCTCCTG |
| 1473 | AGGAGAGTGATGGAGAGTA | TACTCTCCATCACTCTCCT |
| 1474 | GGAGAGTGATGGAGAGTAC | GTACTCTCCATCACTCTCC |
| 1475 | GAGAGTGATGGAGAGTACG | CGTACTCTCCATCACTCTC |
| 1476 | AGAGTGATGGAGAGTACGC | GCGTACTCTCCATCACTCT |
| 1477 | GAGTGATGGAGAGTACGCC | GGCGTACTCTCCATCACTC |
| 1478 | AGTGATGGAGAGTACGCCC | GGGCGTACTCTCCATCACT |
| 1479 | GTGATGGAGAGTACGCCCA | TGGGCGTACTCTCCATCAC |
| 1480 | TGATGGAGAGTACGCCCAG | CTGGGCGTACTCTCCATCA |
| 1481 | GATGGAGAGTACGCCCAGC | GCTGGGCGTACTCTCCATC |
| 1482 | ATGGAGAGTACGCCCAGCT | AGCTGGGCGTACTCTCCAT |
| 1483 | TGGAGAGTACGCCCAGCTT | AAGCTGGGCGTACTCTCCA |
| 1484 | GGAGAGTACGCCCAGCTTC | GAAGCTGGGCGTACTCTCC |
| 1485 | GAGAGTACGCCCAGCTTCC | GGAAGCTGGGCGTACTCTC |
| 1486 | AGAGTACGCCCAGCTTCCT | AGGAAGCTGGGCGTACTCT |
| 1487 | GAGTACGCCCAGCTTCCTG | CAGGAAGCTGGGCGTACTC |
| 1488 | AGTACGCCCAGCTTCCTGA | TCAGGAAGCTGGGCGTACT |
| 1489 | GTACGCCCAGCTTCCTGAA | TTCAGGAAGCTGGGCGTAC |
| 1490 | TACGCCCAGCTTCCTGAAG | CTTCAGGAAGCTGGGCGTA |
| 1491 | ACGCCCAGCTTCCTGAAGG | CCTTCAGGAAGCTGGGCGT |
| 1492 | CGCCCAGCTTCCTGAAGGG | CCCTTCAGGAAGCTGGGCG |
| 1493 | GCCCAGCTTCCTGAAGGGC | GCCCTTCAGGAAGCTGGGC |
| 1494 | CCCAGCTTCCTGAAGGGCA | TGCCCTTCAGGAAGCTGGG |
| 1495 | CCAGCTTCCTGAAGGGCAC | GTGCCCTTCAGGAAGCTGG |
| 1496 | CAGCTTCCTGAAGGGCACC | GGTGCCCTTCAGGAAGCTG |
| 1497 | AGCTTCCTGAAGGGCACCC | GGGTGCCCTTCAGGAAGCT |
| 1498 | GCTTCCTGAAGGGCACCCC | GGGGTGCCCTTCAGGAAGC |
| 1499 | CTTCCTGAAGGGCACCCCA | TGGGGTGCCCTTCAGGAAG |
| 1500 | TTCCTGAAGGGCACCCCAA | TTGGGGTGCCCTTCAGGAA |
| 1501 | TCCTGAAGGGCACCCCAAC | GTTGGGGTGCCCTTCAGGA |
| 1502 | CCTGAAGGGCACCCCAACC | GGTTGGGGTGCCCTTCAGG |
| 1503 | CTGAAGGGCACCCCAACCT | AGGTTGGGGTGCCCTTCAG |
| 1504 | TGAAGGGCACCCCAACCTG | CAGGTTGGGGTGCCCTTCA |
| 1505 | GAAGGGCACCCCAACCTGG | CCAGGTTGGGGTGCCCTTC |
| 1506 | AAGGGCACCCCAACCTGGG | CCCAGGTTGGGGTGCCCTT |
| 1507 | AGGGCACCCCAACCTGGGA | TCCCAGGTTGGGGTGCCCT |
| 1508 | GGGCACCCCAACCTGGGAG | CTCCCAGGTTGGGGTGCCC |
| 1509 | GGCACCCCAACCTGGGAGA | TCTCCCAGGTTGGGGTGCC |
| 1510 | GCACCCCAACCTGGGAGAA | TTCTCCCAGGTTGGGGTGC |
| 1511 | CACCCCAACCTGGGAGAAG | CTTCTCCCAGGTTGGGGTG |
| 1512 | ACCCCAACCTGGGAGAAGA | TCTTCTCCCAGGTTGGGGT |
| 1513 | CCCCAACCTGGGAGAAGAC | GTCTTCTCCCAGGTTGGGG |
| 1514 | CCCAACCTGGGAGAAGACG | CGTCTTCTCCCAGGTTGGG |
| 1515 | CCAACCTGGGAGAAGACGG | CCGTCTTCTCCCAGGTTGG |
| 1516 | CAACCTGGGAGAAGACGGC | GCCGTCTTCTCCCAGGTTG |
| 1517 | AACCTGGGAGAAGACGGCC | GGCCGTCTTCTCCCAGGTT |
| 1518 | ACCTGGGAGAAGACGGCCC | GGGCCGTCTTCTCCCAGGT |
| 1519 | CCTGGGAGAAGACGGCCCC | GGGGCCGTCTTCTCCCAGG |
| 1520 | CTGGGAGAAGACGGCCCCA | TGGGGCCGTCTTCTCCCAG |
| 1521 | TGGGAGAAGACGGCCCCAG | CTGGGGCCGTCTTCTCCCA |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1522 | GGGAGAAGACGGCCCCAGA | TCTGGGGCCGTCTTCTCCC |
| 1523 | GGAGAAGACGGCCCCAGAG | CTCTGGGGCCGTCTTCTCC |
| 1524 | GAGAAGACGGGGCCAGAGA | TCTCTGGGGCCGTCTTCTC |
| 1525 | AGAAGACGGCCCCAGAGAA | TTCTCTGGGGCCGTCTTCT |
| 1526 | GAAGACGGCCCCAGAGAAC | GTTCTCTGGGGCCGTCTTC |
| 1527 | AAGACGGCCCCAGAGAACG | CGTTCTCTGGGGCCGTCTT |
| 1528 | AGACGGCCCCAGAGAACGG | CCGTTCTCTGGGGCCGTCT |
| 1529 | GACGGCCCCAGAGAACGGC | GCCGTTCTCTGGGGCCGTC |
| 1530 | ACGGCCCCAGAGAACGGCA | TGCCGTTCTCTGGGGCCGT |
| 1531 | CGGCCCCAGAGAACGGCAT | ATGCCGTTCTCTGGGGCCG |
| 1532 | GGCCCCAGAGAACGGCATC | GATGCCGTTCTCTGGGGCC |
| 1533 | GCCCCAGAGAACGGCATCG | CGATGCCGTTCTCTGGGGC |
| 1534 | CCCCAGAGAACGGCATCGT | ACGATGCCGTTCTCTGGGG |
| 1535 | CCCAGAGAACGGCATCGTG | CACGATGCCGTTCTCTGGG |
| 1536 | CCAGAGAACGGCATCGTGA | TCACGATGCCGTTCTCTGG |
| 1537 | CAGAGAACGGCATCGTGAG | CTCACGATGCCGTTCTCTG |
| 1538 | AGAGAACGGCATCGTGAGA | TCTCACGATGCCGTTCTCT |
| 1539 | GAGAACGGCATCGTGAGAC | GTCTCACGATGCCGTTCTC |
| 1540 | AGAACGGCATCGTGAGACA | TGTCTCACGATGCCGTTCT |
| 1541 | GAACGGCATCGTGAGACAG | CTGTCTCACGATGCCGTTC |
| 1542 | AACGGCATCGTGAGACAGG | CCTGTCTCACGATGCCGTT |
| 1543 | ACGGCATCGTGAGACAGGA | TCCTGTCTCACGATGCCGT |
| 1544 | CGGCATCGTGAGACAGGAG | CTCCTGTCTCACGATGCCG |
| 1545 | GGCATCGTGAGACAGGAGC | GCTCCTGTCTCACGATGCC |
| 1546 | GCATCGTGAGACAGGAGCC | GGCTCCTGTCTCACGATGC |
| 1547 | CATCGTGAGACAGGAGCCC | GGGCTCCTGTCTCACGATG |
| 1548 | ATCGTGAGACAGGAGCCCG | CGGGCTCCTGTCTCACGAT |
| 1549 | TCGTGAGACAGGAGCCCGG | CCGGGCTCCTGTCTCACGA |
| 1550 | CGTGAGACAGGAGCCCGGC | GCCGGGCTCCTGTCTCACG |
| 1551 | GTGAGACAGGAGCCCGGCA | TGCCGGGCTCCTGTCTCAC |
| 1552 | TGAGACAGGAGCCCGGCAG | CTGCCGGGCTCCTGTCTCA |
| 1553 | GAGACAGGAGCCCGGCAGC | GCTGCCGGGCTCCTGTCTC |
| 1554 | AGACAGGAGCCCGGCAGCC | GGCTGCCGGGCTCCTGTCT |
| 1555 | GACAGGAGCCCGGCAGCCC | GGGCTGCCGGGCTCCTGTC |
| 1556 | ACAGGAGCCCGGCAGCCCG | CGGGCTGCCGGGCTCCTGT |
| 1557 | CAGGAGCCCGGCAGCCCGC | GCGGGCTGCCGGGCTCCTG |
| 1558 | AGGAGCCCGGCAGCCCGCC | GGCGGGCTGCCGGGCTCCT |
| 1559 | GGAGCCCGGCAGCCCGCCT | AGGCGGGCTGCCGGGCTCC |
| 1560 | GAGCCCGGCAGCCCGCCTC | GAGGCGGGCTGCCGGGCTC |
| 1561 | AGCCCGGCAGCCCGCCTCG | CGAGGCGGGCTGCCGGGCT |
| 1562 | GCCCGGCAGCCCGCCTCGA | TCGAGGCGGGCTGCCGGGC |
| 1563 | CCCGGCAGCCCGCCTCGAG | CTCGAGGCGGGCTGCCGGG |
| 1564 | CCGGCAGCCCGCCTCGAGA | TCTCGAGGCGGGCTGCCGG |
| 1565 | CGGCAGCCCGCCTCGAGAT | ATCTCGAGGCGGGCTGCCG |
| 1566 | GGCAGCCCGCCTCGAGATG | CATCTCGAGGCGGGCTGCC |
| 1567 | GCAGCCCGCCTCGAGATGG | CCATCTCGAGGCGGGCTGC |
| 1568 | CAGCCCGCCTCGAGATGGA | TCCATCTCGAGGCGGGCTG |
| 1569 | AGCCCGCCTCGAGATGGAC | GTCCATCTCGAGGCGGGCT |
| 1570 | GCCCGCCTCGAGATGGACT | AGTCCATCTCGAGGCGGGC |
| 1571 | CCCGCCTCGAGATGGACTG | CAGTCCATCTCGAGGCGGG |
| 1572 | CCGCCTCGAGATGGACTGC | GCAGTCCATCTCGAGGCGG |
| 1573 | CGCCTCGAGATGGACTGCA | TGCAGTCCATCTCGAGGCG |
| 1574 | GCCTCGAGATGGACTGCAC | GTGCAGTCCATCTCGAGGC |
| 1575 | CCTCGAGATGGACTGCACC | GGTGCAGTCCATCTCGAGG |
| 1576 | CTCGAGATGGACTGCACCA | TGGTGCAGTCCATCTCGAG |
| 1577 | TCGAGATGGACTGCACCAT | ATGGTGCAGTCCATCTCGA |
| 1578 | CGAGATGGACTGCACCATG | CATGGTGCAGTCCATCTCG |
| 1579 | GAGATGGACTGCACCATGG | CCATGGTGCAGTCCATCTC |
| 1580 | AGATGGACTGCACCATGGG | CCCATGGTGCAGTCCATCT |
| 1581 | GATGGACTGCACCATGGGC | GCCCATGGTGCAGTCCATC |
| 1582 | ATGGACTGCACCATGGGCC | GGCCCATGGTGCAGTCCAT |
| 1583 | TGGACTGCACCATGGGCCG | CGGCCCATGGTGCAGTCCA |
| 1584 | GGACTGCACCATGGGCCGC | GCGGCCCATGGTGCAGTCC |
| 1585 | GACTGCACCATGGGCCGCT | AGCGGCCCATGGTGCAGTC |
| 1586 | ACTGCACCATGGGCCGCTG | CAGCGGCCCATGGTGCAGT |
| 1587 | CTGCACCATGGGCCGCTGT | ACAGCGGCCCATGGTGCAG |
| 1588 | TGCACCATGGGCCGCTGTG | CACAGCGGCCCATGGTGCA |
| 1589 | GCACCATGGGCCGCTGTGC | GCACAGCGGCCCATGGTGC |
| 1590 | CACCATGGGCCGCTGTGCC | GGCACAGCGGCCCATGGTG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 1591 | ACCATGGGCCGCTGTGCCT | AGGCACAGCGGCCCATGGT |
| 1592 | CCATGGGCCGCTGTGCCTG | CAGGCACAGCGGCCCATGG |
| 1593 | CATGGGCCGCTGTGCCTGG | CCAGGCACAGCGGCCCATG |
| 1594 | ATGGGCCGCTGTGCCTGGG | CCCAGGCACAGCGGCCCAT |
| 1595 | TGGGCCGCTGTGCCTGGGA | TCCCAGGCACAGCGGCCCA |
| 1596 | GGGCCGCTGTGCCTGGGAG | CTCCCAGGCACAGCGGCCC |
| 1597 | GGCCGCTGTGCCTGGGAGA | TCTCCCAGGCACAGCGGCC |
| 1598 | GCCGCTGTGCCTGGGAGAG | CTCTCCCAGGCACAGCGGC |
| 1599 | CCGCTGTGCCTGGGAGAGC | GCTCTCCCAGGCACAGCGG |
| 1600 | CGCTGTGCCTGGGAGAGCC | GGCTCTCCCAGGCACAGCG |
| 1601 | GCTGTGCCTGGGAGAGCCT | AGGCTCTCCCAGGCACAGC |
| 1602 | CTGTGCCTGGGAGAGCCTG | CAGGCTCTCCCAGGCACAG |
| 1603 | TGTGCCTGGGAGAGCCTGC | GCAGGCTCTCCCAGGCACA |
| 1604 | GTGCCTGGGAGAGCCTGCT | AGCAGGCTCTCCCAGGCAC |
| 1605 | TGCCTGGGAGAGCCTGCTC | GAGCAGGCTCTCCCAGGCA |
| 1606 | GCCTGGGAGAGCCTGCTCC | GGAGCAGGCTCTCCCAGGC |
| 1607 | CCTGGGAGAGCCTGCTCCC | GGGAGCAGGCTCTCCCAGG |
| 1608 | CTGGGAGAGCCTGCTCCCT | AGGGAGCAGGCTCTCCCAG |
| 1609 | TGGGAGAGCCTGCTCCCTT | AAGGGAGCAGGCTCTCCCA |
| 1610 | GGGAGAGCCTGCTCCCTTT | AAAGGGAGCAGGCTCTCCC |
| 1611 | GGAGAGCCTGCTCCCTTTT | AAAAGGGAGCAGGCTCTCC |
| 1612 | GAGAGCCTGCTCCCTTTTG | CAAAAGGGAGCAGGCTCTC |
| 1613 | AGAGCCTGCTCCCTTTTGG | CCAAAAGGGAGCAGGCTCT |
| 1614 | GAGCCTGCTCCCTTTTGGA | TCCAAAAGGGAGCAGGCTC |
| 1615 | AGCCTGCTCCCTTTTGGAG | CTCCAAAAGGGAGCAGGCT |
| 1616 | GCCTGCTCCCTTTTGGAGG | CCTCCAAAAGGGAGCAGGC |
| 1617 | CCTGCTCCCTTTTGGAGGG | CCCTCCAAAAGGGAGCAGG |
| 1618 | CTGCTCCCTTTTGGAGGGG | CCCCTCCAAAAGGGAGCAG |
| 1619 | TGCTCCCTTTTGGAGGGGC | GCCCCTCCAAAAGGGAGCA |
| 1620 | GCTCCCTTTTGGAGGGGCG | CGCCCCTCCAAAAGGGAGC |
| 1621 | CTCCCTTTTGGAGGGGCGT | ACGCCCCTCCAAAAGGGAG |
| 1622 | TCCCTTTTGGAGGGGCGTC | GACGCCCCTCCAAAAGGGA |
| 1623 | CCCTTTTGGAGGGGCGTCC | GGACGCCCCTCCAAAAGGG |
| 1624 | CCTTTTGGAGGGGCGTCCT | AGGACGCCCCTCCAAAAGG |
| 1625 | CTTTTGGAGGGGCGTCCTG | CAGGACGCCCCTCCAAAAG |
| 1626 | TTTTGGAGGGGCGTCCTGA | TCAGGACGCCCCTCCAAAA |
| 1627 | TTTGGAGGGGCGTCCTGAG | CTCAGGACGCCCCTCCAAA |
| 1628 | TTGGAGGGGCGTCCTGAGC | GCTCAGGACGCCCCTCCAA |
| 1629 | TGGAGGGGCGTCCTGAGCA | TGCTCAGGACGCCCCTCCA |
| 1630 | GGAGGGGCGTCCTGAGCAC | GTGCTCAGGACGCCCCTCC |
| 1631 | GAGGGGCGTCCTGAGCACC | GGTGCTCAGGACGCCCCTC |
| 1632 | AGGGGCGTCCTGAGCACCC | GGGTGCTCAGGACGCCCCT |
| 1633 | GGGGCGTCCTGAGCACCCC | GGGGTGCTCAGGACGCCCC |
| 1634 | GGGCGTCCTGAGCACCCCA | TGGGGTGCTCAGGACGCCC |
| 1635 | GGCGTCCTGAGCACCCCAG | CTGGGGTGCTCAGGACGCC |
| 1636 | GCGTCCTGAGCACCCCAGA | TCTGGGGTGCTCAGGACGC |
| 1637 | CGTCCTGAGCACCCCAGAC | GTCTGGGGTGCTCAGGACG |
| 1638 | GTCCTGAGCACCCCAGACT | AGTCTGGGGTGCTCAGGAC |
| 1639 | TCCTGAGCACCCCAGACTC | GAGTCTGGGGTGCTCAGGA |
| 1640 | CCTGAGCACCCCAGACTCC | GGAGTCTGGGGTGCTCAGG |
| 1641 | CTGAGCACCCCAGACTCCT | AGGAGTCTGGGGTGCTCAG |
| 1642 | TGAGCACCCCAGACTCCTG | CAGGAGTCTGGGGTGCTCA |
| 1643 | GAGCACCCCAGACTCCTGG | CCAGGAGTCTGGGGTGCTC |
| 1644 | AGCACCCCAGACTCCTGGC | GCCAGGAGTCTGGGGTGCT |
| 1645 | GCACCCCAGACTCCTGGCT | AGCCAGGAGTCTGGGGTGC |
| 1646 | CACCCCAGACTCCTGGCTT | AAGCCAGGAGTCTGGGGTG |
| 1647 | ACCCCAGACTCCTGGCTTC | GAAGCCAGGAGTCTGGGGT |
| 1648 | CCCCAGACTCCTGGCTTCC | GGAAGCCAGGAGTCTGGGG |
| 1649 | CCCAGACTCCTGGCTTCCC | GGGAAGCCAGGAGTCTGGG |
| 1650 | CCAGACTCCTGGCTTCCCC | GGGGAAGCCAGGAGTCTGG |
| 1651 | CAGACTCCTGGCTTCCCCC | GGGGGAAGCCAGGAGTCTG |
| 1652 | AGACTCCTGGCTTCCCCCT | AGGGGGAAGCCAGGAGTCT |
| 1653 | GACTCCTGGCTTCCCCCTG | CAGGGGGAAGCCAGGAGTC |
| 1654 | ACTCCTGGCTTCCCCCTGG | CCAGGGGGAAGCCAGGAGT |
| 1655 | CTCCTGGCTTCCCCCTGGC | GCCAGGGGGAAGCCAGGAG |
| 1656 | TCCTGGCTTCCCCCTGGCT | AGCCAGGGGGAAGCCAGGA |
| 1657 | CCTGGCTTCCCCCTGGCTT | AAGCCAGGGGGAAGCCAGG |
| 1658 | CTGGCTTCCCCCTGGCTTC | GAAGCCAGGGGGAAGCCAG |
| 1659 | TGGCTTCCCCCTGGCTTCC | GGAAGCCAGGGGGAAGCCA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 1660 | GGCTTCCCCCTGGCTTCCC | GGGAAGCCAGGGGGAAGCC |
| 1661 | GCTTCCCCCTGGCTTCCCC | GGGGAAGCCAGGGGGAAGC |
| 1662 | CTTCCCCCTGGCTTCCCCC | GGGGGAAGCCAGGGGGAAG |
| 1663 | TTCCCCCTGGCTTCCCCCA | TGGGGGAAGCCAGGGGGAA |
| 1664 | TCCCCCTGGCTTCCCCCAG | CTGGGGGAAGCCAGGGGGA |
| 1665 | CCCCCTGGCTTCCCCCAGG | CCTGGGGGAAGCCAGGGGG |
| 1666 | CCCCTGGCTTCCCCCAGGG | CCCTGGGGGAAGCCAGGGG |
| 1667 | CCCTGGCTTCCCCCAGGGC | GCCCTGGGGGAAGCCAGGG |
| 1668 | CCTGGCTTCCCCCAGGGCC | GGCCCTGGGGGAAGCCAGG |
| 1669 | CTGGCTTCCCCCAGGGCCC | GGGCCCTGGGGGAAGCCAG |
| 1670 | TGGCTTCCCCCAGGGCCCC | GGGGCCCTGGGGGAAGCCA |
| 1671 | GGCTTCCCCCAGGGCCCCA | TGGGGCCCTGGGGGAAGCC |
| 1672 | GCTTCCCCCAGGGCCCCAA | TTGGGGCCCTGGGGGAAGC |
| 1673 | CTTCCCCCAGGGCCCCAAG | CTTGGGGCCCTGGGGGAAG |
| 1674 | TTCCCCCAGGGCCCCAAGG | CCTTGGGGCCCTGGGGGAA |
| 1675 | TCCCCCAGGGCCCCAAGGA | TCCTTGGGGCCCTGGGGGA |
| 1676 | CCCCCAGGGCCCCAAGGAC | GTCCTTGGGGCCCTGGGGG |
| 1677 | CCCCAGGGCCCCAAGGACA | TGTCCTTGGGGCCCTGGGG |
| 1678 | CCCAGGGCCCCAAGGACAT | ATGTCCTTGGGGCCCTGGG |
| 1679 | CCAGGGCCCCAAGGACATG | CATGTCCTTGGGGCCCTGG |
| 1680 | CAGGGCCCCAAGGACATGC | GCATGTCCTTGGGGCCCTG |
| 1681 | AGGGCCCCAAGGACATGCT | AGCATGTCCTTGGGGCCCT |
| 1682 | GGGCCCCAAGGACATGCTC | GAGCATGTCCTTGGGGCCC |
| 1683 | GGCCCCAAGGACATGCTCC | GGAGCATGTCCTTGGGGCC |
| 1684 | GCCCCAAGGACATGCTCCC | GGGAGCATGTCCTTGGGGC |
| 1685 | CCCCAAGGACATGCTCCCA | TGGGAGCATGTCCTTGGGG |
| 1686 | CCCAAGGACATGCTCCCAC | GTGGGAGCATGTCCTTGGG |
| 1687 | CCAAGGACATGCTCCCACT | AGTGGGAGCATGTCCTTGG |
| 1688 | CAAGGACATGCTCCCACTT | AAGTGGGAGCATGTCCTTG |
| 1689 | AAGGACATGCTCCCACTTG | CAAGTGGGAGCATGTCCTT |
| 1690 | AGGACATGCTCCCACTTGT | ACAAGTGGGAGCATGTCCT |
| 1691 | GGACATGCTCCCACTTGTG | CACAAGTGGGAGCATGTCC |
| 1692 | GACATGCTCCCACTTGTGG | CCACAAGTGGGAGCATGTC |
| 1693 | ACATGCTCCCACTTGTGGA | TCCACAAGTGGGAGCATGT |
| 1694 | CATGCTCCCACTTGTGGAG | CTCCACAAGTGGGAGCATG |
| 1695 | ATGCTCCCACTTGTGGAGG | CCTCCACAAGTGGGAGCAT |
| 1696 | TGCTCCCACTTGTGGAGGG | CCCTCCACAAGTGGGAGCA |
| 1697 | GCTCCCACTTGTGGAGGGC | GCCCTCCACAAGTGGGAGC |
| 1698 | CTCCCACTTGTGGAGGGCG | CGCCCTCCACAAGTGGGAG |
| 1699 | TCCCACTTGTGGAGGGCGA | TCGCCCTCCACAAGTGGGA |
| 1700 | CCCACTTGTGGAGGGCGAG | CTCGCCCTCCACAAGTGGG |
| 1701 | CCACTTGTGGAGGGCGAGG | CCTCGCCCTCCACAAGTGG |
| 1702 | CACTTGTGGAGGGCGAGGG | CCCTCGCCCTCCACAAGTG |
| 1703 | ACTTGTGGAGGGCGAGGGC | GCCCTCGCCCTCCACAAGT |
| 1704 | CTTGTGGAGGGCGAGGGCC | GGCCCTCGCCCTCCACAAG |
| 1705 | TTGTGGAGGGCGAGGGCCC | GGGCCCTCGCCCTCCACAA |
| 1706 | TGTGGAGGGCGAGGGCCCC | GGGGCCCTCGCCCTCCACA |
| 1707 | GTGGAGGGCGAGGGCCCCC | GGGGGCCCTCGCCCTCCAC |
| 1708 | TGGAGGGCGAGGGCCCCCA | TGGGGGCCCTCGCCCTCCA |
| 1709 | GGAGGGCGAGGGCCCCCAG | CTGGGGGCCCTCGCCCTCC |
| 1710 | GAGGGCGAGGGCCCCCAGA | TCTGGGGGCCCTCGCCCTC |
| 1711 | AGGGCGAGGGCCCCCAGAA | TTCTGGGGGCCCTCGCCCT |
| 1712 | GGGCGAGGGCCCCCAGAAT | ATTCTGGGGGCCCTCGCCC |
| 1713 | GGCGAGGGCCCCCAGAATG | CATTCTGGGGGCCCTCGCC |
| 1714 | GCGAGGGCCCCCAGAATGG | CCATTCTGGGGGCCCTCGC |
| 1715 | CGAGGGCCCCCAGAATGGG | CCCATTCTGGGGGCCCTCG |
| 1716 | GAGGGCCCCCAGAATGGGG | CCCCATTCTGGGGGCCCTC |
| 1717 | AGGGCCCCCAGAATGGGGA | TCCCCATTCTGGGGGCCCT |
| 1718 | GGGCCCCCAGAATGGGGAG | CTCCCCATTCTGGGGGCCC |
| 1719 | GGCCCCCAGAATGGGGAGA | TCTCCCCATTCTGGGGGCC |
| 1720 | GCCCCCAGAATGGGGAGAG | CTCTCCCCATTCTGGGGGC |
| 1721 | CCCCCAGAATGGGGAGAGG | CCTCTCCCCATTCTGGGGG |
| 1722 | CCCCAGAATGGGGAGAGGA | TCCTCTCCCCATTCTGGGG |
| 1723 | CCCAGAATGGGGAGAGGAA | TTCCTCTCCCCATTCTGGG |
| 1724 | CCAGAATGGGGAGAGGAAG | CTTCCTCTCCCCATTCTGG |
| 1725 | CAGAATGGGGAGAGGAAGG | CCTTCCTCTCCCCATTCTG |
| 1726 | AGAATGGGGAGAGGAAGGT | ACCTTCCTCTCCCCATTCT |
| 1727 | GAATGGGGAGAGGAAGGTC | GACCTTCCTCTCCCCATTC |
| 1728 | AATGGGGAGAGGAAGGTCA | TGACCTTCCTCTCCCCATT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 1729 | ATGGGGAGAGGAAGGTCAA | TTGACCTTCCTCTCCCCAT |
| 1730 | TGGGGAGAGGAAGGTCAAC | GTTGACCTTCCTCTCCCCA |
| 1731 | GGGGAGAGGAAGGTCAACT | AGTTGACCTTCCTCTCCCC |
| 1732 | GGGAGAGGAAGGTCAACTG | CAGTTGACCTTCCTCTCCC |
| 1733 | GGAGAGGAAGGTCAACTGG | CCAGTTGACCTTCCTCTCC |
| 1734 | GAGAGGAAGGTCAACTGGC | GCCAGTTGACCTTCCTCTC |
| 1735 | AGAGGAAGGTCAACTGGCT | AGCCAGTTGACCTTCCTCT |
| 1736 | GAGGAAGGTCAACTGGCTG | CAGCCAGTTGACCTTCCTC |
| 1737 | AGGAAGGTCAACTGGCTGG | CCAGCCAGTTGACCTTCCT |
| 1738 | GGAAGGTCAACTGGCTGGG | CCCAGCCAGTTGACCTTCC |
| 1739 | GAAGGTCAACTGGCTGGGC | GCCCAGCCAGTTGACCTTC |
| 1740 | AAGGTCAACTGGCTGGGCA | TGCCCAGCCAGTTGACCTT |
| 1741 | AGGTCAACTGGCTGGGCAG | CTGCCCAGCCAGTTGACCT |
| 1742 | GGTCAACTGGCTGGGCAGC | GCTGCCCAGCCAGTTGACC |
| 1743 | GTCAACTGGCTGGGCAGCA | TGCTGCCCAGCCAGTTGAC |
| 1744 | TCAACTGGCTGGGCAGCAA | TTGCTGCCCAGCCAGTTGA |
| 1745 | CAACTGGCTGGGCAGCAAA | TTTGCTGCCCAGCCAGTTG |
| 1746 | AACTGGCTGGGCAGCAAAG | CTTTGCTGCCCAGCCAGTT |
| 1747 | ACTGGCTGGGCAGCAAAGA | TCTTTGCTGCCCAGCCAGT |
| 1748 | CTGGCTGGGCAGCAAAGAG | CTCTTTGCTGCCCAGCCAG |
| 1749 | TGGCTGGGCAGCAAAGAGG | CCTCTTTGCTGCCCAGCCA |
| 1750 | GGCTGGGCAGCAAAGAGGG | CCCTCTTTGCTGCCCAGCC |
| 1751 | GCTGGGCAGCAAAGAGGGA | TCCCTCTTTGCTGCCCAGC |
| 1752 | CTGGGCAGCAAAGAGGGAC | GTCCCTCTTTGCTGCCCAG |
| 1753 | TGGGCAGCAAAGAGGGACT | AGTCCCTCTTTGCTGCCCA |
| 1754 | GGGCAGCAAAGAGGGACTG | CAGTCCCTCTTTGCTGCCC |
| 1755 | GGCAGCAAAGAGGGACTGC | GCAGTCCCTCTTTGCTGCC |
| 1756 | GCAGCAAAGAGGGACTGCG | CGCAGTCCCTCTTTGCTGC |
| 1757 | CAGCAAAGAGGGACTGCGC | GCGCAGTCCCTCTTTGCTG |
| 1758 | AGCAAAGAGGGACTGCGCT | AGCGCAGTCCCTCTTTGCT |
| 1759 | GCAAAGAGGGACTGCGCTG | CAGCGCAGTCCCTCTTTGC |
| 1760 | CAAAGAGGGACTGCGCTGG | CCAGCGCAGTCCCTCTTTG |
| 1761 | AAAGAGGGACTGCGCTGGA | TCCAGCGCAGTCCCTCTTT |
| 1762 | AAGAGGGACTGCGCTGGAA | TTCCAGCGCAGTCCCTCTT |
| 1763 | AGAGGGACTGCGCTGGAAG | CTTCCAGCGCAGTCCCTCT |
| 1764 | GAGGGACTGCGCTGGAAGG | CCTTCCAGCGCAGTCCCTC |
| 1765 | AGGGACTGCGCTGGAAGGA | TCCTTCCAGCGCAGTCCCT |
| 1766 | GGGACTGCGCTGGAAGGAG | CTCCTTCCAGCGCAGTCCC |
| 1767 | GGACTGCGCTGGAAGGAGG | CCTCCTTCCAGCGCAGTCC |
| 1768 | GACTGCGCTGGAAGGAGGC | GCCTCCTTCCAGCGCAGTC |
| 1769 | ACTGCGCTGGAAGGAGGCC | GGCCTCCTTCCAGCGCAGT |
| 1770 | CTGCGCTGGAAGGAGGCCA | TGGCCTCCTTCCAGCGCAG |
| 1771 | TGCGCTGGAAGGAGGCCAT | ATGGCCTCCTTCCAGCGCA |
| 1772 | GCGCTGGAAGGAGGCCATG | CATGGCCTCCTTCCAGCGC |
| 1773 | CGCTGGAAGGAGGCCATGC | GCATGGCCTCCTTCCAGCG |
| 1774 | GCTGGAAGGAGGCCATGCT | AGCATGGCCTCCTTCCAGC |
| 1775 | CTGGAAGGAGGCCATGCTT | AAGCATGGCCTCCTTCCAG |
| 1776 | TGGAAGGAGGCCATGCTTA | TAAGCATGGCCTCCTTCCA |
| 1777 | GGAAGGAGGCCATGCTTAC | GTAAGCATGGCCTCCTTCC |
| 1778 | GAAGGAGGCCATGCTTACC | GGTAAGCATGGCCTCCTTC |
| 1779 | AAGGAGGCCATGCTTACCC | GGGTAAGCATGGCCTCCTT |
| 1780 | AGGAGGCCATGCTTACCCA | TGGGTAAGCATGGCCTCCT |
| 1781 | GGAGGCCATGCTTACCCAT | ATGGGTAAGCATGGCCTCC |
| 1782 | GAGGCCATGCTTACCCATC | GATGGGTAAGCATGGCCTC |
| 1783 | AGGCCATGCTTACCCATCC | GGATGGGTAAGCATGGCCT |
| 1784 | GGCCATGCTTACCCATCCG | CGGATGGGTAAGCATGGCC |
| 1785 | GCCATGCTTACCCATCCGC | GCGGATGGGTAAGCATGGC |
| 1786 | CCATGCTTACCCATCCGCT | AGCGGATGGGTAAGCATGG |
| 1787 | CATGCTTACCCATCCGCTG | CAGCGGATGGGTAAGCATG |
| 1788 | ATGCTTACCCATCCGCTGG | CCAGCGGATGGGTAAGCAT |
| 1789 | TGCTTACCCATCCGCTGGC | GCCAGCGGATGGGTAAGCA |
| 1790 | GCTTACCCATCCGCTGGCA | TGCCAGCGGATGGGTAAGC |
| 1791 | CTTACCCATCCGCTGGCAT | ATGCCAGCGGATGGGTAAG |
| 1792 | TTACCCATCCGCTGGCATT | AATGCCAGCGGATGGGTAA |
| 1793 | TACCCATCCGCTGGCATTC | GAATGCCAGCGGATGGGTA |
| 1794 | ACCCATCCGCTGGCATTCT | AGAATGCCAGCGGATGGGT |
| 1795 | CCCATCCGCTGGCATTCTG | CAGAATGCCAGCGGATGGG |
| 1796 | CCATCCGCTGGCATTCTGC | GCAGAATGCCAGCGGATGG |
| 1797 | CATCCGCTGGCATTCTGCG | CGCAGAATGCCAGCGGATG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X - 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1798 | ATCCGCTGGCATTCTGCGG | CCGCAGAATGCCAGCGGAT |
| 1799 | TCCGCTGGCATTCTGCGGG | CCCGCAGAATGCCAGCGGA |
| 1800 | CCGCTGGCATTCTGCGGGC | GCCCGCAGAATGCCAGCGG |
| 1801 | CGCTGGCATTCTGCGGGCC | GGCCCGCAGAATGCCAGCG |
| 1802 | GCTGGCATTCTGCGGGCCA | TGGCCCGCAGAATGCCAGC |
| 1803 | CTGGCATTCTGCGGGCCAG | CTGGCCCGCAGAATGCCAG |
| 1804 | TGGCATTCTGCGGGCCAGC | GCTGGCCCGCAGAATGCCA |
| 1805 | GGCATTCTGCGGGCCAGCG | CGCTGGCCCGCAGAATGCC |
| 1806 | GCATTCTGCGGGCCAGCGT | ACGCTGGCCCGCAGAATGC |
| 1807 | CATTCTGCGGGCCAGCGTG | CACGCTGGCCCGCAGAATG |
| 1808 | ATTCTGCGGGCCAGCGTGC | GCACGCTGGCCCGCAGAAT |
| 1809 | TTCTGCGGGCCAGCGTGCC | GGCACGCTGGCCCGCAGAA |
| 1810 | TCTGCGGGCCAGCGTGCCC | GGGCACGCTGGCCCGCAGA |
| 1811 | CTGCGGGCCAGCGTGCCCA | TGGGCACGCTGGCCCGCAG |
| 1812 | TGCGGGCCAGCGTGCCCAC | GTGGGCACGCTGGCCCGCA |
| 1813 | GCGGGCCAGCGTGCCCACC | GGTGGGCACGCTGGCCCGC |
| 1814 | CGGGCCAGCGTGCCCACCT | AGGTGGGCACGCTGGCCCG |
| 1815 | GGGCCAGCGTGCCCACCTC | GAGGTGGGCACGCTGGCCC |
| 1816 | GGCCAGCGTGCCCACCTCG | CGAGGTGGGCACGCTGGCC |
| 1817 | GCCAGCGTGCCCACCTCGC | GCGAGGTGGGCACGCTGGC |
| 1818 | CCAGCGTGCCCACCTCGCT | AGCGAGGTGGGCACGCTGG |
| 1819 | CAGCGTGCCCACCTCGCTG | CAGCGAGGTGGGCACGCTG |
| 1820 | AGCGTGCCCACCTCGCTGT | ACAGCGAGGTGGGCACGCT |
| 1821 | GCGTGCCCACCTCGCTGTG | CACAGCGAGGTGGGCACGC |
| 1822 | CGTGCCCACCTCGCTGTGG | CCACAGCGAGGTGGGCACG |
| 1823 | GTGCCCACCTCGCTGTGGC | GCCACAGCGAGGTGGGCAC |
| 1824 | TGCCCACCTCGCTGTGGCC | GGCCACAGCGAGGTGGGCA |
| 1825 | GCCCACCTCGCTGTGGCCC | GGGCCACAGCGAGGTGGGC |
| 1826 | CCCACCTCGCTGTGGCCCC | GGGGCCACAGCGAGGTGGG |
| 1827 | CCACCTCGCTGTGGCCCCC | GGGGGCCACAGCGAGGTGG |
| 1828 | CACCTCGCTGTGGCCCCCT | AGGGGGCCACAGCGAGGTG |
| 1829 | ACCTCGCTGTGGCCCCCTG | CAGGGGGCCACAGCGAGGT |
| 1830 | CCTCGCTGTGGCCCCCTGA | TCAGGGGGCCACAGCGAGG |
| 1831 | CTCGCTGTGGCCCCCTGAT | ATCAGGGGGCCACAGCGAG |
| 1832 | TCGCTGTGGCCCCCTGATG | CATCAGGGGGCCACAGCGA |
| 1833 | CGCTGTGGCCCCCTGATGC | GCATCAGGGGGCCACAGCG |
| 1834 | GCTGTGGCCCCCTGATGCC | GGCATCAGGGGGCCACAGC |
| 1835 | CTGTGGCCCCCTGATGCCT | AGGCATCAGGGGGCCACAG |
| 1836 | TGTGGCCCCCTGATGCCTG | CAGGCATCAGGGGGCCACA |
| 1837 | GTGGCCCCCTGATGCCTGA | TCAGGCATCAGGGGGCCAC |
| 1838 | TGGCCCCCTGATGCCTGAG | CTCAGGCATCAGGGGGCCA |
| 1839 | GGCCCCCTGATGCCTGAGC | GCTCAGGCATCAGGGGGCC |
| 1840 | GCCCCCTGATGCCTGAGCA | TGCTCAGGCATCAGGGGGC |
| 1841 | CCCCCTGATGCCTGAGCAT | ATGCTCAGGCATCAGGGGG |
| 1842 | CCCCTGATGCCTGAGCATA | TATGCTCAGGCATCAGGGG |
| 1843 | CCCTGATGCCTGAGCATAG | CTATGCTCAGGCATCAGGG |
| 1844 | CCTGATGCCTGAGCATAGT | ACTATGCTCAGGCATCAGG |
| 1845 | CTGATGCCTGAGCATAGTG | CACTATGCTCAGGCATCAG |
| 1846 | TGATGCCTGAGCATAGTGG | CCACTATGCTCAGGCATCA |
| 1847 | GATGCCTGAGCATAGTGGT | ACCACTATGCTCAGGCATC |
| 1848 | ATGCCTGAGCATAGTGGTG | CACCACTATGCTCAGGCAT |
| 1849 | TGCCTGAGCATAGTGGTGG | CCACCACTATGCTCAGGCA |
| 1850 | GCCTGAGCATAGTGGTGGC | GCCACCACTATGCTCAGGC |
| 1851 | CCTGAGCATAGTGGTGGCC | GGCCACCACTATGCTCAGG |
| 1852 | CTGAGCATAGTGGTGGCCA | TGGCCACCACTATGCTCAG |
| 1853 | TGAGCATAGTGGTGGCCAT | ATGGCCACCACTATGCTCA |
| 1854 | GAGCATAGTGGTGGCCATC | GATGGCCACCACTATGCTC |
| 1855 | AGCATAGTGGTGGCCATCT | AGATGGCCACCACTATGCT |
| 1856 | GCATAGTGGTGGCCATCTC | GAGATGGCCACCACTATGC |
| 1857 | CATAGTGGTGGCCATCTCA | TGAGATGGCCACCACTATG |
| 1858 | ATAGTGGTGGCCATCTCAA | TTGAGATGGCCACCACTAT |
| 1859 | TAGTGGTGGCCATCTCAAG | CTTGAGATGGCCACCACTA |
| 1860 | AGTGGTGGCCATCTCAAGA | TCTTGAGATGGCCACCACT |
| 1861 | GTGGTGGCCATCTCAAGAG | CTCTTGAGATGGCCACCAC |
| 1862 | TGGTGGCCATCTCAAGAGT | ACTCTTGAGATGGCCACCA |
| 1863 | GGTGGCCATCTCAAGAGTG | CACTCTTGAGATGGCCACC |
| 1864 | GTGGCCATCTCAAGAGTGA | TCACTCTTGAGATGGCCAC |
| 1865 | TGGCCATCTCAAGAGTGAC | GTCACTCTTGAGATGGCCA |
| 1866 | GGCCATCTCAAGAGTGACC | GGTCACTCTTGAGATGGCC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X – 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1867 | GCCATCTCAAGAGTGACCC | GGGTCACTCTTGAGATGGC |
| 1868 | CCATCTCAAGAGTGACCCT | AGGGTCACTCTTGAGATGG |
| 1869 | CATCTCAAGAGTGACCCTG | CAGGGTCACTCTTGAGATG |
| 1870 | ATCTCAAGAGTGACCCTGT | ACAGGGTCACTCTTGAGAT |
| 1871 | TCTCAAGAGTGACCCTGTG | CACAGGGTCACTCTTGAGA |
| 1872 | CTCAAGAGTGACCCTGTGG | CCACAGGGTCACTCTTGAG |
| 1873 | TCAAGAGTGACCCTGTGGC | GCCACAGGGTCACTCTTGA |
| 1874 | CAAGAGTGACCCTGTGGCC | GGCCACAGGGTCACTCTTG |
| 1875 | AAGAGTGACCCTGTGGCCT | AGGCCACAGGGTCACTCTT |
| 1876 | AGAGTGACCCTGTGGCCTT | AAGGCCACAGGGTCACTCT |
| 1877 | GAGTGACCCTGTGGCCTTC | GAAGGCCACAGGGTCACTC |
| 1878 | AGTGACCCTGTGGCCTTCC | GGAAGGCCACAGGGTCACT |
| 1879 | GTGACCCTGTGGCCTTCCG | CGGAAGGCCACAGGGTCAC |
| 1880 | TGACCCTGTGGCCTTCCGG | CCGGAAGGCCACAGGGTCA |
| 1881 | GACCCTGTGGCCTTCCGGC | GCCGGAAGGCCACAGGGTC |
| 1882 | ACCCTGTGGCCTTCCGGCC | GGCCGGAAGGCCACAGGGT |
| 1883 | CCCTGTGGCCTTCCGGCCC | GGGCCGGAAGGCCACAGGG |
| 1884 | CCTGTGGCCTTCCGGCCCT | AGGGCCGGAAGGCCACAGG |
| 1885 | CTGTGGCCTTCCGGCCCTG | CAGGGCCGGAAGGCCACAG |
| 1886 | TGTGGCCTTCCGGCCCTGG | CCAGGGCCGGAAGGCCACA |
| 1887 | GTGGCCTTCCGGCCCTGGC | GCCAGGGCCGGAAGGCCAC |
| 1888 | TGGCCTTCCGGCCCTGGCA | TGCCAGGGCCGGAAGGCCA |
| 1889 | GGCCTTCCGGCCCTGGCAC | GTGCCAGGGCCGGAAGGCC |
| 1890 | GCCTTCCGGCCCTGGCACT | AGTGCCAGGGCCGGAAGGC |
| 1891 | CCTTCCGGCCCTGGCACTG | CAGTGCCAGGGCCGGAAGG |
| 1892 | CTTCCGGCCCTGGCACTGC | GCAGTGCCAGGGCCGGAAG |
| 1893 | TTCCGGCCCTGGCACTGCC | GGCAGTGCCAGGGCCGGAA |
| 1894 | TCCGGCCCTGGCACTGCCC | GGGCAGTGCCAGGGCCGGA |
| 1895 | CCGGCCCTGGCACTGCCCT | AGGGCAGTGCCAGGGCCGG |
| 1896 | CGGCCCTGGCACTGCCCTT | AAGGGCAGTGCCAGGGCCG |
| 1897 | GGCCCTGGCACTGCCCTTT | AAAGGGCAGTGCCAGGGCC |
| 1898 | GCCCTGGCACTGCCCTTTC | GAAAGGGCAGTGCCAGGGC |
| 1899 | CCCTGGCACTGCCCTTTCC | GGAAAGGGCAGTGCCAGGG |
| 1900 | CCTGGCACTGCCCTTTCCT | AGGAAAGGGCAGTGCCAGG |
| 1901 | CTGGCACTGCCCTTTCCTT | AAGGAAAGGGCAGTGCCAG |
| 1902 | TGGCACTGCCCTTTCCTTC | GAAGGAAAGGGCAGTGCCA |
| 1903 | GGCACTGCCCTTTCCTTCT | AGAAGGAAAGGGCAGTGCC |
| 1904 | GCACTGCCCTTTCCTTCTG | CAGAAGGAAAGGGCAGTGC |
| 1905 | CACTGCCCTTTCCTTCTGG | CCAGAAGGAAAGGGCAGTG |
| 1906 | ACTGCCCTTTCCTTCTGGA | TCCAGAAGGAAAGGGCAGT |
| 1907 | CTGCCCTTTCCTTCTGGAG | CTCCAGAAGGAAAGGGCAG |
| 1908 | TGCCCTTTCCTTCTGGAGA | TCTCCAGAAGGAAAGGGCA |
| 1909 | GCCCTTTCCTTCTGGAGAC | GTCTCCAGAAGGAAAGGGC |
| 1910 | CCCTTTCCTTCTGGAGACC | GGTCTCCAGAAGGAAAGGG |
| 1911 | CCTTTCCTTCTGGAGACCA | TGGTCTCCAGAAGGAAAGG |
| 1912 | CTTTCCTTCTGGAGACCAA | TTGGTCTCCAGAAGGAAAG |
| 1913 | TTTCCTTCTGGAGACCAAG | CTTGGTCTCCAGAAGGAAA |
| 1914 | TTCCTTCTGGAGACCAAGA | TCTTGGTCTCCAGAAGGAA |
| 1915 | TCCTTCTGGAGACCAAGAT | ATCTTGGTCTCCAGAAGGA |
| 1916 | CCTTCTGGAGACCAAGATC | GATCTTGGTCTCCAGAAGG |
| 1917 | CTTCTGGAGACCAAGATCC | GGATCTTGGTCTCCAGAAG |
| 1918 | TTCTGGAGACCAAGATCCT | AGGATCTTGGTCTCCAGAA |
| 1919 | TCTGGAGACCAAGATCCTG | CAGGATCTTGGTCTCCAGA |
| 1920 | CTGGAGACCAAGATCCTGG | CCAGGATCTTGGTCTCCAG |
| 1921 | TGGAGACCAAGATCCTGGA | TCCAGGATCTTGGTCTCCA |
| 1922 | GGAGACCAAGATCCTGGAG | CTCCAGGATCTTGGTCTCC |
| 1923 | GAGACCAAGATCCTGGAGC | GCTCCAGGATCTTGGTCTC |
| 1924 | AGACCAAGATCCTGGAGCG | CGCTCCAGGATCTTGGTCT |
| 1925 | GACCAAGATCCTGGAGCGA | TCGCTCCAGGATCTTGGTC |
| 1926 | ACCAAGATCCTGGAGCGAG | CTCGCTCCAGGATCTTGGT |
| 1927 | CCAAGATCCTGGAGCGAGC | GCTCGCTCCAGGATCTTGG |
| 1928 | CAAGATCCTGGAGCGAGCT | AGCTCGCTCCAGGATCTTG |
| 1929 | AAGATCCTGGAGCGAGCTC | GAGCTCGCTCCAGGATCTT |
| 1930 | AGATCCTGGAGCGAGCTCC | GGAGCTCGCTCCAGGATCT |
| 1931 | GATCCTGGAGCGAGCTCCC | GGGAGCTCGCTCCAGGATC |
| 1932 | ATCCTGGAGCGAGCTCCCT | AGGGAGCTCGCTCCAGGAT |
| 1933 | TCCTGGAGCGAGCTCCCTT | AAGGGAGCTCGCTCCAGGA |
| 1934 | CCTGGAGCGAGCTCCCTTC | GAAGGGAGCTCGCTCCAGG |
| 1935 | CTGGAGCGAGCTCCCTTCT | AGAAGGGAGCTCGCTCCAG |

TABLE 1-continued cDNA Human Hairless 19-mer Target Sequences and Complement Referenced to NM_005144-
*Homo sapiens* hairless homolog (mouse) (HR), transcript variant 1, complete mRNA (1-5699 bp).
(SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 1936 | TGGAGCGAGCTCCCTTCTG | CAGAAGGGAGCTCGCTCCA |
| 1937 | GGAGCGAGCTCCCTTCTGG | CCAGAAGGGAGCTCGCTCC |
| 1938 | GAGCGAGCTCCCTTCTGGG | CCCAGAAGGGAGCTCGCTC |
| 1939 | AGCGAGCTCCCTTCTGGGT | ACCCAGAAGGGAGCTCGCT |
| 1940 | GCGAGCTCCCTTCTGGGTG | CACCCAGAAGGGAGCTCGC |
| 1941 | CGAGCTCCCTTCTGGGTGC | GCACCCAGAAGGGAGCTCG |
| 1942 | GAGCTCCCTTCTGGGTGCC | GGCACCCAGAAGGGAGCTC |
| 1943 | AGCTCCCTTCTGGGTGCCC | GGGCACCCAGAAGGGAGCT |
| 1944 | GCTCCCTTCTGGGTGCCCA | TGGGCACCCAGAAGGGAGC |
| 1945 | CTCCCTTCTGGGTGCCCAC | GTGGGCACCCAGAAGGGAG |
| 1946 | TCCCTTCTGGGTGCCCACC | GGTGGGCACCCAGAAGGGA |
| 1947 | CCCTTCTGGGTGCCCACCT | AGGTGGGCACCCAGAAGGG |
| 1948 | CCTTCTGGGTGCCCACCTG | CAGGTGGGCACCCAGAAGG |
| 1949 | CTTCTGGGTGCCCACCTGC | GCAGGTGGGCACCCAGAAG |
| 1950 | TTCTGGGTGCCCACCTGCT | AGCAGGTGGGCACCCAGAA |
| 1951 | TCTGGGTGCCCACCTGCTT | AAGCAGGTGGGCACCCAGA |
| 1952 | CTGGGTGCCCACCTGCTTG | CAAGCAGGTGGGCACCCAG |
| 1953 | TGGGTGCCCACCTGCTTGC | GCAAGCAGGTGGGCACCCA |
| 1954 | GGGTGCCCACCTGCTTGCC | GGCAAGCAGGTGGGCACCC |
| 1955 | GGTGCCCACCTGCTTGCCA | TGGCAAGCAGGTGGGCACC |
| 1956 | GTGCCCACCTGCTTGCCAC | GTGGCAAGCAGGTGGGCAC |
| 1957 | TGCCCACCTGCTTGCCACC | GGTGGCAAGCAGGTGGGCA |
| 1958 | GCCCACCTGCTTGCCACCC | GGGTGGCAAGCAGGTGGGC |
| 1959 | CCCACCTGCTTGCCACCCT | AGGGTGGCAAGCAGGTGGG |
| 1960 | CCACCTGCTTGCCACCCTA | TAGGGTGGCAAGCAGGTGG |
| 1961 | CACCTGCTTGCCACCCTAC | GTAGGGTGGCAAGCAGGTG |
| 1962 | ACCTGCTTGCCACCCTACC | GGTAGGGTGGCAAGCAGGT |
| 1963 | CCTGCTTGCCACCCTACCT | AGGTAGGGTGGCAAGCAGG |
| 1964 | CTGCTTGCCACCCTACCTA | TAGGTAGGGTGGCAAGCAG |
| 1965 | TGCTTGCCACCCTACCTAG | CTAGGTAGGGTGGCAAGCA |
| 1966 | GCTTGCCACCCTACCTAGT | ACTAGGTAGGGTGGCAAGC |
| 1967 | CTTGCCACCCTACCTAGTG | CACTAGGTAGGGTGGCAAG |
| 1968 | TTGCCACCCTACCTAGTGT | ACACTAGGTAGGGTGGCAA |
| 1969 | TGCCACCCTACCTAGTGTC | GACACTAGGTAGGGTGGCA |
| 1970 | GCCACCCTACCTAGTGTCT | AGACACTAGGTAGGGTGGC |
| 1971 | CCACCCTACCTAGTGTCTG | CAGACACTAGGTAGGGTGG |
| 1972 | CACCCTACCTAGTGTCTGG | CCAGACACTAGGTAGGGTG |
| 1973 | ACCCTACCTAGTGTCTGGC | GCCAGACACTAGGTAGGGT |
| 1974 | CCCTACCTAGTGTCTGGCC | GGCCAGACACTAGGTAGGG |
| 1975 | CCTACCTAGTGTCTGGCCT | AGGCCAGACACTAGGTAGG |
| 1976 | CTACCTAGTGTCTGGCCTG | CAGGCCAGACACTAGGTAG |
| 1977 | TACCTAGTGTCTGGCCTGC | GCAGGCCAGACACTAGGTA |
| 1978 | ACCTAGTGTCTGGCCTGCC | GGCAGGCCAGACACTAGGT |
| 1979 | CCTAGTGTCTGGCCTGCCC | GGGCAGGCCAGACACTAGG |
| 1980 | CTAGTGTCTGGCCTGCCCC | GGGGCAGGCCAGACACTAG |
| 1981 | TAGTGTCTGGCCTGCCCCC | GGGGGCAGGCCAGACACTA |
| 1982 | AGTGTCTGGCCTGCCCCCA | TGGGGGCAGGCCAGACACT |
| 1983 | GTGTCTGGCCTGCCCCCAG | CTGGGGGCAGGCCAGACAC |
| 1984 | TGTCTGGCCTGCCCCCAGA | TCTGGGGGCAGGCCAGACA |
| 1985 | GTCTGGCCTGCCCCCAGAG | CTCTGGGGGCAGGCCAGAC |
| 1986 | TCTGGCCTGCCCCCAGAGC | GCTCTGGGGGCAGGCCAGA |
| 1987 | CTGGCCTGCCCCCAGAGCA | TGCTCTGGGGGCAGGCCAG |
| 1988 | TGGCCTGCCCCCAGAGCAT | ATGCTCTGGGGGCAGGCCA |
| 1989 | GGCCTGCCCCCAGAGCATC | GATGCTCTGGGGGCAGGCC |
| 1990 | GCCTGCCCCCAGAGCATCC | GGATGCTCTGGGGGCAGGC |
| 1991 | CCTGCCCCCAGAGCATCCA | TGGATGCTCTGGGGGCAGG |
| 1992 | CTGCCCCCAGAGCATCCAT | ATGGATGCTCTGGGGGCAG |
| 1993 | TGCCCCCAGAGCATCCATG | CATGGATGCTCTGGGGGCA |
| 1994 | GCCCCCAGAGCATCCATGT | ACATGGATGCTCTGGGGGC |
| 1995 | CCCCCAGAGCATCCATGTG | CACATGGATGCTCTGGGGG |
| 1996 | CCCCAGAGCATCCATGTGA | TCACATGGATGCTCTGGGG |
| 1997 | CCCAGAGCATCCATGTGAC | GTCACATGGATGCTCTGGG |
| 1998 | CCAGAGCATCCATGTGACT | AGTCACATGGATGCTCTGG |
| 1999 | CAGAGCATCCATGTGACTG | CAGTCACATGGATGCTCTG |
| 2000 | AGAGCATCCATGTGACTGG | CCAGTCACATGGATGCTCT |
| 2001 | GAGCATCCATGTGACTGGC | GCCAGTCACATGGATGCTC |
| 2002 | AGCATCCATGTGACTGGCC | GGCCAGTCACATGGATGCT |
| 2003 | GCATCCATGTGACTGGCCC | GGGCCAGTCACATGGATGC |
| 2004 | CATCCATGTGACTGGCCCC | GGGGCCAGTCACATGGATG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X – 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2005 | ATCCATGTGACTGGCCCCT | AGGGGCCAGTCACATGGAT |
| 2006 | TCCATGTGACTGGCCCCTG | CAGGGGCCAGTCACATGGA |
| 2007 | CCATGTGACTGGCCCCTGA | TCAGGGGCCAGTCACATGG |
| 2008 | CATGTGACTGGCCCCTGAC | GTCAGGGGCCAGTCACATG |
| 2009 | ATGTGACTGGCCCCTGACC | GGTCAGGGGCCAGTCACAT |
| 2010 | TGTGACTGGCCCCTGACCC | GGGTCAGGGGCCAGTCACA |
| 2011 | GTGACTGGCCCCTGACCCC | GGGGTCAGGGGCCAGTCAC |
| 2012 | TGACTGGCCCCTGACCCCG | CGGGGTCAGGGGCCAGTCA |
| 2013 | GACTGGCCCCTGACCCCGC | GCGGGGTCAGGGGCCAGTC |
| 2014 | ACTGGCCCCTGACCCCGCA | TGCGGGGTCAGGGGCCAGT |
| 2015 | CTGGCCCCTGACCCCGCAC | GTGCGGGGTCAGGGGCCAG |
| 2016 | TGGCCCCTGACCCCGCACC | GGTGCGGGGTCAGGGGCCA |
| 2017 | GGCCCCTGACCCCGCACCC | GGGTGCGGGGTCAGGGGCC |
| 2018 | GCCCCTGACCCCGCACCCC | GGGGTGCGGGGTCAGGGGC |
| 2019 | CCCCTGACCCCGCACCCCT | AGGGGTGCGGGGTCAGGGG |
| 2020 | CCCTGACCCCGCACCCCTG | CAGGGGTGCGGGGTCAGGG |
| 2021 | CCTGACCCCGCACCCCTGG | CCAGGGGTGCGGGGTCAGG |
| 2022 | CTGACCCCGCACCCCTGGG | CCCAGGGGTGCGGGGTCAG |
| 2023 | TGACCCCGCACCCCTGGGT | ACCCAGGGGTGCGGGGTCA |
| 2024 | GACCCCGCACCCCTGGGTA | TACCCAGGGGTGCGGGGTC |
| 2025 | ACCCCGCACCCCTGGGTAT | ATACCCAGGGGTGCGGGGT |
| 2026 | CCCCGCACCCCTGGGTATA | TATACCCAGGGGTGCGGGG |
| 2027 | CCCGCACCCCTGGGTATAC | GTATACCCAGGGGTGCGGG |
| 2028 | CCGCACCCCTGGGTATACT | AGTATACCCAGGGGTGCGG |
| 2029 | CGCACCCCTGGGTATACTC | GAGTATACCCAGGGGTGCG |
| 2030 | GCACCCCTGGGTATACTCC | GGAGTATACCCAGGGGTGC |
| 2031 | CACCCCTGGGTATACTCCG | CGGAGTATACCCAGGGGTG |
| 2032 | ACCCCTGGGTATACTCCGG | CCGGAGTATACCCAGGGGT |
| 2033 | CCCCTGGGTATACTCCGGG | CCCGGAGTATACCCAGGGG |
| 2034 | CCCTGGGTATACTCCGGGG | CCCCGGAGTATACCCAGGG |
| 2035 | CCTGGGTATACTCCGGGGG | CCCCCGGAGTATACCCAGG |
| 2036 | CTGGGTATACTCCGGGGGC | GCCCCCGGAGTATACCCAG |
| 2037 | TGGGTATACTCCGGGGGCC | GGCCCCCGGAGTATACCCA |
| 2038 | GGGTATACTCCGGGGGCCA | TGGCCCCCGGAGTATACCC |
| 2039 | GGTATACTCCGGGGGCCAG | CTGGCCCCCGGAGTATACC |
| 2040 | GTATACTCCGGGGGCCAGC | GCTGGCCCCCGGAGTATAC |
| 2041 | TATACTCCGGGGGCCAGCC | GGCTGGCCCCCGGAGTATA |
| 2042 | ATACTCCGGGGGCCAGCCC | GGGCTGGCCCCCGGAGTAT |
| 2043 | TACTCCGGGGGCCAGCCCA | TGGGCTGGCCCCCGGAGTA |
| 2044 | ACTCCGGGGGCCAGCCCAA | TTGGGCTGGCCCCCGGAGT |
| 2045 | CTCCGGGGGCCAGCCCAAA | TTTGGGCTGGCCCCCGGAG |
| 2046 | TCCGGGGGCCAGCCCAAAG | CTTTGGGCTGGCCCCCGGA |
| 2047 | CCGGGGGCCAGCCCAAAGT | ACTTTGGGCTGGCCCCCGG |
| 2048 | CGGGGGCCAGCCCAAAGTG | CACTTTGGGCTGGCCCCCG |
| 2049 | GGGGGCCAGCCCAAAGTGC | GCACTTTGGGCTGGCCCCC |
| 2050 | GGGGCCAGCCCAAAGTGCC | GGCACTTTGGGCTGGCCCC |
| 2051 | GGGCCAGCCCAAAGTGCCC | GGGCACTTTGGGCTGGCCC |
| 2052 | GGCCAGCCCAAAGTGCCCT | AGGGCACTTTGGGCTGGCC |
| 2053 | GCCAGCCCAAAGTGCCCTC | GAGGGCACTTTGGGCTGGC |
| 2054 | CCAGCCCAAAGTGCCCTCT | AGAGGGCACTTTGGGCTGG |
| 2055 | CAGCCCAAAGTGCCCTCTG | CAGAGGGCACTTTGGGCTG |
| 2056 | AGCCCAAAGTGCCCTCTGC | GCAGAGGGCACTTTGGGCT |
| 2057 | GCCCAAAGTGCCCTCTGCC | GGCAGAGGGCACTTTGGGC |
| 2058 | CCCAAAGTGCCCTCTGCCT | AGGCAGAGGGCACTTTGGG |
| 2059 | CCAAAGTGCCCTCTGCCTT | AAGGCAGAGGGCACTTTGG |
| 2060 | CAAAGTGCCCTCTGCCTTC | GAAGGCAGAGGGCACTTTG |
| 2061 | AAAGTGCCCTCTGCCTTCA | TGAAGGCAGAGGGCACTTT |
| 2062 | AAGTGCCCTCTGCCTTCAG | CTGAAGGCAGAGGGCACTT |
| 2063 | AGTGCCCTCTGCCTTCAGC | GCTGAAGGCAGAGGGCACT |
| 2064 | GTGCCCTCTGCCTTCAGCT | AGCTGAAGGCAGAGGGCAC |
| 2065 | TGCCCTCTGCCTTCAGCTT | AAGCTGAAGGCAGAGGGCA |
| 2066 | GCCCTCTGCCTTCAGCTTA | TAAGCTGAAGGCAGAGGGC |
| 2067 | CCCTCTGCCTTCAGCTTAG | CTAAGCTGAAGGCAGAGGG |
| 2068 | CCTCTGCCTTCAGCTTAGG | CCTAAGCTGAAGGCAGAGG |
| 2069 | CTCTGCCTTCAGCTTAGGC | GCCTAAGCTGAAGGCAGAG |
| 2070 | TCTGCCTTCAGCTTAGGCA | TGCCTAAGCTGAAGGCAGA |
| 2071 | CTGCCTTCAGCTTAGGCAG | CTGCCTAAGCTGAAGGCAG |
| 2072 | TGCCTTCAGCTTAGGCAGC | GCTGCCTAAGCTGAAGGCA |
| 2073 | GCCTTCAGCTTAGGCAGCA | TGCTGCCTAAGCTGAAGGC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X – 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2074 | CCTTCAGCTTAGGCAGCAA | TTGCTGCCTAAGCTGAAGG |
| 2075 | CTTCAGCTTAGGCAGCAAG | CTTGCTGCCTAAGCTGAAG |
| 2076 | TTCAGCTTAGGCAGCAAGG | CCTTGCTGCCTAAGCTGAA |
| 2077 | TCAGCTTAGGCAGCAAGGG | CCCTTGCTGCCTAAGCTGA |
| 2078 | CAGCTTAGGCAGCAAGGGC | GCCCTTGCTGCCTAAGCTG |
| 2079 | AGCTTAGGCAGCAAGGGCT | AGCCCTTGCTGCCTAAGCT |
| 2080 | GCTTAGGCAGCAAGGGCTT | AAGCCCTTGCTGCCTAAGC |
| 2081 | CTTAGGCAGCAAGGGCTTT | AAAGCCCTTGCTGCCTAAG |
| 2082 | TTAGGCAGCAAGGGCTTTT | AAAAGCCCTTGCTGCCTAA |
| 2083 | TAGGCAGCAAGGGCTTTTA | TAAAAGCCCTTGCTGCCTA |
| 2084 | AGGCAGCAAGGGCTTTTAC | GTAAAAGCCCTTGCTGCCT |
| 2085 | GGCAGCAAGGGCTTTTACT | AGTAAAAGCCCTTGCTGCC |
| 2086 | GCAGCAAGGGCTTTTACTA | TAGTAAAAGCCCTTGCTGC |
| 2087 | CAGCAAGGGCTTTTACTAC | GTAGTAAAAGCCCTTGCTG |
| 2088 | AGCAAGGGCTTTTACTACA | TGTAGTAAAAGCCCTTGCT |
| 2089 | GCAAGGGCTTTTACTACAA | TTGTAGTAAAAGCCCTTGC |
| 2090 | CAAGGGCTTTTACTACAAG | CTTGTAGTAAAAGCCCTTG |
| 2091 | AAGGGCTTTTACTACAAGG | CCTTGTAGTAAAAGCCCTT |
| 2092 | AGGGCTTTTACTACAAGGA | TCCTTGTAGTAAAAGCCCT |
| 2093 | GGGCTTTTACTACAAGGAT | ATCCTTGTAGTAAAAGCCC |
| 2094 | GGCTTTTACTACAAGGATC | GATCCTTGTAGTAAAAGCC |
| 2095 | GCTTTTACTACAAGGATCC | GGATCCTTGTAGTAAAAGC |
| 2096 | CTTTTACTACAAGGATCCG | CGGATCCTTGTAGTAAAAG |
| 2097 | TTTTACTACAAGGATCCGA | TCGGATCCTTGTAGTAAAA |
| 2098 | TTTACTACAAGGATCCGAG | CTCGGATCCTTGTAGTAAA |
| 2099 | TTACTACAAGGATCCGAGC | GCTCGGATCCTTGTAGTAA |
| 2100 | TACTACAAGGATCCGAGCA | TGCTCGGATCCTTGTAGTA |
| 2101 | ACTACAAGGATCCGAGCAT | ATGCTCGGATCCTTGTAGT |
| 2102 | CTACAAGGATCCGAGCATT | AATGCTCGGATCCTTGTAG |
| 2103 | TACAAGGATCCGAGCATTC | GAATGCTCGGATCCTTGTA |
| 2104 | ACAAGGATCCGAGCATTCC | GGAATGCTCGGATCCTTGT |
| 2105 | CAAGGATCCGAGCATTCCC | GGGAATGCTCGGATCCTTG |
| 2106 | AAGGATCCGAGCATTCCCA | TGGGAATGCTCGGATCCTT |
| 2107 | AGGATCCGAGCATTCCCAG | CTGGGAATGCTCGGATCCT |
| 2108 | GGATCCGAGCATTCCCAGG | CCTGGGAATGCTCGGATCC |
| 2109 | GATCCGAGCATTCCCAGGT | ACCTGGGAATGCTCGGATC |
| 2110 | ATCCGAGCATTCCCAGGTT | AACCTGGGAATGCTCGGAT |
| 2111 | TCCGAGCATTCCCAGGTTG | CAACCTGGGAATGCTCGGA |
| 2112 | CCGAGCATTCCCAGGTTGG | CCAACCTGGGAATGCTCGG |
| 2113 | CGAGCATTCCCAGGTTGGC | GCCAACCTGGGAATGCTCG |
| 2114 | GAGCATTCCCAGGTTGGCA | TGCCAACCTGGGAATGCTC |
| 2115 | AGCATTCCCAGGTTGGCAA | TTGCCAACCTGGGAATGCT |
| 2116 | GCATTCCCAGGTTGGCAAA | TTTGCCAACCTGGGAATGC |
| 2117 | CATTCCCAGGTTGGCAAAG | CTTTGCCAACCTGGGAATG |
| 2118 | ATTCCCAGGTTGGCAAAGG | CCTTTGCCAACCTGGGAAT |
| 2119 | TTCCCAGGTTGGCAAAGGA | TCCTTTGCCAACCTGGGAA |
| 2120 | TCCCAGGTTGGCAAAGGAG | CTCCTTTGCCAACCTGGGA |
| 2121 | CCCAGGTTGGCAAAGGAGC | GCTCCTTTGCCAACCTGGG |
| 2122 | CCAGGTTGGCAAAGGAGCC | GGCTCCTTTGCCAACCTGG |
| 2123 | CAGGTTGGCAAAGGAGCCC | GGGCTCCTTTGCCAACCTG |
| 2124 | AGGTTGGCAAAGGAGCCCT | AGGGCTCCTTTGCCAACCT |
| 2125 | GGTTGGCAAAGGAGCCCTT | AAGGGCTCCTTTGCCAACC |
| 2126 | GTTGGCAAAGGAGCCCTTG | CAAGGGCTCCTTTGCCAAC |
| 2127 | TTGGCAAAGGAGCCCTTGG | CCAAGGGCTCCTTTGCCAA |
| 2128 | TGGCAAAGGAGCCCTTGGC | GCCAAGGGCTCCTTTGCCA |
| 2129 | GGCAAAGGAGCCCTTGGCA | TGCCAAGGGCTCCTTTGCC |
| 2130 | GCAAAGGAGCCCTTGGCAG | CTGCCAAGGGCTCCTTTGC |
| 2131 | CAAAGGAGCCCTTGGCAGC | GCTGCCAAGGGCTCCTTTG |
| 2132 | AAAGGAGCCCTTGGCAGCT | AGCTGCCAAGGGCTCCTTT |
| 2133 | AAGGAGCCCTTGGCAGCTG | CAGCTGCCAAGGGCTCCTT |
| 2134 | AGGAGCCCTTGGCAGCTGC | GCAGCTGCCAAGGGCTCCT |
| 2135 | GGAGCCCTTGGCAGCTGCG | CGCAGCTGCCAAGGGCTCC |
| 2136 | GAGCCCTTGGCAGCTGCGG | CCGCAGCTGCCAAGGGCTC |
| 2137 | AGCCCTTGGCAGCTGCGGA | TCCGCAGCTGCCAAGGGCT |
| 2138 | GCCCTTGGCAGCTGCGGAA | TTCCGCAGCTGCCAAGGGC |
| 2139 | CCCTTGGCAGCTGCGGAAC | GTTCCGCAGCTGCCAAGGG |
| 2140 | CCTTGGCAGCTGCGGAACC | GGTTCCGCAGCTGCCAAGG |
| 2141 | CTTGGCAGCTGCGGAACCT | AGGTTCCGCAGCTGCCAAG |
| 2142 | TTGGCAGCTGCGGAACCTG | CAGGTTCCGCAGCTGCCAA |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 2143 | TGGCAGCTGCGGAACCTGG | CCAGGTTCCGCAGCTGCCA |
| 2144 | GGCAGCTGCGGAACCTGGG | CCCAGGTTCCGCAGCTGCC |
| 2145 | GCAGCTGCGGAACCTGGGT | ACCCAGGTTCCGCAGCTGC |
| 2146 | CAGCTGCGGAACCTGGGTT | AACCCAGGTTCCGCAGCTG |
| 2147 | AGCTGCGGAACCTGGGTTG | CAACCCAGGTTCCGCAGCT |
| 2148 | GCTGCGGAACCTGGGTTGT | ACAACCCAGGTTCCGCAGC |
| 2149 | CTGCGGAACCTGGGTTGTT | AACAACCCAGGTTCCGCAG |
| 2150 | TGCGGAACCTGGGTTGTTT | AAACAACCCAGGTTCCGCA |
| 2151 | GCGGAACCTGGGTTGTTTG | CAAACAACCCAGGTTCCGC |
| 2152 | CGGAACCTGGGTTGTTTGG | CCAAACAACCCAGGTTCCG |
| 2153 | GGAACCTGGGTTGTTTGGC | GCCAAACAACCCAGGTTCC |
| 2154 | GAACCTGGGTTGTTTGGCT | AGCCAAACAACCCAGGTTC |
| 2155 | AACCTGGGTTGTTTGGCTT | AAGCCAAACAACCCAGGTT |
| 2156 | ACCTGGGTTGTTTGGCTTA | TAAGCCAAACAACCCAGGT |
| 2157 | CCTGGGTTGTTTGGCTTAA | TTAAGCCAAACAACCCAGG |
| 2158 | CTGGGTTGTTTGGCTTAAA | TTTAAGCCAAACAACCCAG |
| 2159 | TGGGTTGTTTGGCTTAAAC | GTTTAAGCCAAACAACCCA |
| 2160 | GGGTTGTTTGGCTTAAACT | AGTTTAAGCCAAACAACCC |
| 2161 | GGTTGTTTGGCTTAAACTC | GAGTTTAAGCCAAACAACC |
| 2162 | GTTGTTTGGCTTAAACTCT | AGAGTTTAAGCCAAACAAC |
| 2163 | TTGTTTGGCTTAAACTCTG | CAGAGTTTAAGCCAAACAA |
| 2164 | TGTTTGGCTTAAACTCTGG | CCAGAGTTTAAGCCAAACA |
| 2165 | GTTTGGCTTAAACTCTGGT | ACCAGAGTTTAAGCCAAAC |
| 2166 | TTTGGCTTAAACTCTGGTG | CACCAGAGTTTAAGCCAAA |
| 2167 | TTGGCTTAAACTCTGGTGG | CCACCAGAGTTTAAGCCAA |
| 2168 | TGGCTTAAACTCTGGTGGG | CCCACCAGAGTTTAAGCCA |
| 2169 | GGCTTAAACTCTGGTGGGC | GCCCACCAGAGTTTAAGCC |
| 2170 | GCTTAAACTCTGGTGGGCA | TGCCCACCAGAGTTTAAGC |
| 2171 | CTTAAACTCTGGTGGGCAC | GTGCCCACCAGAGTTTAAG |
| 2172 | TTAAACTCTGGTGGGCACC | GGTGCCCACCAGAGTTTAA |
| 2173 | TAAACTCTGGTGGGCACCT | AGGTGCCCACCAGAGTTTA |
| 2174 | AAACTCTGGTGGGCACCTG | CAGGTGCCCACCAGAGTTT |
| 2175 | AACTCTGGTGGGCACCTGC | GCAGGTGCCCACCAGAGTT |
| 2176 | ACTCTGGTGGGCACCTGCA | TGCAGGTGCCCACCAGAGT |
| 2177 | CTCTGGTGGGCACCTGCAG | CTGCAGGTGCCCACCAGAG |
| 2178 | TCTGGTGGGCACCTGCAGA | TCTGCAGGTGCCCACCAGA |
| 2179 | CTGGTGGGCACCTGCAGAG | CTCTGCAGGTGCCCACCAG |
| 2180 | TGGTGGGCACCTGCAGAGA | TCTCTGCAGGTGCCCACCA |
| 2181 | GGTGGGCACCTGCAGAGAG | CTCTCTGCAGGTGCCCACC |
| 2182 | GTGGGCACCTGCAGAGAGC | GCTCTCTGCAGGTGCCCAC |
| 2183 | TGGGCACCTGCAGAGAGCC | GGCTCTCTGCAGGTGCCCA |
| 2184 | GGGCACCTGCAGAGAGCCG | CGGCTCTCTGCAGGTGCCC |
| 2185 | GGCACCTGCAGAGAGCCGG | CCGGCTCTCTGCAGGTGCC |
| 2186 | GCACCTGCAGAGAGCCGGG | CCCGGCTCTCTGCAGGTGC |
| 2187 | CACCTGCAGAGAGCCGGGG | CCCCGGCTCTCTGCAGGTG |
| 2188 | ACCTGCAGAGAGCCGGGGA | TCCCCGGCTCTCTGCAGGT |
| 2189 | CCTGCAGAGAGCCGGGGAG | CTCCCCGGCTCTCTGCAGG |
| 2190 | CTGCAGAGAGCCGGGGAGG | CCTCCCCGGCTCTCTGCAG |
| 2191 | TGCAGAGAGCCGGGGAGGC | GCCTCCCCGGCTCTCTGCA |
| 2192 | GCAGAGAGCCGGGGAGGCC | GGCCTCCCCGGCTCTCTGC |
| 2193 | CAGAGAGCCGGGGAGGCCG | CGGCCTCCCCGGCTCTCTG |
| 2194 | AGAGAGCCGGGGAGGCCGA | TCGGCCTCCCCGGCTCTCT |
| 2195 | GAGAGCCGGGGAGGCCGAA | TTCGGCCTCCCCGGCTCTC |
| 2196 | AGAGCCGGGGAGGCCGAAC | GTTCGGCCTCCCCGGCTCT |
| 2197 | GAGCCGGGGAGGCCGAACG | CGTTCGGCCTCCCCGGCTC |
| 2198 | AGCCGGGGAGGCCGAACGC | GCGTTCGGCCTCCCCGGCT |
| 2199 | GCCGGGGAGGCCGAACGCC | GGCGTTCGGCCTCCCCGGC |
| 2200 | CCGGGGAGGCCGAACGCCC | GGGCGTTCGGCCTCCCCGG |
| 2201 | CGGGGAGGCCGAACGCCCT | AGGGCGTTCGGCCTCCCCG |
| 2202 | GGGGAGGCCGAACGCCCTT | AAGGGCGTTCGGCCTCCCC |
| 2203 | GGGAGGCCGAACGCCCTTC | GAAGGGCGTTCGGCCTCCC |
| 2204 | GGAGGCCGAACGCCCTTCA | TGAAGGGCGTTCGGCCTCC |
| 2205 | GAGGCCGAACGCCCTTCAC | GTGAAGGGCGTTCGGCCTC |
| 2206 | AGGCCGAACGCCCTTCACT | AGTGAAGGGCGTTCGGCCT |
| 2207 | GGCCGAACGCCCTTCACTG | CAGTGAAGGGCGTTCGGCC |
| 2208 | GCCGAACGCCCTTCACTGC | GCAGTGAAGGGCGTTCGGC |
| 2209 | CCGAACGCCCTTCACTGCA | TGCAGTGAAGGGCGTTCGG |
| 2210 | CGAACGCCCTTCACTGCAC | GTGCAGTGAAGGGCGTTCG |
| 2211 | GAACGCCCTTCACTGCACC | GGTGCAGTGAAGGGCGTTC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 2212 | AACGCCCTTCACTGCACCA | TGGTGCAGTGAAGGGCGTT |
| 2213 | ACGCCCTTCACTGCACCAG | CTGGTGCAGTGAAGGGCGT |
| 2214 | CGCCCTTCACTGCACCAGA | TCTGGTGCAGTGAAGGGCG |
| 2215 | GCCCTTCACTGCACCAGAG | CTCTGGTGCAGTGAAGGGC |
| 2216 | CCCTTCACTGCACCAGAGG | CCTCTGGTGCAGTGAAGGG |
| 2217 | CCTTCACTGCACCAGAGGG | CCCTCTGGTGCAGTGAAGG |
| 2218 | CTTCACTGCACCAGAGGGA | TCCCTCTGGTGCAGTGAAG |
| 2219 | TTCACTGCACCAGAGGGAT | ATCCCTCTGGTGCAGTGAA |
| 2220 | TCACTGCACCAGAGGGATG | CATCCCTCTGGTGCAGTGA |
| 2221 | CACTGCACCAGAGGGATGG | CCATCCCTCTGGTGCAGTG |
| 2222 | ACTGCACCAGAGGGATGGA | TCCATCCCTCTGGTGCAGT |
| 2223 | CTGCACCAGAGGGATGGAG | CTCCATCCCTCTGGTGCAG |
| 2224 | TGCACCAGAGGGATGGAGA | TCTCCATCCCTCTGGTGCA |
| 2225 | GCACCAGAGGGATGGAGAG | CTCTCCATCCCTCTGGTGC |
| 2226 | CACCAGAGGGATGGAGAGA | TCTCTCCATCCCTCTGGTG |
| 2227 | ACCAGAGGGATGGAGAGAT | ATCTCTCCATCCCTCTGGT |
| 2228 | CCAGAGGGATGGAGAGATG | CATCTCTCCATCCCTCTGG |
| 2229 | CAGAGGGATGGAGAGATGG | CCATCTCTCCATCCCTCTG |
| 2230 | AGAGGGATGGAGAGATGGG | CCCATCTCTCCATCCCTCT |
| 2231 | GAGGGATGGAGAGATGGGA | TCCCATCTCTCCATCCCTC |
| 2232 | AGGGATGGAGAGATGGGAG | CTCCCATCTCTCCATCCCT |
| 2233 | GGGATGGAGAGATGGGAGC | GCTCCCATCTCTCCATCCC |
| 2234 | GGATGGAGAGATGGGAGCT | AGCTCCCATCTCTCCATCC |
| 2235 | GATGGAGAGATGGGAGCTG | CAGCTCCCATCTCTCCATC |
| 2236 | ATGGAGAGATGGGAGCTGG | CCAGCTCCCATCTCTCCAT |
| 2237 | TGGAGAGATGGGAGCTGGC | GCCAGCTCCCATCTCTCCA |
| 2238 | GGAGAGATGGGAGCTGGCC | GGCCAGCTCCCATCTCTCC |
| 2239 | GAGAGATGGGAGCTGGCCG | CGGCCAGCTCCCATCTCTC |
| 2240 | AGAGATGGGAGCTGGCCGG | CCGGCCAGCTCCCATCTCT |
| 2241 | GAGATGGGAGCTGGCCGGC | GCCGGCCAGCTCCCATCTC |
| 2242 | AGATGGGAGCTGGCCGGCA | TGCCGGCCAGCTCCCATCT |
| 2243 | GATGGGAGCTGGCCGGCAG | CTGCCGGCCAGCTCCCATC |
| 2244 | ATGGGAGCTGGCCGGCAGC | GCTGCCGGCCAGCTCCCAT |
| 2245 | TGGGAGCTGGCCGGCAGCA | TGCTGCCGGCCAGCTCCCA |
| 2246 | GGGAGCTGGCCGGCAGCAG | CTGCTGCCGGCCAGCTCCC |
| 2247 | GGAGCTGGCCGGCAGCAGA | TCTGCTGCCGGCCAGCTCC |
| 2248 | GAGCTGGCCGGCAGCAGAA | TTCTGCTGCCGGCCAGCTC |
| 2249 | AGCTGGCCGGCAGCAGAAT | ATTCTGCTGCCGGCCAGCT |
| 2250 | GCTGGCCGGCAGCAGAATC | GATTCTGCTGCCGGCCAGC |
| 2251 | CTGGCCGGCAGCAGAATCC | GGATTCTGCTGCCGGCCAG |
| 2252 | TGGCCGGCAGCAGAATCCT | AGGATTCTGCTGCCGGCCA |
| 2253 | GGCCGGCAGCAGAATCCTT | AAGGATTCTGCTGCCGGCC |
| 2254 | GCCGGCAGCAGAATCCTTG | CAAGGATTCTGCTGCCGGC |
| 2255 | CCGGCAGCAGAATCCTTGC | GCAAGGATTCTGCTGCCGG |
| 2256 | CGGCAGCAGAATCCTTGCC | GGCAAGGATTCTGCTGCCG |
| 2257 | GGCAGCAGAATCCTTGCCC | GGGCAAGGATTCTGCTGCC |
| 2258 | GCAGCAGAATCCTTGCCCG | CGGGCAAGGATTCTGCTGC |
| 2259 | CAGCAGAATCCTTGCCCGC | GCGGGCAAGGATTCTGCTG |
| 2260 | AGCAGAATCCTTGCCCGCT | AGCGGGCAAGGATTCTGCT |
| 2261 | GCAGAATCCTTGCCCGCTC | GAGCGGGCAAGGATTCTGC |
| 2262 | CAGAATCCTTGCCCGCTCT | AGAGCGGGCAAGGATTCTG |
| 2263 | AGAATCCTTGCCCGCTCTT | AAGAGCGGGCAAGGATTCT |
| 2264 | GAATCCTTGCCCGCTCTTC | GAAGAGCGGGCAAGGATTC |
| 2265 | AATCCTTGCCCGCTCTTCC | GGAAGAGCGGGCAAGGATT |
| 2266 | ATCCTTGCCCGCTCTTCCT | AGGAAGAGCGGGCAAGGAT |
| 2267 | TCCTTGCCCGCTCTTCCTG | CAGGAAGAGCGGGCAAGGA |
| 2268 | CCTTGCCCGCTCTTCCTGG | CCAGGAAGAGCGGGCAAGG |
| 2269 | CTTGCCCGCTCTTCCTGGG | CCCAGGAAGAGCGGGCAAG |
| 2270 | TTGCCCGCTCTTCCTGGGG | CCCCAGGAAGAGCGGGCAA |
| 2271 | TGCCCGCTCTTCCTGGGGC | GCCCCAGGAAGAGCGGGCA |
| 2272 | GCCCGCTCTTCCTGGGGCA | TGCCCCAGGAAGAGCGGGC |
| 2273 | CCCGCTCTTCCTGGGGCAG | CTGCCCCAGGAAGAGCGGG |
| 2274 | CCGCTCTTCCTGGGGCAGC | GCTGCCCCAGGAAGAGCGG |
| 2275 | CGCTCTTCCTGGGGCAGCC | GGCTGCCCCAGGAAGAGCG |
| 2276 | GCTCTTCCTGGGGCAGCCA | TGGCTGCCCCAGGAAGAGC |
| 2277 | CTCTTCCTGGGGCAGCCAG | CTGGCTGCCCCAGGAAGAG |
| 2278 | TCTTCCTGGGGCAGCCAGA | TCTGGCTGCCCCAGGAAGA |
| 2279 | CTTCCTGGGGCAGCCAGAC | GTCTGGCTGCCCCAGGAAG |
| 2280 | TTCCTGGGGCAGCCAGACA | TGTCTGGCTGCCCCAGGAA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2281 | TCCTGGGGCAGCCAGACAC | GTGTCTGGCTGCCCCAGGA |
| 2282 | CCTGGGGCAGCCAGACACT | AGTGTCTGGCTGCCCCAGG |
| 2283 | CTGGGGCAGCCAGACACTG | CAGTGTCTGGCTGCCCCAG |
| 2284 | TGGGGCAGCCAGACACTGT | ACAGTGTCTGGCTGCCCCA |
| 2285 | GGGGCAGCCAGACACTGTG | CACAGTGTCTGGCTGCCCC |
| 2286 | GGGCAGCCAGACACTGTGC | GCACAGTGTCTGGCTGCCC |
| 2287 | GGCAGCCAGACACTGTGCC | GGCACAGTGTCTGGCTGCC |
| 2288 | GCAGCCAGACACTGTGCCC | GGGCACAGTGTCTGGCTGC |
| 2289 | CAGCCAGACACTGTGCCCT | AGGGCACAGTGTCTGGCTG |
| 2290 | AGCCAGACACTGTGCCCTG | CAGGGCACAGTGTCTGGCT |
| 2291 | GCCAGACACTGTGCCCTGG | CCAGGGCACAGTGTCTGGC |
| 2292 | CCAGACACTGTGCCCTGGA | TCCAGGGCACAGTGTCTGG |
| 2293 | CAGACACTGTGCCCTGGAC | GTCCAGGGCACAGTGTCTG |
| 2294 | AGACACTGTGCCCTGGACC | GGTCCAGGGCACAGTGTCT |
| 2295 | GACACTGTGCCCTGGACCT | AGGTCCAGGGCACAGTGTC |
| 2296 | ACACTGTGCCCTGGACCTC | GAGGTCCAGGGCACAGTGT |
| 2297 | CACTGTGCCCTGGACCTCC | GGAGGTCCAGGGCACAGTG |
| 2298 | ACTGTGCCCTGGACCTCCT | AGGAGGTCCAGGGCACAGT |
| 2299 | CTGTGCCCTGGACCTCCTG | CAGGAGGTCCAGGGCACAG |
| 2300 | TGTGCCCTGGACCTCCTGG | CCAGGAGGTCCAGGGCACA |
| 2301 | GTGCCCTGGACCTCCTGGC | GCCAGGAGGTCCAGGGCAC |
| 2302 | TGCCCTGGACCTCCTGGCC | GGCCAGGAGGTCCAGGGCA |
| 2303 | GCCCTGGACCTCCTGGCCC | GGGCCAGGAGGTCCAGGGC |
| 2304 | CCCTGGACCTCCTGGCCCG | CGGGCCAGGAGGTCCAGGG |
| 2305 | CCTGGACCTCCTGGCCCGC | GCGGGCCAGGAGGTCCAGG |
| 2306 | CTGGACCTCCTGGCCCGCT | AGCGGGCCAGGAGGTCCAG |
| 2307 | TGGACCTCCTGGCCCGCTT | AAGCGGGCCAGGAGGTCCA |
| 2308 | GGACCTCCTGGCCCGCTTG | CAAGCGGGCCAGGAGGTCC |
| 2309 | GACCTCCTGGCCCGCTTGT | ACAAGCGGGCCAGGAGGTC |
| 2310 | ACCTCCTGGCCCGCTTGTC | GACAAGCGGGCCAGGAGGT |
| 2311 | CCTCCTGGCCCGCTTGTCC | GGACAAGCGGGCCAGGAGG |
| 2312 | CTCCTGGCCCGCTTGTCCC | GGGACAAGCGGGCCAGGAG |
| 2313 | TCCTGGCCCGCTTGTCCCC | GGGGACAAGCGGGCCAGGA |
| 2314 | CCTGGCCCGCTTGTCCCCC | GGGGGACAAGCGGGCCAGG |
| 2315 | CTGGCCCGCTTGTCCCCCA | TGGGGGACAAGCGGGCCAG |
| 2316 | TGGCCCGCTTGTCCCCCAG | CTGGGGGACAAGCGGGCCA |
| 2317 | GGCCCGCTTGTCCCCCAGG | CCTGGGGGACAAGCGGGCC |
| 2318 | GCCCGCTTGTCCCCCAGGC | GCCTGGGGGACAAGCGGGC |
| 2319 | CCCGCTTGTCCCCCAGGCC | GGCCTGGGGGACAAGCGGG |
| 2320 | CCGCTTGTCCCCCAGGCCT | AGGCCTGGGGGACAAGCGG |
| 2321 | CGCTTGTCCCCCAGGCCTT | AAGGCCTGGGGGACAAGCG |
| 2322 | GCTTGTCCCCCAGGCCTTG | CAAGGCCTGGGGGACAAGC |
| 2323 | CTTGTCCCCCAGGCCTTGT | ACAAGGCCTGGGGGACAAG |
| 2324 | TTGTCCCCCAGGCCTTGTT | AACAAGGCCTGGGGGACAA |
| 2325 | TGTCCCCCAGGCCTTGTTC | GAACAAGGCCTGGGGGACA |
| 2326 | GTCCCCCAGGCCTTGTTCA | TGAACAAGGCCTGGGGGAC |
| 2327 | TCCCCCAGGCCTTGTTCAT | ATGAACAAGGCCTGGGGGA |
| 2328 | CCCCCAGGCCTTGTTCATA | TATGAACAAGGCCTGGGGG |
| 2329 | CCCCAGGCCTTGTTCATAC | GTATGAACAAGGCCTGGGG |
| 2330 | CCCAGGCCTTGTTCATACT | AGTATGAACAAGGCCTGGG |
| 2331 | CCAGGCCTTGTTCATACTC | GAGTATGAACAAGGCCTGG |
| 2332 | CAGGCCTTGTTCATACTCT | AGAGTATGAACAAGGCCTG |
| 2333 | AGGCCTTGTTCATACTCTT | AAGAGTATGAACAAGGCCT |
| 2334 | GGCCTTGTTCATACTCTTG | CAAGAGTATGAACAAGGCC |
| 2335 | GCCTTGTTCATACTCTTGG | CCAAGAGTATGAACAAGGC |
| 2336 | CCTTGTTCATACTCTTGGC | GCCAAGAGTATGAACAAGG |
| 2337 | CTTGTTCATACTCTTGGCA | TGCCAAGAGTATGAACAAG |
| 2338 | TTGTTCATACTCTTGGCAA | TTGCCAAGAGTATGAACAA |
| 2339 | TGTTCATACTCTTGGCAAC | GTTGCCAAGAGTATGAACA |
| 2340 | GTTCATACTCTTGGCAACG | CGTTGCCAAGAGTATGAAC |
| 2341 | TTCATACTCTTGGCAACGT | ACGTTGCCAAGAGTATGAA |
| 2342 | TCATACTCTTGGCAACGTC | GACGTTGCCAAGAGTATGA |
| 2343 | CATACTCTTGGCAACGTCT | AGACGTTGCCAAGAGTATG |
| 2344 | ATACTCTTGGCAACGTCTG | CAGACGTTGCCAAGAGTAT |
| 2345 | TACTCTTGGCAACGTCTGG | CCAGACGTTGCCAAGAGTA |
| 2346 | ACTCTTGGCAACGTCTGGG | CCCAGACGTTGCCAAGAGT |
| 2347 | CTCTTGGCAACGTCTGGGC | GCCCAGACGTTGCCAAGAG |
| 2348 | TCTTGGCAACGTCTGGGCT | AGCCCAGACGTTGCCAAGA |
| 2349 | CTTGGCAACGTCTGGGCTG | CAGCCCAGACGTTGCCAAG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2350 | TTGGCAACGTCTGGGCTGG | CCAGCCCAGACGTTGCCAA |
| 2351 | TGGCAACGTCTGGGCTGGG | CCCAGCCCAGACGTTGCCA |
| 2352 | GGCAACGTCTGGGCTGGGC | GCCCAGCCCAGACGTTGCC |
| 2353 | GCAACGTCTGGGCTGGGCC | GGCCCAGCCCAGACGTTGC |
| 2354 | CAACGTCTGGGCTGGGCCA | TGGCCCAGCCCAGACGTTG |
| 2355 | AACGTCTGGGCTGGGCCAG | CTGGCCCAGCCCAGACGTT |
| 2356 | ACGTCTGGGCTGGGCCAGG | CCTGGCCCAGCCCAGACGT |
| 2357 | CGTCTGGGCTGGGCCAGGC | GCCTGGCCCAGCCCAGACG |
| 2358 | GTCTGGGCTGGGCCAGGCG | CGCCTGGCCCAGCCCAGAC |
| 2359 | TCTGGGCTGGGCCAGGCGA | TCGCCTGGCCCAGCCCAGA |
| 2360 | CTGGGCTGGGCCAGGCGAT | ATCGCCTGGCCCAGCCCAG |
| 2361 | TGGGCTGGGCCAGGCGATG | CATCGCCTGGCCCAGCCCA |
| 2362 | GGGCTGGGCCAGGCGATGG | CCATCGCCTGGCCCAGCCC |
| 2363 | GGCTGGGCCAGGCGATGGG | CCCATCGCCTGGCCCAGCC |
| 2364 | GCTGGGCCAGGCGATGGGA | TCCCATCGCCTGGCCCAGC |
| 2365 | CTGGGCCAGGCGATGGGAA | TTCCCATCGCCTGGCCCAG |
| 2366 | TGGGCCAGGCGATGGGAAC | GTTCCCATCGCCTGGCCCA |
| 2367 | GGGCCAGGCGATGGGAACC | GGTTCCCATCGCCTGGCCC |
| 2368 | GGCCAGGCGATGGGAACCT | AGGTTCCCATCGCCTGGCC |
| 2369 | GCCAGGCGATGGGAACCTT | AAGGTTCCCATCGCCTGGC |
| 2370 | CCAGGCGATGGGAACCTTG | CAAGGTTCCCATCGCCTGG |
| 2371 | CAGGCGATGGGAACCTTGG | CCAAGGTTCCCATCGCCTG |
| 2372 | AGGCGATGGGAACCTTGGG | CCCAAGGTTCCCATCGCCT |
| 2373 | GGCGATGGGAACCTTGGGT | ACCCAAGGTTCCCATCGCC |
| 2374 | GCGATGGGAACCTTGGGTA | TACCCAAGGTTCCCATCGC |
| 2375 | CGATGGGAACCTTGGGTAC | GTACCCAAGGTTCCCATCG |
| 2376 | GATGGGAACCTTGGGTACC | GGTACCCAAGGTTCCCATC |
| 2377 | ATGGGAACCTTGGGTACCA | TGGTACCCAAGGTTCCCAT |
| 2378 | TGGGAACCTTGGGTACCAG | CTGGTACCCAAGGTTCCCA |
| 2379 | GGGAACCTTGGGTACCAGC | GCTGGTACCCAAGGTTCCC |
| 2380 | GGAACCTTGGGTACCAGCT | AGCTGGTACCCAAGGTTCC |
| 2381 | GAACCTTGGGTACCAGCTG | CAGCTGGTACCCAAGGTTC |
| 2382 | AACCTTGGGTACCAGCTGG | CCAGCTGGTACCCAAGGTT |
| 2383 | ACCTTGGGTACCAGCTGGG | CCCAGCTGGTACCCAAGGT |
| 2384 | CCTTGGGTACCAGCTGGGG | CCCCAGCTGGTACCCAAGG |
| 2385 | CTTGGGTACCAGCTGGGGC | GCCCCAGCTGGTACCCAAG |
| 2386 | TTGGGTACCAGCTGGGGCC | GGCCCCAGCTGGTACCCAA |
| 2387 | TGGGTACCAGCTGGGGCCA | TGGCCCCAGCTGGTACCCA |
| 2388 | GGGTACCAGCTGGGGCCAC | GTGGCCCCAGCTGGTACCC |
| 2389 | GGTACCAGCTGGGGCCACC | GGTGGCCCCAGCTGGTACC |
| 2390 | GTACCAGCTGGGGCCACCA | TGGTGGCCCCAGCTGGTAC |
| 2391 | TACCAGCTGGGGCCACCAG | CTGGTGGCCCCAGCTGGTA |
| 2392 | ACCAGCTGGGGCCACCAGC | GCTGGTGGCCCCAGCTGGT |
| 2393 | CCAGCTGGGGCCACCAGCA | TGCTGGTGGCCCCAGCTGG |
| 2394 | CAGCTGGGGCCACCAGCAA | TTGCTGGTGGCCCCAGCTG |
| 2395 | AGCTGGGGCCACCAGCAAC | GTTGCTGGTGGCCCCAGCT |
| 2396 | GCTGGGGCCACCAGCAACA | TGTTGCTGGTGGCCCCAGC |
| 2397 | CTGGGGCCACCAGCAACAC | GTGTTGCTGGTGGCCCCAG |
| 2398 | TGGGGCCACCAGCAACACC | GGTGTTGCTGGTGGCCCCA |
| 2399 | GGGGCCACCAGCAACACCA | TGGTGTTGCTGGTGGCCCC |
| 2400 | GGGCCACCAGCAACACCAA | TTGGTGTTGCTGGTGGCCC |
| 2401 | GGCCACCAGCAACACCAAG | CTTGGTGTTGCTGGTGGCC |
| 2402 | GCCACCAGCAACACCAAGG | CCTTGGTGTTGCTGGTGGC |
| 2403 | CCACCAGCAACACCAAGGT | ACCTTGGTGTTGCTGGTGG |
| 2404 | CACCAGCAACACCAAGGTG | CACCTTGGTGTTGCTGGTG |
| 2405 | ACCAGCAACACCAAGGTGC | GCACCTTGGTGTTGCTGGT |
| 2406 | CCAGCAACACCAAGGTGCC | GGCACCTTGGTGTTGCTGG |
| 2407 | CAGCAACACCAAGGTGCCC | GGGCACCTTGGTGTTGCTG |
| 2408 | AGCAACACCAAGGTGCCCC | GGGGCACCTTGGTGTTGCT |
| 2409 | GCAACACCAAGGTGCCCCT | AGGGGCACCTTGGTGTTGC |
| 2410 | CAACACCAAGGTGCCCCTC | GAGGGGCACCTTGGTGTTG |
| 2411 | AACACCAAGGTGCCCCTCT | AGAGGGGCACCTTGGTGTT |
| 2412 | ACACCAAGGTGCCCCTCTC | GAGAGGGGCACCTTGGTGT |
| 2413 | CACCAAGGTGCCCCTCTCC | GGAGAGGGGCACCTTGGTG |
| 2414 | ACCAAGGTGCCCCTCTCCT | AGGAGAGGGGCACCTTGGT |
| 2415 | CCAAGGTGCCCCTCTCCTG | CAGGAGAGGGGCACCTTGG |
| 2416 | CAAGGTGCCCCTCTCCTGA | TCAGGAGAGGGGCACCTTG |
| 2417 | AAGGTGCCCCTCTCCTGAG | CTCAGGAGAGGGGCACCTT |
| 2418 | AGGTGCCCCTCTCCTGAGC | GCTCAGGAGAGGGGCACCT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2419 | GGTGCCCTCTCCTGAGCC | GGCTCAGGAGAGGGCACC |
| 2420 | GTGCCCTCTCCTGAGCCG | CGGCTCAGGAGAGGGCAC |
| 2421 | TGCCCCTCTCCTGAGCCGC | GCGGCTCAGGAGAGGGCA |
| 2422 | GCCCCTCTCCTGAGCCGCC | GGCGGCTCAGGAGAGGGC |
| 2423 | CCCCTCTCCTGAGCCGCCT | AGGCGGCTCAGGAGAGGG |
| 2424 | CCCTCTCCTGAGCCGCCTG | CAGGCGGCTCAGGAGAGG |
| 2425 | CCTCTCCTGAGCCGCCTGT | ACAGGCGGCTCAGGAGAG |
| 2426 | CTCTCCTGAGCCGCCTGTC | GACAGGCGGCTCAGGAGAG |
| 2427 | TCTCCTGAGCCGCCTGTCA | TGACAGGCGGCTCAGGAGA |
| 2428 | CTCCTGAGCCGCCTGTCAC | GTGACAGGCGGCTCAGGAG |
| 2429 | TCCTGAGCCGCCTGTCACC | GGTGACAGGCGGCTCAGGA |
| 2430 | CCTGAGCCGCCTGTCACCC | GGGTGACAGGCGGCTCAGG |
| 2431 | CTGAGCCGCCTGTCACCCA | TGGGTGACAGGCGGCTCAG |
| 2432 | TGAGCCGCCTGTCACCCAG | CTGGGTGACAGGCGGCTCA |
| 2433 | GAGCCGCCTGTCACCCAGC | GCTGGGTGACAGGCGGCTC |
| 2434 | AGCCGCCTGTCACCCAGCG | CGCTGGGTGACAGGCGGCT |
| 2435 | GCCGCCTGTCACCCAGCGG | CCGCTGGGTGACAGGCGGC |
| 2436 | CCGCCTGTCACCCAGCGGG | CCCGCTGGGTGACAGGCGG |
| 2437 | CGCCTGTCACCCAGCGGGG | CCCCGCTGGGTGACAGGCG |
| 2438 | GCCTGTCACCCAGCGGGGC | GCCCCGCTGGGTGACAGGC |
| 2439 | CCTGTCACCCAGCGGGGCT | AGCCCCGCTGGGTGACAGG |
| 2440 | CTGTCACCCAGCGGGGCTG | CAGCCCCGCTGGGTGACAG |
| 2441 | TGTCACCCAGCGGGGCTGC | GCAGCCCCGCTGGGTGACA |
| 2442 | GTCACCCAGCGGGGCTGCT | AGCAGCCCCGCTGGGTGAC |
| 2443 | TCACCCAGCGGGGCTGCTG | CAGCAGCCCCGCTGGGTGA |
| 2444 | CACCCAGCGGGGCTGCTGT | ACAGCAGCCCCGCTGGGTG |
| 2445 | ACCCAGCGGGGCTGCTGTT | AACAGCAGCCCCGCTGGGT |
| 2446 | CCCAGCGGGGCTGCTGTTC | GAACAGCAGCCCCGCTGGG |
| 2447 | CCAGCGGGGCTGCTGTTCA | TGAACAGCAGCCCCGCTGG |
| 2448 | CAGCGGGGCTGCTGTTCAT | ATGAACAGCAGCCCCGCTG |
| 2449 | AGCGGGGCTGCTGTTCATC | GATGAACAGCAGCCCCGCT |
| 2450 | GCGGGGCTGCTGTTCATCC | GGATGAACAGCAGCCCCGC |
| 2451 | CGGGGCTGCTGTTCATCCT | AGGATGAACAGCAGCCCCG |
| 2452 | GGGGCTGCTGTTCATCCTA | TAGGATGAACAGCAGCCCC |
| 2453 | GGGCTGCTGTTCATCCTAC | GTAGGATGAACAGCAGCCC |
| 2454 | GGCTGCTGTTCATCCTACC | GGTAGGATGAACAGCAGCC |
| 2455 | GCTGCTGTTCATCCTACCC | GGGTAGGATGAACAGCAGC |
| 2456 | CTGCTGTTCATCCTACCCA | TGGGTAGGATGAACAGCAG |
| 2457 | TGCTGTTCATCCTACCCAC | GTGGGTAGGATGAACAGCA |
| 2458 | GCTGTTCATCCTACCCACC | GGTGGGTAGGATGAACAGC |
| 2459 | CTGTTCATCCTACCCACCC | GGGTCGGTAGGATGAACAG |
| 2460 | TGTTCATCCTACCCACCCA | TGGGTGGGTAGGATGAACA |
| 2461 | GTTCATCCTACCCACCCAC | GTGGGTGGGTAGGATGAAC |
| 2462 | TTCATCCTACCCACCCACT | AGTGGGTGGGTAGGATGAA |
| 2463 | TCATCCTACCCACCCACTA | TAGTGGGTGGGTAGGATGA |
| 2464 | CATCCTACCCACCCACTAA | TTAGTGGGTGGGTAGGATG |
| 2465 | ATCCTACCCACCCACTAAA | TTTAGTGGGTGGGTAGGAT |
| 2466 | TCCTACCCACCCACTAAAG | CTTTAGTGGGTGGGTAGGA |
| 2467 | CCTACCCACCCACTAAAGG | CCTTTAGTGGGTGGGTAGG |
| 2468 | CTACCCACCCACTAAAGGT | ACCTTTAGTGGGTGGGTAG |
| 2469 | TACCCACCCACTAAAGGTG | CACCTTTAGTGGGTGGGTA |
| 2470 | ACCCACCCACTAAAGGTGG | CCACCTTTAGTGGGTGGGT |
| 2471 | CCCACCCACTAAAGGTGGG | CCCACCTTTAGTGGGTGGG |
| 2472 | CCACCCACTAAAGGTGGGG | CCCCACCTTTAGTGGGTGG |
| 2473 | CACCCACTAAAGGTGGGGG | CCCCCACCTTTAGTGGGTG |
| 2474 | ACCCACTAAAGGTGGGGGT | ACCCCCACCTTTAGTGGGT |
| 2475 | CCCACTAAAGGTGGGGGTC | GACCCCCACCTTTAGTGGG |
| 2476 | CCACTAAAGGTGGGGGTCT | AGACCCCCACCTTTAGTGG |
| 2477 | CACTAAAGGTGGGGGTCTT | AAGACCCCCACCTTTAGTG |
| 2478 | ACTAAAGGTGGGGGTCTTG | CAAGACCCCCACCTTTAGT |
| 2479 | CTAAAGGTGGGGGTCTTGG | CCAAGACCCCCACCTTTAG |
| 2480 | TAAAGGTGGGGGTCTTGGC | GCCAAGACCCCCACCTTTA |
| 2481 | AAAGGTGGGGGTCTTGGCC | GGCCAAGACCCCCACCTTT |
| 2482 | AAGGTGGGGGTCTTGGCCC | GGGCCAAGACCCCCACCTT |
| 2483 | AGGTGGGGGTCTTGGCCCT | AGGGCCAAGACCCCCACCT |
| 2484 | GGTGGGGGTCTTGGCCCTT | AAGGGCCAAGACCCCCACC |
| 2485 | GTGGGGGTCTTGGCCCTTG | CAAGGGCCAAGACCCCCAC |
| 2486 | TGGGGGTCTTGGCCCTTGT | ACAAGGGCCAAGACCCCCA |
| 2487 | GGGGGTCTTGGCCCTTGTG | CACAAGGGCCAAGACCCCC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2488 | GGGGTCTTGGCCCTTGTGG | CCACAAGGGCCAAGACCCC |
| 2489 | GGGTCTTGGCCCTTGTGGG | CCCACAAGGGCCAAGACCC |
| 2490 | GGTCTTGGCCCTTGTGGGA | TCCCACAAGGGCCAAGACC |
| 2491 | GTCTTGGCCCTTGTGGGAA | TTCCCACAAGGGCCAAGAC |
| 2492 | TCTTGGCCCTTGTGGGAAG | CTTCCCACAAGGGCCAAGA |
| 2493 | CTTGGCCCTTGTGGGAAGT | ACTTCCCACAAGGGCCAAG |
| 2494 | TTGGCCCTTGTGGGAAGTG | CACTTCCCACAAGGGCCAA |
| 2495 | TGGCCCTTGTGGGAAGTGC | GCACTTCCCACAAGGGCCA |
| 2496 | GGCCCTTGTGGGAAGTGCC | GGCACTTCCCACAAGGGCC |
| 2497 | GCCCTTGTGGGAAGTGCCA | TGGCACTTCCCACAAGGGC |
| 2498 | CCCTTGTGGGAAGTGCCAG | CTGGCACTTCCCACAAGGG |
| 2499 | CCTTGTGGGAAGTGCCAGG | CCTGGCACTTCCCACAAGG |
| 2500 | CTTGTGGGAAGTGCCAGGA | TCCTGGCACTTCCCACAAG |
| 2501 | TTGTGGGAAGTGCCAGGAG | CTCCTGGCACTTCCCACAA |
| 2502 | TGTGGGAAGTGCCAGGAGG | CCTCCTGGCACTTCCCACA |
| 2503 | GTGGGAAGTGCCAGGAGGG | CCCTCCTGGCACTTCCCAC |
| 2504 | TGGGAAGTGCCAGGAGGGC | GCCCTCCTGGCACTTCCCA |
| 2505 | GGGAAGTGCCAGGAGGGCC | GGCCCTCCTGGCACTTCCC |
| 2506 | GGAAGTGCCAGGAGGGCCT | AGGCCCTCCTGGCACTTCC |
| 2507 | GAAGTGCCAGGAGGGCCTG | CAGGCCCTCCTGGCACTTC |
| 2508 | AAGTGCCAGGAGGGCCTGG | CCAGGCCCTCCTGGCACTT |
| 2509 | AGTGCCAGGAGGGCCTGGA | TCCAGGCCCTCCTGGCACT |
| 2510 | GTGCCAGGAGGGCCTGGAG | CTCCAGGCCCTCCTGGCAC |
| 2511 | TGCCAGGAGGGCCTGGAGG | CCTCCAGGCCCTCCTGGCA |
| 2512 | GCCAGGAGGGCCTGGAGGG | CCCTCCAGGCCCTCCTGGC |
| 2513 | CCAGGAGGGCCTGGAGGGG | CCCCTCCAGGCCCTCCTGG |
| 2514 | CAGGAGGGCCTGGAGGGGG | CCCCCTCCAGGCCCTCCTG |
| 2515 | AGGAGGGCCTGGAGGGGGG | CCCCCCTCCAGGCCCTCCT |
| 2516 | GGAGGGCCTGGAGGGGGGT | ACCCCCCTCCAGGCCCTCC |
| 2517 | GAGGGCCTGGAGGGGGGTG | CACCCCCCTCCAGGCCCTC |
| 2518 | AGGGCCTGGAGGGGGGTGC | GCACCCCCCTCCAGGCCCT |
| 2519 | GGGCCTGGAGGGGGGTGCC | GGCACCCCCCTCCAGGCCC |
| 2520 | GGCCTGGAGGGGGGTGCCA | TGGCACCCCCCTCCAGGCC |
| 2521 | GCCTGGAGGGGGGTGCCAG | CTGGCACCCCCCTCCAGGC |
| 2522 | CCTGGAGGGGGGTGCCAGT | ACTGGCACCCCCCTCCAGG |
| 2523 | CTGGAGGGGGGTGCCAGTG | CACTGGCACCCCCCTCCAG |
| 2524 | TGGAGGGGGGTGCCAGTGG | CCACTGGCACCCCCCTCCA |
| 2525 | GGAGGGGGGTGCCAGTGGA | TCCACTGGCACCCCCCTCC |
| 2526 | GAGGGGGGTGCCAGTGGAG | CTCCACTGGCACCCCCCTC |
| 2527 | AGGGGGGTGCCAGTGGAGC | GCTCCACTGGCACCCCCCT |
| 2528 | GGGGGGTGCCAGTGGAGCC | GGCTCCACTGGCACCCCCC |
| 2529 | GGGGGTGCCAGTGGAGCCA | TGGCTCCACTGGCACCCCC |
| 2530 | GGGGTGCCAGTGGAGCCAG | CTGGCTCCACTGGCACCCC |
| 2531 | GGGTGCCAGTGGAGCCAGC | GCTGGCTCCACTGGCACCC |
| 2532 | GGTGCCAGTGGAGCCAGCG | CGCTGGCTCCACTGGCACC |
| 2533 | GTGCCAGTGGAGCCAGCGA | TCGCTGGCTCCACTGGCAC |
| 2534 | TGCCAGTGGAGCCAGCGAA | TTCGCTGGCTCCACTGGCA |
| 2535 | GCCAGTGGAGCCAGCGAAC | GTTCGCTGGCTCCACTGGC |
| 2536 | CCAGTGGAGCCAGCGAACC | GGTTCGCTGGCTCCACTGG |
| 2537 | CAGTGGAGCCAGCGAACCC | GGGTTCGCTGGCTCCACTG |
| 2538 | AGTGGAGCCAGCGAACCCA | TGGGTTCGCTGGCTCCACT |
| 2539 | GTGGAGCCAGCGAACCCAG | CTGGGTTCGCTGGCTCCAC |
| 2540 | TGGAGCCAGCGAACCCAGC | GCTGGGTTCGCTGGCTCCA |
| 2541 | GGAGCCAGCGAACCCAGCG | CGCTGGGTTCGCTGGCTCC |
| 2542 | GAGCCAGCGAACCCAGCGA | TCGCTGGGTTCGCTGGCTC |
| 2543 | AGCCAGCGAACCCAGCGAG | CTCGCTGGGTTCGCTGGCT |
| 2544 | GCCAGCGAACCCAGCGAGG | CCTCGCTGGGTTCGCTGGC |
| 2545 | CCAGCGAACCCAGCGAGGA | TCCTCGCTGGGTTCGCTGG |
| 2546 | CAGCGAACCCAGCGAGGAA | TTCCTCGCTGGGTTCGCTG |
| 2547 | AGCGAACCCAGCGAGGAAG | CTTCCTCGCTGGGTTCGCT |
| 2548 | GCGAACCCAGCGAGGAAGT | ACTTCCTCGCTGGGTTCGC |
| 2549 | CGAACCCAGCGAGGAAGTG | CACTTCCTCGCTGGGTTCG |
| 2550 | GAACCCAGCGAGGAAGTGA | TCACTTCCTCGCTGGGTTC |
| 2551 | AACCCAGCGAGGAAGTGAA | TTCACTTCCTCGCTGGGTT |
| 2552 | ACCCAGCGAGGAAGTGAAC | GTTCACTTCCTCGCTGGGT |
| 2553 | CCCAGCGAGGAAGTGAACA | TGTTCACTTCCTCGCTGGG |
| 2554 | CCAGCGAGGAAGTGAACAA | TTGTTCACTTCCTCGCTGG |
| 2555 | CAGCGAGGAAGTGAACAAG | CTTGTTCACTTCCTCGCTG |
| 2556 | AGCGAGGAAGTGAACAAGG | CCTTGTTCACTTCCTCGCT |

TABLE 1-continued cDNA Human Hairless 19-mer Target Sequences and Complement Referenced to NM_005144-
*Homo sapiens* hairless homolog (mouse) (HR), transcript variant 1, complete mRNA (1-5699 bp).
(SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 2557 | GCGAGGAAGTGAACAAGGC | GCCTTGTTCACTTCCTCGC |
| 2558 | CGAGGAAGTGAACAAGGCC | GGCCTTGTTCACTTCCTCG |
| 2559 | GAGGAAGTGAACAAGGCCT | AGGCCTTGTTCACTTCCTC |
| 2560 | AGGAAGTGAACAAGGCCTC | GAGGCCTTGTTCACTTCCT |
| 2561 | GGAAGTGAACAAGGCCTCT | AGAGGCCTTGTTCACTTCC |
| 2562 | GAAGTGAACAAGGCCTCTG | CAGAGGCCTTGTTCACTTC |
| 2563 | AAGTGAACAAGGCCTCTGG | CCAGAGGCCTTGTTCACTT |
| 2564 | AGTGAACAAGGCCTCTGGC | GCCAGAGGCCTTGTTCACT |
| 2565 | GTGAACAAGGCCTCTGGCC | GGCCAGAGGCCTTGTTCAC |
| 2566 | TGAACAAGGCCTCTGGCCC | GGGCCAGAGGCCTTGTTCA |
| 2567 | GAACAAGGCCTCTGGCCCC | GGGGCCAGAGGCCTTGTTC |
| 2568 | AACAAGGCCTCTGGCCCCA | TGGGGCCAGAGGCCTTGTT |
| 2569 | ACAAGGCCTCTGGCCCCAG | CTGGGGCCAGAGGCCTTGT |
| 2570 | CAAGGCCTCTGGCCCCAGG | CCTGGGGCCAGAGGCCTTG |
| 2571 | AAGGCCTCTGGCCCCAGGG | CCCTGGGGCCAGAGGCCTT |
| 2572 | AGGCCTCTGGCCCCAGGGC | GCCCTGGGGCCAGAGGCCT |
| 2573 | GGCCTCTGGCCCCAGGGCC | GGCCCTGGGGCCAGAGGCC |
| 2574 | GCCTCTGGCCCCAGGGCCT | AGGCCCTGGGGCCAGAGGC |
| 2575 | CCTCTGGCCCCAGGGCCTG | CAGGCCCTGGGGCCAGAGG |
| 2576 | CTCTGGCCCCAGGGCCTGT | ACAGGCCCTGGGGCCAGAG |
| 2577 | TCTGGCCCCAGGGCCTGTC | GACAGGCCCTGGGGCCAGA |
| 2578 | CTGGCCCCAGGGCCTGTCC | GGACAGGCCCTGGGGCCAG |
| 2579 | TGGCCCCAGGGCCTGTCCC | GGGACAGGCCCTGGGGCCA |
| 2580 | GGCCCCAGGGCCTGTCCCC | GGGGACAGGCCCTGGGGCC |
| 2581 | GCCCCAGGGCCTGTCCCCC | GGGGGACAGGCCCTGGGGC |
| 2582 | CCCCAGGGCCTGTCCCCCC | GGGGGGACAGGCCCTGGGG |
| 2583 | CCCAGGGCCTGTCCCCCCA | TGGGGGGACAGGCCCTGGG |
| 2584 | CCAGGGCCTGTCCCCCCAG | CTGGGGGGACAGGCCCTGG |
| 2585 | CAGGGCCTGTCCCCCCAGC | GCTGGGGGGACAGGCCCTG |
| 2586 | AGGGCCTGTCCCCCCAGCC | GGCTGGGGGGACAGGCCCT |
| 2587 | GGGCCTGTCCGCCCAGCCA | TGGCTGGGGGACAGGCCC |
| 2588 | GGCCTGTCCCCCCAGCCAC | GTGGCTGGGGGGACAGGCC |
| 2589 | GCCTGTCCCCCCAGCCACC | GGTGGCTGGGGGGACAGGC |
| 2590 | CCTGTCCCCCCAGCCACCA | TGGTGGCTGGGGGGACAGG |
| 2591 | CTGTCCCCCCAGCGACCAC | GTGGTGGCTGGGGGGACAG |
| 2592 | TGTCCCCCCAGCCACCACA | TGTGGTGGCTGGGGGGACA |
| 2593 | GTCCCCCCAGCCACCACAC | GTGTGGTGGCTGGGGGGAC |
| 2594 | TCCCCCCAGCCACCACACC | GGTGTGGTGGCTGGGGGGA |
| 2595 | CCCCCCAGCCACCACACCA | TGGTGTGGTGGCTGGGGGG |
| 2596 | CCCCCAGCCACCACACCAA | TTGGTGTGGTGGCTGGGGG |
| 2597 | CCCCAGCCACCACACCAAG | CTTGGTGTGGTGGCTGGGG |
| 2598 | CCCAGCCACCACACCAAGC | GCTTGGTGTGGTGGCTGGG |
| 2599 | CCAGCCACCACACCAAGCT | AGCTTGGTGTGGTGGCTGG |
| 2600 | CAGCCACCACACCAAGCTG | CAGCTTGGTGTGGTGGCTG |
| 2601 | AGCCACCACACCAAGCTGA | TCAGCTTGGTGTGGTGGCT |
| 2602 | GCCACCACACCAAGCTGAA | TTCAGCTTGGTGTGGTGGC |
| 2603 | CCACCACACCAAGCTGAAG | CTTCAGCTTGGTGTGGTGG |
| 2604 | CACCACACCAAGCTGAAGA | TCTTCAGCTTGGTGTGGTG |
| 2605 | ACCACACCAAGCTGAAGAA | TTCTTCAGCTTGGTGTGGT |
| 2606 | CCACACCAAGCTGAAGAAG | CTTCTTCAGCTTGGTGTGG |
| 2607 | CACACCAAGCTGAAGAAGA | TCTTCTTCAGCTTGGTGTG |
| 2608 | ACACCAAGCTGAAGAAGAC | GTCTTCTTCAGCTTGGTGT |
| 2609 | CACCAAGCTGAAGAAGACA | TGTCTTCTTCAGCTTGGTG |
| 2610 | ACCAAGCTGAAGAAGACAT | ATGTCTTCTTCAGCTTGGT |
| 2611 | CCAAGCTGAAGAAGACATG | CATGTCTTCTTCAGCTTGG |
| 2612 | CAAGCTGAAGAAGACATGG | CCATGTCTTCTTCAGCTTG |
| 2613 | AAGCTGAAGAAGACATGGC | GCCATGTCTTCTTCAGCTT |
| 2614 | AGCTGAAGAAGACATGGCT | AGCCATGTCTTCTTCAGCT |
| 2615 | GCTGAAGAAGACATGGCTC | GAGCCATGTCTTCTTCAGC |
| 2616 | CTGAAGAAGACATGGCTCA | TGAGCCATGTCTTCTTCAG |
| 2617 | TGAAGAAGACATGGCTCAC | GTGAGCCATGTCTTCTTCA |
| 2618 | GAAGAAGACATGGCTCACA | TGTGAGCCATGTCTTCTTC |
| 2619 | AAGAAGACATGGCTCACAC | GTGTGAGCCATGTCTTCTT |
| 2620 | AGAAGACATGGCTCACACG | CGTGTGAGCCATGTCTTCT |
| 2621 | GAAGACATGGCTCACACGG | CCGTGTGAGCCATGTCTTC |
| 2622 | AAGACATGGCTCACACGGC | GCCGTGTGAGCCATGTCTT |
| 2623 | AGACATGGCTCACACGGCA | TGCCGTGTGAGCCATGTCT |
| 2624 | GACATGGCTCACACGGCAC | GTGCCGTGTGAGCCATGTC |
| 2625 | ACATGGCTCACACGGCACT | AGTGCCGTGTGAGCCATGT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2626 | CATGGCTCACACGGCACTC | GAGTGCCGTGTGAGCCATG |
| 2627 | ATGGCTCACACGGCACTCG | CGAGTGCCGTGTGAGCCAT |
| 2628 | TGGCTCACACGGCACTCGG | CCGAGTGCCGTGTGAGCCA |
| 2629 | GGCTCACACGGCACTCGGA | TCCGAGTGCCGTGTGAGCC |
| 2630 | GCTCACACGGCACTCGGAG | CTCCGAGTGCCGTGTGAGC |
| 2631 | CTCACACGGCACTCGGAGC | GCTCCGAGTGCCGTGTGAG |
| 2632 | TCACACGGCACTCGGAGCA | TGCTCCGAGTGCCGTGTGA |
| 2633 | CACACGGCACTCGGAGCAG | CTGCTCCGAGTGCCGTGTG |
| 2634 | ACACGGCACTCGGAGCAGT | ACTGCTCCGAGTGCCGTGT |
| 2635 | CACGGCACTCGGAGCAGTT | AACTGCTCCGAGTGCCGTG |
| 2636 | ACGGCACTCGGAGCAGTTT | AAACTGCTCCGAGTGCCGT |
| 2637 | CGGCACTCGGAGCAGTTTG | CAAACTGCTCCGAGTGCCG |
| 2638 | GGCACTCGGAGCAGTTTGA | TCAAACTGCTCCGAGTGCC |
| 2639 | GCACTCGGAGCAGTTTGAA | TTCAAACTGCTCCGAGTGC |
| 2640 | CACTCGGAGCAGTTTGAAT | ATTCAAACTGCTCCGAGTG |
| 2641 | ACTCGGAGCAGTTTGAATG | CATTCAAACTGCTCCGAGT |
| 2642 | CTCGGAGCAGTTTGAATGT | ACATTCAAACTGCTCCGAG |
| 2643 | TCGGAGCAGTTTGAATGTC | GACATTCAAACTGCTCCGA |
| 2644 | CGGAGCAGTTTGAATGTCC | GGACATTCAAACTGCTCCG |
| 2645 | GGAGCAGTTTGAATGTCCA | TGGACATTCAAACTGCTCC |
| 2646 | GAGCAGTTTGAATGTCCAC | GTGGACATTCAAACTGCTC |
| 2647 | AGCAGTTTGAATGTCCACG | CGTGGACATTCAAACTGCT |
| 2648 | GCAGTTTGAATGTCCACGC | GCGTGGACATTCAAACTGC |
| 2649 | CAGTTTGAATGTCCACGCG | CGCGTGGACATTCAAACTG |
| 2650 | AGTTTGAATGTCCACGCGG | CCGCGTGGACATTCAAACT |
| 2651 | GTTTGAATGTCCACGCGGC | GCCGCGTGGACATTCAAAC |
| 2652 | TTTGAATGTCCACGCGGCT | AGCCGCGTGGACATTCAAA |
| 2653 | TTGAATGTCCACGCGGCTG | CAGCCGCGTGGACATTCAA |
| 2654 | TGAATGTCCACGCGGCTGC | GCAGCCGCGTGGACATTCA |
| 2655 | GAATGTCCACGCGGCTGCC | GGCAGCCGCGTGGACATTC |
| 2656 | AATGTCCACGCGGCTGCCC | GGGCAGCCGCGTGGACATT |
| 2657 | ATGTCCACGCGGCTGCCCT | AGGGCAGCCGCGTGGACAT |
| 2658 | TGTCCACGCGGCTGCCCTG | CAGGGCAGCCGCGTGGACA |
| 2659 | GTCCACGCGGCTGCCCTGA | TCAGGGCAGCCGCGTGGAC |
| 2660 | TCCACGCGGCTGCCCTGAG | CTCAGGGCAGCCGCGTGGA |
| 2661 | CCACGCGGCTGCCCTGAGG | CCTCAGGGCAGCCGCGTGG |
| 2662 | CACGCGGCTGCCCTGAGGT | ACCTCAGGGCAGCCGCGTG |
| 2663 | ACGCGGCTGCCCTGAGGTC | GACCTCAGGGCAGCCGCGT |
| 2664 | CGCGGCTGCCCTGAGGTCG | CGACCTCAGGGCAGCCGCG |
| 2665 | GCGGCTGCCCTGAGGTCGA | TCGACCTCAGGGCAGCCGC |
| 2666 | CGGCTGCCCTGAGGTCGAG | CTCGACCTCAGGGCAGCCG |
| 2667 | GGCTGCCCTGAGGTCGAGG | CCTCGACCTCAGGGCAGCC |
| 2668 | GCTGCCCTGAGGTCGAGGA | TCCTCGACCTCAGGGCAGC |
| 2669 | CTGCCCTGAGGTCGAGGAG | CTCCTCGACCTCAGGGCAG |
| 2670 | TGCCCTGAGGTCGAGGAGA | TCTCCTCGACCTCAGGGCA |
| 2671 | GCCCTGAGGTCGAGGAGAG | CTCTCCTCGACCTCAGGGC |
| 2672 | CCCTGAGGTCGAGGAGAGG | CCTCTCCTCGACCTCAGGG |
| 2673 | CCTGAGGTCGAGGAGAGGC | GCCTCTCCTCGACCTCAGG |
| 2674 | CTGAGGTCGAGGAGAGGCC | GGCCTCTCCTCGACCTCAG |
| 2675 | TGAGGTCGAGGAGAGGCCG | CGGCCTCTCCTCGACCTCA |
| 2676 | GAGGTCGAGGAGAGGCCGG | CCGGCCTCTCCTCGACCTC |
| 2677 | AGGTCGAGGAGAGGCCGGT | ACCGGCCTCTCCTCGACCT |
| 2678 | GGTCGAGGAGAGGCCGGTT | AACCGGCCTCTCCTCGACC |
| 2679 | GTCGAGGAGAGGCCGGTTG | CAACCGGCCTCTCCTCGAC |
| 2680 | TCGAGGAGAGGCCGGTTGC | GCAACCGGCCTCTCCTCGA |
| 2681 | CGAGGAGAGGCCGGTTGCT | AGCAACCGGCCTCTCCTCG |
| 2682 | GAGGAGAGGCCGGTTGCTC | GAGCAACCGGCCTCTCCTC |
| 2683 | AGGAGAGGCCGGTTGCTCG | CGAGCAACCGGCCTCTCCT |
| 2684 | GGAGAGGCCGGTTGCTCGG | CCGAGCAACCGGCCTCTCC |
| 2685 | GAGAGGCCGGTTGCTCGGC | GCCGAGCAACCGGCCTCTC |
| 2686 | AGAGGCCGGTTGCTCGGCT | AGCCGAGCAACCGGCCTCT |
| 2687 | GAGGCCGGTTGCTCGGCTC | GAGCCGAGCAACCGGCCTC |
| 2688 | AGGCCGGTTGCTCGGCTCC | GGAGCCGAGCAACCGGCCT |
| 2689 | GGCCGGTTGCTCGGCTCCG | CGGAGCCGAGCAACCGGCC |
| 2690 | GCCGGTTGCTCGGCTCCGG | CCGGAGCCGAGCAACCGGC |
| 2691 | CCGGTTGCTCGGCTCCGGG | CCCGGAGCCGAGCAACCGG |
| 2692 | CGGTTGCTCGGCTCCGGGC | GCCCGGAGCCGAGCAACCG |
| 2693 | GGTTGCTCGGCTCCGGGCC | GGCCCGGAGCCGAGCAACC |
| 2694 | GTTGCTCGGCTCCGGGCCC | GGGCCCGGAGCCGAGCAAC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2695 | TTGCTCGGCTCCGGGCCCT | AGGGCCCGGAGCCGAGCAA |
| 2696 | TGCTCGGCTCCGGGCCCTC | GAGGGCCCGGAGCCGAGCA |
| 2697 | GCTCGGCTCCGGGCCCTCA | TGAGGGCCCGGAGCCGAGC |
| 2698 | CTCGGCTCCGGGCCCTCAA | TTGAGGGCCCGGAGCCGAG |
| 2699 | TCGGCTCCGGGCCCTCAAA | TTTGAGGGCCCGGAGCCGA |
| 2700 | CGGCTCCGGGCCCTCAAAA | TTTTGAGGGCCCGGAGCCG |
| 2701 | GGCTCCGGGCCCTCAAAAG | CTTTTGAGGGCCCGGAGCC |
| 2702 | GCTCCGGGCCCTCAAAAGG | CCTTTTGAGGGCCCGGAGC |
| 2703 | CTCCGGGCCCTCAAAAGGG | CCCTTTTGAGGGCCCGGAG |
| 2704 | TCCGGGCCCTCAAAAGGGC | GCCCTTTTGAGGGCCCGGA |
| 2705 | CCGGGCCCTCAAAAGGGCA | TGCCCTTTTGAGGGCCCGG |
| 2706 | CGGGCCCTCAAAAGGGCAG | CTGCCCTTTTGAGGGCCCG |
| 2707 | GGGCCCTCAAAAGGGCAGG | CCTGCCCTTTTGAGGGCCC |
| 2708 | GGCCCTCAAAAGGGCAGGC | GCCTGCCCTTTTGAGGGCC |
| 2709 | GCCCTCAAAAGGGCAGGCA | TGCCTGCCCTTTTGAGGGC |
| 2710 | CCCTCAAAAGGGCAGGCAG | CTGCCTGCCCTTTTGAGGG |
| 2711 | CCTCAAAAGGGCAGGCAGC | GCTGCCTGCCCTTTTGAGG |
| 2712 | CTCAAAAGGGCAGGCAGCC | GGCTGCCTGCCCTTTTGAG |
| 2713 | TCAAAAGGGCAGGCAGCCC | GGGCTGCCTGCCCTTTTGA |
| 2714 | CAAAAGGGCAGGCAGCCCC | GGGGCTGCCTGCCCTTTTG |
| 2715 | AAAAGGGCAGGCAGCCCCG | CGGGGCTGCCTGCCCTTTT |
| 2716 | AAAGGGCAGGCAGCCCCGA | TCGGGGCTGCCTGCCCTTT |
| 2717 | AAGGGCAGGCAGCCCCGAG | CTCGGGGCTGCCTGCCCTT |
| 2718 | AGGGCAGGCAGCCCCGAGG | CCTCGGGGCTGCCTGCCCT |
| 2719 | GGGCAGGCAGCCCCGAGGT | ACCTCGGGGCTGCCTGCCC |
| 2720 | GGCAGGCAGCCCCGAGGTC | GACCTCGGGGCTGCCTGCC |
| 2721 | GCAGGCAGCCCCGAGGTCC | GGACCTCGGGGCTGCCTGC |
| 2722 | CAGGCAGCCCCGAGGTCCA | TGGACCTCGGGGCTGCCTG |
| 2723 | AGGCAGCCCCGAGGTCCAG | CTGGACCTCGGGGCTGCCT |
| 2724 | GGCAGCCCCGAGGTCCAGG | CCTGGACCTCGGGGCTGCC |
| 2725 | GCAGCCCCGAGGTCCAGGG | CCCTGGACCTCGGGGCTGC |
| 2726 | CAGCCCCGAGGTCCAGGGA | TCCCTGGACCTCGGGGCTG |
| 2727 | AGCCCCGAGGTCCAGGGAG | CTCCCTGGACCTCGGGGCT |
| 2728 | GCCCCGAGGTCCAGGGAGC | GCTCCCTGGACCTCGGGGC |
| 2729 | CCCCGAGGTCCAGGGAGCA | TGCTCCCTGGACCTCGGGG |
| 2730 | CCCGAGGTCCAGGGAGCAA | TTGCTCCCTGGACCTCGGG |
| 2731 | CCGAGGTCCAGGGAGCAAT | ATTGCTCCCTGGACCTCGG |
| 2732 | CGAGGTCCAGGGAGCAATG | CATTGCTCCCTGGACCTCG |
| 2733 | GAGGTCCAGGGAGCAATGG | CCATTGCTCCCTGGACCTC |
| 2734 | AGGTCCAGGGAGCAATGGG | CCCATTGCTCCCTGGACCT |
| 2735 | GGTCCAGGGAGCAATGGGC | GCCCATTGCTCCCTGGACC |
| 2736 | GTCCAGGGAGCAATGGGCA | TGCCCATTGCTCCCTGGAC |
| 2737 | TCCAGGGAGCAATGGGCAG | CTGCCCATTGCTCCCTGGA |
| 2738 | CCAGGGAGCAATGGGCAGT | ACTGCCCATTGCTCCCTGG |
| 2739 | CAGGGAGCAATGGGCAGTC | GACTGCCCATTGCTCCCTG |
| 2740 | AGGGAGCAATGGGCAGTCC | GGACTGCCCATTGCTCCCT |
| 2741 | GGGAGCAATGGGCAGTCCA | TGGACTGCCCATTGCTCCC |
| 2742 | GGAGCAATGGGCAGTCCAG | CTGGACTGCCCATTGCTCC |
| 2743 | GAGCAATGGGCAGTCCAGC | GCTGGACTGCCCATTGCTC |
| 2744 | AGCAATGGGCAGTCCAGCC | GGCTGGACTGCCCATTGCT |
| 2745 | GCAATGGGCAGTCCAGCCC | GGGCTGGACTGCCCATTGC |
| 2746 | CAATGGGCAGTCCAGCCCC | GGGGCTGGACTGCCCATTG |
| 2747 | AATGGGCAGTCCAGCCCCC | GGGGGCTGGACTGCCCATT |
| 2748 | ATGGGCAGTCCAGCCCCCA | TGGGGGCTGGACTGCCCAT |
| 2749 | TGGGCAGTCCAGCCCCCAA | TTGGGGGCTGGACTGCCCA |
| 2750 | GGGCAGTCCAGCCCCCAAG | CTTGGGGGCTGGACTGCCC |
| 2751 | GGCAGTCCAGCCCCCAAGC | GCTTGGGGGCTGGACTGCC |
| 2752 | GCAGTCCAGCCCCCAAGCG | CGCTTGGGGGCTGGACTGC |
| 2753 | CAGTCCAGCCCCCAAGCGG | CCGCTTGGGGGCTGGACTG |
| 2754 | AGTCCAGCCCCCAAGCGGC | GCCGCTTGGGGGCTGGACT |
| 2755 | GTCCAGCCCCCAAGCGGCC | GGCCGCTTGGGGGCTGGAC |
| 2756 | TCCAGCCCCCAAGCGGCCA | TGGCCGCTTGGGGGCTGGA |
| 2757 | CCAGCCCCCAAGCGGCCAC | GTGGCCGCTTGGGGGCTGG |
| 2758 | CAGCCCCCAAGCGGCCACC | GGTGGCCGCTTGGGGGCTG |
| 2759 | AGCCCCCAAGCGGCCACCG | CGGTGGCCGCTTGGGGGCT |
| 2760 | GCCCCCAAGCGGCCACCGG | CCGGTGGCCGCTTGGGGGC |
| 2761 | CCCCCAAGCGGCCACCGGA | TCCGGTGGCCGCTTGGGGG |
| 2762 | CCCCAAGCGGCCACCGGAC | GTCCGGTGGCCGCTTGGGG |
| 2763 | CCCAAGCGGCCACCGGACC | GGTCCGGTGGCCGCTTGGG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2764 | CCAAGCGGCCACCGGACCC | GGGTCCGGTGGCCGCTTGG |
| 2765 | CAAGCGGCCACCGGACCCT | AGGGTCCGGTGGCCGCTTG |
| 2766 | AAGCGGCCACCGGACCCTT | AAGGGTCCGGTGGCCGCTT |
| 2767 | AGCGGCCACCGGACCCTTT | AAAGGGTCCGGTGGCCGCT |
| 2768 | GCGGCCACCGGACCCTTTT | AAAAGGGTCCGGTGGCCGC |
| 2769 | CGGCCACCGGACCCTTTTC | GAAAAGGGTCCGGTGGCCG |
| 2770 | GGCCACCGGACCCTTTTCC | GGAAAAGGGTCCGGTGGCC |
| 2771 | GCCACCGGACCCTTTTCCA | TGGAAAAGGGTCCGGTGGC |
| 2772 | CCACCGGACCCTTTTCCAG | CTGGAAAAGGGTCCGGTGG |
| 2773 | CACCGGACCCTTTTCCAGG | CCTGGAAAAGGGTCCGGTG |
| 2774 | ACCGGACCCTTTTCCAGGC | GCCTGGAAAAGGGTCCGGT |
| 2775 | CCGGACCCTTTTCCAGGCA | TGCCTGGAAAAGGGTCCGG |
| 2776 | CGGACCCTTTTCCAGGCAC | GTGCCTGGAAAAGGGTCCG |
| 2777 | GGACCCTTTTCCAGGCACT | AGTGCCTGGAAAAGGGTCC |
| 2778 | GACCCTTTTCCAGGCACTG | CAGTGCCTGGAAAAGGGTC |
| 2779 | ACCCTTTTCCAGGCACTGC | GCAGTGCCTGGAAAAGGGT |
| 2780 | CCCTTTTCCAGGCACTGCA | TGCAGTGCCTGGAAAAGGG |
| 2781 | CCTTTTCCAGGCACTGCAG | CTGCAGTGCCTGGAAAAGG |
| 2782 | CTTTTCCAGGCACTGCAGA | TCTGCAGTGCCTGGAAAAG |
| 2783 | TTTTCCAGGCACTGCAGAA | TTCTGCAGTGCCTGGAAAA |
| 2784 | TTTCCAGGCACTGCAGAAC | GTTCTGCAGTGCCTGGAAA |
| 2785 | TTCCAGGCACTGCAGAACA | TGTTCTGCAGTGCCTGGAA |
| 2786 | TCCAGGCACTGCAGAACAG | CTGTTCTGCAGTGCCTGGA |
| 2787 | CCAGGCACTGCAGAACAGG | CCTGTTCTGCAGTGCCTGG |
| 2788 | CAGGCACTGCAGAACAGGG | CCCTGTTCTGCAGTGCCTG |
| 2789 | AGGCACTGCAGAACAGGGG | CCCCTGTTCTGCAGTGCCT |
| 2790 | GGCACTGCAGAACAGGGGG | CCCCCTGTTCTGCAGTGCC |
| 2791 | GCACTGCAGAACAGGGGGC | GCCCCCTGTTCTGCAGTGC |
| 2792 | CACTGCAGAACAGGGGGCT | AGCCCCCTGTTCTGCAGTG |
| 2793 | ACTGCAGAACAGGGGGCTG | CAGCCCCCTGTTCTGCAGT |
| 2794 | CTGCAGAACAGGGGGCTGG | CCAGCCCCCTGTTCTGCAG |
| 2795 | TGCAGAACAGGGGGCTGGG | CCCAGCCCCCTGTTCTGCA |
| 2796 | GCAGAACAGGGGGCTGGGG | CCCCAGCCCCCTGTTCTGC |
| 2797 | CAGAACAGGGGGCTGGGGG | CCCCCAGCCCCCTGTTCTG |
| 2798 | AGAACAGGGGGCTGGGGGT | ACCCCCAGCCCCCTGTTCT |
| 2799 | GAACAGGGGGCTGGGGGTT | AACCCCCAGCCCCCTGTTC |
| 2800 | AACAGGGGGCTGGGGGTTG | CAACCCCCAGCCCCCTGTT |
| 2801 | ACAGGGGGCTGGGGGTTGG | CCAACCCCCAGCCCCCTGT |
| 2802 | CAGGGGGCTGGGGGTTGGC | GCCAACCCCCAGCCCCCTG |
| 2803 | AGGGGGCTGGGGGTTGGCA | TGCCAACCCCCAGCCCCCT |
| 2804 | GGGGGCTGGGGGTTGGCAG | CTGCCAACCCCCAGCCCCC |
| 2805 | GGGGCTGGGGGTTGGCAGG | CCTGCCAACCCCCAGCCCC |
| 2806 | GGGCTGGGGGTTGGCAGGA | TCCTGCCAACCCCCAGCCC |
| 2807 | GGCTGGGGGTTGGCAGGAG | CTCCTGCCAACCCCCAGCC |
| 2808 | GCTGGGGGTTGGCAGGAGG | CCTCCTGCCAACCCCCAGC |
| 2809 | CTGGGGGTTGGCAGGAGGT | ACCTCCTGCCAACCCCCAG |
| 2810 | TGGGGGTTGGCAGGAGGTG | CACCTCCTGCCAACCCCCA |
| 2811 | GGGGGTTGGCAGGAGGTGC | GCACCTCCTGCCAACCCCC |
| 2812 | GGGGTTGGCAGGAGGTGCG | CGCACCTCCTGCCAACCCC |
| 2813 | GGGTTGGCAGGAGGTGCGG | CCGCACCTCCTGCCAACCC |
| 2814 | GGTTGGCAGGAGGTGCGGG | CCCGCACCTCCTGCCAACC |
| 2815 | GTTGGCAGGAGGTGCGGGA | TCCCGCACCTCCTGCCAAC |
| 2816 | TTGGCAGGAGGTGCGGGAC | GTCCCGCACCTCCTGCCAA |
| 2817 | TGGCAGGAGGTGCGGGACA | TGTCCCGCACCTCCTGCCA |
| 2818 | GGCAGGAGGTGCGGGACAC | GTGTCCCGCACCTCCTGCC |
| 2819 | GCAGGAGGTGCGGGACACA | TGTGTCCCGCACCTCCTGC |
| 2820 | CAGGAGGTGCGGGACACAT | ATGTGTCCCGCACCTCCTG |
| 2821 | AGGAGGTGCGGGACACATC | GATGTGTCCCGCACCTCCT |
| 2822 | GGAGGTGCGGGACACATCG | CGATGTGTCCCGCACCTCC |
| 2823 | GAGGTGCGGGACACATCGA | TCGATGTGTCCCGCACCTC |
| 2824 | AGGTGCGGGACACATCGAT | ATCGATGTGTCCCGCACCT |
| 2825 | GGTGCGGGACACATCGATA | TATCGATGTGTCCCGCACC |
| 2826 | GTGCGGGACACATCGATAG | CTATCGATGTGTCCCGCAC |
| 2827 | TGCGGGACACATCGATAGG | CCTATCGATGTGTCCCGCA |
| 2828 | GCGGGACACATCGATAGGG | CCCTATCGATGTGTCCCGC |
| 2829 | CGGGACACATCGATAGGGA | TCCCTATCGATGTGTCCCG |
| 2830 | GGGACACATCGATAGGGAA | TTCCCTATCGATGTGTCCC |
| 2831 | GGACACATCGATAGGGAAC | GTTCCCTATCGATGTGTCC |
| 2832 | GACACATCGATAGGGAACA | TGTTCCCTATCGATGTGTC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 2833 | ACACATCGATAGGGAACAA | TTGTTCCCTATCGATGTGT |
| 2834 | CACATCGATAGGGAACAAG | CTTGTTCCCTATCGATGTG |
| 2835 | ACATCGATAGGGAACAAGG | CCTTGTTCCCTATCGATGT |
| 2836 | CATCGATAGGGAACAAGGA | TCCTTGTTCCCTATCGATG |
| 2837 | ATCGATAGGGAACAAGGAT | ATCCTTGTTCCCTATCGAT |
| 2838 | TCGATAGGGAACAAGGATG | CATCCTTGTTCCCTATCGA |
| 2839 | CGATAGGGAACAAGGATGT | ACATCCTTGTTCCCTATCG |
| 2840 | GATAGGGAACAAGGATGTG | CACATCCTTGTTCCCTATC |
| 2841 | ATAGGGAACAAGGATGTGG | CCACATCCTTGTTCCCTAT |
| 2842 | TAGGGAACAAGGATGTGGA | TCCACATCCTTGTTCCCTA |
| 2843 | AGGGAACAAGGATGTGGAC | GTCCACATCCTTGTTCCCT |
| 2844 | GGGAACAAGGATGTGGACT | AGTCCACATCCTTGTTCCC |
| 2845 | GGAACAAGGATGTGGACTC | GAGTCCACATCCTTGTTCC |
| 2846 | GAACAAGGATGTGGACTCG | CGAGTCCACATCCTTGTTC |
| 2847 | AACAAGGATGTGGACTCGG | CCGAGTCCACATCCTTGTT |
| 2848 | ACAAGGATGTGGACTCGGG | CCCGAGTCCACATCCTTGT |
| 2849 | CAAGGATGTGGACTCGGGA | TCCCGAGTCCACATCCTTG |
| 2850 | AAGGATGTGGACTCGGGAC | GTCCCGAGTCCACATCCTT |
| 2851 | AGGATGTGGACTCGGGACA | TGTCCCGAGTCCACATCCT |
| 2852 | GGATGTGGACTCGGGACAG | CTGTCCCGAGTCCACATCC |
| 2853 | GATGTGGACTCGGGACAGC | GCTGTCCCGAGTCCACATC |
| 2854 | ATGTGGACTCGGGACAGCA | TGCTGTCCCGAGTCCACAT |
| 2855 | TGTGGACTCGGGACAGCAT | ATGCTGTCCCGAGTCCACA |
| 2856 | GTGGACTCGGGACAGCATG | CATGCTGTCCCGAGTCCAC |
| 2857 | TGGACTCGGGACAGCATGA | TCATGCTGTCCCGAGTCCA |
| 2858 | GGACTCGGGACAGCATGAT | ATCATGCTGTCCCGAGTCC |
| 2859 | GACTCGGGACAGCATGATG | CATCATGCTGTCCCGAGTC |
| 2860 | ACTCGGGACAGCATGATGA | TCATCATGCTGTCCCGAGT |
| 2861 | CTCGGGACAGCATGATGAG | CTCATCATGCTGTCCCGAG |
| 2862 | TCGGGACAGCATGATGAGC | GCTCATCATGCTGTCCCGA |
| 2863 | CGGGACAGCATGATGAGCA | TGCTCATCATGCTGTCCCG |
| 2864 | GGGACAGCATGATGAGCAG | CTGCTCATCATGCTGTCCC |
| 2865 | GGACAGCATGATGAGCAGA | TCTGCTCATCATGCTGTCC |
| 2866 | GACAGCATGATGAGCAGAA | TTCTGCTCATCATGCTGTC |
| 2867 | ACAGCATGATGAGCAGAAA | TTTCTGCTCATCATGCTGT |
| 2868 | CAGCATGATGAGCAGAAAG | CTTTCTGCTCATCATGCTG |
| 2869 | AGCATGATGAGCAGAAAGG | CCTTTCTGCTCATCATGCT |
| 2870 | GCATGATGAGCAGAAAGGA | TCCTTTCTGCTCATCATGC |
| 2871 | CATGATGAGCAGAAAGGAC | GTCCTTTCTGCTCATCATG |
| 2872 | ATGATGAGCAGAAAGGACC | GGTCCTTTCTGCTCATCAT |
| 2873 | TGATGAGCAGAAAGGACCC | GGGTCCTTTCTGCTCATCA |
| 2874 | GATGAGCAGAAAGGACCCC | GGGGTCCTTTCTGCTCATC |
| 2875 | ATGAGCAGAAAGGACCCCA | TGGGGTCCTTTCTGCTCAT |
| 2876 | TGAGCAGAAAGGACCCCAA | TTGGGGTCCTTTCTGCTCA |
| 2877 | GAGCAGAAAGGACCCCAAG | CTTGGGGTCCTTTCTGCTC |
| 2878 | AGCAGAAAGGACCCCAAGA | TCTTGGGGTCCTTTCTGCT |
| 2879 | GCAGAAAGGACCCCAAGAT | ATCTTGGGGTCCTTTCTGC |
| 2880 | CAGAAAGGACCCCAAGATG | CATCTTGGGGTCCTTTCTG |
| 2881 | AGAAAGGACCCCAAGATGG | CCATCTTGGGGTCCTTTCT |
| 2882 | GAAAGGACCCCAAGATGGC | GCCATCTTGGGGTCCTTTC |
| 2883 | AAAGGACCCCAAGATGGCC | GGCCATCTTGGGGTCCTTT |
| 2884 | AAGGACCCCAAGATGGCCA | TGGCCATCTTGGGGTCCTT |
| 2885 | AGGACCCCAAGATGGCCAG | CTGGCCATCTTGGGGTCCT |
| 2886 | GGACCCCAAGATGGCCAGG | CCTGGCCATCTTGGGGTCC |
| 2887 | GACCCCAAGATGGCCAGGC | GCCTGGCCATCTTGGGGTC |
| 2888 | ACCCCAAGATGGCCAGGCC | GGCCTGGCCATCTTGGGGT |
| 2889 | CCCCAAGATGGCCAGGCCA | TGGCCTGGCCATCTTGGGG |
| 2890 | CCCAAGATGGCCAGGCCAG | CTGGCCTGGCCATCTTGGG |
| 2891 | CCAAGATGGCCAGGCCAGT | ACTGGCCTGGCCATCTTGG |
| 2892 | CAAGATGGCCAGGCCAGTC | GACTGGCCTGGCCATCTTG |
| 2893 | AAGATGGCCAGGCCAGTCT | AGACTGGCCTGGCCATCTT |
| 2894 | AGATGGCCAGGCCAGTCTC | GAGACTGGCCTGGCCATCT |
| 2895 | GATGGCCAGGCCAGTCTCC | GGAGACTGGCCTGGCCATC |
| 2896 | ATGGCCAGGCCAGTCTCCA | TGGAGACTGGCCTGGCCAT |
| 2897 | TGGCCAGGCCAGTCTCCAG | CTGGAGACTGGCCTGGCCA |
| 2898 | GGCCAGGCCAGTCTCCAGG | CCTGGAGACTGGCCTGGCC |
| 2899 | GCCAGGCCAGTCTCCAGGA | TCCTGGAGACTGGCCTGGC |
| 2900 | CCAGGCCAGTCTCCAGGAC | GTCCTGGAGACTGGCCTGG |
| 2901 | CAGGCCAGTCTCCAGGACC | GGTCCTGGAGACTGGCCTG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 2902 | AGGCCAGTCTCCAGGACCC | GGGTCCTGGAGACTGGCCT |
| 2903 | GGCCAGTCTCCAGGACCCG | CGGGTCCTGGAGACTGGCC |
| 2904 | GCCAGTCTCCAGGACCCGG | CCGGGTCCTGGAGACTGGC |
| 2905 | CCAGTCTCCAGGACCCGGG | CCCGGGTCCTGGAGACTGG |
| 2906 | CAGTCTCCAGGACCCGGGA | TCCCGGGTCCTGGAGACTG |
| 2907 | AGTCTCCAGGACCCGGGAC | GTCCCGGGTCCTGGAGACT |
| 2908 | GTCTCCAGGACCCGGGACT | AGTCCCGGGTCCTGGAGAC |
| 2909 | TCTCCAGGACCCGGGACTT | AAGTCCCGGGTCCTGGAGA |
| 2910 | CTCCAGGACCCGGGACTTC | GAAGTCCCGGGTCCTGGAG |
| 2911 | TCCAGGACCCGGGACTTCA | TGAAGTCCCGGGTCCTGGA |
| 2912 | CCAGGACCCGGGACTTCAG | CTGAAGTCCCGGGTCCTGG |
| 2913 | CAGGACCCGGGACTTCAGG | CCTGAAGTCCCGGGTCCTG |
| 2914 | AGGACCCGGGACTTCAGGA | TCCTGAAGTCCCGGGTCCT |
| 2915 | GGACCCGGGACTTCAGGAC | GTCCTGAAGTCCCGGGTCC |
| 2916 | GACCCGGGACTTCAGGACA | TGTCCTGAAGTCCCGGGTC |
| 2917 | ACCCGGGACTTCAGGACAT | ATGTCCTGAAGTCCCGGGT |
| 2918 | CCCGGGACTTCAGGACATA | TATGTCCTGAAGTCCCGGG |
| 2919 | CCGGGACTTCAGGACATAC | GTATGTCCTGAAGTCCCGG |
| 2920 | CGGGACTTCAGGACATACC | GGTATGTCCTGAAGTCCCG |
| 2921 | GGGACTTCAGGACATACCA | TGGTATGTCCTGAAGTCCC |
| 2922 | GGACTTCAGGACATACCAT | ATGGTATGTCCTGAAGTCC |
| 2923 | GACTTCAGGACATACCATG | CATGGTATGTCCTGAAGTC |
| 2924 | ACTTCAGGACATACCATGC | GCATGGTATGTCCTGAAGT |
| 2925 | CTTCAGGACATACCATGCC | GGCATGGTATGTCCTGAAG |
| 2926 | TTCAGGACATACCATGCCT | AGGCATGGTATGTCCTGAA |
| 2927 | TCAGGACATACCATGCCTG | CAGGCATGGTATGTCCTGA |
| 2928 | CAGGACATACCATGCCTGG | CCAGGCATGGTATGTCCTG |
| 2929 | AGGACATACCATGCCTGGC | GCCAGGCATGGTATGTCCT |
| 2930 | GGACATACCATGCCTGGCT | AGCCAGGCATGGTATGTCC |
| 2931 | GACATACCATGCCTGGCTC | GAGCCAGGCATGGTATGTC |
| 2932 | ACATACCATGCCTGGCTCT | AGAGCCAGGCATGGTATGT |
| 2933 | CATACCATGCCTGGCTCTC | GAGAGCCAGGCATGGTATG |
| 2934 | ATACCATGCCTGGCTCTCC | GGAGAGCCAGGCATGGTAT |
| 2935 | TACCATGCCTGGCTCTCCC | GGGAGAGCCAGGCATGGTA |
| 2936 | ACCATGCCTGGCTCTCCCT | AGGGAGAGCCAGGCATGGT |
| 2937 | CCATGCCTGGCTCTCCCTG | CAGGGAGAGCCAGGCATGG |
| 2938 | CATGCCTGGCTCTCCCTGC | GCAGGGAGAGCCAGGCATG |
| 2939 | ATGCCTGGCTCTCCCTGCA | TGCAGGGAGAGCCAGGCAT |
| 2940 | TGCCTGGCTCTCCCTGCAA | TTGCAGGGAGAGCCAGGCA |
| 2941 | GCCTGGCTCTCCCTGCAAA | TTTGCAGGGAGAGCCAGGC |
| 2942 | CCTGGCTCTCCCTGCAAAA | TTTTGCAGGGAGAGCCAGG |
| 2943 | CTGGCTCTCCCTGCAAAAC | GTTTTGCAGGGAGAGCCAG |
| 2944 | TGGCTCTCCCTGCAAAACT | AGTTTTGCAGGGAGAGCCA |
| 2945 | GGCTCTCCCTGCAAAACTG | CAGTTTTGCAGGGAGAGCC |
| 2946 | GCTCTCCCTGCAAAACTGG | CCAGTTTTGCAGGGAGAGC |
| 2947 | CTCTCCCTGCAAAACTGGC | GCCAGTTTTGCAGGGAGAG |
| 2948 | TCTCCCTGCAAAACTGGCT | AGCCAGTTTTGCAGGGAGA |
| 2949 | CTCCCTGCAAAACTGGCTC | GAGCCAGTTTTGCAGGGAG |
| 2950 | TCCCTGCAAAACTGGCTCA | TGAGCCAGTTTTGCAGGGA |
| 2951 | CCCTGCAAAACTGGCTCAA | TTGAGCCAGTTTTGCAGGG |
| 2952 | CCTGCAAAACTGGCTCAAT | ATTGAGCCAGTTTTGCAGG |
| 2953 | CTGCAAAACTGGCTCAATG | CATTGAGCCAGTTTTGCAG |
| 2954 | TGCAAAACTGGCTCAATGC | GCATTGAGCCAGTTTTGCA |
| 2955 | GCAAAACTGGCTCAATGCC | GGCATTGAGCCAGTTTTGC |
| 2956 | CAAAACTGGCTCAATGCCA | TGGCATTGAGCCAGTTTTG |
| 2957 | AAAACTGGCTCAATGCCAA | TTGGCATTGAGCCAGTTTT |
| 2958 | AAACTGGCTCAATGCCAAA | TTTGGCATTGAGCCAGTTT |
| 2959 | AACTGGCTCAATGCCAAAG | CTTTGGCATTGAGCCAGTT |
| 2960 | ACTGGCTCAATGCCAAAGT | ACTTTGGCATTGAGCCAGT |
| 2961 | CTGGCTCAATGCCAAAGTT | AACTTTGGCATTGAGCCAG |
| 2962 | TGGCTCAATGCCAAAGTTG | CAACTTTGGCATTGAGCCA |
| 2963 | GGCTCAATGCCAAAGTTGT | ACAACTTTGGCATTGAGCC |
| 2964 | GCTCAATGCCAAAGTTGTG | CACAACTTTGGCATTGAGC |
| 2965 | CTCAATGCCAAAGTTGTGC | GCACAACTTTGGCATTGAG |
| 2966 | TCAATGCCAAAGTTGTGCC | GGCACAACTTTGGCATTGA |
| 2967 | CAATGCCAAAGTTGTGCCC | GGGCACAACTTTGGCATTG |
| 2968 | AATGCCAAAGTTGTGCCCA | TGGGCACAACTTTGGCATT |
| 2969 | ATGCCAAAGTTGTGCCCAG | CTGGGCACAACTTTGGCAT |
| 2970 | TGCCAAAGTTGTGCCCAGG | CCTGGGCACAACTTTGGCA |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 2971 | GCCAAAGTTGTGCCCAGGC | GCCTGGGCACAACTTTGGC |
| 2972 | CCAAAGTTGTGCCCAGGCA | TGCCTGGGCACAACTTTGG |
| 2973 | CAAAGTTGTGCCCAGGCAG | CTGCCTGGGCACAACTTTG |
| 2974 | AAAGTTGTGCCCAGGCAGC | GCTGCCTGGGCACAACTTT |
| 2975 | AAGTTGTGCCCAGGCAGCT | AGCTGCCTGGGCACAACTT |
| 2976 | AGTTGTGCCCAGGCAGCTG | CAGCTGCCTGGGCACAACT |
| 2977 | GTTGTGCCCAGGCAGCTGG | CCAGCTGCCTGGGCACAAC |
| 2978 | TTGTGCCCAGGCAGCTGGA | TCCAGCTGCCTGGGCACAA |
| 2979 | TGTGCCCAGGCAGCTGGAG | CTCCAGCTGCCTGGGCACA |
| 2980 | GTGCCCAGGCAGCTGGAGA | TCTCCAGCTGCCTGGGCAC |
| 2981 | TGCCCAGGCAGCTGGAGAG | CTCTCCAGCTGCCTGGGCA |
| 2982 | GCCCAGGCAGCTGGAGAGG | CCTCTCCAGCTGCCTGGGC |
| 2983 | CCCAGGCAGCTGGAGAGGG | CCCTCTCCAGCTGCCTGGG |
| 2984 | CCAGGCAGCTGGAGAGGGA | TCCCTCTCCAGCTGCCTGG |
| 2985 | CAGGCAGCTGGAGAGGGAG | CTCCCTCTCCAGCTGCCTG |
| 2986 | AGGCAGCTGGAGAGGGAGG | CCTCCCTCTCCAGCTGCCT |
| 2987 | GGCAGCTGGAGAGGGAGGA | TCCTCCCTCTCCAGCTGCC |
| 2988 | GCAGCTGGAGAGGGAGGAG | CTCCTCCCTCTCCAGCTGC |
| 2989 | CAGCTGGAGAGGGAGGAGG | CCTCCTCCCTCTCCAGCTG |
| 2990 | AGCTGGAGAGGGAGGAGGG | CCCTCCTCCCTCTCCAGCT |
| 2991 | GCTGGAGAGGGAGGAGGGC | GCCCTCCTCCCTCTCCAGC |
| 2992 | CTGGAGAGGGAGGAGGGCA | TGCCCTCCTCCCTCTCCAG |
| 2993 | TGGAGAGGGAGGAGGGCAC | GTGCCCTCCTCCCTCTCCA |
| 2994 | GGAGAGGGAGGAGGGCACG | CGTGCCCTCCTCCCTCTCC |
| 2995 | GAGAGGGAGGAGGGCACGC | GCGTGCCCTCCTCCCTCTC |
| 2996 | AGAGGGAGGAGGGCACGCC | GGCGTGCCCTCCTCCCTCT |
| 2997 | GAGGGAGGAGGGCACGCCT | AGGCGTGCCCTCCTCCCTC |
| 2998 | AGGGAGGAGGGCACGCCTG | CAGGCGTGCCCTCCTCCCT |
| 2999 | GGGAGGAGGGCACGCCTGC | GCAGGCGTGCCCTCCTCCC |
| 3000 | GGAGGAGGGCACGCCTGCC | GGCAGGCGTGCCCTCCTCC |
| 3001 | GAGGAGGGCACGCCTGCCA | TGGCAGGCGTGCCCTCCTC |
| 3002 | AGGAGGGCACGCCTGCCAC | GTGGCAGGCGTGCCCTCCT |
| 3003 | GGAGGGCACGCCTGCCACT | AGTGGCAGGCGTGCCCTCC |
| 3004 | GAGGGCACGCCTGCCACTC | GAGTGGCAGGCGTGCCCTC |
| 3005 | AGGGCACGCCTGCCACTCT | AGAGTGGCAGGCGTGCCCT |
| 3006 | GGGCACGCCTGCCACTCTC | GAGAGTGGCAGGCGTGCCC |
| 3007 | GGCACGCCTGCCACTCTCA | TGAGAGTGGCAGGCGTGCC |
| 3008 | GCACGCCTGCCACTCTCAG | CTGAGAGTGGCAGGCGTGC |
| 3009 | CACGCCTGCCACTCTCAGC | GCTGAGAGTGGCAGGCGTG |
| 3010 | ACGCCTGCCACTCTCAGCA | TGCTGAGAGTGGCAGGCGT |
| 3011 | CGCCTGCCACTCTCAGCAA | TTGCTGAGAGTGGCAGGCG |
| 3012 | GCCTGCCACTCTCAGCAAG | CTTGCTGAGAGTGGCAGGC |
| 3013 | CCTGCCACTCTCAGCAAGT | ACTTGCTGAGAGTGGCAGG |
| 3014 | CTGCCACTCTCAGCAAGTG | CACTTGCTGAGAGTGGCAG |
| 3015 | TGCCACTCTCAGCAAGTGC | GCACTTGCTGAGAGTGGCA |
| 3016 | GCCACTCTCAGCAAGTGCG | CGCACTTGCTGAGAGTGGC |
| 3017 | CCACTCTCAGCAAGTGCGG | CCGCACTTGCTGAGAGTGG |
| 3018 | CACTCTCAGCAAGTGCGGA | TCCGCACTTGCTGAGAGTG |
| 3019 | ACTCTCAGCAAGTGCGGAG | CTCCGCACTTGCTGAGAGT |
| 3020 | CTCTCAGCAAGTGCGGAGA | TCTCCGCACTTGCTGAGAG |
| 3021 | TCTCAGCAAGTGCGGAGAT | ATCTCCGCACTTGCTGAGA |
| 3022 | CTCAGCAAGTGCGGAGATC | GATCTCCGCACTTGCTGAG |
| 3023 | TCAGCAAGTGCGGAGATCG | CGATCTCCGCACTTGCTGA |
| 3024 | CAGCAAGTGCGGAGATCGC | GCGATCTCCGCACTTGCTG |
| 3025 | AGCAAGTGCGGAGATCGCC | GGCGATCTCCGCACTTGCT |
| 3026 | GCAAGTGCGGAGATCGCCT | AGGCGATCTCCGCACTTGC |
| 3027 | CAAGTGCGGAGATCGCCTC | GAGGCGATCTCCGCACTTG |
| 3028 | AAGTGCGGAGATCGCCTCT | AGAGGCGATCTCCGCACTT |
| 3029 | AGTGCGGAGATCGCCTCTG | CAGAGGCGATCTCCGCACT |
| 3030 | GTGCGGAGATCGCCTCTGG | CCAGAGGCGATCTCCGCAC |
| 3031 | TGCGGAGATCGCCTCTGGG | CCCAGAGGCGATCTCCGCA |
| 3032 | GCGGAGATCGCCTCTGGGA | TCCCAGAGGCGATCTCCGC |
| 3033 | CGGAGATCGCCTCTGGGAG | CTCCCAGAGGCGATCTCCG |
| 3034 | GGAGATCGCCTCTGGGAGG | CCTCCCAGAGGCGATCTCC |
| 3035 | GAGATCGCCTCTGGGAGGG | CCCTCCCAGAGGCGATCTC |
| 3036 | AGATCGCCTCTGGGAGGGG | CCCCTCCCAGAGGCGATCT |
| 3037 | GATCGCCTCTGGGAGGGGA | TCCCCTCCCAGAGGCGATC |
| 3038 | ATCGCCTCTGGGAGGGGAG | CTCCCCTCCCAGAGGCGAT |
| 3039 | TCGCCTCTGGGAGGGGAGC | GCTCCCCTCCCAGAGGCGA |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 3040 | CGCCTCTGGGAGGGGAGCT | AGCTCCCCTCCCAGAGGCG |
| 3041 | GCCTCTGGGAGGGGAGCTG | CAGCTCCCCTCCCAGAGGC |
| 3042 | CCTCTGGGAGGGGAGCTGC | GCAGCTCCCCTCCCAGAGG |
| 3043 | CTCTGGGAGGGGAGCTGCA | TGCAGCTCCCCTCCCAGAG |
| 3044 | TCTGGGAGGGGAGCTGCAG | CTGCAGCTCCCCTCCCAGA |
| 3045 | CTGGGAGGGGAGCTGCAGC | GCTGCAGCTCCCCTCCCAG |
| 3046 | TGGGAGGGGAGCTGCAGCA | TGCTGCAGCTCCCCTCCCA |
| 3047 | GGGAGGGGAGCTGCAGCAG | CTGCTGCAGCTCCCCTCCC |
| 3048 | GGAGGGGAGCTGCAGCAGG | CCTGCTGCAGCTCCCCTCC |
| 3049 | GAGGGGAGCTGCAGCAGGA | TCCTGCTGCAGCTCCCCTC |
| 3050 | AGGGGAGCTGCAGCAGGAG | CTCCTGCTGCAGCTCCCCT |
| 3051 | GGGGAGCTGCAGCAGGAGG | CCTCCTGCTGCAGCTCCCC |
| 3052 | GGGAGCTGCAGCAGGAGGA | TCCTCCTGCTGCAGCTCCC |
| 3053 | GGAGCTGCAGCAGGAGGAA | TTCCTCCTGCTGCAGCTCC |
| 3054 | GAGCTGCAGCAGGAGGAAG | CTTCCTCCTGCTGCAGCTC |
| 3055 | AGCTGCAGCAGGAGGAAGA | TCTTCCTCCTGCTGCAGCT |
| 3056 | GCTGCAGCAGGAGGAAGAC | GTCTTCCTCCTGCTGCAGC |
| 3057 | CTGCAGCAGGAGGAAGACA | TGTCTTCCTCCTGCTGCAG |
| 3058 | TGCAGCAGGAGGAAGACAC | GTGTCTTCCTCCTGCTGCA |
| 3059 | GCAGCAGGAGGAAGACACA | TGTGTCTTCCTCCTGCTGC |
| 3060 | CAGCAGGAGGAAGACACAG | CTGTGTCTTCCTCCTGCTG |
| 3061 | AGCAGGAGGAAGACACAGC | GCTGTGTCTTCCTCCTGCT |
| 3062 | GCAGGAGGAAGACACAGCC | GGCTGTGTCTTCCTCCTGC |
| 3063 | CAGGAGGAAGACACAGCCA | TGGCTGTGTCTTCCTCCTG |
| 3064 | AGGAGGAAGACACAGCCAC | GTGGCTGTGTCTTCCTCCT |
| 3065 | GGAGGAAGACACAGCCACC | GGTGGCTGTGTCTTCCTCC |
| 3066 | GAGGAAGAGACAGCCACCA | TGGTGGCTGTGTCTTCCTC |
| 3067 | AGGAAGACACAGCCACCAA | TTGGTGGCTGTGTCTTCCT |
| 3068 | GGAAGACACAGCCACCAAC | GTTGGTGGCTGTGTCTTCC |
| 3069 | GAAGACACAGCCACCAACT | AGTTGGTGGCTGTGTCTTC |
| 3070 | AAGACACAGCCACCAACTC | GAGTTGGTGGCTGTGTCTT |
| 3071 | AGACACAGCCACCAACTCC | GGAGTTGGTGGCTGTGTCT |
| 3072 | GACACAGCCACCAACTCCA | TGGAGTTGGTGGCTGTGTC |
| 3073 | ACACAGCCACCAACTCCAG | CTGGAGTTGGTGGCTGTGT |
| 3074 | CACAGCCACCAACTCCAGC | GCTGGAGTTGGTGGCTGTG |
| 3075 | ACAGCCACCAACTCCAGCT | AGCTGGAGTTGGTGGCTGT |
| 3076 | CAGCCACCAACTCCAGCTC | GAGCTGGAGTTGGTGGCTG |
| 3077 | AGCCACCAACTCCAGCTCT | AGAGCTGGAGTTGGTGGCT |
| 3078 | GCCACCAACTCCAGCTCTG | CAGAGCTGGAGTTGGTGGC |
| 3079 | CCACCAACTCCAGCTCTGA | TCAGAGCTGGAGTTGGTGG |
| 3080 | CACCAACTCCAGCTCTGAG | CTCAGAGCTGGAGTTGGTG |
| 3081 | ACCAACTCCAGCTCTGAGG | CCTCAGAGCTGGAGTTGGT |
| 3082 | CCAACTCCAGCTCTGAGGA | TCCTCAGAGCTGGAGTTGG |
| 3083 | CAACTCCAGCTCTGAGGAA | TTCCTCAGAGCTGGAGTTG |
| 3084 | AACTCCAGCTCTGAGGAAG | CTTCCTCAGAGCTGGAGTT |
| 3085 | ACTCCAGCTCTGAGGAAGG | CCTTCCTCAGAGCTGGAGT |
| 3086 | CTCCAGCTCTGAGGAAGGC | GCCTTCCTCAGAGCTGGAG |
| 3087 | TCCAGCTCTGAGGAAGGCC | GGCCTTCCTCAGAGCTGGA |
| 3088 | CCAGCTCTGAGGAAGGCCC | GGGCCTTCCTCAGAGCTGG |
| 3089 | CAGCTCTGAGGAAGGCCCA | TGGGCCTTCCTCAGAGCTG |
| 3090 | AGCTCTGAGGAAGGCCCAG | CTGGGCCTTCCTCAGAGCT |
| 3091 | GCTCTGAGGAAGGCCCAGG | CCTGGGCCTTCCTCAGAGC |
| 3092 | CTCTGAGGAAGGCCCAGGG | CCCTGGGCCTTCCTCAGAG |
| 3093 | TCTGAGGAAGGCCCAGGGT | ACCCTGGGCCTTCCTCAGA |
| 3094 | CTGAGGAAGGCCCAGGGTC | GACCCTGGGCCTTCCTCAG |
| 3095 | TGAGGAAGGCCCAGGGTCC | GGACCCTGGGCCTTCCTCA |
| 3096 | GAGGAAGGCCCAGGGTCCG | CCGACCCTGGGCCTTCCTC |
| 3097 | AGGAAGGCCCAGGGTCCGG | CCGGACCCTGGGCCTTCCT |
| 3098 | GGAAGGCCCAGGGTCCGGC | GCCGGACCCTGGGCCTTCC |
| 3099 | GAAGGCCCAGGGTCCGGCC | GGCCGGACCCTGGGCCTTC |
| 3100 | AAGGCCCAGGGTCCGGCCC | GGGCCGGACCCTGGGCCTT |
| 3101 | AGGCCCAGGGTCCGGCCCT | AGGGCCGGACCCTGGGCCT |
| 3102 | GGCCCAGGGTCCGGCCCTG | CAGGGCCGGACCCTGGGCC |
| 3103 | GCCCAGGGTCCGGCCCTGA | TCAGGGCCGGACCCTGGGC |
| 3104 | CCCAGGGTCCGGCCCTGAC | GTCAGGGCCGGACCCTGGG |
| 3105 | CCAGGGTCCGGCCCTGACA | TGTCAGGGCCGGACCCTGG |
| 3106 | CAGGGTCCGGCCCTGACAG | CTGTCAGGGCCGGACCCTG |
| 3107 | AGGGTCCGGCCCTGACAGC | GCTGTCAGGGCCGGACCCT |
| 3108 | GGGTCCGGCCCTGACAGCG | GGCTGTCAGGGCCGGACCC |

TABLE 1-continued cDNA Human Hairless 19-mer Target Sequences and Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3109 | GGTCCGGCCCTGACAGCCG | CGGCTGTCAGGGCCGGACC |
| 3110 | GTCCGGCCCTGACAGCCGG | CCGGCTGTCAGGGCCGGAC |
| 3111 | TCCGGCCCTGACAGCCGGC | GCCGGCTGTCAGGGCCGGA |
| 3112 | CCGGCCCTGACAGCCGGCT | AGCCGGCTGTCAGGGCCGG |
| 3113 | CGGCCCTGACAGCCGGCTC | GAGCCGGCTGTCAGGGCCG |
| 3114 | GGCCCTGACAGCCGGCTCA | TGAGCCGGCTGTCAGGGCC |
| 3115 | GCCCTGACAGCCGGCTCAG | CTGAGCCGGCTGTCAGGGC |
| 3116 | CCCTGACAGCCGGCTCAGC | GCTGAGCCGGCTGTCAGGG |
| 3117 | CCTGACAGCCGGCTCAGCA | TGCTGAGCCGGCTGTCAGG |
| 3118 | CTGACAGCCGGCTCAGCAC | GTGCTGAGCCGGCTGTCAG |
| 3119 | TGACAGCCGGCTCAGCACA | TGTGCTGAGCCGGCTGTCA |
| 3120 | GACAGCCGGCTCAGCACAG | CTGTGCTGAGCCGGCTGTC |
| 3121 | ACAGCCGGCTCAGCACAGG | CCTGTGCTGAGCCGGCTGT |
| 3122 | CAGCCGGCTCAGCACAGGC | GCCTGTGCTGAGCCGGCTG |
| 3123 | AGCCGGCTCAGCACAGGCC | GGCCTGTGCTGAGCCGGCT |
| 3124 | GCCGGCTCAGCACAGGCCT | AGGCCTGTGCTGAGCCGGC |
| 3125 | CCGGCTCAGCACAGGCCTC | GAGGCCTGTGCTGAGCCGG |
| 3126 | CGGCTCAGCACAGGCCTCG | CGAGGCCTGTGCTGAGCCG |
| 3127 | GGCTCAGCACAGGCCTCGC | GCGAGGCCTGTGCTGAGCC |
| 3128 | GCTCAGCACAGGCCTCGCC | GGCGAGGCCTGTGCTGAGC |
| 3129 | CTCAGCACAGGCCTCGCCA | TGGCGAGGCCTGTGCTGAG |
| 3130 | TCAGCACAGGCCTCGCCAA | TTGGCGAGGCCTGTGCTGA |
| 3131 | CAGCACAGGCCTCGCCAAG | CTTGGCGAGGCCTGTGCTG |
| 3132 | AGCACAGGCCTCGCCAAGC | GCTTGGCGAGGCCTGTGCT |
| 3133 | GCACAGGCCTCGCCAAGCA | TGCTTGGCGAGGCCTGTGC |
| 3134 | CACAGGCCTCGCCAAGCAC | GTGCTTGGCGAGGCCTGTG |
| 3135 | ACAGGCCTCGCCAAGCACC | GGTGCTTGGCGAGGCCTGT |
| 3136 | CAGGCCTCGCCAAGCACCT | AGGTGCTTGGCGAGGCCTG |
| 3137 | AGGCCTCGCCAAGCACCTG | CAGGTGCTTGGCGAGGCCT |
| 3138 | GGCCTCGCCAAGCACCTGC | GCAGGTGCTTGGCGAGGCC |
| 3139 | GCCTCGCCAAGCACCTGCT | AGCAGGTGCTTGGCGAGGC |
| 3140 | CCTCGCCAAGCACCTGCTC | GAGCAGGTGCTTGGCGAGG |
| 3141 | CTCGCCAAGCACCTGCTCA | TGAGCAGGTGCTTGGCGAG |
| 3142 | TCGCCAAGCACCTGCTCAG | CTGAGCAGGTGCTTGGCGA |
| 3143 | CGCCAAGCACCTGCTCAGT | ACTGAGCAGGTGCTTGGCG |
| 3144 | GCCAAGCACCTGCTCAGTG | CACTGAGCAGGTGCTTGGC |
| 3145 | CCAAGCACCTGCTCAGTGG | CCACTGAGCAGGTGCTTGG |
| 3146 | CAAGCACCTGCTCAGTGGT | ACCACTGAGCAGGTGCTTG |
| 3147 | AAGCACCTGCTCAGTGGTT | AACCACTGAGCAGGTCCTT |
| 3148 | AGCACCTGCTCAGTGGTTT | AAACCACTGAGCAGGTGCT |
| 3149 | GCACCTGCTCAGTGGTTTG | CAAACCACTGAGCAGGTGC |
| 3150 | CACCTGCTCAGTGGTTTGG | CCAAACCACTGAGCAGGTG |
| 3151 | ACCTGCTCAGTGGTTTGGG | CCCAAACCACTGAGCAGGT |
| 3152 | CCTGCTCAGTGGTTTGGGG | CCCCAAACCACTGAGCAGG |
| 3153 | CTGCTCAGTGGTTTGGGGG | CCCCCAAACCACTGAGCAG |
| 3154 | TGCTCAGTGGTTTGGGGGA | TCCCCAAACCACTGAGCA |
| 3155 | GCTCAGTGGTTTGGGGGAC | GTCCCCAAACCACTGAGC |
| 3156 | CTCAGTGGTTTGGGGGACC | GGTCCCCAAACCACTGAG |
| 3157 | TCAGTGGTTTGGGGGACCG | CGGTCCCCAAACCACTGA |
| 3158 | CAGTGGTTTGGGGGACCGA | TCGGTCCCCAAACCACTG |
| 3159 | AGTGGTTTGGGGGACCGAC | GTCGGTCCCCAAACCACT |
| 3160 | GTGGTTTGGGGGACCGACT | AGTCGGTCCCCAAACCAC |
| 3161 | TGGTTTGGGGGACCGACTG | CAGTCGGTCCCCAAACCA |
| 3162 | GGTTTGGGGGACCGACTGT | ACAGTCGGTCCCCAAACC |
| 3163 | GTTTGGGGGACCGACTGTG | CACAGTCGGTCCCCAAAC |
| 3164 | TTTGGGGGACCGACTGTGC | GCACAGTCGGTCCCCAAA |
| 3165 | TTGGGGGACCGACTGTGCC | GGCACAGTCGGTCCCCAA |
| 3166 | TGGGGGACCGACTGTGCCG | CGGCACAGTCGGTCCCCCA |
| 3167 | GGGGGACCGACTGTGCCGC | GCGGCACAGTCGGTCCCCC |
| 3168 | GGGGACCGACTGTGCCGCC | GGCGGCACAGTCGGTCCCC |
| 3169 | GGGACCGACTGTGCCGCCT | AGGCGGCACAGTCGGTCCC |
| 3170 | GGACCGACTGTGCCGCCTG | CAGGCGGCACAGTCGGTCC |
| 3171 | GACCGACTGTGCCGCCTGC | GCAGGCGGCACAGTCGGTC |
| 3172 | ACCGACTGTGCCGCCTGCT | AGCAGGCGGCACAGTCGGT |
| 3173 | CCGACTGTGCCGCCTGCTG | CAGCAGGCGGCACAGTCGG |
| 3174 | CGACTGTGCCGCCTGCTGC | GCAGCAGGCGGCACAGTCG |
| 3175 | GACTGTGCCGCCTGCTGCG | CGCAGCAGGCGGCACAGTC |
| 3176 | ACTGTGCCGCCTGCTGCGG | CCGCAGCAGGCGGCACAGT |
| 3177 | CTGTGCCGCCTGCTGCGGA | TCCGCAGCAGGCGGCACAG |

TABLE 1-continued cDNA Human Hairless 19-mer Target Sequences and Complement Referenced to NM_005144-
*Homo sapiens* hairless homolog (mouse) (HR), transcript variant 1, complete mRNA (1-5699 bp).
(SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 3178 | TGTGCCGCCTGCTGCGGAG | CTCCGCAGCAGGCGGCACA |
| 3179 | GTGCCGCCTGCTGCGGAGG | CCTCCGCAGCAGGCGGCAC |
| 3180 | TGCCGCCTGCTGCGGAGGG | CCCTCCGCAGCAGGCGGCA |
| 3181 | GCCGCCTGCTGCGGAGGGA | TCCCTCCGCAGCAGGCGGC |
| 3182 | CCGCCTGCTGCGGAGGGAG | CTCCCTCCGCAGCAGGCGG |
| 3183 | CGCCTGCTGCGGAGGGAGC | GCTCCCTCCGCAGCAGGCG |
| 3184 | GCCTGCTGCGGAGGGAGCG | CGCTCCCTCCGCAGCAGGC |
| 3185 | CCTGCTGCGGAGGGAGCGG | CCGCTCCCTCCGCAGCAGG |
| 3186 | CTGCTGCGGAGGGAGCGGG | CCCGCTCCGTCCGCAGCAG |
| 3187 | TGCTGCGGAGGGAGCGGGA | TCCCGCTCCCTCCGCAGCA |
| 3188 | GCTGCGGAGGGAGCGGGAG | CTCCCGCTCCCTCCGCAGC |
| 3189 | CTGCGGAGGGAGCGGGAGG | CCTCCCGCTCCCTCCGCAG |
| 3190 | TGCGGAGGGAGCGGGAGGC | GCCTCCCGCTCCCTCCGCA |
| 3191 | GCGGAGGGAGCGGGAGGCC | GGCCTCCCGCTCCCTCCGC |
| 3192 | CGGAGGGAGCGGGAGGCCC | GGGCCTCCCGCTCCCTCCG |
| 3193 | GGAGGGAGCGGGAGGCCCT | AGGGCCTCCCGCTCCCTCC |
| 3194 | GAGGGAGCGGGAGGCCCTG | CAGGGCCTCCCGCTCCCTC |
| 3195 | AGGGAGCGGGAGGCCCTGG | CCAGGGCCTCCCGCTCCCT |
| 3196 | GGGAGCGGGAGGCCCTGGC | GCCAGGGCCTCCCGCTCCC |
| 3197 | GGAGCGGGAGGCCCTGGCT | AGCCAGGGCCTCCCGCTCC |
| 3198 | GAGCGGGAGGCCCTGGCTT | AAGCCAGGGCCTCCCGCTC |
| 3199 | AGCGGGAGGCCCTGGCTTG | CAAGCCAGGGCCTCCCGCT |
| 3200 | GCGGGAGGCCCTGGCTTGG | CCAAGCCAGGGCCTCCCGC |
| 3201 | CGGGAGGCCCTGGCTTGGG | CCCAAGCCAGGGCCTCCCG |
| 3202 | GGGAGGCCCTGGCTTGGGC | GCCCAAGCCAGGGCCTCCC |
| 3203 | GGAGGCCCTGGCTTGGGCC | GGCCCAAGCCAGGGCCTCC |
| 3204 | GAGGCCCTGGCTTGGGCCC | GGGCCCAAGCCAGGGCCTC |
| 3205 | AGGCCCTGGCTTGGGCCCA | TGGGCCCAAGCCAGGGCCT |
| 3206 | GGCCCTGGCTTGGGCCCAG | CTGGGCCCAAGCCAGGGCC |
| 3207 | GCCCTGGCTTGGGCCCAGC | GCTGGGCCCAAGCCAGGGC |
| 3208 | CCCTGGCTTGGGCCCAGCG | CGCTGGGCCCAAGCCAGGG |
| 3209 | CCTGGCTTGGGCCCAGCGG | CCGCTGGGCCCAAGCCAGG |
| 3210 | CTGGCTTGGGCCCAGCGGG | CCCGCTGGGCCCAAGCCAG |
| 3211 | TGGCTTGGGCCCAGCGGGA | TCCCGCTGGGCCCAAGCCA |
| 3212 | GGCTTGGGCCCAGCGGGAA | TTCCCGCTGGGCCCAAGCC |
| 3213 | GCTTGGGCCCAGCGGGAAG | CTTCCCGCTGGGCCCAAGC |
| 3214 | CTTGGGCCCAGCGGGAAGG | CCTTCCCGCTGGGCCCAAG |
| 3215 | TTGGGCCCAGCGGGAAGGC | GCCTTCCCGCTGGGCCCAA |
| 3216 | TGGGCCCAGCGGGAAGGCC | GGCCTTCCCGCTGGGCCCA |
| 3217 | GGGCCCAGCGGGAAGGCCA | TGGCCTTCCCGCTGGGCCC |
| 3218 | GGCCCAGCGGGAAGGCCAA | TTGGCCTTCCCGCTGGGCC |
| 3219 | GCCCAGCGGGAAGGCCAAG | CTTGGCCTTCCCGCTGGGC |
| 3220 | CCCAGCGGGAAGGCCAAGG | CCTTGGCCTTCCCGCTGGG |
| 3221 | CCAGCGGGAAGGCCAAGGG | CCCTTGGCCTTCCCGCTGG |
| 3222 | CAGCGGGAAGGCCAAGGGC | GCCCTTGGCCTTCCCGCTG |
| 3223 | AGCGGGAAGGCCAAGGGCC | GGCCCTTGGCCTTCCCGCT |
| 3224 | GCGGGAAGGCCAAGGGCCA | TGGCCCTTGGCCTTCCCGC |
| 3225 | CGGGAAGGCCAAGGGCCAG | CTGGCCCTTGGCCTTCCCG |
| 3226 | GGGAAGGCCAAGGGCCAGC | GCTGGCCCTTGGCCTTCCC |
| 3227 | GGAAGGCCAAGGGCCAGCC | GGCTGGCCCTTGGCCTTCC |
| 3228 | GAAGGCCAAGGGCCAGCCG | CGGCTGGCCCTTGGCCTTC |
| 3229 | AAGGCCAAGGGCCAGCCGT | ACGGCTGGCCCTTGGCCTT |
| 3230 | AGGCCAAGGGCCAGCCGTG | CACGGCTGGCCCTTGGCCT |
| 3231 | GGCCAAGGGCCAGCCGTGA | TCACGGCTGGCCCTTGGCC |
| 3232 | GCCAAGGGCCAGCCGTGAC | GTCACGGCTGGCCCTTGGC |
| 3233 | CCAAGGGCCAGCCGTGACA | TGTCACGGCTGGCCCTTGG |
| 3234 | CAAGGGCCAGCCGTGACAG | CTGTCACGGCTGGCCCTTG |
| 3235 | AAGGGCCAGCCGTGACAGA | TCTGTCACGGCTGGCCCTT |
| 3236 | AGGGCCAGCCGTGACAGAG | CTCTGTCACGGCTGGCCCT |
| 3237 | GGGCCAGCCGTGACAGAGG | CCTCTGTCACGGCTGGCCC |
| 3238 | GGCCAGCCGTGACAGAGGA | TCCTCTGTCACGGCTGGCC |
| 3239 | GCCAGCCGTGACAGAGGAC | GTCCTCTGTCACGGCTGGC |
| 3240 | CCAGCCGTGACAGAGGACA | TGTCCTCTGTCACGGCTGG |
| 3241 | CAGCCGTGACAGAGGACAG | CTGTCCTCTGTCACGGCTG |
| 3242 | AGCCGTGACAGAGGACAGC | GCTGTCCTCTGTCACGGCT |
| 3243 | GCCGTGACAGAGGACAGCC | GGCTGTCCTCTGTCACGGC |
| 3244 | CCGTGACACAGGACAGCCC | GGGCTGTCCTCTGTCACGG |
| 3245 | CGTGACAGAGGACAGCCCA | TGGGCTGTCCTCTGTCACG |
| 3246 | GTGACAGAGGACAGCCCAG | CTGGGCTGTCCTCTGTCAC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3247 | TGACAGAGGACAGCCCAGG | CCTGGGCTGTCCTCTGTCA |
| 3248 | GACAGAGGACAGCCCAGGC | GCCTGGGCTGTCCTCTGTC |
| 3249 | ACAGAGGACAGCCCAGGCA | TGCCTGGGCTGTCCTCTGT |
| 3250 | CAGAGGACAGCCCAGGCAT | ATGCCTGGGCTGTCCTCTG |
| 3251 | AGAGGACAGCCCAGGCATT | AATGCCTGGGCTGTCCTCT |
| 3252 | GAGGACAGCCCAGGCATTC | GAATGCCTGGGCTGTCCTC |
| 3253 | AGGACAGCCCAGGCATTCC | GGAATGCCTGGGCTGTCCT |
| 3254 | GGACAGCCCAGGCATTCCA | TGGAATGCCTGGGCTGTCC |
| 3255 | GACAGCCCAGGCATTCCAC | GTGGAATGCCTGGGCTGTC |
| 3256 | ACAGCCCAGGCATTCCACG | CGTGGAATGCCTGGGCTGT |
| 3257 | CAGCCCAGGCATTCCACGC | GCGTGGAATGCCTGGGCTG |
| 3258 | AGCCCAGGCATTCCACGCT | AGCGTGGAATGCCTGGGCT |
| 3259 | GCCCAGGCATTCCACGCTG | CAGCGTGGAATGCCTGGGC |
| 3260 | CCCAGGCATTCCACGCTGC | GCAGCGTGGAATGCCTGGG |
| 3261 | CCAGGCATTCCACGCTGCT | AGCAGCGTGGAATGCCTGG |
| 3262 | CAGGCATTCCACGCTGCTG | CAGCAGCGTGGAATGCCTG |
| 3263 | AGGCATTCCACGCTGCTGC | GCAGCAGCGTGGAATGCCT |
| 3264 | GGCATTCCACGCTGCTGCA | TGCAGCAGCGTGGAATGCC |
| 3265 | GCATTCCACGCTGCTGCAG | CTGCAGCAGCGTGGAATGC |
| 3266 | CATTCCACGCTGCTGCAGC | GCTGCAGCAGCGTGGAATG |
| 3267 | ATTCCACGCTGCTGCAGCC | GGCTGCAGCAGCGTGGAAT |
| 3268 | TTCCACGCTGCTGCAGCCG | CGGCTGCAGCAGCGTGGAA |
| 3269 | TCCACGCTGCTGCAGCCGT | ACGGCTGCAGCAGCGTGGA |
| 3270 | CCACGCTGCTGCAGCCGTT | AACGGCTGCAGCAGCGTGG |
| 3271 | CACGCTGCTGCAGCCGTTG | CAACGGCTGCAGCAGCGTG |
| 3272 | ACGCTGCTGCAGCCGTTGC | GCAACGGCTGCAGCAGCGT |
| 3273 | CGCTGCTGCAGCCGTTGCC | GGCAACGGCTGCAGCAGCG |
| 3274 | GCTGCTGCAGCCGTTGCCA | TGGCAACGGCTGCAGCAGC |
| 3275 | CTGCTGCAGCCGTTGCCAC | GTGGCAACGGCTGCAGCAG |
| 3276 | TGCTGCAGCCGTTGCCACC | GGTGGCAACGGCTGCAGCA |
| 3277 | GCTGCAGCCGTTGCCACCA | TGGTGGCAACGGCTGCAGC |
| 3278 | CTGCAGCCGTTGCCACCAT | ATGGTGGCAACGGCTGCAG |
| 3279 | TGCAGCCGTTGCCACCATG | CATGGTGGCAACGGCTGCA |
| 3280 | GCAGCCGTTGCCACCATGG | CCATGGTGGCAACGGCTGC |
| 3281 | CAGCCGTTGCCACCATGGA | TCCATGGTGGCAACGGCTG |
| 3282 | AGCCGTTGCCACCATGGAC | GTCCATGGTGGCAACGGCT |
| 3283 | GCCGTTGCCACCATGGACT | AGTCCATGGTGGCAAGGGC |
| 3284 | CCGTTGCCACCATGGACTC | GAGTCCATGGTGGCAACGG |
| 3285 | CGTTGCCACCATGGACTCT | AGAGTCCATGGTGGCAACG |
| 3286 | GTTGCCACCATGGACTCTT | AAGAGTCCATGGTGGCAAC |
| 3287 | TTGCCACCATGGACTCTTC | GAAGAGTCCATGGTGGCAA |
| 3288 | TGCCACCATGGACTCTTCA | TGAAGAGTCCATGGTGGCA |
| 3289 | GCCACCATGGACTCTTCAA | TTGAAGAGTCCATGGTGGC |
| 3290 | CCACCATGGACTCTTCAAC | GTTGAAGAGTCCATGGTGG |
| 3291 | CACCATGGACTCTTCAACA | TGTTGAAGAGTCCATGGTG |
| 3292 | ACCATGGACTCTTCAACAC | GTGTTGAAGAGTCCATGGT |
| 3293 | CCATGGACTCTTCAACACC | GGTGTTGAAGAGTCCATGG |
| 3294 | CATGGACTCTTCAACACCC | GGGTGTTGAAGAGTCCATG |
| 3295 | ATGGACTCTTCAACACCCA | TGGGTGTTGAAGAGTCCAT |
| 3296 | TGGACTCTTCAACACCCAC | GTGGGTGTTGAAGAGTCCA |
| 3297 | GGACTCTTCAACACCCACT | AGTGGGTGTTGAAGAGTCC |
| 3298 | GACTCTTCAACACCCACTG | CAGTGGGTGTTGAAGAGTC |
| 3299 | ACTCTTCAACACCCACTGG | CCAGTGGGTGTTGAAGAGT |
| 3300 | CTCTTCAACACCCACTGGC | GCCAGTGGGTGTTGAAGAG |
| 3301 | TCTTCAACACCCACTGGCG | CGCCAGTGGGTGTTGAAGA |
| 3302 | CTTCAACACCCACTGGCGA | TCGCCAGTGGGTGTTGAAG |
| 3303 | TTCAACACCCACTGGCGAT | ATCGCCAGTGGGTGTTGAA |
| 3304 | TCAACACCCACTGGCGATG | CATCGCCAGTGGGTGTTGA |
| 3305 | CAACACCCACTGGCGATGT | ACATCGCCAGTGGGTGTTG |
| 3306 | AACACCCACTGGCGATGTC | GACATCGCCAGTGGGTGTT |
| 3307 | ACACCCACTGGCGATGTCC | GGACATCGCCAGTGGGTGT |
| 3308 | CACCCACTGGCGATGTCCC | GGGACATCGCCAGTGGGTG |
| 3309 | ACCCACTGGCGATGTCCCC | GGGGACATCGCCAGTGGGT |
| 3310 | CCCACTGGCGATGTCCCCG | CGGGGACATCGCCAGTGGG |
| 3311 | CCACTGGCGATGTCCCCGC | GCGGGGACATCGCCAGTGG |
| 3312 | CACTGGCGATGTCCCCGCT | AGCGGGGACATCGCCAGTG |
| 3313 | ACTGGCGATGTCCCCGCTG | CAGCGGGGACATCGCCAGT |
| 3314 | CTGGCGATGTCCCCGCTGC | GCAGCGGGGACATCGCCAG |
| 3315 | TGGCGATGTCCCCGCTGCA | TGCAGCGGGGACATCGCCA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3316 | GGCGATGTCCCCGCTGCAG | CTGCAGCGGGGACATCGCC |
| 3317 | GCGATGTCCCCGCTGCAGC | GCTGCAGCGGGGACATCGC |
| 3318 | CGATGTCCCCGCTGCAGCC | GGCTGCAGCGGGGACATCG |
| 3319 | GATGTCCCCGCTGCAGCCA | TGGCTGCAGCGGGGACATC |
| 3320 | ATGTCCCCGCTGCAGCCAC | GTGGCTGCAGCGGGGACAT |
| 3321 | TGTCCCCGCTGCAGCCACC | GGTGGCTGCAGCGGGGACA |
| 3322 | GTCCCCGCTGCAGCCACCG | CGGTGGCTGCAGCGGGGAC |
| 3323 | TCCCCGCTGCAGCCACCGG | CCGGTGGCTGCAGCGGGGA |
| 3324 | CCCCGCTGCAGCCACCGGC | GCCGGTGGCTGCAGCGGGG |
| 3325 | CCCGCTGCAGCCACCGGCT | AGCCGGTGGCTGCAGCGGG |
| 3326 | CCGCTGCAGCCACCGGCTG | CAGCCGGTGGCTGCAGCGG |
| 3327 | CGCTGCAGCCACCGGCTGT | ACAGCCGGTGGCTGCAGCG |
| 3328 | GCTGCAGCCACCGGCTGTG | CACAGCCGGTGGCTGCAGC |
| 3329 | CTGCAGCCACCGGCTGTGT | ACACAGCCGGTGGCTGCAG |
| 3330 | TGCAGCCACCGGCTGTGTG | CACACAGCCGGTGGCTGCA |
| 3331 | GCAGCCACCGGCTGTGTGT | ACACACAGCCGGTGGCTGC |
| 3332 | CAGCCACCGGCTGTGTGTG | CACACACAGCCGGTGGCTG |
| 3333 | AGCCACCGGCTGTGTGTGG | CCACACACAGCCGGTGGCT |
| 3334 | GCCACCGGCTGTGTGTGGC | GCCACACACAGCCGGTGGC |
| 3335 | CCACCGGCTGTGTGTGGCC | GGCCACACACAGCCGGTGG |
| 3336 | CACCGGCTGTGTGTGGCCT | AGGCCACACACAGCCGGTG |
| 3337 | ACCGGCTGTGTGTGGCCTG | CAGGCCACACACAGCCGGT |
| 3338 | CCGGCTGTGTGTGGCCTGT | ACAGGCCACACACAGCCGG |
| 3339 | CGGCTGTGTGTGGCCTGTG | CACAGGCCACACACAGCCG |
| 3340 | GGCTGTGTGTGGCCTGTGG | CCACAGGCCACACACAGCC |
| 3341 | GCTGTGTGTGGCCTGTGGT | ACCACAGGCCACACACAGC |
| 3342 | CTGTGTGTGGCCTGTGGTC | GACCACAGGCCACACACAG |
| 3343 | TGTGTGTGGCCTGTGGTCG | CGACCACAGGCCACACACA |
| 3344 | GTGTGTGGCCTGTGGTCGT | ACGACCACAGGCCACACAC |
| 3345 | TGTGTGGCCTGTGGTCGTG | CACGACCACAGGCCACACA |
| 3346 | GTGTGGCCTGTGGTCGTGT | ACACGACCACAGGCCACAC |
| 3347 | TGTGGCCTGTGGTCGTGTG | CACACGACCACAGGCCACA |
| 3348 | GTGGCCTGTGGTCGTGTGG | CCACACGACCACAGGCCAC |
| 3349 | TGGCCTGTGGTCGTGTGGC | GCCACACGACCACAGGCCA |
| 3350 | GGCCTGTGGTCGTGTGGCA | TGCCACACGACCACAGGCC |
| 3351 | GCCTGTGGTCGTGTGGCAG | CTGCCACACGACCACAGGC |
| 3352 | CCTGTGGTCGTGTGGCAGG | CCTGCCACACGACCACAGG |
| 3353 | CTGTGGTCGTGTGGCAGGC | GCCTGCCACACGACCACAG |
| 3354 | TGTGGTCGTGTGGCAGGCA | TGCCTGCCACACGACCACA |
| 3355 | GTGGTCGTGTGGCAGGCAC | GTGCCTGCCACACGACCAC |
| 3356 | TGGTCGTGTGGCAGGCACT | AGTGCCTGCCACACGACCA |
| 3357 | GGTCGTGTGGCAGGCACTG | CAGTGCCTGCCACACGACC |
| 3358 | GTCGTGTGGCAGGCACTGG | CCAGTGCCTGCCACACGAC |
| 3359 | TCGTGTGGCAGGCACTGGG | CCCAGTGCCTGCCACACGA |
| 3360 | CGTGTGGCAGGCACTGGGC | GCCCAGTGCCTGCCACACG |
| 3361 | GTGTGGCAGGCACTGGGCG | CGCCCAGTGCCTGCCACAC |
| 3362 | TGTGGCAGGCACTGGGCGG | CCGCCCAGTGCCTGCCACA |
| 3363 | GTGGCAGGCACTGGGCGGG | CCCGCCCAGTGCCTGCCAC |
| 3364 | TGGCAGGCACTGGGCGGGC | GCCCGCCCAGTGCCTGCCA |
| 3365 | GGCAGGCACTGGGCGGGCC | GGCCCGCCCAGTGCCTGCC |
| 3366 | GCAGGCACTGGGCGGGCCA | TGGCCCGCCCAGTGCCTGC |
| 3367 | CAGGCACTGGGCGGGCCAG | CTGGCCCGCCCAGTGCCTG |
| 3368 | AGGCACTGGGCGGGCCAGG | CCTGGCCCGCCCAGTGCCT |
| 3369 | GGCACTGGGCGGGCCAGGG | CCCTGGCCCGCCCAGTGCC |
| 3370 | GCACTGGGCGGGCCAGGGA | TCCCTGGCCCGCCCAGTGC |
| 3371 | CACTGGGCGGGCCAGGGAG | CTCCCTGGCCCGCCCAGTG |
| 3372 | ACTGGGCGGGCCAGGGAGA | TCTCCCTGGCCCGCCCAGT |
| 3373 | CTGGGCGGGCCAGGGAGAA | TTCTCCCTGGCCCGCCCAG |
| 3374 | TGGGCGGGCCAGGGAGAAA | TTTCTCCCTGGCCCGCCCA |
| 3375 | GGGCGGGCCAGGGAGAAAG | CTTTCTCCCTGGCCCGCCC |
| 3376 | GGCGGGCCAGGGAGAAAGC | GCTTTCTCCCTGGCCCGCC |
| 3377 | GCGGGCCAGGGAGAAAGCA | TGCTTTCTCCCTGGCCCGC |
| 3378 | CGGGCCAGGGAGAAAGCAG | CTGCTTTCTCCCTGGCCCG |
| 3379 | GGGCCAGGGAGAAAGCAGG | CCTGCTTTCTCCCTGGCCC |
| 3380 | GGCCAGGGAGAAAGCAGGC | GCCTGCTTTCTCCCTGGCC |
| 3381 | GCCAGGGAGAAAGCAGGCT | AGCCTGCTTTCTCCCTGGC |
| 3382 | CCAGGGAGAAAGCAGGCTT | AAGCCTGCTTTCTCCCTGG |
| 3383 | CAGGGAGAAAGCAGGCTTT | AAAGCCTGCTTTCTCCCTG |
| 3384 | AGGGAGAAAGCAGGCTTTC | GAAAGCCTGCTTTCTCCCT |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X - 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 3385 | GGGAGAAAGCAGGCTTTCA | TGAAAGCCTGCTTTCTCCC |
| 3386 | GGAGAAAGCAGGCTTTCAG | CTGAAAGCCTGCTTTCTCC |
| 3387 | GAGAAAGCAGGCTTTCAGG | CCTGAAAGCCTGCTTTCTC |
| 3388 | AGAAAGCAGGCTTTCAGGA | TCCTGAAAGCCTGCTTTCT |
| 3389 | GAAAGCAGGCTTTCAGGAG | CTCCTGAAAGCCTGCTTTC |
| 3390 | AAAGCAGGCTTTCAGGAGC | GCTCCTGAAAGCCTGCTTT |
| 3391 | AAGCAGGCTTTCAGGAGCA | TGCTCCTGAAAGCCTGCTT |
| 3392 | AGCAGGCTTTCAGGAGCAG | CTGCTCCTGAAAGCCTGCT |
| 3393 | GCAGGCTTTCAGGAGCAGT | ACTGCTCCTGAAAGCCTGC |
| 3394 | CAGGCTTTCAGGAGCAGTC | GACTGCTCCTGAAAGCCTG |
| 3395 | AGGCTTTCAGGAGCAGTCC | GGACTGCTCCTGAAAGCCT |
| 3396 | GGCTTTCAGGAGCAGTCCG | CGGACTGCTCCTGAAAGCC |
| 3397 | GCTTTCAGGAGCAGTCCGC | GCGGACTGCTCCTGAAAGC |
| 3398 | CTTTCAGGAGCAGTCCGCG | CGCGGACTGCTCCTGAAAG |
| 3399 | TTTCAGGAGCAGTCCGCGG | CCGCGGACTGCTCCTGAAA |
| 3400 | TTCAGGAGCAGTCCGCGGA | TCCGCGGACTGCTCCTGAA |
| 3401 | TCAGGAGCAGTCCGCGGAG | CTCCGCGGACTGCTCCTGA |
| 3402 | CAGGAGCAGTCCGCGGAGG | CCTCCGCGGACTGCTCCTG |
| 3403 | AGGAGCAGTCCGCGGAGGA | TCCTCCGCGGACTGCTCCT |
| 3404 | GGAGCAGTCCGCGGAGGAG | CTCCTCCGCGGACTGCTCC |
| 3405 | GAGCAGTCCGCGGAGGAGT | ACTCCTCCGCGGACTGCTC |
| 3406 | AGCAGTCCGCGGAGGAGTG | CACTCCTCCGCGGACTGCT |
| 3407 | GCAGTCCGCGGAGGAGTGC | GCACTCCTCCGCGGACTGC |
| 3408 | CAGTCCGCGGAGGAGTGCA | TGCACTCCTCCGCGGACTG |
| 3409 | AGTCCGCGGAGGAGTGCAC | GTGCACTCCTCCGCGGACT |
| 3410 | GTCCGCGGAGGAGTGCACG | CGTGCACTCCTCCGCGGAC |
| 3411 | TCCGCGGAGGAGTGCACGC | GCGTGCACTCCTCCGCGGA |
| 3412 | CCGCGGAGGAGTGCACGCA | TGCGTGCACTCCTCCGCGG |
| 3413 | CGCGGAGGAGTGCACGCAG | CTGCGTGCACTCCTCCGCG |
| 3414 | GCGGAGGAGTGCACGCAGG | CCTGCGTGCACTCCTCCGC |
| 3415 | CGGAGGAGTGCACGCAGGA | TCCTGCGTGCACTCCTCCG |
| 3416 | GGAGGAGTGCACGCAGGAG | CTCCTGCGTGCACTCCTCC |
| 3417 | GAGGAGTGCACGCAGGAGG | CCTCCTGCGTGCACTCCTC |
| 3418 | AGGAGTGCACGCAGGAGGC | GCCTCCTGCGTGCACTCCT |
| 3419 | GGAGTGCACGCAGGAGGCC | GGCCTCCTGCGTGCACTCC |
| 3420 | GAGTGCACGCAGGAGGCCG | CGGCCTCCTGCGTGCACTC |
| 3421 | AGTGCACGCAGGAGGCCGG | CCGGCCTCCTGCGTGCACT |
| 3422 | GTGCACGCAGGAGGCCGGG | CCCGGCCTCCTGCGTGCAC |
| 3423 | TGCACGCAGGAGGCCGGGC | GCCCGGCCTCCTGCGTGCA |
| 3424 | GCACGCAGGAGGCCGGGCA | TGCCCGGCCTCCTGCGTGC |
| 3425 | CACGCAGGAGGCCGGGCAC | GTGCCCGGCCTCCTGCGTG |
| 3426 | ACGCAGGAGGCCGGGCACG | CGTGCCCGGCCTCCTGCGT |
| 3427 | CGCAGGAGGCCGGGCACGC | GCGTGCCCGGCCTCCTGCG |
| 3428 | GCAGGAGGCCGGGCACGCT | AGCGTGCCCGGCCTCCTGC |
| 3429 | CAGGAGGCCGGGCACGCTG | CAGCGTGCCCGGCCTCCTG |
| 3430 | AGGAGGCCGGGCACGCTGC | GCAGCGTGCCCGGCCTCCT |
| 3431 | GGAGGCCGGGCACGCTGCC | GGCAGCGTGCCCGGCCTCC |
| 3432 | GAGGCCGGGCACGCTGCCT | AGGCAGCGTGCCCGGCCTC |
| 3433 | AGGCCGGGCACGCTGCCTG | CAGGCAGCGTGCCCGGCCT |
| 3434 | GGCCGGGCACGCTGCCTGT | ACAGGCAGCGTGCCCGGCC |
| 3435 | GCCGGGCACGCTGCCTGTT | AACAGGCAGCGTGCCCGGC |
| 3436 | CCGGGCACGCTGCCTGTTC | GAACAGGCAGCGTGCCCGG |
| 3437 | CGGGCACGCTGCCTGTTCC | GGAACAGGCAGCGTGCCCG |
| 3438 | GGGCACGCTGCCTGTTCCC | GGGAACAGGCAGCGTGCCC |
| 3439 | GGCACGCTGCCTGTTCCCT | AGGGAACAGGCAGCGTGCC |
| 3440 | GCACGCTGCCTGTTCCCTG | CAGGGAACAGGCAGCGTGC |
| 3441 | CACGCTGCCTGTTCCCTGA | TCAGGGAACAGGCAGCGTG |
| 3442 | ACGCTGCCTGTTCCCTGAT | ATCAGGGAACAGGCAGCGT |
| 3443 | CGCTGCCTGTTCCCTGATG | CATCAGGGAACAGGCAGCG |
| 3444 | GCTGCCTGTTCCCTGATGC | GCATCAGGGAACAGGCAGC |
| 3445 | CTGCCTGTTCCCTGATGCT | AGCATCAGGGAACAGGCAG |
| 3446 | TGCCTGTTCCCTGATGCTG | CAGCATCAGGGAACAGGCA |
| 3447 | GCCTGTTCCCTGATGCTGA | TCAGCATCAGGGAACAGGC |
| 3448 | CCTGTTCCCTGATGCTGAC | GTCAGCATCAGGGAACAGG |
| 3449 | CTGTTCCCTGATGCTGACC | GGTCAGCATCAGGGAACAG |
| 3450 | TGTTCCCTGATGCTGACCC | GGGTCAGCATCAGGGAACA |
| 3451 | GTTCCCTGATGCTGACCCA | TGGGTCAGCATCAGGGAAC |
| 3452 | TTCCCTGATGCTGACCCAG | CTGGGTCAGCATCAGGGAA |
| 3453 | TCCCTGATGCTGACCCAGT | ACTGGGTCAGCATCAGGGA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3454 | CCCTGATGCTGACCCAGTT | AACTGGGTCAGCATCAGGG |
| 3455 | CCTGATGCTGACCCAGTTT | AAACTGGGTCAGCATCAGG |
| 3456 | CTGATGCTGACCCAGTTTG | CAAACTGGGTCAGCATCAG |
| 3457 | TGATGCTGACCCAGTTTGT | ACAAACTGGGTCAGCATCA |
| 3458 | GATGCTGACCCAGTTTGTC | GACAAACTGGGTCAGCATC |
| 3459 | ATGCTGACCCAGTTTGTCT | AGACAAACTGGGTCAGCAT |
| 3460 | TGCTGACCCAGTTTGTCTC | GAGACAAACTGGGTCAGCA |
| 3461 | GCTGACCCAGTTTGTCTCC | GGAGACAAACTGGGTCAGC |
| 3462 | CTGACCCAGTTTGTCTCCA | TGGAGACAAACTGGGTCAG |
| 3463 | TGACCCAGTTTGTCTCCAG | CTGGAGACAAACTGGGTCA |
| 3464 | GACCCAGTTTGTCTCCAGC | GCTGGAGACAAACTGGGTC |
| 3465 | ACCCAGTTTGTCTCCAGCC | GGCTGGAGACAAACTGGGT |
| 3466 | CCCAGTTTGTCTCCAGCCA | TGGCTGGAGACAAACTGGG |
| 3467 | CCAGTTTGTCTCCAGCCAG | CTGGCTGGAGACAAACTGG |
| 3468 | CAGTTTGTCTCCAGCCAGG | CCTGGCTGGAGACAAACTG |
| 3469 | AGTTTGTCTCCAGCCAGGC | GCCTGGCTGGAGACAAACT |
| 3470 | GTTTGTCTCCAGCCAGGCT | AGCCTGGCTGGAGACAAAC |
| 3471 | TTTGTCTCCAGCCAGGCTT | AAGCCTGGCTGGAGACAAA |
| 3472 | TTGTCTCCAGCCAGGCTTT | AAAGCCTGGCTGGAGACAA |
| 3473 | TGTCTCCAGCCAGGCTTTG | CAAAGCCTGGCTGGAGACA |
| 3474 | GTCTCCAGCCAGGCTTTGG | CCAAAGCCTGGCTGGAGAC |
| 3475 | TCTCCAGCCAGGCTTTGGC | GCCAAAGCCTGGCTGGAGA |
| 3476 | CTCCAGCCAGGCTTTGGCA | TGCCAAAGCCTGGCTGGAG |
| 3477 | TCCAGCCAGGCTTTGGCAG | CTGCCAAAGCCTGGCTGGA |
| 3478 | CCAGCCAGGCTTTGGCAGA | TCTGCCAAAGCCTGGCTGG |
| 3479 | CAGCCAGGCTTTGGCAGAG | CTCTGCCAAAGCCTGGCTG |
| 3480 | AGCCAGGCTTTGGCAGAGC | GCTCTGCCAAAGCCTGGCT |
| 3481 | GCCAGGCTTTGGCAGAGCT | AGCTCTGCCAAAGCCTGGC |
| 3482 | CCAGGCTTTGGCAGAGCTG | CAGCTCTGCCAAAGCCTGG |
| 3483 | CAGGCTTTGGCAGAGCTGA | TCAGCTCTGCCAAAGCCTG |
| 3484 | AGGCTTTGGCAGAGCTGAG | CTCAGCTCTGCCAAAGCCT |
| 3485 | GGCTTTGGCAGAGCTGAGC | GCTCAGCTCTGCCAAAGCC |
| 3486 | GCTTTGGCAGAGCTGAGCA | TGCTCAGCTCTGCCAAAGC |
| 3487 | CTTTGGCAGAGCTGAGCAC | GTGCTCAGCTCTGCCAAAG |
| 3488 | TTTGGCAGAGCTGAGCACT | AGTGCTCAGCTCTGCCAAA |
| 3489 | TTGGCAGAGCTGAGCACTG | CAGTGCTCAGCTCTGCCAA |
| 3490 | TGGCAGAGCTGAGCACTGC | GCAGTGCTCAGCTCTGCCA |
| 3491 | GGCAGAGCTGAGCACTGCA | TGCAGTGCTCAGCTCTGCC |
| 3492 | GCAGAGCTGAGCACTGCAA | TTGCAGTGCTCAGCTCTGC |
| 3493 | CAGAGCTGAGCACTGCAAT | ATTGCAGTGCTCAGCTCTG |
| 3494 | AGAGCTGAGCACTGCAATG | CATTGCAGTGCTCAGCTCT |
| 3495 | GAGCTGAGCACTGCAATGC | GCATTGCAGTGCTCAGCTC |
| 3496 | AGCTGAGCACTGCAATGCA | TGCATTGCAGTGCTCAGCT |
| 3497 | GCTGAGCACTGCAATGCAC | GTGCATTGCAGTGCTCAGC |
| 3498 | CTGAGCACTGCAATGCACC | GGTGCATTGCAGTGCTCAG |
| 3499 | TGAGCACTGCAATGCACCA | TGGTGCATTGCAGTGCTCA |
| 3500 | GAGCACTGCAATGCACCAG | CTGGTGCATTGCAGTGCTC |
| 3501 | AGCACTGCAATGCACCAGG | CCTGGTGCATTGCAGTGCT |
| 3502 | GCACTGCAATGCACCAGGT | ACCTGGTGCATTGCAGTGC |
| 3503 | CACTGCAATGCACCAGGTC | GACCTGGTGCATTGCAGTG |
| 3504 | ACTGCAATGCACCAGGTCT | AGACCTGGTGCATTGCAGT |
| 3505 | CTGCAATGCACCAGGTCTG | CAGACCTGGTGCATTGCAG |
| 3506 | TGCAATGCACCAGGTCTGG | CCAGACCTGGTGCATTGCA |
| 3507 | GCAATGCACCAGGTCTGGG | CCCAGACCTGGTGCATTGC |
| 3508 | CAATGCACCAGGTCTGGGT | ACCCAGACCTGGTGCATTG |
| 3509 | AATGCACCAGGTCTGGGTC | GACCCAGACCTGGTGCATT |
| 3510 | ATGCACCAGGTCTGGGTCA | TGACCCAGACCTGGTGCAT |
| 3511 | TGCACCAGGTCTGGGTCAA | TTGACCCAGACCTGGTGCA |
| 3512 | GCACCAGGTCTGGGTCAAG | CTTGACCCAGACCTGGTGC |
| 3513 | CACCAGGTCTGGGTCAAGT | ACTTGACCCAGACCTGGTG |
| 3514 | ACCAGGTCTGGGTCAAGTT | AACTTGACCCAGACCTGGT |
| 3515 | CCAGGTCTGGGTCAAGTTT | AAACTTGACCCAGACCTGG |
| 3516 | CAGGTCTGGGTCAAGTTTG | CAAACTTGACCCAGACCTG |
| 3517 | AGGTCTGGGTCAAGTTTGA | TCAAACTTGACCCAGACCT |
| 3518 | GGTCTGGGTCAAGTTTGAT | ATCAAACTTGACCCAGACC |
| 3519 | GTCTGGGTCAAGTTTGATA | TATCAAACTTGACCCAGAC |
| 3520 | TCTGGGTCAAGTTTGATAT | ATATCAAACTTGACCCAGA |
| 3521 | CTGGGTCAAGTTTGATATC | GATATCAAACTTGACCCAG |
| 3522 | TGGGTCAAGTTTGATATCC | GGATATCAAACTTGACCCA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3523 | GGGTCAAGTTTGATATCCG | CGGATATCAAACTTGACCC |
| 3524 | GGTCAAGTTTGATATCCGG | CCGGATATCAAACTTGACC |
| 3525 | GTCAAGTTTGATATCCGGG | CCCGGATATCAAACTTGAC |
| 3526 | TCAAGTTTGATATCCGGGG | CCCCGGATATCAAACTTGA |
| 3527 | CAAGTTTGATATCCGGGGG | CCCCCGGATATCAAACTTG |
| 3528 | AAGTTTGATATCCGGGGGC | GCCCCCGGATATCAAACTT |
| 3529 | AGTTTGATATCCGGGGGCA | TGCCCCCGGATATCAAACT |
| 3530 | GTTTGATATCCGGGGGCAC | GTGCCCCCGGATATCAAAC |
| 3531 | TTTGATATCCGGGGGCACT | AGTGCCCCCGGATATCAAA |
| 3532 | TTGATATCCGGGGGCACTG | CAGTGCCCCCGGATATCAA |
| 3533 | TGATATCCGGGGGCACTGC | GCAGTGCCCCCGGATATCA |
| 3534 | GATATCCGGGGGCACTGCC | GGCAGTGCCCCCGGATATC |
| 3535 | ATATCCGGGGGCACTGCCC | GGGCAGTGCCCCCGGATAT |
| 3536 | TATCCGGGGGCACTGCCCC | GGGGCAGTGCCCCCGGATA |
| 3537 | ATCCGGGGGCACTGCCCCT | AGGGGCAGTGCCCCCGGAT |
| 3538 | TCCGGGGGCACTGCCCCTG | CAGGGGCAGTGCCCCCGGA |
| 3539 | CCGGGGGCACTGCCCCTGC | GCAGGGGCAGTGCCCCCGG |
| 3540 | CGGGGGCACTGCCCCTGCC | GGCAGGGGCAGTGCCCCCG |
| 3541 | GGGGGCACTGCCCCTGCCA | TGGCAGGGGCAGTGCCCCC |
| 3542 | GGGGCACTGCCCCTGCCAA | TTGGCAGGGGCAGTGCCCC |
| 3543 | GGGCACTGCCCCTGCCAAG | CTTGGCAGGGGCAGTGCCC |
| 3544 | GGCACTGCCCCTGCCAAGC | GCTTGGCAGGGGCAGTGCC |
| 3545 | GCACTGCCCCTGCCAAGCT | AGCTTGGCAGGGGCAGTGC |
| 3546 | CACTGCCCCTGCCAAGCTG | CAGCTTGGCAGGGGCAGTG |
| 3547 | ACTGCCCCTGCCAAGCTGA | TCAGCTTGGCAGGGGCAGT |
| 3548 | CTGCCCCTGCCAAGCTGAT | ATCAGCTTGGCAGGGGCAG |
| 3549 | TGCCCCTGCCAAGCTGATG | CATCAGCTTGGCAGGGGCA |
| 3550 | GCCCCTGCCAAGCTGATGC | GCATCAGCTTGGCAGGGGC |
| 3551 | CCCCTGCCAAGCTGATGCC | GGCATCAGCTTGGCAGGGG |
| 3552 | CCCTGCCAAGCTGATGCCC | GGGCATCAGCTTGGCAGGG |
| 3553 | CCTGCCAAGCTGATGCCCG | CGGGCATCAGCTTGGCAGG |
| 3554 | CTGCCAAGCTGATGCCCGG | CCGGGCATCAGCTTGGCAG |
| 3555 | TGCCAAGCTGATGCCCGGG | CCCGGGCATCAGCTTGGCA |
| 3556 | GCCAAGCTGATGCCCGGGT | ACCCGGGCATCAGCTTGGC |
| 3557 | CCAAGCTGATGCCCGGGTA | TACCCGGGCATCAGCTTGG |
| 3558 | CAAGCTGATGCCCGGGTAT | ATACCCGGGCATCAGCTTG |
| 3559 | AAGCTGATGCCCGGGTATG | CATACCCGGGCATCAGCTT |
| 3560 | AGCTGATGCCCGGGTATGG | CCATACCCGGGCATCAGCT |
| 3561 | GCTGATGCCCGGGTATGGG | CCCATACCCGGGCATCAGC |
| 3562 | CTGATGCCCGGGTATGGGC | GCCCATACCCGGGCATCAG |
| 3563 | TGATGCCCGGGTATGGGCC | GGCCCATACCCGGGCATCA |
| 3564 | GATGCCCGGGTATGGGCCC | GGGCCCATACCCGGGCATC |
| 3565 | ATGCCCGGGTATGGGCCCC | GGGGCCCATACCCGGGCAT |
| 3566 | TGCCCGGGTATGGGCCCCC | GGGGGCCCATACCCGGGCA |
| 3567 | GCCCGGGTATGGGCCCCCG | CGGGGGCCCATACCCGGGC |
| 3568 | CCCGGGTATGGGCCCCCGG | CCGGGGGCCCATACCCGGG |
| 3569 | CCGGGTATGGGCCCCCGGG | CCCGGGGGCCCATACCCGG |
| 3570 | CGGGTATGGGCCCCCGGGG | CCCCGGGGGCCCATACCCG |
| 3571 | GGGTATGGGCCCCCGGGGA | TCCCCGGGGGCCCATACCC |
| 3572 | GGTATGGGCCCCCGGGGAT | ATCCCCGGGGGCCCATACC |
| 3573 | GTATGGGCCCCCGGGGATG | CATCCCCGGGGGCCCATAC |
| 3574 | TATGGGCCCCCGGGGATGC | GCATCCCCGGGGGCCCATA |
| 3575 | ATGGGCCCCCGGGGATGCA | TGCATCCCCGGGGGCCCAT |
| 3576 | TGGGCCCCCGGGGATGCAG | CTGCATCCCCGGGGGCCCA |
| 3577 | GGGCCCCCGGGGATGCAGG | CCTGCATCCCCGGGGGCCC |
| 3578 | GGCCCCCGGGGATGCAGGC | GCCTGCATCCCCGGGGGCC |
| 3579 | GCCCCCGGGGATGCAGGCC | GGCCTGCATCCCCGGGGGC |
| 3580 | CCCCCGGGGATGCAGGCCA | TGGCCTGCATCCCCGGGGG |
| 3581 | CCCCGGGGATGCAGGCCAG | CTGGCCTGCATCCCCGGGG |
| 3582 | CCCGGGGATGCAGGCCAGC | GCTGGCCTGCATCCCCGGG |
| 3583 | CCGGGGATGCAGGCCAGCA | TGCTGGCCTGCATCCCCGG |
| 3584 | CGGGGATGCAGGCCAGCAG | CTGCTGGCCTGCATCCCCG |
| 3585 | GGGGATGCAGGCCAGCAGA | TCTGCTGGCCTGCATCCCC |
| 3586 | GGGATGCAGGCCAGCAGAA | TTCTGCTGGCCTGCATCCC |
| 3587 | GGATGCAGGCCAGCAGAAG | CTTCTGCTGGCCTGCATCC |
| 3588 | GATGCAGGCCAGCAGAAGG | CCTTCTGCTGGCCTGCATC |
| 3589 | ATGCAGGCCAGCAGAAGGA | TCCTTCTGCTGGCCTGCAT |
| 3590 | TGCAGGCCAGCAGAAGGAA | TTCCTTCTGCTGGCCTGCA |
| 3591 | GCAGGCCAGCAGAAGGAAT | ATTCCTTCTGCTGGCCTGC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 3592 | CAGGCCAGCAGAAGGAATC | GATTCCTTCTGCTGGCCTG |
| 3593 | AGGCCAGCAGAAGGAATCA | TGATTCCTTCTGCTGGCCT |
| 3594 | GGCCAGCAGAAGGAATCAA | TTGATTCCTTCTGCTGGCC |
| 3595 | GCCAGCAGAAGGAATCAAC | GTTGATTCCTTCTGCTGGC |
| 3596 | CCAGCAGAAGGAATCAACA | TGTTGATTCCTTCTGCTGG |
| 3597 | CAGCAGAAGGAATCAACAC | GTGTTGATTCCTTCTGCTG |
| 3598 | AGCAGAAGGAATCAACACA | TGTGTTGATTCCTTCTGCT |
| 3599 | GCAGAAGGAATCAACACAG | CTGTGTTGATTCCTTCTGC |
| 3600 | CAGAAGGAATCAACACAGA | TCTGTGTTGATTCCTTCTG |
| 3601 | AGAAGGAATCAACACAGAA | TTCTGTGTTGATTCCTTCT |
| 3602 | GAAGGAATCAACACAGAAA | TTTCTGTGTTGATTCCTTC |
| 3603 | AAGGAATCAACACAGAAAA | TTTTCTGTGTTGATTCCTT |
| 3604 | AGGAATCAACACAGAAAAC | GTTTTCTGTGTTGATTCCT |
| 3605 | GGAATCAACACAGAAAACG | CGTTTTCTGTGTTGATTCC |
| 3606 | GAATCAACACAGAAAACGC | GCGTTTTCTGTGTTGATTC |
| 3607 | AATCAACACAGAAAACGCC | GGCGTTTTCTGTGTTGATT |
| 3608 | ATCAACACAGAAAACGCCC | GGGCGTTTTCTGTGTTGAT |
| 3609 | TCAACACAGAAAACGCCCC | GGGGCGTTTTCTGTGTTGA |
| 3610 | CAACACAGAAAACGCCCCC | GGGGGCGTTTTCTGTGTTG |
| 3611 | AACACAGAAAACGCCCCCA | TGGGGGCGTTTTCTGTGTT |
| 3612 | ACACAGAAAACGCCCCCAA | TTGGGGGCGTTTTCTGTGT |
| 3613 | CACAGAAAACGCCCCCAAC | GTTGGGGGCGTTTTCTGTG |
| 3614 | ACAGAAAACGCCCCCAACT | AGTTGGGGGCGTTTTCTGT |
| 3615 | CAGAAAACGCCCCCAACTC | GAGTTGGGGGCGTTTTCTG |
| 3616 | AGAAAACGCCCCCAACTCC | GGAGTTGGGGGCGTTTTCT |
| 3617 | GAAAACGCCCCCAACTCCA | TGGAGTTGGGGGCGTTTTC |
| 3618 | AAAACGCCCCCAACTCCAC | GTGGAGTTGGGGGCGTTTT |
| 3619 | AAACGCCCCCAACTCCACA | TGTGGAGTTGGGGGCGTTT |
| 3620 | AACGCCCCCAACTCCACAA | TTGTGGAGTTGGGGGCGTT |
| 3621 | ACGCCCCCAACTCCACAAC | GTTGTGGAGTTGGGGGCGT |
| 3622 | CGCCCCCAACTCCACAACC | GGTTGTGGAGTTGGGGGCG |
| 3623 | GCCCCCAACTCCACAACCT | AGGTTGTGGAGTTGGGGGC |
| 3624 | CCCCCAACTCCACAACCTT | AAGGTTGTGGAGTTGGGGG |
| 3625 | CCCCAACTCCACAACCTTC | GAAGGTTGTGGAGTTGGGG |
| 3626 | CCCAACTCCACAACCTTCC | GGAAGGTTGTGGAGTTGGG |
| 3627 | CCAACTCCACAACCTTCCT | AGGAAGGTTGTGGAGTTGG |
| 3628 | CAACTCCACAACCTTCCTG | CAGGAAGGTTGTGGAGTTG |
| 3629 | AACTCCACAACCTTCCTGC | GCAGGAAGGTTGTGGAGTT |
| 3630 | ACTCCACAACCTTCCTGCA | TGCAGGAAGGTTGTGGAGT |
| 3631 | CTCCACAACCTTCCTGCAA | TTGCAGGAAGGTTGTGGAG |
| 3632 | TCCACAACCTTCCTGCAAT | ATTGCAGGAAGGTTGTGGA |
| 3633 | CCACAACCTTCCTGCAATG | CATTGCAGGAAGGTTGTGG |
| 3634 | CACAACCTTCCTGCAATGG | CCATTGCAGGAAGGTTGTG |
| 3635 | ACAACCTTCCTGCAATGGC | GCCATTGCAGGAAGGTTGT |
| 3636 | CAACCTTCCTGCAATGGCG | CGCCATTGCAGGAAGGTTG |
| 3637 | AACCTTCCTGCAATGGCGA | TCGCCATTGCAGGAAGGTT |
| 3638 | ACCTTCCTGCAATGGCGAC | GTCGCCATTGCAGGAAGGT |
| 3639 | CCTTCCTGCAATGGCGACA | TGTCGCCATTGCAGGAAGG |
| 3640 | CTTCCTGCAATGGCGACAC | GTGTCGCCATTGCAGGAAG |
| 3641 | TTCCTGCAATGGCGACACC | GGTGTCGCCATTGCAGGAA |
| 3642 | TCCTGCAATGGCGACACCC | GGGTGTCGCCATTGCAGGA |
| 3643 | CCTGCAATGGCGACACCCA | TGGGTGTCGCCATTGCAGG |
| 3644 | CTGCAATGGCGACACCCAC | GTGGGTGTCGCCATTGCAG |
| 3645 | TGCAATGGCGACACCCACA | TGTGGGTGTCGCCATTGCA |
| 3646 | GCAATGGCGACACCCACAG | CTGTGGGTGTCGCCATTGC |
| 3647 | CAATGGCGACACCCACAGG | CCTGTGGGTGTCGCCATTG |
| 3648 | AATGGCGACACCCACAGGA | TCCTGTGGGTGTCGCCATT |
| 3649 | ATGGCGACACCCACAGGAC | GTCCTGTGGGTGTCGCCAT |
| 3650 | TGGCGACACCCACAGGACC | GGTCCTGTGGGTGTCGCCA |
| 3651 | GGCGACACCCACAGGACCA | TGGTCCTGTGGGTGTCGCC |
| 3652 | GCGACACCCACAGGACCAA | TTGGTCCTGTGGGTGTCGC |
| 3653 | CGACACCCACAGGACCAAG | CTTGGTCCTGTGGGTGTCG |
| 3654 | GACACCCACAGGACCAAGA | TCTTGGTCCTGTGGGTGTC |
| 3655 | ACACCCACAGGACCAAGAG | CTCTTGGTCCTGTGGGTGT |
| 3656 | CACCCACAGGACCAAGAGC | GCTCTTGGTCCTGTGGGTG |
| 3657 | ACCCACAGGACCAAGAGCA | TGCTCTTGGTCCTGTGGGT |
| 3658 | CCCACAGGACCAAGAGCAT | ATGCTCTTGGTCCTGTGGG |
| 3659 | CCACAGGACCAAGAGCATC | GATGCTCTTGGTCCTGTGG |
| 3660 | CACAGGACCAAGAGCATCA | TGATGCTCTTGGTCCTGTG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 3661 | ACAGGACCAAGAGCATCAA | TTGATGCTCTTGGTCCTGT |
| 3662 | CAGGACCAAGAGCATCAAA | TTTGATGCTCTTGGTCCTG |
| 3663 | AGGACCAAGAGCATCAAAG | CTTTGATGCTCTTGGTCCT |
| 3664 | GGACCAAGAGCATCAAAGA | TCTTTGATGCTCTTGGTCC |
| 3665 | GACCAAGAGCATCAAAGAG | CTCTTTGATGCTCTTGGTC |
| 3666 | ACCAAGAGCATCAAAGAGG | CCTCTTTGATGCTCTTGGT |
| 3667 | CCAAGAGCATCAAAGAGGA | TCCTCTTTGATGCTCTTGG |
| 3668 | CAAGAGCATCAAAGAGGAG | CTCCTCTTTGATGCTCTTG |
| 3669 | AAGAGCATCAAAGAGGAGA | TCTCCTCTTTGATGCTCTT |
| 3670 | AGAGCATCAAAGAGGAGAC | GTCTCCTCTTTGATGCTCT |
| 3671 | GAGCATCAAAGAGGAGACC | GGTCTCCTCTTTGATGCTC |
| 3672 | AGCATCAAAGAGGAGACCC | GGGTCTCCTCTTTGATGCT |
| 3673 | GCATCAAAGAGGAGACCCC | GGGGTCTCCTCTTTGATGC |
| 3674 | CATCAAAGAGGAGACCCCC | GGGGGTCTCCTCTTTGATG |
| 3675 | ATCAAAGAGGAGACCCCCG | CGGGGGTCTCCTCTTTGAT |
| 3676 | TCAAAGAGGAGACCCCCGA | TCGGGGGTCTCCTCTTTGA |
| 3677 | CAAAGAGGAGACCCCCGAT | ATCGGGGGTCTCCTCTTTG |
| 3678 | AAAGAGGAGACCCCCGATT | AATCGGGGGTCTCCTCTTT |
| 3679 | AAGAGGAGACCCCCGATTC | GAATCGGGGGTCTCCTCTT |
| 3680 | AGAGGAGACCCCCGATTCC | GGAATCGGGGGTCTCCTCT |
| 3681 | GAGGAGACCCCCGATTCCG | CGGAATCGGGGGTCTCCTC |
| 3682 | AGGAGACCCCCGATTCCGC | GCGGAATCGGGGGTCTCCT |
| 3683 | GGAGACCCCCGATTCCGCT | AGCGGAATCGGGGGTCTCC |
| 3684 | GAGACCCCCGATTCCGCTG | CAGCGGAATCGGGGGTCTC |
| 3685 | AGACCCCCGATTCCGCTGA | TCAGCGGAATCGGGGGTCT |
| 3686 | GACCCCCGATTCCGCTGAG | CTCAGCGGAATCGGGGGTC |
| 3687 | ACCCCCGATTCCGCTGAGA | TCTCAGCGGAATCGGGGGT |
| 3688 | CCCCCGATTCCGCTGAGAC | GTCTCAGCGGAATCGGGGG |
| 3689 | CCCCGATTCCGCTGAGACC | GGTCTCAGCGGAATCGGGG |
| 3690 | CCCGATTCCGCTGAGACCC | GGGTCTCAGCGGAATCGGG |
| 3691 | CCGATTCCGCTGAGACCCC | GGGGTCTCAGCGGAATCGG |
| 3692 | CGATTCCGCTGAGACCCCA | TGGGGTCTCAGCGGAATCG |
| 3693 | GATTCCGCTGAGACCCCAG | CTGGGGTCTCAGCGGAATC |
| 3694 | ATTCCGCTGAGACCCCAGC | GCTGGGGTCTCAGCGGAAT |
| 3695 | TTCCGCTGAGACCCCAGCA | TGCTGGGGTCTCAGCGGAA |
| 3696 | TCCGCTGAGACCCCAGCAG | CTGCTGGGGTCTCAGCGGA |
| 3697 | CCGCTGAGACCCCAGCAGA | TCTGCTGGGGTCTCAGCGG |
| 3698 | CGCTGAGACCCCAGCAGAG | CTCTGCTGGGGTCTCAGCG |
| 3699 | GCTGAGACCCCAGCAGAGG | CCTCTGCTGGGGTCTCAGC |
| 3700 | CTGAGACCCCAGCAGAGGA | TCCTCTGCTGGGGTCTCAG |
| 3701 | TGAGACCCCAGCAGAGGAC | GTCCTCTGCTGGGGTCTCA |
| 3702 | GAGACCCCAGCAGAGGACC | GGTCCTCTGCTGGGGTCTC |
| 3703 | AGACCCCAGCAGAGGACCG | CGGTCCTCTGCTGGGGTCT |
| 3704 | GACCCCAGCAGAGGACCGT | ACGGTCCTCTGCTGGGGTC |
| 3705 | ACCCCAGCAGAGGACCGTG | CACGGTCCTCTGCTGGGGT |
| 3706 | CCCCAGCAGAGGACCGTGC | GCACGGTCCTCTGCTGGGG |
| 3707 | CCCAGCAGAGGACCGTGCT | AGCACGGTCCTCTGCTGGG |
| 3708 | CCAGCAGAGGACCGTGCTG | CAGCACGGTCCTCTGCTGG |
| 3709 | CAGCAGAGGACCGTGCTGG | CCAGCACGGTCCTCTGCTG |
| 3710 | AGCAGAGGACCGTGCTGGC | GCCAGCACGGTCCTCTGCT |
| 3711 | GCAGAGGACCGTGCTGGCC | GGCCAGCACGGTCCTCTGC |
| 3712 | CAGAGGACCGTGCTGGCCG | CGGCCAGCACGGTCCTCTG |
| 3713 | AGAGGACCGTGCTGGCCGA | TCGGCCAGCACGGTCCTCT |
| 3714 | GAGGACCGTGCTGGCCGAG | CTCGGCCAGCACGGTCCTC |
| 3715 | AGGACCGTGCTGGCCGAGG | CCTCGGCCAGCACGGTCCT |
| 3716 | GGACCGTGCTGGCCGAGGG | CCCTCGGCCAGCACGGTCC |
| 3717 | GACCGTGCTGGCCGAGGGC | GCCCTCGGCCAGCACGGTC |
| 3718 | ACCGTGCTGGCCGAGGGCC | GGCCCTCGGCCAGCACGGT |
| 3719 | CCGTGCTGGCCGAGGGCCC | GGGCCCTCGGCCAGCACGG |
| 3720 | CGTGCTGGCCGAGGGCCCC | GGGGCCCTCGGCCAGCACG |
| 3721 | GTGCTGGCCGAGGGCCCCT | AGGGGCCCTCGGCCAGCAC |
| 3722 | TGCTGGCCGAGGGCCCCTG | CAGGGGCCCTCGGCCAGCA |
| 3723 | GCTGGCCGAGGGCCCCTGC | GCAGGGGCCCTCGGCCAGC |
| 3724 | CTGGCCGAGGGCCCCTGCC | GGCAGGGGCCCTCGGCCAG |
| 3725 | TGGCCGAGGGCCCCTGCCT | AGGCAGGGGCCCTCGGCCA |
| 3726 | GGCCGAGGGCCCCTGCCTT | AAGGCAGGGGCCCTCGGCC |
| 3727 | GCCGAGGGCCCCTGCCTTG | CAAGGCAGGGGCCCTCGGC |
| 3728 | CCGAGGGCCCCTGCCTTGT | ACAAGGCAGGGGCCCTCGG |
| 3729 | CGAGGGCCCCTGCCTTGTC | GACAAGGCAGGGGCCCTCG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3730 | GAGGGCCCCTGCCTTGTCC | GGACAAGGCAGGGGCCCTC |
| 3731 | AGGGCCCCTGCCTTGTCCT | AGGACAAGGCAGGGGCCCT |
| 3732 | GGGCCCCTGCCTTGTCCTT | AAGGACAAGGCAGGGGCCC |
| 3733 | GGCCCCTGCCTTGTCCTTC | GAAGGACAAGGCAGGGGCC |
| 3734 | GCCCCTGCCTTGTCCTTCT | AGAAGGACAAGGCAGGGGC |
| 3735 | CCCCTGCCTTGTCCTTCTC | GAGAAGGACAAGGCAGGGG |
| 3736 | CCCTGCCTTGTCCTTCTCT | AGAGAAGGACAAGGCAGGG |
| 3737 | CCTGCCTTGTCCTTCTCTC | GAGAGAAGGACAAGGCAGG |
| 3738 | CTGCCTTGTCCTTCTCTCT | AGAGAGAAGGACAAGGCAG |
| 3739 | TGCCTTGTCCTTCTCTCTG | CAGAGAGAAGGACAAGGCA |
| 3740 | GCCTTGTCCTTCTCTCTGC | GCAGAGAGAAGGACAAGGC |
| 3741 | CCTTGTCCTTCTCTCTGCG | CGCAGAGAGAAGGACAAGG |
| 3742 | CTTGTCCTTCTCTCTGCGA | TCGCAGAGAGAAGGACAAG |
| 3743 | TTGTCCTTCTCTCTGCGAA | TTCGCAGAGAGAAGGACAA |
| 3744 | TGTCCTTCTCTCTGCGAAC | GTTCGCAGAGAGAAGGACA |
| 3745 | GTCCTTCTCTCTGCGAACT | AGTTCGCAGAGAGAAGGAC |
| 3746 | TCCTTCTCTCTGCGAACTG | CAGTTCGCAGAGAGAAGGA |
| 3747 | CCTTCTCTCTGCGAACTGC | GCAGTTCGCAGAGAGAAGG |
| 3748 | CTTCTCTCTGCGAACTGCT | AGCAGTTCGCAGAGAGAAG |
| 3749 | TTCTCTCTGCGAACTGCTG | CAGCAGTTCGCAGAGAGAA |
| 3750 | TCTCTCTGCGAACTGCTGG | CCAGCAGTTCGCAGAGAGA |
| 3751 | CTCTCTGCGAACTGCTGGC | GCCAGCAGTTCGCAGAGAG |
| 3752 | TCTCTGCGAACTGCTGGCT | AGCCAGCAGTTCGCAGAGA |
| 3753 | CTCTGCGAACTGCTGGCTT | AAGCCAGCAGTTCGCAGAG |
| 3754 | TCTGCGAACTGCTGGCTTC | GAAGCCAGCAGTTCGCAGA |
| 3755 | CTGCGAACTGCTGGCTTCT | AGAAGCCAGCAGTTCGCAG |
| 3756 | TGCGAACTGCTGGCTTCTA | TAGAAGCCAGCAGTTCGCA |
| 3757 | GCGAACTGCTGGCTTCTAC | GTAGAAGCCAGCAGTTCGC |
| 3758 | CGAACTGCTGGCTTCTACC | GGTAGAAGCCAGCAGTTCG |
| 3759 | GAACTGCTGGCTTCTACCG | CGGTAGAAGCCAGCAGTTC |
| 3760 | AACTGCTGGCTTCTACCGC | GCGGTAGAAGCCAGCAGTT |
| 3761 | ACTGCTGGCTTCTACCGCG | CGCGGTAGAAGCCAGCAGT |
| 3762 | CTGCTGGCTTCTACCGCGG | CCGCGGTAGAAGCCAGCAG |
| 3763 | TGCTGGCTTCTACCGCGGT | ACCGCGGTAGAAGCCAGCA |
| 3764 | GCTGGCTTCTACCGCGGTC | GACCGCGGTAGAAGCCAGC |
| 3765 | CTGGCTTCTACCGCGGTCA | TGACCGCGGTAGAAGCCAG |
| 3766 | TGGCTTCTACCGCGGTCAA | TTGACCGCGGTAGAAGCCA |
| 3767 | GGCTTCTACCGCGGTCAAA | TTTGACCGCGGTAGAAGCC |
| 3768 | GCTTCTACCGCGGTCAAAC | GTTTGACCGCGGTAGAAGC |
| 3769 | CTTCTACCGCGGTCAAACT | AGTTTGACCGCGGTAGAAG |
| 3770 | TTCTACCGCGGTCAAACTC | GAGTTTGACCGCGGTAGAA |
| 3771 | TCTACCGCGGTCAAACTCT | AGAGTTTGACCGCGGTAGA |
| 3772 | CTACCGCGGTCAAACTCTG | CAGAGTTTGACCGCGGTAG |
| 3773 | TACCGCGGTCAAACTCTGC | GCAGAGTTTGACCGCGGTA |
| 3774 | ACCGCGGTCAAACTCTGCT | AGCAGAGTTTGACCGCGGT |
| 3775 | CCGCGGTCAAACTCTGCTT | AAGCAGAGTTTGACCGCGG |
| 3776 | CGCGGTCAAACTCTGCTTG | CAAGCAGAGTTTGACCGCG |
| 3777 | GCGGTCAAACTCTGCTTGG | CCAAGCAGAGTTTGACCGC |
| 3778 | CGGTCAAACTCTGCTTGGG | CCCAAGCAGAGTTTGACCG |
| 3779 | GGTCAAACTCTGCTTGGGC | GCCCAAGCAGAGTTTGACC |
| 3780 | GTCAAACTCTGCTTGGGCC | GGCCCAAGCAGAGTTTGAC |
| 3781 | TCAAACTCTGCTTGGGCCA | TGGCCCAAGCAGAGTTTGA |
| 3782 | CAAACTCTGCTTGGGCCAT | ATGGCCCAAGCAGAGTTTG |
| 3783 | AAACTCTGCTTGGGCCATG | CATGGCCCAAGCAGAGTTT |
| 3784 | AACTCTGCTTGGGCCATGA | TCATGGCCCAAGCAGAGTT |
| 3785 | ACTCTGCTTGGGCCATGAG | CTCATGGCCCAAGCAGAGT |
| 3786 | CTCTGCTTGGGCCATGAGC | GCTCATGGCCCAAGCAGAG |
| 3787 | TCTGCTTGGGCCATGAGCG | CGCTCATGGCCCAAGCAGA |
| 3788 | CTGCTTGGGCCATGAGCGA | TCGCTCATGGCCCAAGCAG |
| 3789 | TGCTTGGGCCATGAGCGAA | TTCGCTCATGGCCCAAGCA |
| 3790 | GCTTGGGCCATGAGCGAAT | ATTCGCTCATGGCCCAAGC |
| 3791 | CTTGGGCCATGAGCGAATA | TATTCGCTCATGGCCCAAG |
| 3792 | TTGGGCCATGAGCGAATAC | GTATTCGCTCATGGCCCAA |
| 3793 | TGGGCCATGAGCGAATACA | TGTATTCGCTCATGGCCCA |
| 3794 | GGGCCATGAGCGAATACAC | GTGTATTCGCTCATGGCCC |
| 3795 | GGCCATGAGCGAATACACA | TGTGTATTCGCTCATGGCC |
| 3796 | GCCATGAGCGAATACACAT | ATGTGTATTCGCTCATGGC |
| 3797 | CCATGAGCGAATACACATG | CATGTGTATTCGCTCATGG |
| 3798 | CATGAGCGAATACACATGG | CCATGTGTATTCGCTCATG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3799 | ATGAGCGAATACACATGGC | GCCATGTGTATTCGCTCAT |
| 3800 | TGAGCGAATACACATGGCC | GGCCATGTGTATTCGCTCA |
| 3801 | GAGCGAATACACATGGCCT | AGGCCATGTGTATTCGCTC |
| 3802 | AGCGAATACACATGGCCTT | AAGGCCATGTGTATTCGCT |
| 3803 | GCGAATACACATGGCCTTC | GAAGGCCATGTGTATTCGC |
| 3804 | CGAATACACATGGCCTTCG | CGAAGGCCATGTGTATTCG |
| 3805 | GAATACACATGGCCTTCGC | GCGAAGGCCATGTGTATTC |
| 3806 | AATACACATGGCCTTCGCC | GGCGAAGGCCATGTGTATT |
| 3807 | ATACACATGGCCTTCGCCC | GGGCGAAGGCCATGTGTAT |
| 3808 | TACACATGGCCTTCGCCCC | GGGGCGAAGGCCATGTGTA |
| 3809 | ACACATGGCCTTCGCCCCC | GGGGGCGAAGGCCATGTGT |
| 3810 | CACATGGCCTTCGCCCCCG | CGGGGGCGAAGGCCATGTG |
| 3811 | ACATGGCCTTCGCCCCCGT | ACGGGGGCGAAGGCCATGT |
| 3812 | CATGGCCTTCGCCCCCGTC | GACGGGGGCGAAGGCCATG |
| 3813 | ATGGCCTTCGCCCCCGTCA | TGACGGGGGCGAAGGCCAT |
| 3814 | TGGCCTTCGCCCCCGTCAC | GTGACGGGGGCGAAGGCCA |
| 3815 | GGCCTTCGCCCCCGTCACT | AGTGACGGGGGCGAAGGCC |
| 3816 | GCCTTCGCCCCCGTCACTC | GAGTGACGGGGGCGAAGGC |
| 3817 | CCTTCGCCCCCGTCACTCC | GGAGTGACGGGGGCGAAGG |
| 3818 | CTTCGCCCCCGTCACTCCG | CGGAGTGACGGGGGCGAAG |
| 3819 | TTCGCCCCCGTCACTCCGG | CCGGAGTGACGGGGGCGAA |
| 3820 | TCGCCCCCGTCACTCCGGC | GCCGGAGTGACGGGGGCGA |
| 3821 | CGCCCCCGTCACTCCGGCC | GGCCGGAGTGACGGGGGCG |
| 3822 | GCCCCCGTCACTCCGGCCC | GGGCCGGAGTGACGGGGGC |
| 3823 | CCCCCGTCACTCCGGCCCT | AGGGCCGGAGTGACGGGGG |
| 3824 | CCCCGTCACTCCGGCCCTG | CAGGGCCGGAGTGACGGGG |
| 3825 | CCCGTCACTCCGGCCCTGC | GCAGGGCCGGAGTGACGGG |
| 3826 | CCGTCACTCCGGCCCTGCC | GGCAGGGCCGGAGTGACGG |
| 3827 | CGTCACTCCGGCCCTGCCC | GGGCAGGGCCGGAGTGACG |
| 3828 | GTCACTCCGGCCCTGCCCA | TGGGCAGGGCCGGAGTGAC |
| 3829 | TCACTCCGGCCCTGCCCAG | CTGGGCAGGGCCGGAGTGA |
| 3830 | CACTCCGGCCCTGCCCAGT | ACTGGGCAGGGCCGGAGTG |
| 3831 | ACTCCGGCCCTGCCCAGTG | CACTGGGCAGGGCCGGAGT |
| 3832 | CTCCGGCCCTGCCCAGTGA | TCACTGGGCAGGGCCGGAG |
| 3833 | TCCGGCCCTGCCCAGTGAT | ATCACTGGGCAGGGCCGGA |
| 3834 | CCGGCCCTGCCCAGTGATG | CATCACTGGGCAGGGCCGG |
| 3835 | CGGCCCTGCCCAGTGATGA | TCATCACTGGGCAGGGCCG |
| 3836 | GGCCCTGCCCAGTGATGAC | GTCATCACTGGGCAGGGCC |
| 3837 | GCCCTGCCCAGTGATGACC | GGTCATCACTGGGCAGGGC |
| 3838 | CCCTGCCCAGTGATGACCG | CGGTCATCACTGGGCAGGG |
| 3839 | CCTGCCCAGTGATGACCGC | GCGGTCATCACTGGGCAGG |
| 3840 | CTGCCCAGTGATGACCGCA | TGCGGTCATCACTGGGCAG |
| 3841 | TGCCCAGTGATGACCGCAT | ATGCGGTCATCACTGGGCA |
| 3842 | GCCCAGTGATGACCGCATC | GATGCGGTCATCACTGGGC |
| 3843 | CCCAGTGATGACCGCATCA | TGATGCGGTCATCACTGGG |
| 3844 | CCAGTGATGACCGCATCAC | GTGATGCGGTCATCACTGG |
| 3845 | CAGTGATGACCGCATCACC | GGTGATGCGGTCATCACTG |
| 3846 | AGTGATGACCGCATCACCA | TGGTGATGCGGTCATCACT |
| 3847 | GTGATGACCGCATCACCAA | TTGGTGATGCGGTCATCAC |
| 3848 | TGATGACCGCATCACCAAC | GTTGGTGATGCGGTCATCA |
| 3849 | GATGACCGCATCACCAACA | TGTTGGTGATGCGGTCATC |
| 3850 | ATGACCGCATCACCAACAT | ATGTTGGTGATGCGGTCAT |
| 3851 | TGACCGCATCACCAACATC | GATGTTGGTGATGCGGTCA |
| 3852 | GACCGCATCACCAACATCC | GGATGTTGGTGATGCGGTC |
| 3853 | ACCGCATCACCAACATCCT | AGGATGTTGGTGATGCGGT |
| 3854 | CCGCATCACCAACATCCTG | CAGGATGTTGGTGATGCGG |
| 3855 | CGCATCACCAACATCCTGG | CCAGGATGTTGGTGATGCG |
| 3856 | GCATCACCAACATCCTGGA | TCCAGGATGTTGGTGATGC |
| 3857 | CATCACCAACATCCTGGAC | GTCCAGGATGTTGGTGATG |
| 3858 | ATCACCAACATCCTGGACA | TGTCCAGGATGTTGGTGAT |
| 3859 | TCACCAACATCCTGGACAG | CTGTCCAGGATGTTGGTGA |
| 3860 | CACCAACATCCTGGACAGC | GCTGTCCAGGATGTTGGTG |
| 3861 | ACCAACATCCTGGACAGCA | TGCTGTCCAGGATGTTGGT |
| 3862 | CCAACATCCTGGACAGCAT | ATGCTGTCCAGGATGTTGG |
| 3863 | CAACATCCTGGACAGCATT | AATGCTGTCCAGGATGTTG |
| 3864 | AACATCCTGGACAGCATTA | TAATGCTGTCCAGGATGTT |
| 3865 | ACATCCTGGACAGCATTAT | ATAATGCTGTCCAGGATGT |
| 3866 | CATCCTGGACAGCATTATC | GATAATGCTGTCCAGGATG |
| 3867 | ATCCTGGACAGCATTATCG | CGATAATGCTGTCCAGGAT |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 3868 | TCCTGGACAGCATTATCGC | GCGATAATGCTGTCCAGGA |
| 3869 | CCTGGACAGCATTATCGCA | TGCGATAATGCTGTCCAGG |
| 3870 | CTGGACAGCATTATCGCAC | GTGCGATAATGCTGTCCAG |
| 3871 | TGGACAGCATTATCGCACA | TGTGCGATAATGCTGTCCA |
| 3872 | GGACAGCATTATCGCACAG | CTGTGCGATAATGCTGTCC |
| 3873 | GACAGCATTATCGCACAGG | CCTGTGCGATAATGCTGTC |
| 3874 | ACAGCATTATCGCACAGGT | ACCTGTGCGATAATGCTGT |
| 3875 | CAGCATTATCGCACAGGTG | CACCTGTGCGATAATGCTG |
| 3876 | AGCATTATCGCACAGGTGG | CCACCTGTGCGATAATGCT |
| 3877 | GCATTATCGCACAGGTGGT | ACCACCTGTGCGATAATGC |
| 3878 | CATTATCGCACAGGTGGTG | CACCACCTGTGCGATAATG |
| 3879 | ATTATCGCACAGGTGGTGG | CCACCACCTGTGCGATAAT |
| 3880 | TTATCGCACAGGTGGTGGA | TCCACCACCTGTGCGATAA |
| 3881 | TATCGCACAGGTGGTGGAA | TTCCACCACCTGTGCGATA |
| 3882 | ATCGCACAGGTGGTGGAAC | GTTCCACCACCTGTGCGAT |
| 3883 | TCGCACAGGTGGTGGAACG | CGTTCCACCACCTGTGCGA |
| 3884 | CGCACAGGTGGTGGAACGG | CCGTTCCACCACCTGTGCG |
| 3885 | GCACAGGTGGTGGAACGGA | TCCGTTCCACCACCTGTGC |
| 3886 | CACAGGTGGTGGAACGGAA | TTCCGTTCCACCACCTGTG |
| 3887 | ACAGGTGGTGGAACGGAAG | CTTCCGTTCCACCACCTGT |
| 3888 | CAGGTGGTGGAACGGAAGA | TCTTCCGTTCCACCACCTG |
| 3889 | AGGTGGTGGAACGGAAGAT | ATCTTCCGTTCCACCACCT |
| 3890 | GGTGGTGGAACGGAAGATC | GATCTTCCGTTCCACCACC |
| 3891 | GTGGTGGAACGGAAGATCC | GGATCTTCCGTTCCACCAC |
| 3892 | TGGTGGAACGGAAGATCCA | TGGATCTTCCGTTCCACCA |
| 3893 | GGTGGAACGGAAGATCCAG | CTGGATCTTCCGTTCCACC |
| 3894 | GTGGAACGGAAGATCCAGG | CCTGGATCTTCCGTTCCAC |
| 3895 | TGGAACGGAAGATCCAGGA | TCCTGGATCTTCCGTTCCA |
| 3896 | GGAACGGAAGATCCAGGAG | CTCCTGGATCTTCCGTTCC |
| 3897 | GAACGGAAGATCCAGGAGA | TCTCCTGGATCTTCCGTTC |
| 3898 | AACGGAAGATCCAGGAGAA | TTCTCCTGGATCTTCCGTT |
| 3899 | ACGGAAGATCCAGGAGAAA | TTTCTCCTGGATCTTCCGT |
| 3900 | CGGAAGATCCAGGAGAAAG | CTTTCTCCTGGATCTTCCG |
| 3901 | GGAAGATCCAGGAGAAAGC | GCTTTCTCCTGGATCTTCC |
| 3902 | GAAGATCCAGGAGAAAGCC | GGCTTTCTCCTGGATCTTC |
| 3903 | AAGATCCAGGAGAAAGCCC | GGGCTTTCTCCTGGATCTT |
| 3904 | AGATCCAGGAGAAAGCCCT | AGGGCTTTCTCCTGGATCT |
| 3905 | GATCCAGGAGAAAGCCCTG | CAGGGCTTTCTCCTGGATC |
| 3906 | ATCCAGGAGAAAGCCCTGG | CCAGGGCTTTCTCCTGGAT |
| 3907 | TCCAGGAGAAAGCCCTGGG | CCCAGGGCTTTCTCCTGGA |
| 3908 | CCAGGAGAAAGCCCTGGGG | CCCCAGGGCTTTCTCCTGG |
| 3909 | CAGGAGAAAGCCCTGGGGC | GCCCCAGGGCTTTCTCCTG |
| 3910 | AGGAGAAAGCCCTGGGGCC | GGCCCCAGGGCTTTCTCCT |
| 3911 | GGAGAAAGCCCTGGGGCCG | CGGCCCCAGGGCTTTCTCC |
| 3912 | GAGAAAGCCCTGGGGCCGG | CCGGCCCCAGGGCTTTCTC |
| 3913 | AGAAAGCCCTGGGGCCGGG | CCCGGCCCCAGGGCTTTCT |
| 3914 | GAAAGCCCTGGGGCCGGGG | CCCCGGCCCCAGGGCTTTC |
| 3915 | AAAGCCCTGGGGCCGGGGC | GCCCCGGCCCCAGGGCTTT |
| 3916 | AAGCCCTGGGGCCGGGGCT | AGCCCCGGCCCCAGGGCTT |
| 3917 | AGCCCTGGGGCCGGGGCTT | AAGCCCCGGCCCCAGGGCT |
| 3918 | GCCCTGGGGCCGGGGCTTC | GAAGCCCCGGCCCCAGGGC |
| 3919 | CCCTGGGGCCGGGGCTTCG | CGAAGCCCCGGCCCCAGGG |
| 3920 | CCTGGGGCCGGGGCTTCGA | TCGAAGCCCCGGCCCCAGG |
| 3921 | CTGGGGCCGGGGCTTCGAG | CTCGAAGCCCCGGCCCCAG |
| 3922 | TGGGGCCGGGGCTTCGAGC | GCTCGAAGCCCCGGCCCCA |
| 3923 | GGGGCCGGGGCTTCGAGCT | AGCTCGAAGCCCCGGCCCC |
| 3924 | GGGCCGGGGCTTCGAGCTG | CAGCTCGAAGCCCCGGCCC |
| 3925 | GGCCGGGGCTTCGAGCTGG | CCAGCTCGAAGCCCCGGCC |
| 3926 | GCCGGGGCTTCGAGCTGGC | GCCAGCTCGAAGCCCCGGC |
| 3927 | CCGGGGCTTCGAGCTGGCC | GGCCAGCTCGAAGCCCCGG |
| 3928 | CGGGGCTTCGAGCTGGCCC | GGGCCAGCTCGAAGCCCCG |
| 3929 | GGGGCTTCGAGCTGGCCCG | CGGGCCAGCTCGAAGCCCC |
| 3930 | GGGCTTCGAGCTGGCCCGG | CCGGGCCAGCTCGAAGCCC |
| 3931 | GGCTTCGAGCTGGCCCGGG | CCCGGGCCAGCTCGAAGCC |
| 3932 | GCTTCGAGCTGGCCCGGGT | ACCCGGGCCAGCTCGAAGC |
| 3933 | CTTCGAGCTGGCCCGGGTC | GACCCGGGCCAGCTCGAAG |
| 3934 | TTCGAGCTGGCCCGGGTCT | AGACCCGGGCCAGCTCGAA |
| 3935 | TCGAGCTGGCCCGGGTCTG | CAGACCCGGGCCAGCTCGA |
| 3936 | CGAGCTGGCCCGGGTCTGC | GCAGACCCGGGCCAGCTCG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 3937 | GAGCTGGCCCGGGTCTGCG | CGCAGACCCGGGCCAGCTC |
| 3938 | AGCTGGCCCGGGTCTGCGC | GCGCAGACCCGGGCCAGCT |
| 3939 | GCTGGCCCGGGTCTGCGCA | TGCGCAGACCCGGGCCAGC |
| 3940 | CTGGCCCGGGTCTGCGCAA | TTGCGCAGACCCGGGCCAG |
| 3941 | TGGCCCGGGTCTGCGCAAG | CTTGCGCAGACCCGGGCCA |
| 3942 | GGCCCGGGTCTGCGCAAGG | CCTTGCGCAGACCCGGGCC |
| 3943 | GCCCGGGTCTGCGCAAGGG | CCCTTGCGCAGACCCGGGC |
| 3944 | CCCGGGTCTGCGCAAGGGC | GCCCTTGCGCAGACCCGGG |
| 3945 | CCGGGTCTGCGCAAGGGCC | GGCCCTTGCGCAGACCCGG |
| 3946 | CGGGTCTGCGCAAGGGCCT | AGGCCCTTGCGCAGACCCG |
| 3947 | GGGTCTGCGCAAGGGCCTG | CAGGCCCTTGCGCAGACCC |
| 3948 | GGTCTGCGCAAGGGCCTGG | CCAGGCCCTTGCGCAGACC |
| 3949 | GTCTGCGCAAGGGCCTGGG | CCCAGGCCCTTGCGCAGAC |
| 3950 | TCTGCGCAAGGGCCTGGGC | GCCCAGGCCCTTGCGCAGA |
| 3951 | CTGCGCAAGGGCCTGGGCC | GGCCCAGGCCCTTGCGCAG |
| 3952 | TGCGCAAGGGCCTGGGCCT | AGGCCCAGGCCCTTGCGCA |
| 3953 | GCGCAAGGGCCTGGGCCTG | CAGGCCCAGGCCCTTGCGC |
| 3954 | CGCAAGGGCCTGGGCCTGC | GCAGGCCCAGGCCCTTGCG |
| 3955 | GCAAGGGCCTGGGCCTGCC | GGCAGGCCCAGGCCCTTGC |
| 3956 | CAAGGGCCTGGGCCTGCCC | GGGCAGGCCCAGGCCCTTG |
| 3957 | AAGGGCCTGGGCCTGCCCC | GGGGCAGGCCCAGGCCCTT |
| 3958 | AGGGCCTGGGCCTGCCCCT | AGGGGCAGGCCCAGGCCCT |
| 3959 | GGGCCTGGGCCTGCCCCTC | GAGGGGCAGGCCCAGGCCC |
| 3960 | GGCCTGGGCCTGCCCCTCT | AGAGGGGCAGGCCCAGGCC |
| 3961 | GCCTGGGCCTGCCCCTCTC | GAGAGGGGCAGGCCCAGGC |
| 3962 | CCTGGGCCTGCCCCTCTCT | AGAGAGGGGCAGGCCCAGG |
| 3963 | CTGGGCCTGCCCCTCTCTC | GAGAGAGGGGCAGGCCCAG |
| 3964 | TGGGCCTGCCCCTCTCTCC | GGAGAGAGGGGCAGGCCCA |
| 3965 | GGGCCTGCCCCTCTCTCCA | TGGAGAGAGGGGCAGGCCC |
| 3966 | GGCCTGCCCCTCTCTCCAG | CTGGAGAGAGGGGCAGGCC |
| 3967 | GCCTGCCCCTCTCTCCAGT | ACTGGAGAGAGGGGCAGGC |
| 3968 | CCTGCCCCTCTCTCCAGTG | CACTGGAGAGAGGGGCAGG |
| 3969 | CTGCCCCTCTCTCCAGTGC | GCACTGGAGAGAGGGGCAG |
| 3970 | TGCCCCTCTCTCCAGTGCG | CGCACTGGAGAGAGGGGCA |
| 3971 | GCCCCTCTCTCCAGTGCGG | CCGCACTGGAGAGAGGGGC |
| 3972 | CCCCTCTCTCCAGTGCGGC | GCCGCACTGGAGAGAGGGG |
| 3973 | CCCTCTCTCCAGTGCGGCC | GGCCGCACTGGAGAGAGGG |
| 3974 | CCTCTCTCCAGTGCGGCCC | GGGCCGCACTGGAGAGAGG |
| 3975 | CTCTCTCCAGTGCGGCCCC | GGGGCCGCACTGGAGAGAG |
| 3976 | TCTCTCCAGTGCGGCCCCG | CGGGGCCGCACTGGAGAGA |
| 3977 | CTCTCCAGTGCGGCCCCGG | CCGGGGCCGCACTGGAGAG |
| 3978 | TCTCCAGTGCGGCCCCGGC | GCCGGGGCCGCACTGGAGA |
| 3979 | CTCCAGTGCGGCCCCGGCT | AGCCGGGGCCGCACTGGAG |
| 3980 | TCCAGTGCGGCCCCGGCTG | CAGCCGGGGCCGCACTGGA |
| 3981 | CCAGTGCGGCCCCGGCTGC | GCAGCCGGGGCCGCACTGG |
| 3982 | CAGTGCGGCCCCGGCTGCC | GGCAGCCGGGGCCGCACTG |
| 3983 | AGTGCGGCCCCGGCTGCCT | AGGCAGCCGGGGCCGCACT |
| 3984 | GTGCGGCCCCGGCTGCCTC | GAGGCAGCCGGGGCCGCAC |
| 3985 | TGCGGCCCCGGCTGCCTCC | GGAGGCAGCCGGGGCCGCA |
| 3986 | GCGGCCCCGGCTGCCTCCC | GGGAGGCAGCCGGGGCCGC |
| 3987 | CGGCCCCGGCTGCCTCCCC | GGGGAGGCAGCCGGGGCCG |
| 3988 | GGCCCCGGCTGCCTCCCCC | GGGGGAGGCAGCCGGGGCC |
| 3989 | GCCCCGGCTGCCTCCCCCA | TGGGGGAGGCAGCCGGGGC |
| 3990 | CCCCGGCTGCCTCCCCCAG | CTGGGGGAGGCAGCCGGGG |
| 3991 | CCCGGCTGCCTCCCCCAGG | CCTGGGGGAGGCAGCCGGG |
| 3992 | CCGGCTGCCTCCCCCAGGG | CCCTGGGGGAGGCAGCCGG |
| 3993 | CGGCTGCCTCCCCCAGGGG | CCCCTGGGGGAGGCAGCCG |
| 3994 | GGCTGCCTCCCCCAGGGGC | GCCCCTGGGGGAGGCAGCC |
| 3995 | GCTGCCTCCCCCAGGGGCT | AGCCCCTGGGGGAGGCAGC |
| 3996 | CTGCCTCCCCCAGGGGCTT | AAGCCCCTGGGGGAGGCAG |
| 3997 | TGCCTCCCCCAGGGGCTTT | AAAGCCCCTGGGGGAGGCA |
| 3998 | GCCTCCCCCAGGGGCTTTG | CAAAGCCCCTGGGGGAGGC |
| 3999 | CCTCCCCCAGGGGCTTTGC | GCAAAGCCCCTGGGGGAGG |
| 4000 | CTCCCCCAGGGGCTTTGCT | AGCAAAGCCCCTGGGGGAG |
| 4001 | TCCCCCAGGGGCTTTGCTG | CAGCAAAGCCCCTGGGGGA |
| 4002 | CCCCCAGGGGCTTTGCTGT | ACAGCAAAGCCCCTGGGGG |
| 4003 | CCCCAGGGGCTTTGCTGTG | CACAGCAAAGCCCCTGGGG |
| 4004 | CCCAGGGGCTTTGCTGTGG | CCACAGCAAAGCCCCTGGG |
| 4005 | CCAGGGGCTTTGCTGTGGC | GCCACAGCAAAGCCCCTGG |

TABLE 1-continued cDNA Human Hairless 19-mer Target Sequences and Complement Referenced to NM_005144-
*Homo sapiens* hairless homolog (mouse) (HR), transcript variant 1, complete mRNA (1-5699 bp).
(SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 4006 | CAGGGGCTTTGCTGTGGCT | AGCCACAGCAAAGCCCCTG |
| 4007 | AGGGGCTTTGCTGTGGCTG | CAGCCACAGCAAAGCCCCT |
| 4008 | GGGGCTTTGCTGTGGCTGC | GCAGCCACAGCAAAGCCCC |
| 4009 | GGGCTTTGCTGTGGCTGCA | TGCAGCCACAGCAAAGCCC |
| 4010 | GGCTTTGCTGTGGCTGCAG | CTGCAGCCACAGCAAAGCC |
| 4011 | GCTTTGCTGTGGCTGCAGG | CCTGCAGCCACAGCAAAGC |
| 4012 | CTTTGCTGTGGCTGCAGGA | TCCTGCAGCCACAGCAAAG |
| 4013 | TTTGCTGTGGCTGCAGGAG | CTCCTGCAGCCACAGCAAA |
| 4014 | TTGCTGTGGCTGCAGGAGC | GCTCCTGCAGCCACAGCAA |
| 4015 | TGCTGTGGCTGCAGGAGCC | GGCTCCTGCAGCCACAGCA |
| 4016 | GCTGTGGCTGCAGGAGCCC | GGGCTCCTGCAGCCACAGC |
| 4017 | CTGTGGCTGCAGGAGCCCC | GGGGCTCCTGCAGCCACAG |
| 4018 | TGTGGCTGCAGGAGCCCCA | TGGGGCTCCTGCAGCCACA |
| 4019 | GTGGCTGCAGGAGCCCCAG | CTGGGGCTCCTGCAGCCAC |
| 4020 | TGGCTGCAGGAGCCCCAGC | GCTGGGGCTCCTGCAGCCA |
| 4021 | GGCTGCAGGAGCCCCAGCC | GGCTGGGGCTCCTGCAGCC |
| 4022 | GCTGCAGGAGCCCCAGCCT | AGGCTGGGGCTCCTGCAGC |
| 4023 | CTGCAGGAGCCCCAGCCTT | AAGGCTGGGGCTCCTGCAG |
| 4024 | TGCAGGAGCCCCAGCCTTG | CAAGGCTGGGGCTCCTGCA |
| 4025 | GCAGGAGCCCCAGCCTTGC | GCAAGGCTGGGGCTCCTGC |
| 4026 | CAGGAGCCCCAGCCTTGCC | GGCAAGGCTGGGGCTCCTG |
| 4027 | AGGAGCCCCAGCCTTGCCC | GGGCAAGGCTGGGGCTCCT |
| 4028 | GGAGCCCCAGCCTTGCCCT | AGGGCAAGGCTGGGGCTCC |
| 4029 | GAGCCCCAGCCTTGCCCTC | GAGGGCAAGGCTGGGGCTC |
| 4030 | AGCCCCAGCCTTGCCCTCG | CGAGGGCAAGGCTGGGGCT |
| 4031 | GCCCCAGCCTTGCCCTCGG | CCGAGGGCAAGGCTGGGGC |
| 4032 | CCCCAGCCTTGCCCTCGGC | GCCGAGGGCAAGGCTGGGG |
| 4033 | CCCAGCCTTGCCCTCGGCG | CGCCGAGGGCAAGGCTGGG |
| 4034 | CCAGCCTTGCCCTCGGCGT | ACGCCGAGGGCAAGGCTGG |
| 4035 | CAGCCTTGCCCTCGGCGTG | CACGCCGAGGGCAAGGCTG |
| 4036 | AGCCTTGCCCTCGGCGTGG | CCACGCCGAGGGCAAGGCT |
| 4037 | GCCTTGCCCTCGGCGTGGC | GCCACGCCGAGGGCAAGGC |
| 4038 | CCTTGCCCTCGGCGTGGCT | AGCCACGCCGAGGGCAAGG |
| 4039 | CTTGCCCTCGGCGTGGCTT | AAGCCACGCCGAGGGCAAG |
| 4040 | TTGCCCTCGGCGTGGCTTC | GAAGCCACGCCGAGGGCAA |
| 4041 | TGCCCTCGGCGTGGCTTCC | GGAAGCCACGCCGAGGGCA |
| 4042 | GCCCTCGGCGTGGCTTCCA | TGGAAGCCACGCCGAGGGC |
| 4043 | CCCTCGGCGTGGCTTCCAC | GTGGAAGCCACGCCGAGGG |
| 4044 | CCTCGGCGTGGCTTCCACC | GGTGGAAGCCACGCCGAGG |
| 4045 | CTCGGCGTGGCTTCCACCT | AGGTGGAAGCCACGCCGAG |
| 4046 | TCGGCGTGGCTTCCACCTC | GAGGTGGAAGCCACGCCGA |
| 4047 | CGGCGTGGCTTCCACCTCT | AGAGGTGGAAGCCACGCCG |
| 4048 | GGCGTGGCTTCCACCTCTT | AAGAGGTGGAAGCCACGCC |
| 4049 | GCGTGGCTTCCACCTCTTC | GAAGAGGTGGAAGCCACGC |
| 4050 | CGTGGCTTCCACCTCTTCC | GGAAGAGGTGGAAGCCACG |
| 4051 | GTGGCTTCCACCTCTTCCA | TGGAAGAGGTGGAAGCCAC |
| 4052 | TGGCTTCCACCTCTTCCAG | CTGGAAGAGGTGGAAGCCA |
| 4053 | GGCTTCCACCTCTTCCAGG | CCTGGAAGAGGTGGAAGCC |
| 4054 | GCTTCCACCTCTTCCAGGA | TCCTGGAAGAGGTGGAAGC |
| 4055 | CTTCCACCTCTTCCAGGAG | CTCCTGGAAGAGGTGGAAG |
| 4056 | TTCCACCTCTTCCAGGAGC | GCTCCTGGAAGAGGTGGAA |
| 4057 | TCCACCTCTTCCAGGAGCA | TGCTCCTGGAAGAGGTGGA |
| 4058 | CCACCTCTTCCAGGAGCAC | GTGCTCCTGGAAGAGGTGG |
| 4059 | CACCTCTTCCAGGAGCACT | AGTGCTCCTGGAAGAGGTG |
| 4060 | ACCTCTTCCAGGAGCACTG | CAGTGCTCCTGGAAGAGGT |
| 4061 | CCTCTTCCAGGAGCACTGG | CCAGTGCTCCTGGAAGAGG |
| 4062 | CTCTTCCAGGAGCACTGGA | TCCAGTGCTCCTGGAAGAG |
| 4063 | TCTTCCAGGAGCACTGGAG | CTCCAGTGCTCCTGGAAGA |
| 4064 | CTTCCAGGAGCACTGGAGG | CCTCCAGTGCTCCTGGAAG |
| 4065 | TTCCAGGAGCACTGGAGGC | GCCTCCAGTGCTCCTGGAA |
| 4066 | TCCAGGAGCACTGGAGGCA | TGCCTCCAGTGCTCCTGGA |
| 4067 | CCAGGAGCACTGGAGGCAG | CTGCCTCCAGTGCTCCTGG |
| 4068 | CAGGAGCACTGGAGGCAGG | CCTGCCTCCAGTGCTCCTG |
| 4069 | AGGAGCACTGGAGGCAGGG | CCCTGCCTCCAGTGCTCCT |
| 4070 | GGAGCACTGGAGGCAGGGC | GCCCTGCCTCCAGTGCTCC |
| 4071 | GAGCACTGGAGGCAGGGCC | GGCCCTGCCTCCAGTGCTC |
| 4072 | AGCACTGGAGGCAGGGCCA | TGGCCCTGCCTCCAGTGCT |
| 4073 | GCACTGGAGGCAGGGCCAG | CTGGCCCTGCCTCCAGTGC |
| 4074 | CACTGGAGGCAGGGCCAGC | GCTGGCCCTGCCTCCAGTG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4075 | ACTGGAGGCAGGGCCAGCC | GGCTGGCCCTGCCTCCAGT |
| 4076 | CTGGAGGCAGGGCCAGCCT | AGGCTGGCCCTGCCTCCAG |
| 4077 | TGGAGGCAGGGCCAGCCTG | CAGGCTGGCCCTGCCTCCA |
| 4078 | GGAGGCAGGGCCAGCCTGT | ACAGGCTGGCCCTGCCTCC |
| 4079 | GAGGCAGGGCCAGCCTGTG | CACAGGCTGGCCCTGCCTC |
| 4080 | AGGCAGGGCCAGCCTGTGT | ACACAGGCTGGCCCTGCCT |
| 4081 | GGCAGGGCCAGCCTGTGTT | AACACAGGCTGGCCCTGCC |
| 4082 | GCAGGGCCAGCCTGTGTTG | CAACACAGGCTGGCCCTGC |
| 4083 | CAGGGCCAGCCTGTGTTGG | CCAACACAGGCTGGCCCTG |
| 4084 | AGGGCCAGCCTGTGTTGGT | ACCAACACAGGCTGGCCCT |
| 4085 | GGGCCAGCCTGTGTTGGTG | CACCAACACAGGCTGGCCC |
| 4086 | GGCCAGCCTGTGTTGGTGT | ACACCAACACAGGCTGGCC |
| 4087 | GCCAGCCTGTGTTGGTGTC | GACACCAACACAGGCTGGC |
| 4088 | CCAGCCTGTGTTGGTGTCA | TGACACCAACACAGGCTGG |
| 4089 | CAGCCTGTGTTGGTGTCAG | CTGACACCAACACAGGCTG |
| 4090 | AGCCTGTGTTGGTGTCAGG | CCTGACACCAACACAGGCT |
| 4091 | GCCTGTGTTGGTGTCAGGG | CCCTGACACCAACACAGGC |
| 4092 | CCTGTGTTGGTGTCAGGGA | TCCCTGACACCAACACAGG |
| 4093 | CTGTGTTGGTGTCAGGGAT | ATCCCTGACACCAACACAG |
| 4094 | TGTGTTGGTGTCAGGGATC | GATCCCTGACACCAACACA |
| 4095 | GTGTTGGTGTCAGGGATCC | GGATCCCTGACACCAACAC |
| 4096 | TGTTGGTGTCAGGGATCCA | TGGATCCCTGACACCAACA |
| 4097 | GTTGGTGTCAGGGATCCAA | TTGGATCCCTGACACCAAC |
| 4098 | TTGGTGTCAGGGATCCAAA | TTTGGATCCCTGACACCAA |
| 4099 | TGGTGTCAGGGATCCAAAG | CTTTGGATCCCTGACACCA |
| 4100 | GGTGTCAGGGATCCAAAGG | CCTTTGGATCCCTGACACC |
| 4101 | GTGTCAGGGATCCAAAGGA | TCCTTTGGATCCCTGACAC |
| 4102 | TGTCAGGGATCCAAAGGAC | GTCCTTTGGATCCCTGACA |
| 4103 | GTCAGGGATCCAAAGGACA | TGTCCTTTGGATCCCTGAC |
| 4104 | TCAGGGATCCAAAGGACAT | ATGTCCTTTGGATCCCTGA |
| 4105 | CAGGGATCCAAAGGACATT | AATGTCCTTTGGATCCCTG |
| 4106 | AGGGATCCAAAGGACATTG | CAATGTCCTTTGGATCCCT |
| 4107 | GGGATCCAAAGGACATTGC | GCAATGTCCTTTGGATCCC |
| 4108 | GGATCCAAAGGACATTGCA | TGCAATGTCCTTTGGATCC |
| 4109 | GATCCAAAGGACATTGCAG | CTGCAATGTCCTTTGGATC |
| 4110 | ATCCAAAGGACATTGCAGG | CCTGCAATGTCCTTTGGAT |
| 4111 | TCCAAAGGACATTGCAGGG | CCCTGCAATGTCCTTTGGA |
| 4112 | CCAAAGGACATTGCAGGGC | GCCCTGCAATGTCCTTTGG |
| 4113 | CAAAGGACATTGCAGGGCA | TGCCCTGCAATGTCCTTTG |
| 4114 | AAAGGACATTGCAGGGCAA | TTGCCCTGCAATGTCCTTT |
| 4115 | AAGGACATTGCAGGGCAAC | GTTGCCCTGCAATGTCCTT |
| 4116 | AGGACATTGCAGGGCAACC | GGTTGCCCTGCAATGTCCT |
| 4117 | GGACATTGCAGGGCAACCT | AGGTTGCCCTGCAATGTCC |
| 4118 | GACATTGCAGGGCAACCTG | CAGGTTGCCCTGCAATGTC |
| 4119 | ACATTGCAGGGCAACCTGT | ACAGGTTGCCCTGCAATGT |
| 4120 | CATTGCAGGGCAACCTGTG | CACAGGTTGCCCTGCAATG |
| 4121 | ATTGCAGGGCAACCTGTGG | CCACAGGTTGCCCTGCAAT |
| 4122 | TTGCAGGGCAACCTGTGGG | CCCACAGGTTGCCCTGCAA |
| 4123 | TGCAGGGCAACCTGTGGGG | CCCCACAGGTTGCCCTGCA |
| 4124 | GCAGGGCAACCTGTGGGGG | CCCCCACAGGTTGCCCTGC |
| 4125 | CAGGGCAACCTGTGGGGGA | TCCCCCACAGGTTGCCCTG |
| 4126 | AGGGCAACCTGTGGGGGAC | GTCCCCCACAGGTTGCCCT |
| 4127 | GGGCAACCTGTGGGGGACA | TGTCCCCCACAGGTTGCCC |
| 4128 | GGCAACCTGTGGGGGACAG | CTGTCCCCCACAGGTTGCC |
| 4129 | GCAACCTGTGGGGGACAGA | TCTGTCCCCCACAGGTTGC |
| 4130 | CAACCTGTGGGGGACAGAA | TTCTGTCCCCCACAGGTTG |
| 4131 | AACCTGTGGGGGACAGAAG | CTTCTGTCCCCCACAGGTT |
| 4132 | ACCTGTGGGGGACAGAAGC | GCTTCTGTCCCCCACAGGT |
| 4133 | CCTGTGGGGGACAGAAGCT | AGCTTCTGTCCCCCACAGG |
| 4134 | CTGTGGGGGACAGAAGCTC | GAGCTTCTGTCCCCCACAG |
| 4135 | TGTGGGGGACAGAAGCTCT | AGAGCTTCTGTCCCCCACA |
| 4136 | GTGGGGGACAGAAGCTCTT | AAGAGCTTCTGTCCCCCAC |
| 4137 | TGGGGGACAGAAGCTCTTG | CAAGAGCTTCTGTCCCCCA |
| 4138 | GGGGGACAGAAGCTCTTGG | CCAAGAGCTTCTGTCCCCC |
| 4139 | GGGGACAGAAGCTCTTGGG | CCCAAGAGCTTCTGTCCCC |
| 4140 | GGGACAGAAGCTCTTGGGG | CCCCAAGAGCTTCTGTCCC |
| 4141 | GGACAGAAGCTCTTGGGGC | GCCCCAAGAGCTTCTGTCC |
| 4142 | GACAGAAGCTCTTGGGGCA | TGCCCCAAGAGCTTCTGTC |
| 4143 | ACAGAAGCTCTTGGGGCAC | GTGCCCCAAGAGCTTCTGT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4144 | CAGAAGCTCTTGGGGCACT | AGTGCCCCAAGAGCTTCTG |
| 4145 | AGAAGCTGTTGGGGCACTT | AAGTGCCCCAAGAGCTTCT |
| 4146 | GAAGCTCTTGGGGCACTTG | CAAGTGCCCCAAGAGCTTC |
| 4147 | AAGCTCTTGGGGCACTTGG | CCAAGTGCCCCAAGAGCTT |
| 4148 | AGCTCTTGGGGCACTTGGA | TCCAAGTGCCCCAAGAGCT |
| 4149 | GCTCTTGGGGCACTTGGAG | CTCCAAGTGCCCCAAGAGC |
| 4150 | CTCTTGGGGCACTTGGAGG | CCTCCAAGTGCCCCAAGAG |
| 4151 | TCTTGGGGCACTTGGAGGC | GCCTCCAAGTGCCCCAAGA |
| 4152 | CTTGGGGCACTTGGAGGCC | GGCCTCCAAGTGCCCCAAG |
| 4153 | TTGGGGCACTTGGAGGCCA | TGGCCTCCAAGTGCCCCAA |
| 4154 | TGGGGCACTTGGAGGCCAG | CTGGCCTCCAAGTGCCCCA |
| 4155 | GGGGCACTTGGAGGCCAGG | CCTGGCCTCCAAGTGCCCC |
| 4156 | GGGCACTTGGAGGCCAGGT | ACCTGGCCTCCAAGTGCCC |
| 4157 | GGCACTTGGAGGCCAGGTG | CACCTGGCCTCCAAGTGCC |
| 4158 | GCACTTGGAGGCCAGGTGC | GCACCTGGCCTCCAAGTGC |
| 4159 | CACTTGGAGGCCAGGTGCA | TGCACCTGGCCTCCAAGTG |
| 4160 | ACTTGGAGGCCAGGTGCAG | CTGCACCTGGCCTCCAAGT |
| 4161 | CTTGGAGGCCAGGTGCAGG | CCTGCACCTGGCCTCCAAG |
| 4162 | TTGGAGGCCAGGTGCAGGC | GCCTGCACCTGGCCTCCAA |
| 4163 | TGGAGGCCAGGTGCAGGCG | CGCCTGCACCTGGCCTCCA |
| 4164 | GGAGGCCAGGTGCAGGCGC | GCGCCTGCACCTGGCCTCC |
| 4165 | GAGGCCAGGTGCAGGCGCT | AGCGCCTGCACCTGGCCTC |
| 4166 | AGGCCAGGTGCAGGCGCTG | CAGCGCCTGCACCTGGCCT |
| 4167 | GGCCAGGTGCAGGCGCTGA | TCAGCGCCTGCACCTGGCC |
| 4168 | GCCAGGTGCAGGCGCTGAG | CTCAGCGCCTGCACCTGGC |
| 4169 | CCAGGTGCAGGCGCTGAGC | GCTCAGCGCCTGCACCTGG |
| 4170 | CAGGTGCAGGCGCTGAGCC | GGCTCAGCGCCTGCACCTG |
| 4171 | AGGTGCAGGCGCTGAGCCC | GGGCTCAGCGCCTGCACCT |
| 4172 | GGTGCAGGCGCTGAGCCCC | GGGGCTCAGCGCCTGCACC |
| 4173 | GTGCAGGCGCTGAGCCCCC | GGGGGCTCAGCGCCTGCAC |
| 4174 | TGCAGGCGCTGAGCCCCCT | AGGGGGCTCAGCGCCTGCA |
| 4175 | GCAGGCGCTGAGCCCCCTC | GAGGGGGCTCAGCGCCTGC |
| 4176 | CAGGCGCTGAGCCCCCTCG | CGAGGGGGCTCAGCGCCTG |
| 4177 | AGGCGCTGAGCCCCCTCGG | CCGAGGGGGCTCAGCGCCT |
| 4178 | GGCGCTGAGCCCCCTCGGA | TCCGAGGGGGCTCAGCGCC |
| 4179 | GCGCTGAGCCCCCTCGGAC | GTCCGAGGGGGCTCAGCGC |
| 4180 | CGCTGAGCCCCCTCGGACC | GGTCCGAGGGGGCTCAGCG |
| 4181 | GCTGAGCCCCCTCGGACCT | AGGTCCGAGGGGGCTCAGC |
| 4182 | CTGAGCCCCCTCGGACCTC | GAGGTCCGAGGGGGCTCAG |
| 4183 | TGAGCCCCCTCGGACCTCC | GGAGGTCCGAGGGGGCTCA |
| 4184 | GAGCCCCCTCGGACCTCCC | GGGAGGTCCGAGGGGGCTC |
| 4185 | AGCCCCCTCGGACCTCCCC | GGGGAGGTCCGAGGGGGCT |
| 4186 | GCCCCCTCGGACCTCCCCA | TGGGGAGGTCCGAGGGGGC |
| 4187 | CCCCCTCGGACCTCCCCAG | CTGGGGAGGTCCGAGGGGG |
| 4188 | CCCCTCGGACCTCCCCAGC | GCTGGGGAGGTCCGAGGGG |
| 4189 | CCCTCGGACCTCCCCAGCC | GGCTGGGGAGGTCCGAGGG |
| 4190 | CCTCGGACCTCCCCAGCCC | GGGCTGGGGAGGTCCGAGG |
| 4191 | CTCGGACCTCCCCAGCCCA | TGGGCTGGGGAGGTCCGAG |
| 4192 | TCGGACCTCCCCAGCCCAG | CTGGGCTGGGGAGGTCCGA |
| 4193 | CGGACCTCCCCAGCCCAGC | GCTGGGCTGGGGAGGTCCG |
| 4194 | GGACCTCCCCAGCCCAGCA | TGCTGGGCTGGGGAGGTCC |
| 4195 | GACCTCCCCAGCCCAGCAG | CTGCTGGGCTGGGGAGGTC |
| 4196 | ACCTCCCCAGCCCAGCAGC | GCTGCTGGGCTGGGGAGGT |
| 4197 | CCTCCCCAGCCCAGCAGCC | GGCTGCTGGGCTGGGGAGG |
| 4198 | CTCCCCAGCCCAGCAGCCT | AGGCTGCTGGGCTGGGGAG |
| 4199 | TCCCCAGCCCAGCAGCCTG | CAGGCTGCTGGGCTGGGGA |
| 4200 | CCCCAGCCCAGCAGCCTGG | CCAGGCTGCTGGGCTGGGG |
| 4201 | CCCAGCCCAGCAGCCTGGG | CCCAGGCTGCTGGGCTGGG |
| 4202 | CCAGCCCAGCAGCCTGGGC | GCCCAGGCTGCTGGGCTGG |
| 4203 | CAGCCCAGCAGCCTGGGCA | TGCCCAGGCTGCTGGGCTG |
| 4204 | AGCCCAGCAGCCTGGGCAG | CTGCCCAGGCTGCTGGGCT |
| 4205 | GCCCAGCAGCCTGGGCAGC | GCTGCCCAGGCTGCTGGGC |
| 4206 | CCCAGCAGCCTGGGCAGCA | TGCTGCCCAGGCTGCTGGG |
| 4207 | CCAGCAGCCTGGGCAGCAC | GTGCTGCCCAGGCTGCTGG |
| 4208 | CAGCAGCCTGGGCAGCACA | TGTGCTGCCCAGGCTGCTG |
| 4209 | AGCAGCCTGGGCAGCACAA | TTGTGCTGCCCAGGCTGCT |
| 4210 | GCAGCCTGGGCAGCACAAC | GTTGTGCTGCCCAGGCTGC |
| 4211 | CAGCCTGGGCAGCACAACA | TGTTGTGCTGCCCAGGCTG |
| 4212 | AGCCTGGGCAGCACAACAT | ATGTTGTGCTGCCCAGGCT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4213 | GCCTGGGCAGCACAACATT | AATGTTGTGCTGCCCAGGC |
| 4214 | CCTGGGCAGCACAACATTC | GAATGTTGTGCTGCCCAGG |
| 4215 | CTGGGCAGCACAACATTCT | AGAATGTTGTGCTGCCCAG |
| 4216 | TGGGCAGCACAACATTCTG | CAGAATGTTGTGCTGCCCA |
| 4217 | GGGCAGCACAACATTCTGG | CCAGAATGTTGTGCTGCCC |
| 4218 | GGCAGCACAACATTCTGGG | CCCAGAATGTTGTGCTGCC |
| 4219 | GCAGCACAACATTCTGGGA | TCCCAGAATGTTGTGCTGC |
| 4220 | CAGCACAACATTCTGGGAG | CTCCCAGAATGTTGTGCTG |
| 4221 | AGCACAACATTCTGGGAGG | CCTCCCAGAATGTTGTGCT |
| 4222 | GCACAACATTCTGGGAGGG | CCCTCCCAGAATGTTGTGC |
| 4223 | CACAACATTCTGGGAGGGC | GCCCTCCCAGAATGTTGTG |
| 4224 | ACAACATTCTGGGAGGGCT | AGCCCTCCCAGAATGTTGT |
| 4225 | CAACATTCTGGGAGGGCTT | AAGCCCTCCCAGAATGTTG |
| 4226 | AACATTCTGGGAGGGCTTC | GAAGCCCTCCCAGAATGTT |
| 4227 | ACATTCTGGGAGGGCTTCT | AGAAGCCCTCCCAGAATGT |
| 4228 | CATTCTGGGAGGGCTTCTC | GAGAAGCCCTCCCAGAATG |
| 4229 | ATTCTGGGAGGGCTTCTCC | GGAGAAGCCCTCCCAGAAT |
| 4230 | TTCTGGGAGGGCTTCTCCT | AGGAGAAGCCCTCCCAGAA |
| 4231 | TCTGGGAGGGCTTCTCCTG | CAGGAGAAGCCCTCCCAGA |
| 4232 | CTGGGAGGGCTTCTCCTGG | CCAGGAGAAGCCCTCCCAG |
| 4233 | TGGGAGGGCTTCTCCTGGC | GCCAGGAGAAGCCCTCCCA |
| 4234 | GGGAGGGCTTCTCCTGGCC | GGCCAGGAGAAGCCCTCCC |
| 4235 | GGAGGGCTTCTCCTGGCCT | AGGCCAGGAGAAGCCCTCC |
| 4236 | GAGGGCTTCTCCTGGCCTG | CAGGCCAGGAGAAGCCCTC |
| 4237 | AGGGCTTCTCCTGGCCTGA | TCAGGCCAGGAGAAGCCCT |
| 4238 | GGGCTTCTCCTGGCCTGAG | CTCAGGCCAGGAGAAGCCC |
| 4239 | GGCTTCTCCTGGCCTGAGC | GCTCAGGCCAGGAGAAGCC |
| 4240 | GCTTCTCCTGGCCTGAGCT | AGCTCAGGCCAGGAGAAGC |
| 4241 | CTTCTCCTGGCCTGAGCTT | AAGCTCAGGCCAGGAGAAG |
| 4242 | TTCTCCTGGCCTGAGCTTC | GAAGCTCAGGCCAGGAGAA |
| 4243 | TCTCCTGGCCTGAGCTTCG | CGAAGCTCAGGCCAGGAGA |
| 4244 | CTCCTGGCCTGAGCTTCGC | GCGAAGCTCAGGCCAGGAG |
| 4245 | TCCTGGCCTGAGCTTCGCC | GGCGAAGCTCAGGCCAGGA |
| 4246 | CCTGGCCTGAGCTTCGCCC | GGGCGAAGCTCAGGCCAGG |
| 4247 | CTGGCCTGAGCTTCGCCCA | TGGGCGAAGCTCAGGCCAG |
| 4248 | TGGCCTGAGCTTCGCCCAA | TTGGGCGAAGCTCAGGCCA |
| 4249 | GGCCTGAGCTTCGCCCAAA | TTTGGGCGAAGCTCAGGCC |
| 4250 | GCCTGAGCTTCGCCCAAAG | CTTTGGGCGAAGCTCAGGC |
| 4251 | CCTGAGCTTCGCCCAAAGT | ACTTTGGGCGAAGCTCAGG |
| 4252 | CTGAGCTTCGCCCAAAGTC | GACTTTGGGCGAAGCTCAG |
| 4253 | TGAGCTTCGCCCAAAGTCA | TGACTTTGGGCGAAGCTCA |
| 4254 | GAGCTTCGCCCAAAGTCAG | CTGACTTTGGGCGAAGCTC |
| 4255 | AGCTTCGCCCAAAGTCAGA | TCTGACTTTGGGCGAAGCT |
| 4256 | GCTTCGCCCAAAGTCAGAC | GTCTGACTTTGGGCGAAGC |
| 4257 | CTTCGCCCAAAGTCAGACG | CGTCTGACTTTGGGCGAAG |
| 4258 | TTCGCCCAAAGTCAGACGA | TCGTCTGACTTTGGGCGAA |
| 4259 | TCGCCCAAAGTCAGACGAG | CTCGTCTGACTTTGGGCGA |
| 4260 | CGCCCAAAGTCAGACGAGG | CCTCGTCTGACTTTGGGCG |
| 4261 | GCCCAAAGTCAGACGAGGG | CCCTCGTCTGACTTTGGGC |
| 4262 | CCCAAAGTCAGACGAGGGC | GCCCTCGTCTGACTTTGGG |
| 4263 | CCAAAGTCAGACGAGGGCT | AGCCCTCGTCTGACTTTGG |
| 4264 | CAAAGTCAGACGAGGGCTC | GAGCCCTCGTCTGACTTTG |
| 4265 | AAAGTCAGACGAGGGCTCT | AGAGCCCTCGTCTGACTTT |
| 4266 | AAGTCAGACGAGGGCTCTG | CAGAGCCCTCGTCTGACTT |
| 4267 | AGTCAGACGAGGGCTCTGT | ACAGAGCCCTCGTCTGACT |
| 4268 | GTCAGACGAGGGCTCTGTC | GACAGAGCCCTCGTCTGAC |
| 4269 | TCAGACGAGGGCTCTGTCC | GGACAGAGCCCTCGTCTGA |
| 4270 | CAGACGAGGGCTCTGTCCT | AGGACAGAGCCCTCGTCTG |
| 4271 | AGACGAGGGCTCTGTCCTC | GAGGACAGAGCCCTCGTCT |
| 4272 | GACGAGGGCTCTGTCCTCC | GGAGGACAGAGCCCTCGTC |
| 4273 | ACGAGGGCTCTGTCCTCCT | AGGAGGACAGAGCCCTCGT |
| 4274 | CGAGGGCTCTGTCCTCCTG | CAGGAGGACAGAGCCCTCG |
| 4275 | GAGGGCTCTGTCCTCCTGC | GCAGGAGGACAGAGCCCTC |
| 4276 | AGGGCTCTGTCCTCCTGCT | AGCAGGAGGACAGAGCCCT |
| 4277 | GGGCTCTGTCCTCCTGCTG | CAGCAGGAGGACAGAGCCC |
| 4278 | GGCTCTGTCCTCCTGCTGC | GCAGCAGGAGGACAGAGCC |
| 4279 | GCTCTGTCCTCCTGCTGCA | TGCAGCAGGAGGACAGAGC |
| 4280 | CTCTGTCCTCCTGCTGCAC | GTGCAGCAGGAGGACAGAG |
| 4281 | TCTGTCCTCCTGCTGCACC | GGTGCAGCAGGAGGACAGA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4282 | CTGTCCTCCTGCTGCACCG | CGGTGCAGCAGGAGGACAG |
| 4283 | TGTCCTCCTGCTGCACCGA | TCGGTGCAGCAGGAGGACA |
| 4284 | GTCCTCCTGCTGCACCGAG | CTCGGTGCAGCAGGAGGAC |
| 4285 | TCCTCCTGCTGCACCGAGC | GCTCGGTGCAGCAGGAGGA |
| 4286 | CCTCCTGCTGCACCGAGCT | AGCTCGGTGCAGCAGGAGG |
| 4287 | CTCCTGCTGCACCGAGCTT | AAGCTCGGTGCAGCAGGAG |
| 4288 | TCCTGCTGCACCGAGCTTT | AAAGCTCGGTGCAGCAGGA |
| 4289 | CCTGCTGCACCGAGCTTTG | CAAAGCTCGGTGCAGCAGG |
| 4290 | CTGCTGCACCGAGCTTTGG | CCAAAGCTCGGTGCAGCAG |
| 4291 | TGCTGCACCGAGCTTTGGG | CCCAAAGCTCGGTGCAGCA |
| 4292 | GCTGCACCGAGCTTTGGGG | CCCCAAAGCTCGGTGCAGC |
| 4293 | CTGCACCGAGCTTTGGGGG | CCCCCAAAGCTCGGTGCAG |
| 4294 | TGCACCGAGCTTTGGGGGA | TCCCCCAAAGCTCGGTGCA |
| 4295 | GCACCGAGCTTTGGGGGAT | ATCCCCCAAAGCTCGGTGC |
| 4296 | CACCGAGCTTTGGGGGATG | CATCCCCCAAAGCTCGGTG |
| 4297 | ACCGAGCTTTGGGGGATGA | TCATCCCCCAAAGCTCGGT |
| 4298 | CCGAGCTTTGGGGGATGAG | CTCATCCCCCAAAGCTCGG |
| 4299 | CGAGCTTTGGGGGATGAGG | CCTCATCCCCCAAAGCTCG |
| 4300 | GAGCTTTGGGGGATGAGGA | TCCTCATCCCCCAAAGCTC |
| 4301 | AGCTTTGGGGGATGAGGAC | GTCCTCATCCCCCAAAGCT |
| 4302 | GCTTTGGGGGATGAGGACA | TGTCCTCATCCCCCAAAGC |
| 4303 | CTTTGGGGGATGAGGACAC | GTGTCCTCATCCCCCAAAG |
| 4304 | TTTGGGGGATGAGGACACC | GGTGTCCTCATCCCCCAAA |
| 4305 | TTGGGGGATGAGGACACCA | TGGTGTCCTCATCCCCCAA |
| 4306 | TGGGGGATGAGGACACCAG | CTGGTGTCCTCATCCCCCA |
| 4307 | GGGGGATGAGGACACCAGC | GCTGGTGTCCTCATCCCCC |
| 4308 | GGGGATGAGGACACCAGCA | TGCTGGTGTCCTCATCCCC |
| 4309 | GGGATGAGGACACCAGCAG | CTGCTGGTGTCCTCATCCC |
| 4310 | GGATGAGGACACCAGCAGG | CCTGCTGGTGTCCTCATCC |
| 4311 | GATGAGGACACCAGCAGGG | CCCTGCTGGTGTCCTCATC |
| 4312 | ATGAGGACACCAGCAGGGT | ACCCTGCTGGTGTCCTCAT |
| 4313 | TGAGGACACCAGCAGGGTG | CACCCTGCTGGTGTCCTCA |
| 4314 | GAGGACACCAGCAGGGTGG | CCACCCTGCTGGTGTCCTC |
| 4315 | AGGACACCAGCAGGGTGGA | TCCACCCTGCTGGTGTCCT |
| 4316 | GGACACCAGCAGGGTGGAG | CTCCACCCTGCTGGTGTCC |
| 4317 | GACACCAGCAGGGTGGAGA | TCTCCACCCTGCTGGTGTC |
| 4318 | ACACCAGCAGGGTGGAGAA | TTCTCCACCCTGCTGGTGT |
| 4319 | CACCAGCAGGGTGGAGAAC | GTTCTCCACCCTGCTGGTG |
| 4320 | ACCAGCAGGGTGGAGAACC | GGTTCTCCACCCTGCTGGT |
| 4321 | CCAGCAGGGTGGAGAACCT | AGGTTCTCCACCCTGCTGG |
| 4322 | CAGCAGGGTGGAGAACCTA | TAGGTTCTCCACCCTGCTG |
| 4323 | AGCAGGGTGGAGAACCTAG | CTAGGTTCTCCACCCTGCT |
| 4324 | GCAGGGTGGAGAACCTAGC | GCTAGGTTCTCCACCCTGC |
| 4325 | CAGGGTGGAGAACCTAGCT | AGCTAGGTTCTCCACCCTG |
| 4326 | AGGGTGGAGAACCTAGCTG | CAGCTAGGTTCTCCACCCT |
| 4327 | GGGTGGAGAACCTAGCTGC | GCAGCTAGGTTCTCCACCC |
| 4328 | GGTGGAGAACCTAGCTGCC | GGCAGCTAGGTTCTCCACC |
| 4329 | GTGGAGAACCTAGCTGCCA | TGGCAGCTAGGTTCTCCAC |
| 4330 | TGGAGAACCTAGCTGCCAG | CTGGCAGCTAGGTTCTCCA |
| 4331 | GGAGAACCTAGCTGCCAGT | ACTGGCAGCTAGGTTCTCC |
| 4332 | GAGAACCTAGCTGCCAGTC | GACTGGCAGCTAGGTTCTC |
| 4333 | AGAACCTAGCTGCCAGTCT | AGACTGGCAGCTAGGTTCT |
| 4334 | GAACCTAGCTGCCAGTCTG | CAGACTGGCAGCTAGGTTC |
| 4335 | AACCTAGCTGCCAGTCTGC | GCAGACTGGCAGCTAGGTT |
| 4336 | ACCTAGCTGCCAGTCTGCC | GGCAGACTGGCAGCTAGGT |
| 4337 | CCTAGCTGCCAGTCTGCCA | TGGCAGACTGGCAGCTAGG |
| 4338 | CTAGCTGCCAGTCTGCCAC | GTGGCAGACTGGCAGCTAG |
| 4339 | TAGCTGCCAGTCTGCCACT | AGTGGCAGACTGGCAGCTA |
| 4340 | AGCTGCCAGTCTGCCACTT | AAGTGGCAGACTGGCAGCT |
| 4341 | GCTGCCAGTCTGCCACTTC | GAAGTGGCAGACTGGCAGC |
| 4342 | CTGCCAGTCTGCCACTTCC | GGAAGTGGCAGACTGGCAG |
| 4343 | TGCCAGTCTGCCACTTCCG | CGGAAGTGGCAGACTGGCA |
| 4344 | GCCAGTCTGCCACTTCCGG | CCGGAAGTGGCAGACTGGC |
| 4345 | CCAGTCTGCCACTTCCGGA | TCCGGAAGTGGCAGACTGG |
| 4346 | CAGTCTGCCACTTCCGGAG | CTCCGGAAGTGGCAGACTG |
| 4347 | AGTCTGCCACTTCCGGAGT | ACTCCGGAAGTGGCAGACT |
| 4348 | GTCTGCCACTTCCGGAGTA | TACTCCGGAAGTGGCAGAC |
| 4349 | TCTGCCACTTCCGGAGTAC | GTACTCCGGAAGTGGCAGA |
| 4350 | CTGCCACTTCCGGAGTACT | AGTACTCCGGAAGTGGCAG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4351 | TGCCACTTCCGGAGTACTG | CAGTACTCCGGAAGTGGCA |
| 4352 | GCCACTTCCGGAGTACTGC | GCAGTACTCCGGAAGTGGC |
| 4353 | CCACTTCCGGAGTACTGCG | CGCAGTACTCCGGAAGTGG |
| 4354 | CACTTCCGGAGTACTGCGC | GCGCAGTACTCCGGAAGTG |
| 4355 | ACTTCCGGAGTACTGCGCC | GGCGCAGTACTCCGGAAGT |
| 4356 | CTTCCGGAGTACTGCGCCC | GGGCGCAGTACTCCGGAAG |
| 4357 | TTCCGGAGTACTGCGCCCT | AGGGCGCAGTACTCCGGAA |
| 4358 | TCCGGAGTACTGCGCCCTC | GAGGGCGCAGTACTCCGGA |
| 4359 | CCGGAGTACTGCGCCCTCC | GGAGGGCGCAGTACTCCGG |
| 4360 | CGGAGTACTGCGCCCTCCA | TGGAGGGCGCAGTACTCCG |
| 4361 | GGAGTACTGCGCCCTCCAT | ATGGAGGGCGCAGTACTCC |
| 4362 | GAGTACTGCGCCCTCCATG | CATGGAGGGCGCAGTACTC |
| 4363 | AGTACTGCGCCCTCCATGG | CCATGGAGGGCGCAGTACT |
| 4364 | GTACTGCGCCCTCCATGGA | TCCATGGAGGGCGCAGTAC |
| 4365 | TACTGCGCCCTCCATGGAA | TTCCATGGAGGGCGCAGTA |
| 4366 | ACTGCGCCCTCCATGGAAA | TTTCCATGGAGGGCGCAGT |
| 4367 | CTGCGCCCTCCATGGAAAA | TTTTCCATGGAGGGCGCAG |
| 4368 | TGCGCCCTCCATGGAAAAC | GTTTTCCATGGAGGGCGCA |
| 4369 | GCGCCCTCCATGGAAAACT | AGTTTTCCATGGAGGGCGC |
| 4370 | CGCCCTCCATGGAAAACTC | GAGTTTTCCATGGAGGGCG |
| 4371 | GCCCTCCATGGAAAACTCA | TGAGTTTTCCATGGAGGGC |
| 4372 | CCCTCCATGGAAAACTCAA | TTGAGTTTTCCATGGAGGG |
| 4373 | CCTCCATGGAAAACTCAAC | GTTGAGTTTTCCATGGAGG |
| 4374 | CTCCATGGAAAACTCAACC | GGTTGAGTTTTCCATGGAG |
| 4375 | TCCATGGAAAACTCAACCT | AGGTTGAGTTTTCCATGGA |
| 4376 | CCATGGAAAACTCAACCTG | CAGGTTGAGTTTTCCATGG |
| 4377 | CATGGAAAACTCAACCTGG | CCAGGTTGAGTTTTCCATG |
| 4378 | ATGGAAAACTCAACCTGGC | GCCAGGTTGAGTTTTCCAT |
| 4379 | TGGAAAACTCAACCTGGCT | AGCCAGGTTGAGTTTTCCA |
| 4380 | GGAAAACTCAACCTGGCTT | AAGCCAGGTTGAGTTTTCC |
| 4381 | GAAAACTCAACCTGGCTTC | GAAGCCAGGTTGAGTTTTC |
| 4382 | AAAACTCAACCTGGCTTCC | GGAAGCCAGGTTGAGTTTT |
| 4383 | AAACTCAACCTGGCTTCCT | AGGAAGCCAGGTTGAGTTT |
| 4384 | AACTCAACCTGGCTTCCTA | TAGGAAGCCAGGTTGAGTT |
| 4385 | ACTCAACCTGGCTTCCTAC | GTAGGAAGCCAGGTTGAGT |
| 4386 | CTCAACCTGGCTTCCTACC | GGTAGGAAGCCAGGTTGAG |
| 4387 | TCAACCTGGCTTCCTACCT | AGGTAGGAAGCCAGGTTGA |
| 4388 | CAACCTGGCTTCCTACCTC | GAGGTAGGAAGCCAGGTTG |
| 4389 | AACCTGGCTTCCTACCTCC | GGAGGTAGGAAGCCAGGTT |
| 4390 | ACCTGGCTTCCTACCTCCC | GGGAGGTAGGAAGCCAGGT |
| 4391 | CCTGGCTTCCTACCTCCCA | TGGGAGGTAGGAAGCCAGG |
| 4392 | CTGGCTTCCTACCTCCCAC | GTGGGAGGTAGGAAGCCAG |
| 4393 | TGGCTTCCTACCTCCCACC | GGTGGGAGGTAGGAAGCCA |
| 4394 | GGCTTCCTACCTCCCACCG | CGGTGGGAGGTAGGAAGCC |
| 4395 | GCTTCCTACCTCCCACCGG | CCGGTGGGAGGTAGGAAGC |
| 4396 | CTTCCTACCTCCCACCGGG | CCCGGTGGGAGGTAGGAAG |
| 4397 | TTCCTACCTCCCACCGGGC | GCCCGGTGGGAGGTAGGAA |
| 4398 | TCCTACCTCCCACCGGGCC | GGCCCGGTGGGAGGTAGGA |
| 4399 | CCTACCTCCCACCGGGCCT | AGGCCCGGTGGGAGGTAGG |
| 4400 | CTACCTCCCACCGGGCCTT | AAGGCCCGGTGGGAGGTAG |
| 4401 | TACCTCCCACCGGGCCTTG | CAAGGCCCGGTGGGAGGTA |
| 4402 | ACCTCCCACCGGGCCTTGC | GCAAGGCCCGGTGGGAGGT |
| 4403 | CCTCCCACCGGGCCTTGCC | GGCAAGGCCCGGTGGGAGG |
| 4404 | CTCCCACCGGGCCTTGCCC | GGGCAAGGCCCGGTGGGAG |
| 4405 | TCCCACCGGGCCTTGCCCT | AGGGCAAGGCCCGGTGGGA |
| 4406 | CCCACCGGGCCTTGCCCTG | CAGGGCAAGGCCCGGTGGG |
| 4407 | CCACCGGGCCTTGCCCTGC | GCAGGGCAAGGCCCGGTGG |
| 4408 | CACCGGGCCTTGCCCTGCG | CGCAGGGCAAGGCCCGGTG |
| 4409 | ACCGGGCCTTGCCCTGCGT | ACGCAGGGCAAGGCCCGGT |
| 4410 | CCGGGCCTTGCCCTGCGTC | GACGCAGGGCAAGGCCCGG |
| 4411 | CGGGCCTTGCCCTGCGTCC | GGACGCAGGGCAAGGCCCG |
| 4412 | GGGCCTTGCCCTGCGTCCA | TGGACGCAGGGCAAGGCCC |
| 4413 | GGCCTTGCCCTGCGTCCAC | GTGGACGCAGGGCAAGGCC |
| 4414 | GCCTTGCCCTGCGTCCACT | AGTGGACGCAGGGCAAGGC |
| 4415 | CCTTGCCCTGCGTCCACTG | CAGTGGACGCAGGGCAAGG |
| 4416 | CTTGCCCTGCGTCCACTGG | CCAGTGGACGCAGGGCAAG |
| 4417 | TTGCCCTGCGTCCACTGGA | TCCAGTGGACGCAGGGCAA |
| 4418 | TGCCCTGCGTCCACTGGAG | CTCCAGTGGACGCAGGGCA |
| 4419 | GCCCTGCGTCCACTGGAGC | GCTCCAGTGGACGCAGGGC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4420 | CCCTGCGTCCACTGGAGCC | GGCTCCAGTGGACGCAGGG |
| 4421 | CCTGCGTCCACTGGAGCCC | GGGCTCCAGTGGACGCAGG |
| 4422 | CTGCGTCCACTGGAGCCCC | GGGGCTCCAGTGGACGCAG |
| 4423 | TGCGTCCACTGGAGCCCCA | TGGGGCTCCAGTGGACGCA |
| 4424 | GCGTCCACTGGAGCCCCAG | CTGGGGCTCCAGTGGACGC |
| 4425 | CGTCCACTGGAGCCCCAGC | GCTGGGGCTCCAGTGGACG |
| 4426 | GTCCACTGGAGCCCCAGCT | AGCTGGGGCTCCAGTGGAC |
| 4427 | TCCACTGGAGCCCCAGCTC | GAGCTGGGGCTCCAGTGGA |
| 4428 | CCACTGGAGCCCCAGCTCT | AGAGCTGGGGCTCCAGTGG |
| 4429 | CACTGGAGCCCCAGCTCTG | CAGAGCTGGGGCTCCAGTG |
| 4430 | ACTGGAGCCCCAGCTCTGG | CCAGAGCTGGGGCTCCAGT |
| 4431 | CTGGAGCCCCAGCTCTGGG | CCCAGAGCTGGGGCTCCAG |
| 4432 | TGGAGCCCCAGCTCTGGGC | GCCCAGAGCTGGGGCTCCA |
| 4433 | GGAGCCCCAGCTCTGGGCA | TGCCCAGAGCTGGGGCTCC |
| 4434 | GAGCCCCAGCTCTGGGCAG | CTGCCCAGAGCTGGGGCTC |
| 4435 | AGCCCCAGCTCTGGGCAGC | GCTGCCCAGAGCTGGGGCT |
| 4436 | GCCCCAGCTCTGGGCAGCC | GGCTGCCCAGAGCTGGGGC |
| 4437 | CCCCAGCTCTGGGCAGCCT | AGGCTGCCCAGAGCTGGGG |
| 4438 | CCCAGCTCTGGGCAGCCTA | TAGGCTGCCCAGAGCTGGG |
| 4439 | CCAGCTCTGGGCAGCCTAT | ATAGGCTGCCCAGAGCTGG |
| 4440 | CAGCTCTGGGCAGCCTATG | CATAGGCTGCCCAGAGCTG |
| 4441 | AGCTCTGGGCAGCCTATGG | CCATAGGCTGCCCAGAGCT |
| 4442 | GCTCTGGGCAGCCTATGGT | ACCATAGGCTGCCCAGAGC |
| 4443 | CTCTGGGCAGCCTATGGTG | CACCATAGGCTGCCCAGAG |
| 4444 | TCTGGGCAGCCTATGGTGT | ACACCATAGGCTGCCCAGA |
| 4445 | CTGGGCAGCCTATGGTGTG | CACACCATAGGCTGCCCAG |
| 4446 | TGGGCAGCCTATGGTGTGA | TCACACCATAGGCTGCCCA |
| 4447 | GGGCAGCCTATGGTGTGAG | CTCACACCATAGGCTGCCC |
| 4448 | GGCAGCCTATGGTGTGAGC | GCTCACACCATAGGCTGCC |
| 4449 | GCAGCCTATGGTGTGAGCC | GGCTCACACCATAGGCTGC |
| 4450 | CAGCCTATGGTGTGAGCCC | GGGCTCACACCATAGGCTG |
| 4451 | AGCCTATGGTGTGAGCCCG | CGGGCTCACACCATAGGCT |
| 4452 | GCCTATGGTGTGAGCCCGC | GCGGGCTCACACCATAGGC |
| 4453 | CCTATGGTGTGAGCCCGCA | TGCGGGCTCACACCATAGG |
| 4454 | CTATGGTGTGAGCCCGCAC | GTGCGGGCTCACACCATAG |
| 4455 | TATGGTGTGAGCCCGCACC | GGTGCGGGCTCACACCATA |
| 4456 | ATGGTGTGAGCCCGCACCG | CGGTGCGGGCTCACACCAT |
| 4457 | TGGTGTGAGCCCGCACCGG | CCGGTGCGGGCTCACACCA |
| 4458 | GGTGTGAGCCCGCACCGGG | CCCGGTGCGGGCTCACACC |
| 4459 | GTGTGAGCCCGCACCGGGG | CCCCGGTGCGGGCTCACAC |
| 4460 | TGTGAGCCCGCACCGGGGA | TCCCCGGTGCGGGCTCACA |
| 4461 | GTGAGCCCGCACCGGGGAC | GTCCCCGGTGCGGGCTCAC |
| 4462 | TGAGCCCGCACCGGGGACA | TGTCCCCGGTGCGGGCTCA |
| 4463 | GAGCCCGCACCGGGGACAC | GTGTCCCCGGTGCGGGCTC |
| 4464 | AGCCCGCACCGGGGACACC | GGTGTCCCCGGTGCGGGCT |
| 4465 | GCCCGCACCGGGGACACCT | AGGTGTCCCCGGTGCGGGC |
| 4466 | CCCGCACCGGGGACACCTG | CAGGTGTCCCCGGTGCGGG |
| 4467 | CCGCACCGGGGACACCTGG | CCAGGTGTCCCCGGTGCGG |
| 4468 | CGCACCGGGGACACCTGGG | CCCAGGTGTCCCCGGTGCG |
| 4469 | GCACCGGGGACACCTGGGG | CCCCAGGTGTCCCCGGTGC |
| 4470 | CACCGGGGACACCTGGGGA | TCCCCAGGTGTCCCCGGTG |
| 4471 | ACCGGGGACACCTGGGGAC | GTCCCCAGGTGTCCCCGGT |
| 4472 | CCGGGGACACCTGGGGACC | GGTCCCCAGGTGTCCCCGG |
| 4473 | CGGGGACACCTGGGGACCA | TGGTCCCCAGGTGTCCCCG |
| 4474 | GGGGACACCTGGGGACCAA | TTGGTCCCCAGGTGTCCCC |
| 4475 | GGGACACCTGGGGACCAAG | CTTGGTCCCCAGGTGTCCC |
| 4476 | GGACACCTGGGGACCAAGA | TCTTGGTCCCCAGGTGTCC |
| 4477 | GACACCTGGGGACCAAGAA | TTCTTGGTCCCCAGGTGTC |
| 4478 | ACACCTGGGGACCAAGAAC | GTTCTTGGTCCCCAGGTGT |
| 4479 | CACCTGGGGACCAAGAACC | GGTTCTTGGTCCCCAGGTG |
| 4480 | ACCTGGGGACCAAGAACCT | AGGTTCTTGGTCCCCAGGT |
| 4481 | CCTGGGGACCAAGAACCTC | GAGGTTCTTGGTCCCCAGG |
| 4482 | CTGGGGACCAAGAACCTCT | AGAGGTTCTTGGTCCCCAG |
| 4483 | TGGGGACCAAGAACCTCTG | CAGAGGTTCTTGGTCCCCA |
| 4484 | GGGGACCAAGAACCTCTGT | ACAGAGGTTCTTGGTCCCC |
| 4485 | GGGACCAAGAACCTCTGTG | CACAGAGGTTCTTGGTCCC |
| 4486 | GGACCAAGAACCTCTGTGT | ACACAGAGGTTCTTGGTCC |
| 4487 | GACCAAGAACCTCTGTGTG | CACACAGAGGTTCTTGGTC |
| 4488 | ACCAAGAACCTCTGTGTGG | CCACACAGAGGTTCTTGGT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4489 | CCAAGAACCTCTGTGTGGA | TCCACACAGAGGTTCTTGG |
| 4490 | CAAGAACCTCTGTGTGGAG | CTCCACACAGAGGTTCTTG |
| 4491 | AAGAACCTCTGTGTGGAGG | CCTCCACACAGAGGTTCTT |
| 4492 | AGAACCTCTGTGTGGAGGT | ACCTCCACACAGAGGTTCT |
| 4493 | GAACCTCTGTGTGGAGGTG | CACCTCCACACAGAGGTTC |
| 4494 | AACCTCTGTGTGGAGGTGG | CCACCTCCACACAGAGGTT |
| 4495 | ACCTCTGTGTGGAGGTGGC | GCCACCTCCACACAGAGGT |
| 4496 | CCTCTGTGTGGAGGTGGCC | GGCCACCTCCACACAGAGG |
| 4497 | CTCTGTGTGGAGGTGGCCG | CGGCCACCTCCACACAGAG |
| 4498 | TCTGTGTGGAGGTGGCCGA | TCGGCCACCTCCACACAGA |
| 4499 | CTGTGTGGAGGTGGCCGAC | GTCGGCCACCTCCACACAG |
| 4500 | TGTGTGGAGGTGGCCGACC | GGTCGGCCACCTCCACACA |
| 4501 | GTGTGGAGGTGGCCGACCT | AGGTCGGCCACCTCCACAC |
| 4502 | TGTGGAGGTGGCCGACCTG | CAGGTCGGCCACCTCCACA |
| 4503 | GTGGAGGTGGCCGACCTGG | CCAGGTCGGCCACCTCCAC |
| 4504 | TGGAGGTGGCCGACCTGGT | ACCAGGTCGGCCACCTCCA |
| 4505 | GGAGGTGGCCGACCTGGTC | GACCAGGTCGGCCACCTCC |
| 4506 | GAGGTGGCCGACCTGGTCA | TGACCAGGTCGGCCACCTC |
| 4507 | AGGTGGCCGACCTGGTCAG | CTGACCAGGTCGGCCACCT |
| 4508 | GGTGGCCGACCTGGTCAGC | GCTGACCAGGTCGGCCACC |
| 4509 | GTGGCCGACCTGGTCAGCA | TGCTGACCAGGTCGGCCAC |
| 4510 | TGGCCGACCTGGTCAGCAT | ATGCTGACCAGGTCGGCCA |
| 4511 | GGCCGACCTGGTCAGCATC | GATGCTGACCAGGTCGGCC |
| 4512 | GCCGACCTGGTCAGCATCC | GGATGCTGACCAGGTCGGC |
| 4513 | CCGACCTGGTCAGCATCCT | AGGATGCTGACCAGGTCGG |
| 4514 | CGACCTGGTCAGCATCCTG | CAGGATGCTGACCAGGTCG |
| 4515 | GACCTGGTCAGCATCCTGG | CCAGGATGCTGACCAGGTC |
| 4516 | ACCTGGTCAGCATCCTGGT | ACCAGGATGCTGACCAGGT |
| 4517 | CCTGGTCAGCATCCTGGTG | CACCAGGATGCTGACCAGG |
| 4518 | CTGGTCAGCATCCTGGTGC | GCACCAGGATGCTGACCAG |
| 4519 | TGGTCAGCATCCTGGTGCA | TGCACCAGGATGCTGACCA |
| 4520 | GGTCAGCATCCTGGTGCAT | ATGCACCAGGATGCTGACC |
| 4521 | GTCAGCATCCTGGTGCATG | CATGCACCAGGATGCTGAC |
| 4522 | TCAGCATCCTGGTGCATGC | GCATGCACCAGGATGCTGA |
| 4523 | CAGCATCCTGGTGCATGCC | GGCATGCACCAGGATGCTG |
| 4524 | AGCATCCTGGTGCATGCCG | CGGCATGCACCAGGATGCT |
| 4525 | GCATCCTGGTGCATGCCGA | TCGGCATGCACCAGGATGC |
| 4526 | CATCCTGGTGCATGCCGAC | GTCGGCATGCACCAGGATG |
| 4527 | ATCCTGGTGCATGCCGACA | TGTCGGCATGCACCAGGAT |
| 4528 | TCCTGGTGCATGCCGACAC | GTGTCGGCATGCACCAGGA |
| 4529 | CCTGGTGCATGCCGACACA | TGTGTCGGCATGCACCAGG |
| 4530 | CTGGTGCATGCCGACACAC | GTGTGTCGGCATGCACCAG |
| 4531 | TGGTGCATGCCGACACACC | GGTGTGTCGGCATGCACCA |
| 4532 | GGTGCATGCCGACACACCA | TGGTGTGTCGGCATGCACC |
| 4533 | GTGCATGCCGACACACCAC | GTGGTGTGTCGGCATGCAC |
| 4534 | TGCATGCCGACACACCACT | AGTGGTGTGTCGGCATGCA |
| 4535 | GCATGCCGACACACCACTG | CAGTGGTGTGTCGGCATGC |
| 4536 | CATGCCGACACACCACTGC | GCAGTGGTGTGTCGGCATG |
| 4537 | ATGCCGACACACCACTGCC | GGCAGTGGTGTGTCGGCAT |
| 4538 | TGCCGACACACCACTGCCT | AGGCAGTGGTGTGTCGGCA |
| 4539 | GCCGACACACCACTGCCTG | CAGGCAGTGGTGTGTCGGC |
| 4540 | CCGACACACCACTGCCTGC | GCAGGCAGTGGTGTGTCGG |
| 4541 | CGACACACCACTGCCTGCC | GGCAGGCAGTGGTGTGTCG |
| 4542 | GACACACCACTGCCTGCCT | AGGCAGGCAGTGGTGTGTC |
| 4543 | ACACACCACTGCCTGCCTG | CAGGCAGGCAGTGGTGTGT |
| 4544 | CACACCACTGCCTGCCTGG | CCAGGCAGGCAGTGGTGTG |
| 4545 | ACACCACTGCCTGCCTGGC | GCCAGGCAGGCAGTGGTGT |
| 4546 | CACCACTGCCTGCCTGGCA | TGCCAGGCAGGCAGTGGTG |
| 4547 | ACCACTGCCTGCCTGGCAC | GTGCCAGGCAGGCAGTGGT |
| 4548 | CCACTGCCTGCCTGGCACC | GGTGCCAGGCAGGCAGTGG |
| 4549 | CACTGCCTGCCTGGCACCG | CGGTGCCAGGCAGGCAGTG |
| 4550 | ACTGCCTGCCTGGCACCGG | CCGGTGCCAGGCAGGCAGT |
| 4551 | CTGCCTGCCTGGCACCGGG | CCCGGTGCCAGGCAGGCAG |
| 4552 | TGCCTGCCTGGCACCGGGC | GCCCGGTGCCAGGCAGGCA |
| 4553 | GCCTGCCTGGCACCGGGCA | TGCCCGGTGCCAGGCAGGC |
| 4554 | CCTGCCTGGCACCGGGCAC | GTGCCCGGTGCCAGGCAGG |
| 4555 | CTGCCTGGCACCGGGCACA | TGTGCCCGGTGCCAGGCAG |
| 4556 | TGCCTGGCACCGGGCACAG | CTGTGCCCGGTGCCAGGCA |
| 4557 | GCCTGGCACCGGGCACAGA | TCTGTGCCCGGTGCCAGGC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4558 | CCTGGCACCGGGCACAGAA | TTCTGTGCCCGGTGCCAGG |
| 4559 | CTGGCACCGGGCACAGAAA | TTTCTGTGCCCGGTGCCAG |
| 4560 | TGGCACCGGGCACAGAAAG | CTTTCTGTGCCCGGTGCCA |
| 4561 | GGCACCGGGCACAGAAAGA | TCTTTCTGTGCCCGGTGCC |
| 4562 | GCACCGGGCACAGAAAGAC | GTCTTTCTGTGCCCGGTGC |
| 4563 | CACCGGGCACAGAAAGACT | AGTCTTTCTGTGCCCGGTG |
| 4564 | ACCGGGCACAGAAAGACTT | AAGTCTTTCTGTGCCCGGT |
| 4565 | CCGGGCACAGAAAGACTTC | GAAGTCTTTCTGTGCCCGG |
| 4566 | CGGGCACAGAAAGACTTCC | GGAAGTCTTTCTGTGCCCG |
| 4567 | GGGCACAGAAAGACTTCCT | AGGAAGTCTTTCTGTGCCC |
| 4568 | GGCACAGAAAGACTTCCTT | AAGGAAGTCTTTCTGTGCC |
| 4569 | GCACAGAAAGACTTCCTTT | AAAGGAAGTCTTTCTGTGC |
| 4570 | CACAGAAAGACTTCCTTTC | GAAAGGAAGTCTTTCTGTG |
| 4571 | ACAGAAAGACTTCCTTTCA | TGAAAGGAAGTCTTTCTGT |
| 4572 | CAGAAAGACTTCCTTTCAG | CTGAAAGGAAGTCTTTCTG |
| 4573 | AGAAAGACTTCCTTTCAGG | CCTGAAAGGAAGTCTTTCT |
| 4574 | GAAAGACTTCCTTTCAGGC | GCCTGAAAGGAAGTCTTTC |
| 4575 | AAAGACTTCCTTTCAGGCC | GGCCTGAAAGGAAGTCTTT |
| 4576 | AAGACTTCCTTTCAGGCCT | AGGCCTGAAAGGAAGTCTT |
| 4577 | AGACTTCCTTTCAGGCCTG | CAGGCCTGAAAGGAAGTCT |
| 4578 | GACTTCCTTTCAGGCCTGG | CCAGGCCTGAAAGGAAGTC |
| 4579 | ACTTCCTTTCAGGCCTGGA | TCCAGGCCTGAAAGGAAGT |
| 4580 | CTTCCTTTCAGGCCTGGAC | GTCCAGGCCTGAAAGGAAG |
| 4581 | TTCCTTTCAGGCCTGGACG | CGTCCAGGCCTGAAAGGAA |
| 4582 | TCCTTTCAGGCCTGGACGG | CCGTCCAGGCCTGAAAGGA |
| 4583 | CCTTTCAGGCCTGGACGGG | CCCGTCCAGGCCTGAAAGG |
| 4584 | CTTTCAGGCCTGGACGGGG | CCCCGTCCAGGCCTGAAAG |
| 4585 | TTTCAGGCCTGGACGGGGA | TCCCCGTCCAGGCCTGAAA |
| 4586 | TTCAGGCCTGGACGGGGAG | CTCCCCGTCCAGGCCTGAA |
| 4587 | TCAGGCCTGGACGGGGAGG | CCTCCCCGTCCAGGCCTGA |
| 4588 | CAGGCCTGGACGGGGAGGG | CCCTCCCCGTCCAGGCCTG |
| 4589 | AGGCCTGGACGGGGAGGGG | CCCCTCCCCGTCCAGGCCT |
| 4590 | GGCCTGGACGGGGAGGGGC | GCCCCTCCCCGTCCAGGCC |
| 4591 | GCCTGGACGGGGAGGGGCT | AGCCCCTCCCCGTCCAGGC |
| 4592 | CCTGGACGGGGAGGGGCTC | GAGCCCCTCCCCGTCCAGG |
| 4593 | CTGGACGGGGAGGGGCTCT | AGAGCCCCTCCCCGTCCAG |
| 4594 | TGGACGGGGAGGGGCTCTG | CAGAGCCCCTCCCCGTCCA |
| 4595 | GGACGGGGAGGGGCTCTGG | CCAGAGCCCCTCCCCGTCC |
| 4596 | GACGGGGAGGGGCTCTGGT | ACCAGAGCCCCTCCCCGTC |
| 4597 | ACGGGGAGGGGCTCTGGTC | GACCAGAGCCCCTCCCCGT |
| 4598 | CGGGGAGGGGCTCTGGTCT | AGACCAGAGCCCCTCCCCG |
| 4599 | GGGGAGGGGCTCTGGTCTC | GAGACCAGAGCCCCTCCCC |
| 4600 | GGGAGGGGCTCTGGTCTCC | GGAGACCAGAGCCCCTCCC |
| 4601 | GGAGGGGCTCTGGTCTCCG | CGGAGACCAGAGCCCCTCC |
| 4602 | GAGGGGCTCTGGTCTCCGG | CCGGAGACCAGAGCCCCTC |
| 4603 | AGGGGCTCTGGTCTCCGGG | CCCGGAGACCAGAGCCCCT |
| 4604 | GGGGCTCTGGTCTCCGGGC | GCCCGGAGACCAGAGCCCC |
| 4605 | GGGCTCTGGTCTCCGGGCA | TGCCCGGAGACCAGAGCCC |
| 4606 | GGCTCTGGTCTCCGGGCAG | CTGCCCGGAGACCAGAGCC |
| 4607 | GCTCTGGTCTCCGGGCAGC | GCTGCCCGGAGACCAGAGC |
| 4608 | CTCTGGTCTCCGGGCAGCC | GGCTGCCCGGAGACCAGAG |
| 4609 | TCTGGTCTCCGGGCAGCCA | TGGCTGCCCGGAGACCAGA |
| 4610 | CTGGTCTCCGGGCAGCCAG | CTGGCTGCCCGGAGACCAG |
| 4611 | TGGTCTCCGGGCAGCCAGG | CCTGGCTGCCCGGAGACCA |
| 4612 | GGTCTCCGGGCAGCCAGGT | ACCTGGCTGCCCGGAGACC |
| 4613 | GTCTCCGGGCAGCCAGGTC | GACCTGGCTGCCCGGAGAC |
| 4614 | TCTCCGGGCAGCCAGGTCA | TGACCTGGCTGCCCGGAGA |
| 4615 | CTCCGGGCAGCCAGGTCAG | CTGACCTGGCTGCCCGGAG |
| 4616 | TCCGGGCAGCCAGGTCAGC | GCTGACCTGGCTGCCCGGA |
| 4617 | CCGGGCAGCCAGGTCAGCA | TGCTGACCTGGCTGCCCGG |
| 4618 | CGGGCAGCCAGGTCAGCAC | GTGCTGACCTGGCTGCCCG |
| 4619 | GGGCAGCCAGGTCAGCACT | AGTGCTGACCTGGCTGCCC |
| 4620 | GGCAGCCAGGTCAGCACTG | CAGTGCTGACCTGGCTGCC |
| 4621 | GCAGCCAGGTCAGCACTGT | ACAGTGCTGACCTGGCTGC |
| 4622 | CAGCCAGGTCAGCACTGTG | CACAGTGCTGACCTGGCTG |
| 4623 | AGCCAGGTCAGCACTGTGT | ACACAGTGCTGACCTGGCT |
| 4624 | GCCAGGTCAGCACTGTGTG | CACACAGTGCTGACCTGGC |
| 4625 | CCAGGTCAGCACTGTGTGG | CCACACAGTGCTGACCTGG |
| 4626 | CAGGTCAGCACTGTGTGGC | GCCACACAGTGCTGACCTG |

TABLE 1-continued cDNA Human Hairless 19-mer Target Sequences and Complement Referenced to NM_005144-
*Homo sapiens* hairless homolog (mouse) (HR), transcript variant 1, complete mRNA (1-5699 bp).
(SEQ ID NO: for Sense equals (2X - 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 4627 | AGGTCAGCACTGTGTGGCA | TGCCACACAGTGCTGACCT |
| 4628 | GGTCAGCACTGTGTGGCAC | GTGCCACACAGTGCTGACC |
| 4629 | GTCAGCACTGTGTGGCACG | CGTGCCACACAGTGCTGAC |
| 4630 | TCAGCACTGTGTGGCACGT | ACGTGCCACACAGTGCTGA |
| 4631 | CAGCACTGTGTGGCACGTG | CACGTGCCACACAGTGCTG |
| 4632 | AGCACTGTGTGGCACGTGT | ACACGTGCCACACAGTGCT |
| 4633 | GCACTGTGTGGCACGTGTT | AACACGTGCCACACAGTGC |
| 4634 | CACTGTGTGGCACGTGTTC | GAACACGTGCCACACAGTG |
| 4635 | ACTGTGTGGCACGTGTTCC | GGAACACGTGCCACACAGT |
| 4636 | CTGTGTGGCACGTGTTCCG | CGGAACACGTGCCACACAG |
| 4637 | TGTGTGGCACGTGTTCCGG | CCGGAACACGTGCCACACA |
| 4638 | GTGTGGCACGTGTTCCGGG | CCCGGAACACGTGCCACAC |
| 4639 | TGTGGCACGTGTTCCGGGC | GCCCGGAACACGTGCCACA |
| 4640 | GTGGCACGTGTTCCGGGCA | TGCCCGGAACACGTGCCAC |
| 4641 | TGGCACGTGTTCCGGGCAC | GTGCCCGGAACACGTGCCA |
| 4642 | GGCACGTGTTCCGGGCACA | TGTGCCCGGAACACGTGCC |
| 4643 | GCACGTGTTCCGGGCACAG | CTGTGCCCGGAACACGTGC |
| 4644 | CACGTGTTCCGGGCACAGG | CCTGTGCCCGGAACACGTG |
| 4645 | ACGTGTTCCGGGCACAGGA | TCCTGTGCCCGGAACACGT |
| 4646 | CGTGTTCCGGGCACAGGAC | GTCCTGTGCCCGGAACACG |
| 4647 | GTGTTCCGGGCACAGGACG | CGTCCTGTGCCCGGAACAC |
| 4648 | TGTTCCGGGCACAGGACGC | GCGTCCTGTGCCCGGAACA |
| 4649 | GTTCCGGGCACAGGACGCC | GGCGTCCTGTGCCCGGAAC |
| 4650 | TTCCGGGCACAGGACGCCC | GGGCGTCCTGTGCCCGGAA |
| 4651 | TCCGGGCACAGGACGCCCA | TGGGCGTCCTGTGCCCGGA |
| 4652 | CCGGGCACAGGACGCCCAG | CTGGGCGTCCTGTGCCCGG |
| 4653 | CGGGCACAGGACGCCCAGC | GCTGGGCGTCCTGTGCCCG |
| 4654 | GGGCACAGGACGCCCAGCG | CGCTGGGCGTCCTGTGCCC |
| 4655 | GGCACAGGACGCCCAGCGC | GCGCTGGGCGTCCTGTGCC |
| 4656 | GCACAGGACGCCCAGCGCA | TGCGCTGGGCGTCCTGTGC |
| 4657 | CACAGGACGCCCAGCGCAT | ATGCGCTGGGCGTCCTGTG |
| 4658 | ACAGGACGCCCAGCGCATC | GATGCGCTGGGCGTCCTGT |
| 4659 | CAGGACGCCCAGCGCATCC | GGATGCGCTGGGCGTCCTG |
| 4660 | AGGACGCCCAGCGCATCCG | CGGATGCGCTGGGCGTCCT |
| 4661 | GGACGCCCAGCGCATCCGC | GCGGATGCGCTGGGCGTCC |
| 4662 | GACGCCCAGCGCATCCGCC | GGCGGATGCGCTGGGCGTC |
| 4663 | ACGCCCAGCGCATCCGCCG | CGGCGGATGCGCTGGGCGT |
| 4664 | CGCCCAGCGCATCCGCCGC | GCGGCGGATGCGCTGGGCG |
| 4665 | GCCCAGCGCATCCGCCGCT | AGCGGCGGATGCGCTGGGC |
| 4666 | CCCAGCGCATCCGCCGCTT | AAGCGGCGGATGCGCTGGG |
| 4667 | CCAGCGCATCCGCCGCTTT | AAAGCGGCGGATGCGCTGG |
| 4668 | CAGCGCATCCGCCGCTTTC | GAAAGCGGCGGATGCGCTG |
| 4669 | AGCGCATCCGCCGCTTTCT | AGAAAGCGGCGGATGCGCT |
| 4670 | GCGCATCCGCCGCTTTCTC | GAGAAAGCGGCGGATGCGC |
| 4671 | CGCATCCGCCGCTTTCTCC | GGAGAAAGCGGCGGATGCG |
| 4672 | GCATCCGCCGCTTTCTCCA | TGGAGAAAGCGGCGGATGC |
| 4673 | CATCCGCCGCTTTCTCCAG | CTGGAGAAAGCGGCGGATG |
| 4674 | ATCCGCCGCTTTCTCCAGA | TCTGGAGAAAGCGGCGGAT |
| 4675 | TCCGCCGCTTTCTCCAGAT | ATCTGGAGAAAGCGGCGGA |
| 4676 | CCGCCGCTTTCTCCAGATG | CATCTGGAGAAAGCGGCGG |
| 4677 | CGCCGCTTTCTCCAGATGG | CCATCTGGAGAAAGCGGCG |
| 4678 | GCCGCTTTCTCCAGATGGT | ACCATCTGGAGAAAGCGGC |
| 4679 | CCGCTTTCTCCAGATGGTG | CACCATCTGGAGAAAGCGG |
| 4680 | CGCTTTCTCCAGATGGTGT | ACACCATCTGGAGAAAGCG |
| 4681 | GCTTTCTCCAGATGGTGTG | CACACCATCTGGAGAAAGC |
| 4682 | CTTTCTCCAGATGGTGTGC | GCACACCATCTGGAGAAAG |
| 4683 | TTTCTCCAGATGGTGTGCC | GGCACACCATCTGGAGAAA |
| 4684 | TTCTCCAGATGGTGTGCCC | GGGCACACCATCTGGAGAA |
| 4685 | TCTCCAGATGGTGTGCCCG | CGGGCACACCATCTGGAGA |
| 4686 | CTCCAGATGGTGTGCCCGG | CCGGGCACACCATCTGGAG |
| 4687 | TCCAGATGGTGTGCCCGGC | GCCGGGCACACCATCTGGA |
| 4688 | CCAGATGGTGTGCCCGGCC | GGCCGGGCACACCATCTGG |
| 4689 | CAGATGGTGTGCCCGGCCG | CGGCCGGGCACACCATCTG |
| 4690 | AGATGGTGTGCCCGGCCGG | CCGGCCGGGCACACCATCT |
| 4691 | GATGGTGTGCCCGGCCGGG | CCCGGCCGGGCACACCATC |
| 4692 | ATGGTGTGCCCGGCCGGGG | CCCCGGCCGGGCACACCAT |
| 4693 | TGGTGTGCCCGGCCGGGGC | GCCCCGGCCGGGCACACCA |
| 4694 | GGTGTGCCCGGCCGGGGCA | TGCCCCGGCCGGGCACACC |
| 4695 | GTGTGCCCGGCCGGGGCAG | CTGCCCCGGCCGGGCACAC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4696 | TGTGCCCGGCCGGGGCAGG | CCTGCCCCGGCCGGGCACA |
| 4697 | GTGCCCGGCCGGGGCAGGC | GCCTGCCCCGGCCGGGCAC |
| 4698 | TGCCCGGCCGGGGCAGGCG | CGCCTGCCCCGGCCGGGCA |
| 4699 | GCCCGGCCGGGGCAGGCGC | GCGCCTGCCCCGGCCGGGC |
| 4700 | CCCGGCCGGGGCAGGCGCC | GGCGCCTGCCCCGGCCGGG |
| 4701 | CCGGCCGGGGCAGGCGCCC | GGGCGCCTGCCCCGGCCGG |
| 4702 | CGGCCGGGGCAGGCGCCCT | AGGGCGCCTGCCCCGGCCG |
| 4703 | GGCCGGGGCAGGCGCCCTG | CAGGGCGCCTGCCCCGGCC |
| 4704 | GCCGGGGCAGGCGCCCTGG | CCAGGGCGCCTGCCCCGGC |
| 4705 | CCGGGGCAGGCGCCCTGGA | TCCAGGGCGCCTGCCCCGG |
| 4706 | CGGGGCAGGCGCCCTGGAG | CTCCAGGGCGCCTGCCCCG |
| 4707 | GGGGCAGGCGCCCTGGAGC | GCTCCAGGGCGCCTGCCCC |
| 4708 | GGGCAGGCGCCCTGGAGCC | GGCTCCAGGGCGCCTGCCC |
| 4709 | GGCAGGCGCCCTGGAGCCT | AGGCTCCAGGGCGCCTGCC |
| 4710 | GCAGGCGCCCTGGAGCCTG | CAGGCTCCAGGGCGCCTGC |
| 4711 | CAGGCGCCCTGGAGCCTGG | CCAGGCTCCAGGGCGCCTG |
| 4712 | AGGCGCCCTGGAGCCTGGC | GCCAGGCTCCAGGGCGCCT |
| 4713 | GGCGCCCTGGAGCCTGGCG | CGCCAGGCTCCAGGGCGCC |
| 4714 | GCGCCCTGGAGCCTGGCGC | GCGCCAGGCTCCAGGGCGC |
| 4715 | CGCCCTGGAGCCTGGCGCC | GGCGCCAGGCTCCAGGGCG |
| 4716 | GCCCTGGAGCCTGGCGCCC | GGGCGCCAGGCTCCAGGGC |
| 4717 | CCCTGGAGCCTGGCGCCCC | GGGGCGCCAGGCTCCAGGG |
| 4718 | CCTGGAGCCTGGCGCCCCA | TGGGGCGCCAGGCTCCAGG |
| 4719 | CTGGAGCCTGGCGCCCCAG | CTGGGGCGCCAGGCTCCAG |
| 4720 | TGGAGCCTGGCGCCCCAGG | CCTGGGGCGCCAGGCTCCA |
| 4721 | GGAGCCTGGCGCCCCAGGC | GCCTGGGGCGCCAGGCTCC |
| 4722 | GAGCCTGGCGCCCCAGGCA | TGCCTGGGGCGCCAGGCTC |
| 4723 | AGCCTGGCGCCCCAGGCAG | CTGCCTGGGGCGCCAGGCT |
| 4724 | GCCTGGCGCCCCAGGCAGC | GCTGCCTGGGGCGCCAGGC |
| 4725 | CCTGGCGCCCCAGGCAGCT | AGCTGCCTGGGGCGCCAGG |
| 4726 | CTGGCGCCCCAGGCAGCTG | CAGCTGCCTGGGGCGCCAG |
| 4727 | TGGCGCCCCAGGCAGCTGC | GCAGCTGCCTGGGGCGCCA |
| 4728 | GGCGCCCCAGGCAGCTGCT | AGCAGCTGCCTGGGGCGCC |
| 4729 | GCGCCCCAGGCAGCTGCTA | TAGCAGCTGCCTGGGGCGC |
| 4730 | CGCCCCAGGCAGCTGCTAC | GTAGCAGCTGCCTGGGGCG |
| 4731 | GCCCCAGGCAGCTGCTACC | GGTAGCAGCTGCCTGGGGC |
| 4732 | CCCCAGGCAGCTGCTACCT | AGGTAGCAGCTGCCTGGGG |
| 4733 | CCCAGGCAGCTGCTACCTG | CAGGTAGCAGCTGCCTGGG |
| 4734 | CCAGGCAGCTGCTACCTGG | CCAGGTAGCAGCTGCCTGG |
| 4735 | CAGGCAGCTGCTACCTGGA | TCCAGGTAGCAGCTGCCTG |
| 4736 | AGGCAGCTGCTACCTGGAT | ATCCAGGTAGCAGCTGCCT |
| 4737 | GGCAGCTGCTACCTGGATG | CATCCAGGTAGCAGCTGCC |
| 4738 | GCAGCTGCTACCTGGATGC | GCATCCAGGTAGCAGCTGC |
| 4739 | CAGCTGCTACCTGGATGCA | TGCATCCAGGTAGCAGCTG |
| 4740 | AGCTGCTACCTGGATGCAG | CTGCATCCAGGTAGCAGCT |
| 4741 | GCTGCTACCTGGATGCAGG | CCTGCATCCAGGTAGCAGC |
| 4742 | CTGCTACCTGGATGCAGGG | CCCTGCATCCAGGTAGCAG |
| 4743 | TGCTACCTGGATGCAGGGC | GCCCTGCATCCAGGTAGCA |
| 4744 | GCTACCTGGATGCAGGGCT | AGCCCTGCATCCAGGTAGC |
| 4745 | CTACCTGGATGCAGGGCTG | CAGCCCTGCATCCAGGTAG |
| 4746 | TACCTGGATGCAGGGCTGC | GCAGCCCTGCATCCAGGTA |
| 4747 | ACCTGGATGCAGGGCTGCG | CGCAGCCCTGCATCCAGGT |
| 4748 | CCTGGATGCAGGGCTGCGG | CCGCAGCCCTGCATCCAGG |
| 4749 | CTGGATGCAGGGCTGCGGC | GCCGCAGCCCTGCATCCAG |
| 4750 | TGGATGCAGGGCTGCGGCG | CGCCGCAGCCCTGCATCCA |
| 4751 | GGATGCAGGGCTGCGGCGG | CCGCCGCAGCCCTGCATCC |
| 4752 | GATGCAGGGCTGCGGCGGC | GCCGCCGCAGCCCTGCATC |
| 4753 | ATGCAGGGCTGCGGCGGCG | CGCCGCCGCAGCCCTGCAT |
| 4754 | TGCAGGGCTGCGGCGGCGC | GCGCCGCCGCAGCCCTGCA |
| 4755 | GCAGGGCTGCGGCGGCGCC | GGCGCCGCCGCAGCCCTGC |
| 4756 | CAGGGCTGCGGCGGCGCCT | AGGCGCCGCCGCAGCCCTG |
| 4757 | AGGGCTGCGGCGGCGCCTG | CAGGCGCCGCCGCAGCCCT |
| 4758 | GGGCTGCGGCGGCGCCTGC | GCAGGCGCCGCCGCAGCCC |
| 4759 | GGCTGCGGCGGCGCCTGCG | CGCAGGCGCCGCCGCAGCC |
| 4760 | GCTGCGGCGGCGCCTGCGG | CCGCAGGCGCCGCCGCAGC |
| 4761 | CTGCGGCGGCGCCTGCGGG | CCCGCAGGCGCCGCCGCAG |
| 4762 | TGCGGCGGCGCCTGCGGGA | TCCCGCAGGCGCCGCCGCA |
| 4763 | GCGGCGGCGCCTGCGGGAG | CTCCCGCAGGCGCCGCCGC |
| 4764 | CGGCGGCGCCTGCGGGAGG | CCTCCCGCAGGCGCCGCCG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 4765 | GGCGGCGCCTGCGGGAGGA | TCCTCCCGCAGGCGCCGCC |
| 4766 | GCGGCGCCTGCGGGAGGAG | CTCCTCCCGCAGGCGCCGC |
| 4767 | CGGCGCCTGCGGGAGGAGT | ACTCCTCCCGCAGGCGCCG |
| 4768 | GGCGCCTGCGGGAGGAGTG | CACTCCTCCCGCAGGCGCC |
| 4769 | GCGCCTGCGGGAGGAGTGG | CCACTCCTCCCGCAGGCGC |
| 4770 | CGCCTGCGGGAGGAGTGGG | CCCACTCCTCCCGCAGGCG |
| 4771 | GCCTGCGGGAGGAGTGGGG | CCCCACTCCTCCCGCAGGC |
| 4772 | CCTGCGGGAGGAGTGGGGC | GCCCCACTCCTCCCGCAGG |
| 4773 | CTGCGGGAGGAGTGGGGCG | CGCCCCACTCCTCCCGCAG |
| 4774 | TGCGGGAGGAGTGGGGCGT | ACGCCCCACTCCTCCCGCA |
| 4775 | GCGGGAGGAGTGGGGCGTG | CACGCCCCACTCCTCCCGC |
| 4776 | CGGGAGGAGTGGGGCGTGA | TCACGCCCCACTCCTCCCG |
| 4777 | GGGAGGAGTGGGGCGTGAG | CTCACGCCCCACTCCTCCC |
| 4778 | GGAGGAGTGGGGCGTGAGC | GCTCACGCCCCACTCCTCC |
| 4779 | GAGGAGTGGGGCGTGAGCT | AGCTCACGCCCCACTCCTC |
| 4780 | AGGAGTGGGGCGTGAGCTG | CAGCTCACGCCCCACTCCT |
| 4781 | GGAGTGGGGCGTGAGCTGC | GCAGCTCACGCCCCACTCC |
| 4782 | GAGTGGGGCGTGAGCTGCT | AGCAGCTCACGCCCCACTC |
| 4783 | AGTGGGGCGTGAGCTGCTG | CAGCAGCTCACGCCCCACT |
| 4784 | GTGGGGCGTGAGCTGCTGG | CCAGCAGCTCACGCCCCAC |
| 4785 | TGGGGCGTGAGCTGCTGGA | TCCAGCAGCTCACGCCCCA |
| 4786 | GGGGCGTGAGCTGCTGGAC | GTCCAGCAGCTCACGCCCC |
| 4787 | GGGCGTGAGCTGCTGGACC | GGTCCAGCAGCTCACGCCC |
| 4788 | GGCGTGAGCTGCTGGACCC | GGGTCCAGCAGCTCACGCC |
| 4789 | GCGTGAGCTGCTGGACCCT | AGGGTCCAGCAGCTCACGC |
| 4790 | CGTGAGCTGCTGGACCCTG | CAGGGTCCAGCAGCTCACG |
| 4791 | GTGAGCTGCTGGACCCTGC | GCAGGGTCCAGCAGCTCAC |
| 4792 | TGAGCTGCTGGACCCTGCT | AGCAGGGTCCAGCAGCTCA |
| 4793 | GAGCTGCTGGACCCTGCTC | GAGCAGGGTCCAGCAGCTC |
| 4794 | AGCTGCTGGACCCTGCTCC | GGAGCAGGGTCCAGCAGCT |
| 4795 | GCTGCTGGACCCTGCTCCA | TGGAGCAGGGTCCAGCAGC |
| 4796 | CTGCTGGACCCTGCTCCAG | CTGGAGCAGGGTCCAGCAG |
| 4797 | TGCTGGACCCTGCTCCAGG | CCTGGAGCAGGGTCCAGCA |
| 4798 | GCTGGACCCTGCTCCAGGC | GCCTGGAGCAGGGTCCAGC |
| 4799 | CTGGACCCTGCTCCAGGCC | GGCCTGGAGCAGGGTCCAG |
| 4800 | TGGACCCTGCTCCAGGCCC | GGGCCTGGAGCAGGGTCCA |
| 4801 | GGACCCTGCTCCAGGCCCC | GGGGCCTGGAGCAGGGTCC |
| 4802 | GACCCTGCTCCAGGCCCCC | GGGGGCCTGGAGCAGGGTC |
| 4803 | ACCCTGCTCCAGGCCCCCG | CGGGGGCCTGGAGCAGGGT |
| 4804 | CCCTGCTCCAGGCCCCCGG | CCGGGGGCCTGGAGCAGGG |
| 4805 | CCTGCTCCAGGCCCCCGGA | TCCGGGGGCCTGGAGCAGG |
| 4806 | CTGCTCCAGGCCCCCGGAG | CTCCGGGGGCCTGGAGCAG |
| 4807 | TGCTCCAGGCCCCCGGAGA | TCTCCGGGGGCCTGGAGCA |
| 4808 | GCTCCAGGCCCCCGGAGAG | CTCTCCGGGGGCCTGGAGC |
| 4809 | CTCCAGGCCCCCGGAGAGG | CCTCTCCGGGGGCCTGGAG |
| 4810 | TCCAGGCCCCCGGAGAGGC | GCCTCTCCGGGGGCCTGGA |
| 4811 | CCAGGCCCCCGGAGAGGCC | GGCCTCTCCGGGGGCCTGG |
| 4812 | CAGGCCCCCGGAGAGGCCG | CGGCCTCTCCGGGGGCCTG |
| 4813 | AGGCCCCCGGAGAGGCCGT | ACGGCCTCTCCGGGGGCCT |
| 4814 | GGCCCCCGGAGAGGCCGTG | CACGGCCTCTCCGGGGGCC |
| 4815 | GCCCCCGGAGAGGCCGTGC | GCACGGCCTCTCCGGGGGC |
| 4816 | CCCCCGGAGAGGCCGTGCT | AGCACGGCCTCTCCGGGGG |
| 4817 | CCCCGGAGAGGCCGTGCTG | CAGCACGGCCTCTCCGGGG |
| 4818 | CCCGGAGAGGCCGTGCTGG | CCAGCACGGCCTCTCCGGG |
| 4819 | CCGGAGAGGCCGTGCTGGT | ACCAGCACGGCCTCTCCGG |
| 4820 | CGGAGAGGCCGTGCTGGTG | CACCAGCACGGCCTCTCCG |
| 4821 | GGAGAGGCCGTGCTGGTGC | GCACCAGCACGGCCTCTCC |
| 4822 | GAGAGGCCGTGCTGGTGCC | GGCACCAGCACGGCCTCTC |
| 4823 | AGAGGCCGTGCTGGTGCCT | AGGCACCAGCACGGCCTCT |
| 4824 | GAGGCCGTGCTGGTGCCTG | CAGGCACCAGCACGGCCTC |
| 4825 | AGGCCGTGCTGGTGCCTGC | GCAGGCACCAGCACGGCCT |
| 4826 | GGCCGTGCTGGTGCCTGCA | TGCAGGCACCAGCACGGCC |
| 4827 | GCCGTGCTGGTGCCTGCAG | CTGCAGGCACCAGCACGGC |
| 4828 | CCGTGCTGGTGCCTGCAGG | CCTGCAGGCACCAGCACGG |
| 4829 | CGTGCTGGTGCCTGCAGGG | CCCTGCAGGCACCAGCACG |
| 4830 | GTGCTGGTGCCTGCAGGGG | CCCCTGCAGGCACCAGCAC |
| 4831 | TGCTGGTGCCTGCAGGGGC | GCCCCTGCAGGCACCAGCA |
| 4832 | GCTGGTGCCTGCAGGGGCT | AGCCCCTGCAGGCACCAGC |
| 4833 | CTGGTGCCTGCAGGGGCTC | GAGCCCCTGCAGGCACCAG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4834 | TGGTGCCTGCAGGGGCTCC | GGAGCCCCTGCAGGCACCA |
| 4835 | GGTGCCTGCAGGGGCTCCC | GGGAGCCCCTGCAGGCACC |
| 4836 | GTGCCTGCAGGGGCTCCCC | GGGGAGCCCCTGCAGGCAC |
| 4837 | TGCCTGCAGGGGCTCCCCA | TGGGGAGCCCCTGCAGGCA |
| 4838 | GCCTGCAGGGGCTCCCCAC | GTGGGGAGCCCCTGCAGGC |
| 4839 | CCTGCAGGGGCTCCCCACC | GGTGGGGAGCCCCTGCAGG |
| 4840 | CTGCAGGGGCTCCCCACCA | TGGTGGGGAGCCCCTGCAG |
| 4841 | TGCAGGGGCTCCCCACCAG | CTGGTGGGGAGCCCCTGCA |
| 4842 | GCAGGGGCTCCCCACCAGG | CCTGGTGGGGAGCCCCTGC |
| 4843 | CAGGGGCTCCCCACCAGGT | ACCTGGTGGGGAGCCCCTG |
| 4844 | AGGGGCTCCCCACCAGGTG | CACCTGGTGGGGAGCCCCT |
| 4845 | GGGGCTCCCCACCAGGTGC | GCACCTGGTGGGGAGCCCC |
| 4846 | GGGCTCCCCACCAGGTGCA | TGCACCTGGTGGGGAGCCC |
| 4847 | GGCTCCCCACCAGGTGCAG | CTGCACCTGGTGGGGAGCC |
| 4848 | GCTCCCCACCAGGTGCAGG | CCTGCACCTGGTGGGGAGC |
| 4849 | CTCCCCACCAGGTGCAGGG | CCCTGCACCTGGTGGGGAG |
| 4850 | TCCCCACCAGGTGCAGGGC | GCCCTGCACCTGGTGGGGA |
| 4851 | CCCCACCAGGTGCAGGGCC | GGCCCTGCACCTGGTGGGG |
| 4852 | CCCACCAGGTGCAGGGCCT | AGGCCCTGCACCTGGTGGG |
| 4853 | CCACCAGGTGCAGGGCCTG | CAGGCCCTGCACCTGGTGG |
| 4854 | CACCAGGTGCAGGGCCTGG | CCAGGCCCTGCACCTGGTG |
| 4855 | ACCAGGTGCAGGGCCTGGT | ACCAGGCCCTGCACCTGGT |
| 4856 | CCAGGTGCAGGGCCTGGTG | CACCAGGCCCTGCACCTGG |
| 4857 | CAGGTGCAGGGCCTGGTGA | TCACCAGGCCCTGCACCTG |
| 4858 | AGGTGCAGGGCCTGGTGAG | CTCACCAGGCCCTGCACCT |
| 4859 | GGTGCAGGGCCTGGTGAGC | GCTCACCAGGCCCTGCACC |
| 4860 | GTGCAGGGCCTGGTGAGCA | TGCTCACCAGGCCCTGCAC |
| 4861 | TGCAGGGCCTGGTGAGCAC | GTGCTCACCAGGCCCTGCA |
| 4862 | GCAGGGCCTGGTGAGCACA | TGTGCTCACCAGGCCCTGC |
| 4863 | CAGGGCCTGGTGAGCACAG | CTGTGCTCACCAGGCCCTG |
| 4864 | AGGGCCTGGTGAGCACAGT | ACTGTGCTCACCAGGCCCT |
| 4865 | GGGCCTGGTGAGCACAGTC | GACTGTGCTCACCAGGCCC |
| 4866 | GGCCTGGTGAGCACAGTCA | TGACTGTGCTCACCAGGCC |
| 4867 | GCCTGGTGAGCACAGTCAG | CTGACTGTGCTCACCAGGC |
| 4868 | CCTGGTGAGCACAGTCAGC | GCTGACTGTGCTCACCAGG |
| 4869 | CTGGTGAGCACAGTCAGCG | CGCTGACTGTGCTCACCAG |
| 4870 | TGGTGAGCACAGTCAGCGT | ACGCTGACTGTGCTCACCA |
| 4871 | GGTGAGCACAGTCAGCGTC | GACGCTGACTGTGCTCACC |
| 4872 | GTGAGCACAGTCAGCGTCA | TGACGCTGACTGTGCTCAC |
| 4873 | TGAGCACAGTCAGCGTCAC | GTGACGCTGACTGTGCTCA |
| 4874 | GAGCACAGTCAGCGTCACT | AGTGACGCTGACTGTGCTC |
| 4875 | AGCACAGTCAGCGTCACTC | GAGTGACGCTGACTGTGCT |
| 4876 | GCACAGTCAGCGTCACTCA | TGAGTGACGCTGACTGTGC |
| 4877 | CACAGTCAGCGTCACTCAG | CTGAGTGACGCTGACTGTG |
| 4878 | ACAGTCAGCGTCACTCAGC | GCTGAGTGACGCTGACTGT |
| 4879 | CAGTCAGCGTCACTCAGCA | TGCTGAGTGACGCTGACTG |
| 4880 | AGTCAGCGTCACTCAGCAC | GTGCTGAGTGACGCTGACT |
| 4881 | GTCAGCGTCACTCAGCACT | AGTGCTGAGTGACGCTGAC |
| 4882 | TCAGCGTCACTCAGCACTT | AAGTGCTGAGTGACGCTGA |
| 4883 | CAGCGTCACTCAGCACTTC | GAAGTGCTGAGTGACGCTG |
| 4884 | AGCGTCACTCAGCACTTCC | GGAAGTGCTGAGTGACGCT |
| 4885 | GCGTCACTCAGCACTTCCT | AGGAAGTGCTGAGTGACGC |
| 4886 | CGTCACTCAGCACTTCCTC | GAGGAAGTGCTGAGTGACG |
| 4887 | GTCACTCAGCACTTCCTCT | AGAGGAAGTGCTGAGTGAC |
| 4888 | TCACTCAGCACTTCCTCTC | GAGAGGAAGTGCTGAGTGA |
| 4889 | CACTCAGCACTTCCTCTCC | GGAGAGGAAGTGCTGAGTG |
| 4890 | ACTCAGCACTTCCTCTCCC | GGGAGAGGAAGTGCTGAGT |
| 4891 | CTCAGCACTTCCTCTCCCC | GGGGAGAGGAAGTGCTGAG |
| 4892 | TCAGCACTTCCTCTCCCCT | AGGGGAGAGGAAGTGCTGA |
| 4893 | CAGCACTTCCTCTCCCCTG | CAGGGGAGAGGAAGTGCTG |
| 4894 | AGCACTTCCTCTCCCCTGA | TCAGGGGAGAGGAAGTGCT |
| 4895 | GCACTTCCTCTCCCCTGAG | CTCAGGGGAGAGGAAGTGC |
| 4896 | CACTTCCTCTCCCCTGAGA | TCTCAGGGGAGAGGAAGTG |
| 4897 | ACTTCCTCTCCCCTGAGAC | GTCTCAGGGGAGAGGAAGT |
| 4898 | CTTCCTCTCCCCTGAGACC | GGTCTCAGGGGAGAGGAAG |
| 4899 | TTCCTCTCCCCTGAGACCT | AGGTCTCAGGGGAGAGGAA |
| 4900 | TCCTCTCCCCTGAGACCTC | GAGGTCTCAGGGGAGAGGA |
| 4901 | CCTCTCCCCTGAGACCTCT | AGAGGTCTCAGGGGAGAGG |
| 4902 | CTCTCCCCTGAGACCTCTG | CAGAGGTCTCAGGGGAGAG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 4903 | TCTCCCCTGAGACCTCTGC | GCAGAGGTCTCAGGGGAGA |
| 4904 | CTCCCCTGAGACCTCTGCC | GGCAGAGGTCTCAGGGGAG |
| 4905 | TCCCCTGAGACCTCTGCCC | GGGCAGAGGTCTCAGGGGA |
| 4906 | CCCCTGAGACCTCTGCCCT | AGGGCAGAGGTCTCAGGGG |
| 4907 | CCCTGAGACCTCTGCCCTC | GAGGGCAGAGGTCTCAGGG |
| 4908 | CCTGAGACCTCTGCCCTCT | AGAGGGCAGAGGTCTCAGG |
| 4909 | CTGAGACCTCTGCCCTCTC | GAGAGGGCAGAGGTCTCAG |
| 4910 | TGAGACCTCTGCCCTCTCT | AGAGAGGGCAGAGGTCTCA |
| 4911 | GAGACCTCTGCCCTCTCTG | CAGAGAGGGCAGAGGTCTC |
| 4912 | AGACCTCTGCCCTCTCTGC | GCAGAGAGGGCAGAGGTCT |
| 4913 | GACCTCTGCCCTCTCTGCT | AGCAGAGAGGGCAGAGGTC |
| 4914 | ACCTCTGCCCTCTCTGCTC | GAGCAGAGAGGGCAGAGGT |
| 4915 | CCTCTGCCCTCTCTGCTCA | TGAGCAGAGAGGGCAGAGG |
| 4916 | CTCTGCCCTCTCTGCTCAG | CTGAGCAGAGAGGGCAGAG |
| 4917 | TCTGCCCTCTCTGCTCAGC | GCTGAGCAGAGAGGGCAGA |
| 4918 | CTGCCCTCTCTGCTCAGCT | AGCTGAGCAGAGAGGGCAG |
| 4919 | TGCCCTCTCTGCTCAGCTC | GAGCTGAGCAGAGAGGGCA |
| 4920 | GCCCTCTCTGCTCAGCTCT | AGAGCTGAGCAGAGAGGGC |
| 4921 | CCCTCTCTGCTCAGCTCTG | CAGAGCTGAGCAGAGAGGG |
| 4922 | CCTCTCTGCTCAGCTCTGC | GCAGAGCTGAGCAGAGAGG |
| 4923 | CTCTCTGCTCAGCTCTGCC | GGCAGAGCTGAGCAGAGAG |
| 4924 | TCTCTGCTCAGCTCTGCCA | TGGCAGAGCTGAGCAGAGA |
| 4925 | CTCTGCTCAGCTCTGCCAC | GTGGCAGAGCTGAGCAGAG |
| 4926 | TCTGCTCAGCTCTGCCACC | GGTGGCAGAGCTGAGCAGA |
| 4927 | CTGCTCAGCTCTGCCACCA | TGGTGGCAGAGCTGAGCAG |
| 4928 | TGCTCAGCTCTGCCACCAG | CTGGTGGCAGAGCTGAGCA |
| 4929 | GCTCAGCTCTGCCACCAGG | CCTGGTGGCAGAGCTGAGC |
| 4930 | CTCAGCTCTGCCACCAGGG | CCCTGGTGGCAGAGCTGAG |
| 4931 | TCAGCTCTGCCACCAGGGA | TCCCTGGTGGCAGAGCTGA |
| 4932 | CAGCTCTGCCACCAGGGAC | GTCCCTGGTGGCAGAGCTG |
| 4933 | AGCTCTGCCACCAGGGACC | GGTCCCTGGTGGCAGAGCT |
| 4934 | GCTCTGCCACCAGGGACCC | GGGTCCCTGGTGGCAGAGC |
| 4935 | CTCTGCCACCAGGGACCCA | TGGGTCCCTGGTGGCAGAG |
| 4936 | TCTGCCACCAGGGACCCAG | CTGGGTCCCTGGTGGCAGA |
| 4937 | CTGCCACCAGGGACCCAGC | GCTGGGTCCCTGGTGGCAG |
| 4938 | TGCCACCAGGGACCCAGCC | GGCTGGGTCCCTGGTGGCA |
| 4939 | GCCACCAGGGACCCAGCCT | AGGCTGGGTCCCTGGTGGC |
| 4940 | CCACCAGGGACCCAGCCTT | AAGGCTGGGTCCCTGGTGG |
| 4941 | CACCAGGGACCCAGCCTTC | GAAGGCTGGGTCCCTGGTG |
| 4942 | ACCAGGGACCCAGCCTTCC | GGAAGGCTGGGTCCCTGGT |
| 4943 | CCAGGGACCCAGCCTTCCC | GGGAAGGCTGGGTCCCTGG |
| 4944 | CAGGGACCCAGCCTTCCCC | GGGGAAGGCTGGGTCCCTG |
| 4945 | AGGGACCCAGCCTTCCCCC | GGGGGAAGGCTGGGTCCCT |
| 4946 | GGGACCCAGCCTTCCCCCT | AGGGGGAAGGCTGGGTCCC |
| 4947 | GGACCCAGCCTTCCCCCTG | CAGGGGGAAGGCTGGGTCC |
| 4948 | GACCCAGCCTTCCCCCTGA | TCAGGGGAAGGCTGGGTC |
| 4949 | ACCCAGCCTTCCCCCTGAC | GTCAGGGGAAGGCTGGGT |
| 4950 | CCCAGCCTTCCCCCTGACT | AGTCAGGGGAAGGCTGGG |
| 4951 | CCAGCCTTCCCCCTGACTG | CAGTCAGGGGAAGGCTGG |
| 4952 | CAGCCTTCCCCCTGACTGC | GCAGTCAGGGGAAGGCTG |
| 4953 | AGCCTTCCCCCTGACTGCC | GGCAGTCAGGGGAAGGCT |
| 4954 | GCCTTCCCCCTGACTGCCA | TGGCAGTCAGGGGAAGGC |
| 4955 | CCTTCCCCCTGACTGCCAC | GTGGCAGTCAGGGGAAGG |
| 4956 | CTTCCCCCTGACTGCCACC | GGTGGCAGTCAGGGGAAG |
| 4957 | TTCCCCCTGACTGCCACCT | AGGTGGCAGTCAGGGGAA |
| 4958 | TCCCCCTGACTGCCACCTG | CAGGTGGCAGTCAGGGGA |
| 4959 | CCCCCTGACTGCCACCTGC | GCAGGTGGCAGTCAGGGG |
| 4960 | CCCCTGACTGCCACCTGCT | AGCAGGTGGCAGTCAGGGG |
| 4961 | CCCTGACTGCCACCTGCTT | AAGCAGGTGGCAGTCAGGG |
| 4962 | CCTGACTGCCACCTGCTTT | AAAGCAGGTGGCAGTCAGG |
| 4963 | CTGACTGCCACCTGCTTTA | TAAAGCAGGTGGCAGTCAG |
| 4964 | TGACTGCCACCTGCTTTAT | ATAAAGCAGGTGGCAGTCA |
| 4965 | GACTGCCACCTGCTTTATG | CATAAAGCAGGTGGCAGTC |
| 4966 | ACTGCCACCTGCTTTATGC | GCATAAAGCAGGTGGCAGT |
| 4967 | CTGCCACCTGCTTTATGCC | GGCATAAAGCAGGTGGCAG |
| 4968 | TGCCACCTGCTTTATGCCC | GGGCATAAAGCAGGTGGCA |
| 4969 | GCCACCTGCTTTATGCCCA | TGGGCATAAAGCAGGTGGC |
| 4970 | CCACCTGCTTTATGCCCAG | CTGGGCATAAAGCAGGTGG |
| 4971 | CACCTGCTTTATGCCCAGA | TCTGGGCATAAAGCAGGTG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 4972 | ACCTGCTTTATGCCCAGAT | ATCTGGGCATAAAGCAGGT |
| 4973 | CCTGCTTTATGCCCAGATG | CATCTGGGCATAAAGCAGG |
| 4974 | CTGCTTTATGCCCAGATGG | CCATCTGGGCATAAAGCAG |
| 4975 | TGCTTTATGCCCAGATGGA | TCCATCTGGGCATAAAGCA |
| 4976 | GCTTTATGCCCAGATGGAC | GTCCATCTGGGCATAAAGC |
| 4977 | CTTTATGCCCAGATGGACT | AGTCCATCTGGGCATAAAG |
| 4978 | TTTATGCCCAGATGGACTG | CAGTCCATCTGGGCATAAA |
| 4979 | TTATGCCCAGATGGACTGG | CCAGTCCATCTGGGCATAA |
| 4980 | TATGCCCAGATGGACTGGG | CCCAGTCCATCTGGGCATA |
| 4981 | ATGCCCAGATGGACTGGGC | GCCCAGTCCATCTGGGCAT |
| 4982 | TGCCCAGATGGACTGGGCT | AGCCCAGTCCATCTGGGCA |
| 4983 | GCCCAGATGGACTGGGCTG | CAGCCCAGTCCATCTGGGC |
| 4984 | CCCAGATGGACTGGGCTGT | ACAGCCCAGTCCATCTGGG |
| 4985 | CCAGATGGACTGGGCTGTG | CACAGCCCAGTCCATCTGG |
| 4986 | CAGATGGACTGGGCTGTGT | ACACAGCCCAGTCCATCTG |
| 4987 | AGATGGACTGGGCTGTGTT | AACACAGCCCAGTCCATCT |
| 4988 | GATGGACTGGGCTGTGTTC | GAACACAGCCCAGTCCATC |
| 4989 | ATGGACTGGGCTGTGTTCC | GGAACACAGCCCAGTCCAT |
| 4990 | TGGACTGGGCTGTGTTCCA | TGGAACACAGCCCAGTCCA |
| 4991 | GGACTGGGCTGTGTTCCAA | TTGGAACACAGCCCAGTCC |
| 4992 | GACTGGGCTGTGTTCCAAG | CTTGGAACACAGCCCAGTC |
| 4993 | ACTGGGCTGTGTTCCAAGC | GCTTGGAACACAGCCCAGT |
| 4994 | CTGGGCTGTGTTCCAAGCA | TGCTTGGAACACAGCCCAG |
| 4995 | TGGGCTGTGTTCCAAGCAG | CTGCTTGGAACACAGCCCA |
| 4996 | GGGCTGTGTTCCAAGCAGT | ACTGCTTGGAACACAGCCC |
| 4997 | GGCTGTGTTCCAAGCAGTG | CACTGCTTGGAACACAGCC |
| 4998 | GCTGTGTTCCAAGCAGTGA | TCACTGCTTGGAACACAGC |
| 4999 | CTGTGTTCCAAGCAGTGAA | TTCACTGCTTGGAACACAG |
| 5000 | TGTGTTCCAAGCAGTGAAG | CTTCACTGCTTGGAACACA |
| 5001 | GTGTTCCAAGCAGTGAAGG | CCTTCACTGCTTGGAACAC |
| 5002 | TGTTCCAAGCAGTGAAGGT | ACCTTCACTGCTTGGAACA |
| 5003 | GTTCCAAGCAGTGAAGGTG | CACCTTCACTGCTTGGAAC |
| 5004 | TTCCAAGCAGTGAAGGTGG | CCACCTTCACTGCTTGGAA |
| 5005 | TCCAAGCAGTGAAGGTGGC | GCCACCTTCACTGCTTGGA |
| 5006 | CCAAGCAGTGAAGGTGGCC | GGCCACCTTCACTGCTTGG |
| 5007 | CAAGCAGTGAAGGTGGCCG | CGGCCACCTTCACTGCTTG |
| 5008 | AAGCAGTGAAGGTGGCCGT | ACGGCCACCTTCACTGCTT |
| 5009 | AGCAGTGAAGGTGGCCGTG | CACGGCCACCTTCACTGCT |
| 5010 | GCAGTGAAGGTGGCCGTGG | CCACGGCCACCTTCACTGC |
| 5011 | CAGTGAAGGTGGCCGTGGG | CCCACGGCCACCTTCACTG |
| 5012 | AGTGAAGGTGGCCGTGGGG | CCCCACGGCCACCTTCACT |
| 5013 | GTGAAGGTGGCCGTGGGGA | TCCCCACGGCCACCTTCAC |
| 5014 | TGAAGGTGGCCGTGGGGAC | GTCCCCACGGCCACCTTCA |
| 5015 | GAAGGTGGCCGTGGGGACA | TGTCCCCACGGCCACCTTC |
| 5016 | AAGGTGGCCGTGGGGACAT | ATGTCCCCACGGCCACCTT |
| 5017 | AGGTGGCCGTGGGGACATT | AATGTCCCCACGGCCACCT |
| 5018 | GGTGGCCGTGGGGACATTA | TAATGTCCCCACGGCCACC |
| 5019 | GTGGCCGTGGGGACATTAC | GTAATGTCCCCACGGCCAC |
| 5020 | TGGCCGTGGGGACATTACA | TGTAATGTCCCCACGGCCA |
| 5021 | GGCCGTGGGGACATTACAG | CTGTAATGTCCCCACGGCC |
| 5022 | GCCGTGGGGACATTACAGG | CCTGTAATGTCCCCACGGC |
| 5023 | CCGTGGGGACATTACAGGA | TCCTGTAATGTCCCCACGG |
| 5024 | CGTGGGGACATTACAGGAG | CTCCTGTAATGTCCCCACG |
| 5025 | GTGGGGACATTACAGGAGG | CCTCCTGTAATGTCCCCAC |
| 5026 | TGGGGACATTACAGGAGGC | GCCTCCTGTAATGTCCCCA |
| 5027 | GGGGACATTACAGGAGGCC | GGCCTCCTGTAATGTCCCC |
| 5028 | GGGACATTACAGGAGGCCA | TGGCCTCCTGTAATGTCCC |
| 5029 | GGACATTACAGGAGGCCAA | TTGGCCTCCTGTAATGTCC |
| 5030 | GACATTACAGGAGGCCAAA | TTTGGCCTCCTGTAATGTC |
| 5031 | ACATTACAGGAGGCCAAAT | ATTTGGCCTCCTGTAATGT |
| 5032 | CATTACAGGAGGCCAAATA | TATTTGGCCTCCTGTAATG |
| 5033 | ATTACAGGAGGCCAAATAG | CTATTTGGCCTCCTGTAAT |
| 5034 | TTACAGGAGGCCAAATAGA | TCTATTTGGCCTCCTGTAA |
| 5035 | TACAGGAGGCCAAATAGAG | CTCTATTTGGCCTCCTGTA |
| 5036 | ACAGGAGGCCAAATAGAGG | CCTCTATTTGGCCTCCTGT |
| 5037 | CAGGAGGCCAAATAGAGGG | CCCTCTATTTGGCCTCCTG |
| 5038 | AGGAGGCCAAATAGAGGGA | TCCCTCTATTTGGCCTCCT |
| 5039 | GGAGGCCAAATAGAGGGAT | ATCCCTCTATTTGGCCTCC |
| 5040 | GAGGCCAAATAGAGGGATG | CATCCCTCTATTTGGCCTC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 5041 | AGGCCAAATAGAGGGATGC | GCATCCCTCTATTTGGCCT |
| 5042 | GGCCAAATAGAGGGATGCT | AGCATCCCTCTATTTGGCC |
| 5043 | GCCAAATAGAGGGATGCTA | TAGCATCCCTCTATTTGGC |
| 5044 | CCAAATAGAGGGATGCTAG | CTAGCATCCCTCTATTTGG |
| 5045 | CAAATAGAGGGATGCTAGG | CCTAGCATCCCTCTATTTG |
| 5046 | AAATAGAGGGATGCTAGGT | ACCTAGCATCCCTCTATTT |
| 5047 | AATAGAGGGATGCTAGGTG | CACCTAGCATCCCTCTATT |
| 5048 | ATAGAGGGATGCTAGGTGT | ACACCTAGCATCCCTCTAT |
| 5049 | TAGAGGGATGCTAGGTGTC | GACACCTAGCATCCCTCTA |
| 5050 | AGAGGGATGCTAGGTGTCT | AGACACCTAGCATCCCTCT |
| 5051 | GAGGGATGCTAGGTGTCTG | CAGACACCTAGCATCCCTC |
| 5052 | AGGGATGCTAGGTGTCTGG | CCAGACACCTAGCATCCCT |
| 5053 | GGGATGCTAGGTGTCTGGG | CCCAGACACCTAGCATCCC |
| 5054 | GGATGCTAGGTGTCTGGGA | TCCCAGACACCTAGCATCC |
| 5055 | GATGCTAGGTGTCTGGGAT | ATCCCAGACACCTAGCATC |
| 5056 | ATGCTAGGTGTCTGGGATC | GATCCCAGACACCTAGCAT |
| 5057 | TGCTAGGTGTCTGGGATCG | CGATCCCAGACACCTAGCA |
| 5058 | GCTAGGTGTCTGGGATCGG | CCGATCCCAGACACCTAGC |
| 5059 | CTAGGTGTCTGGGATCGGG | CCCGATCCCAGACACCTAG |
| 5060 | TAGGTGTCTGGGATCGGGG | CCCCGATCCCAGACACCTA |
| 5061 | AGGTGTCTGGGATCGGGGT | ACCCCGATCCCAGACACCT |
| 5062 | GGTGTCTGGGATCGGGGTG | CACCCCGATCCCAGACACC |
| 5063 | GTGTCTGGGATCGGGGTGG | CCACCCCGATCCCAGACAC |
| 5064 | TGTCTGGGATCGGGGTGGG | CCCACCCCGATCCCAGACA |
| 5065 | GTCTGGGATCGGGGTGGGG | CCCCACCCCGATCCCAGAC |
| 5066 | TCTGGGATCGGGGTGGGGA | TCCCCACCCCGATCCCAGA |
| 5067 | CTGGGATCGGGGTGGGGAC | GTCCCCACCCCGATCCCAG |
| 5068 | TGGGATCGGGGTGGGGACA | TGTCCCCACCCCGATCCCA |
| 5069 | GGGATCGGGGTGGGGACAG | CTGTCCCCACCCCGATCCC |
| 5070 | GGATCGGGGTGGGGACAGG | CCTGTCCCCACCCCGATCC |
| 5071 | GATCGGGGTGGGGACAGGT | ACCTGTCCCCACCCCGATC |
| 5072 | ATCGGGGTGGGGACAGGTA | TACCTGTCCCCACCCCGAT |
| 5073 | TCGGGGTGGGGACAGGTAG | CTACCTGTCCCCACCCCGA |
| 5074 | CGGGGTGGGGACAGGTAGA | TCTACCTGTCCCCACCCCG |
| 5075 | GGGGTGGGGACAGGTAGAC | GTCTACCTGTCCCCACCCC |
| 5076 | GGGTGGGGACAGGTAGACC | GGTCTACCTGTCCCCACCC |
| 5077 | GGTGGGGACAGGTAGACCA | TGGTCTACCTGTCCCCACC |
| 5078 | GTGGGGACAGGTAGACCAG | CTGGTCTACCTGTCCCCAC |
| 5079 | TGGGGACAGGTAGACCAGG | CCTGGTCTACCTGTCCCCA |
| 5080 | GGGGACAGGTAGACCAGGT | ACCTGGTCTACCTGTCCCC |
| 5081 | GGGACAGGTAGACCAGGTG | CACCTGGTCTACCTGTCCC |
| 5082 | GGACAGGTAGACCAGGTGC | GCACCTGGTCTACCTGTCC |
| 5083 | GACAGGTAGACCAGGTGCT | AGCACCTGGTCTACCTGTC |
| 5084 | ACAGGTAGACCAGGTGCTC | GAGCACCTGGTCTACCTGT |
| 5085 | CAGGTAGACCAGGTGCTCA | TGAGCACCTGGTCTACCTG |
| 5086 | AGGTAGACCAGGTGCTCAG | CTGAGCACCTGGTCTACCT |
| 5087 | GGTAGACCAGGTGCTCAGC | GCTGAGCACCTGGTCTACC |
| 5088 | GTAGACCAGGTGCTCAGCC | GGCTGAGCACCTGGTCTAC |
| 5089 | TAGACCAGGTGCTCAGCCC | GGGCTGAGCACCTGGTCTA |
| 5090 | AGACCAGGTGCTCAGCCCA | TGGGCTGAGCACCTGGTCT |
| 5091 | GACCAGGTGCTCAGCCCAG | CTGGGCTGAGCACCTGGTC |
| 5092 | ACCAGGTGCTCAGCCCAGG | CCTGGGCTGAGCACCTGGT |
| 5093 | CCAGGTGCTCAGCCCAGGC | GCCTGGGCTGAGCACCTGG |
| 5094 | CAGGTGCTCAGCCCAGGCA | TGCCTGGGCTGAGCACCTG |
| 5095 | AGGTGCTCAGCCCAGGCAC | GTGCCTGGGCTGAGCACCT |
| 5096 | GGTGCTCAGCCCAGGCACA | TGTGCCTGGGCTGAGCACC |
| 5097 | GTGCTCAGCCCAGGCACAA | TTGTGCCTGGGCTGAGCAC |
| 5098 | TGCTCAGCCCAGGCACAAC | GTTGTGCCTGGGCTGAGCA |
| 5099 | GCTCAGCCCAGGCACAACT | AGTTGTGCCTGGGCTGAGC |
| 5100 | CTCAGCCCAGGCACAACTT | AAGTTGTGCCTGGGCTGAG |
| 5101 | TCAGCCCAGGCACAACTTC | GAAGTTGTGCCTGGGCTGA |
| 5102 | CAGCCCAGGCACAACTTCA | TGAAGTTGTGCCTGGGCTG |
| 5103 | AGCCCAGGCACAACTTCAG | CTGAAGTTGTGCCTGGGCT |
| 5104 | GCCCAGGCACAACTTCAGC | GCTGAAGTTGTGCCTGGGC |
| 5105 | CCCAGGCACAACTTCAGCA | TGCTGAAGTTGTGCCTGGG |
| 5106 | CCAGGCACAACTTCAGCAG | CTGCTGAAGTTGTGCCTGG |
| 5107 | CAGGCACAACTTCAGCAGG | CCTGCTGAAGTTGTGCCTG |
| 5108 | AGGCACAACTTCAGCAGGG | CCCTGCTGAAGTTGTGCCT |
| 5109 | GGCACAACTTCAGCAGGGG | CCCCTGCTGAAGTTGTGCC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 5110 | GCACAACTTCAGCAGGGGA | TCCCCTGCTGAAGTTGTGC |
| 5111 | GACAACTTCAGCAGGGGAT | ATCCCCTGCTGAAGTTGTG |
| 5112 | ACAACTTCAGCAGGGGATG | CATCCCCTGCTGAAGTTGT |
| 5113 | CAACTTCAGCAGGGGATGG | CCATCCCCTGCTGAAGTTG |
| 5114 | AACTTCAGCAGGGGATGGC | GCCATCCCCTGCTGAAGTT |
| 5115 | ACTTCAGCAGGGGATGGCG | CGCCATCCCCTGCTGAAGT |
| 5116 | CTTCAGCAGGGGATGGCGC | GCGCCATCCCCTGCTGAAG |
| 5117 | TTCAGCAGGGGATGGCGCT | AGCGCCATCCCCTGCTGAA |
| 5118 | TCAGCAGGGGATGGCGCTA | TAGCGCCATCCCCTGCTGA |
| 5119 | CAGCAGGGGATGGCGCTAG | CTAGCGCCATCCCCTGCTG |
| 5120 | AGCAGGGGATGGCGCTAGG | CCTAGCGCCATCCCCTGCT |
| 5121 | GCAGGGGATGGCGCTAGGG | CCCTAGCGCCATCCCCTGC |
| 5122 | CAGGGGATGGCGCTAGGGG | CCCCTAGCGCCATCCCCTG |
| 5123 | AGGGGATGGCGCTAGGGGA | TCCCCTAGCGCCATCCCCT |
| 5124 | GGGGATGGCGCTAGGGGAC | GTCCCCTAGCGCCATCCCC |
| 5125 | GGGATGGCGCTAGGGGACT | AGTCCCCTAGCGCCATCCC |
| 5126 | GGATGGCGCTAGGGGACTT | AAGTCCCCTAGCGCCATCC |
| 5127 | GATGGCGCTAGGGGACTTG | CAAGTCCCCTAGCGCCATC |
| 5128 | ATGGCGCTAGGGGACTTGG | CCAAGTCCCCTAGCGCCAT |
| 5129 | TGGCGCTAGGGGACTTGGG | CCCAAGTCCCCTAGCGCCA |
| 5130 | GGCGCTAGGGGACTTGGGG | CCCCAAGTCCCCTAGCGCC |
| 5131 | GCGCTAGGGGACTTGGGGA | TCCCCAAGTCCCCTAGCGC |
| 5132 | CGCTAGGGGACTTGGGGAT | ATCCCCAAGTCCCCTAGCG |
| 5133 | GCTAGGGGACTTGGGGATT | AATCCCCAAGTCCCCTAGC |
| 5134 | CTAGGGGACTTGGGGATTT | AAATCCCCAAGTCCCCTAG |
| 5135 | TAGGGGACTTGGGGATTTC | GAAATCCCCAAGTCCCCTA |
| 5136 | AGGGGACTTGGGGATTTCT | AGAAATCCCCAAGTCCCCT |
| 5137 | GGGGACTTGGGGATTTCTG | CAGAAATCCCCAAGTCCCC |
| 5138 | GGGACTTGGGGATTTCTGG | CCAGAAATCCCCAAGTCCC |
| 5139 | GGACTTGGGGATTTCTGGT | ACCAGAAATCCCCAAGTCC |
| 5140 | GACTTGGGGATTTCTGGTC | GACCAGAAATCCCCAAGTC |
| 5141 | ACTTGGGGATTTCTGGTCA | TGACCAGAAATCCCCAAGT |
| 5142 | CTTGGGGATTTCTGGTCAA | TTGACCAGAAATCCCCAAG |
| 5143 | TTGGGGATTTCTGGTCAAC | GTTGACCAGAAATCCCCAA |
| 5144 | TGGGGATTTCTGGTCAACC | GGTTGACCAGAAATCCCCA |
| 5145 | GGGGATTTCTGGTCAACCC | GGGTTGACCAGAAATCCCC |
| 5146 | GGGATTTCTGGTCAACCCC | GGGGTTGACCAGAAATCCC |
| 5147 | GGATTTCTGGTCAACCCCA | TGGGGTTGACCAGAAATCC |
| 5148 | GATTTCTGGTCAACCCCAC | GTGGGGTTGACCAGAAATC |
| 5149 | ATTTCTGGTCAACCCCACA | TGTGGGGTTGACCAGAAAT |
| 5150 | TTTCTGGTCAACCCCACAA | TTGTGGGGTTGACCAGAAA |
| 5151 | TTCTGGTCAACCCCACAAG | CTTGTGGGGTTGACCAGAA |
| 5152 | TCTGGTCAACCCCACAAGC | GCTTGTGGGGTTGACCAGA |
| 5153 | CTGGTCAACCCCACAAGCA | TGCTTGTGGGGTTGACCAG |
| 5154 | TGGTCAACCCCACAAGCAC | GTGCTTGTGGGGTTGACCA |
| 5155 | GGTCAACCCCACAAGCACC | GGTGCTTGTGGGGTTGACC |
| 5156 | GTCAACCCCACAAGCACCA | TGGTGCTTGTGGGGTTGAC |
| 5157 | TCAACCCCACAAGCACCAC | GTGGTGCTTGTGGGGTTGA |
| 5158 | CAACCCCACAAGCACCACT | AGTGGTGCTTGTGGGGTTG |
| 5159 | AACCCCACAAGCACCACTC | GAGTGGTGCTTGTGGGGTT |
| 5160 | ACCCCACAAGCACCACTCT | AGAGTGGTGCTTGTGGGGT |
| 5161 | CCCCACAAGCACCACTCTG | CAGAGTGGTGCTTGTGGGG |
| 5162 | CCCACAAGCACCACTCTGG | CCAGAGTGGTGCTTGTGGG |
| 5163 | CCACAAGCACCACTCTGGG | CCCAGAGTGGTGCTTGTGG |
| 5164 | CACAAGCACCACTCTGGGC | GCCCAGAGTGGTGCTTGTG |
| 5165 | ACAAGCACCACTCTGGGCA | TGCCCAGAGTGGTGCTTGT |
| 5166 | CAAGCACCACTCTGGGCAC | GTGCCCAGAGTGGTGCTTG |
| 5167 | AAGCACCACTCTGGGCACA | TGTGCCCAGAGTGGTGCTT |
| 5168 | AGCACCACTCTGGGCACAA | TTGTGCCCAGAGTGGTGCT |
| 5169 | GCACCACTCTGGGCACAAG | CTTGTGCCCAGAGTGGTGC |
| 5170 | CACCACTCTGGGCACAAGC | GCTTGTGCCCAGAGTGGTG |
| 5171 | ACCACTCTGGGCACAAGCA | TGCTTGTGCCCAGAGTGGT |
| 5172 | CCACTCTGGGCACAAGCAG | CTGCTTGTGCCCAGAGTGG |
| 5173 | CACTCTGGGCACAAGCAGG | CCTGCTTGTGCCCAGAGTG |
| 5174 | ACTCTGGGCACAAGCAGGG | CCCTGCTTGTGCCCAGAGT |
| 5175 | CTCTGGGCACAAGCAGGGC | GCCCTGCTTGTGCCCAGAG |
| 5176 | TCTGGGCACAAGCAGGGCA | TGCCCTGCTTGTGCCCAGA |
| 5177 | CTGGGCACAAGCAGGGCAC | GTGCCCTGCTTGTGCCCAG |
| 5178 | TGGGCACAAGCAGGGCACT | AGTGCCCTGCTTGTGCCCA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 5179 | GGGCACAAGCAGGGCACTC | GAGTGCCCTGCTTGTGCCC |
| 5180 | GGCACAAGCAGGGCACTCT | AGAGTGCCCTGCTTGTGCC |
| 5181 | GCACAAGCAGGGCACTCTG | CAGAGTGCCCTGCTTGTGC |
| 5182 | CACAAGCAGGGCACTCTGT | ACAGAGTGCCCTGCTTGTG |
| 5183 | ACAAGCAGGGCACTCTGTT | AACAGAGTGCCCTGCTTGT |
| 5184 | CAAGCAGGGCACTCTGTTC | GAACAGAGTGCCCTGCTTG |
| 5185 | AAGCAGGGCACTCTGTTCC | GGAACAGAGTGCCCTGCTT |
| 5186 | AGCAGGGCACTCTGTTCCC | GGGAACAGAGTGCCCTGCT |
| 5187 | GCAGGGCACTCTGTTCCCC | GGGGAACAGAGTGCCCTGC |
| 5188 | CAGGGCACTCTGTTCCCCT | AGGGGAACAGAGTGCCCTG |
| 5189 | AGGGCACTCTGTTCCCCTC | GAGGGGAACAGAGTGCCCT |
| 5190 | GGGCACTCTGTTCCCCTCC | GGAGGGGAACAGAGTGCCC |
| 5191 | GGCACTCTGTTCCCCTCCC | GGGAGGGGAACAGAGTGCC |
| 5192 | GCACTCTGTTCCCCTCCCC | GGGGAGGGGAACAGAGTGC |
| 5193 | CACTCTGTTCCCCTCCCCC | GGGGGAGGGGAACAGAGTG |
| 5194 | ACTCTGTTCCCCTCCCCCT | AGGGGGAGGGGAACAGAGT |
| 5195 | CTCTGTTCCCCTCCCCCTT | AAGGGGGAGGGGAACAGAG |
| 5196 | TCTGTTCCCCTCCCCCTTA | TAAGGGGGAGGGGAACAGA |
| 5197 | CTGTTCCCCTCCCCCTTAA | TTAAGGGGGAGGGGAACAG |
| 5198 | TGTTCCCCTCCCCCTTAAG | CTTAAGGGGGAGGGGAACA |
| 5199 | GTTCCCCTCCCCCTTAAGC | GCTTAAGGGGGAGGGGAAC |
| 5200 | TTCCCCTCCCCCTTAAGCC | GGCTTAAGGGGGAGGGGAA |
| 5201 | TCCCCTCCCCCTTAAGCCA | TGGCTTAAGGGGGAGGGGA |
| 5202 | CCCCTCCCCCTTAAGCCAA | TTGGCTTAAGGGGGAGGGG |
| 5203 | CCCTCCCCCTTAAGCCAAC | GTTGGCTTAAGGGGGAGGG |
| 5204 | CCTCCCCCTTAAGCCAACA | TGTTGGCTTAAGGGGGAGG |
| 5205 | CTCCCCCTTAAGCCAACAA | TTGTTGGCTTAAGGGGGAG |
| 5206 | TCCCCCTTAAGCCAACAAC | GTTGTTGGCTTAAGGGGGA |
| 5207 | CCCCCTTAAGCCAACAACC | GGTTGTTGGCTTAAGGGGG |
| 5208 | CCCCTTAAGCCAACAACCA | TGGTTGTTGGCTTAAGGGG |
| 5209 | CCCTTAAGCCAACAACCAC | GTGGTTGTTGGCTTAAGGG |
| 5210 | CCTTAAGCCAACAACCACA | TGTGGTTGTTGGCTTAAGG |
| 5211 | CTTAAGCCAACAACCACAG | CTGTGGTTGTTGGCTTAAG |
| 5212 | TTAAGCCAACAACCACAGT | ACTGTGGTTGTTGGCTTAA |
| 5213 | TAAGCCAACAACCACAGTG | CACTGTGGTTGTTGGCTTA |
| 5214 | AAGCCAACAACCACAGTGC | GCACTGTGGTTGTTGGCTT |
| 5215 | AGCCAACAACCACAGTGCC | GGCACTGTGGTTGTTGGCT |
| 5216 | GCCAACAACCACAGTGCCA | TGGCACTGTGGTTGTTGGC |
| 5217 | CCAACAACCACAGTGCCAC | GTGGCACTGTGGTTGTTGG |
| 5218 | CAACAACCACAGTGCCACC | GGTGGCACTGTGGTTGTTG |
| 5219 | AACAACCACAGTGCCACCA | TGGTGGCACTGTGGTTGTT |
| 5220 | ACAACCACAGTGCCACCAA | TTGGTGGCACTGTGGTTGT |
| 5221 | CAACCACAGTGCCACCAAG | CTTGGTGGCACTGTGGTTG |
| 5222 | AACCACAGTGCCACCAAGC | GCTTGGTGGCACTGTGGTT |
| 5223 | ACCACAGTGCCACCAAGCT | AGCTTGGTGGCACTGTGGT |
| 5224 | CCACAGTGCCACCAAGCTC | GAGCTTGGTGGCACTGTGG |
| 5225 | CACAGTGCCACCAAGCTCA | TGAGCTTGGTGGCACTGTG |
| 5226 | ACAGTGCCACCAAGCTCAC | GTGAGCTTGGTGGCACTGT |
| 5227 | CAGTGCCACCAAGCTCACA | TGTGAGCTTGGTGGCACTG |
| 5228 | AGTGCCACCAAGCTCACAC | GTGTGAGCTTGGTGGCACT |
| 5229 | GTGCCACCAAGCTCACACC | GGTGTGAGCTTGGTGGCAC |
| 5230 | TGCCACCAAGCTCACACCT | AGGTGTGAGCTTGGTGGCA |
| 5231 | GCCACCAAGCTCACACCTG | CAGGTGTGAGCTTGGTGGC |
| 5232 | CCACCAAGCTCACACCTGT | ACAGGTGTGAGCTTGGTGG |
| 5233 | CACCAAGCTCACACCTGTC | GACAGGTGTGAGCTTGGTG |
| 5234 | ACCAAGCTCACACCTGTCC | GGACAGGTGTGAGCTTGGT |
| 5235 | CCAAGCTCACACCTGTCCT | AGGACAGGTGTGAGCTTGG |
| 5236 | CAAGCTCACACCTGTCCTT | AAGGACAGGTGTGAGCTTG |
| 5237 | AAGCTCACACCTGTCCTTC | GAAGGACAGGTGTGAGCTT |
| 5238 | AGCTCACACCTGTCCTTCT | AGAAGGACAGGTGTGAGCT |
| 5239 | GCTCACACCTGTCCTTCTC | GAGAAGGACAGGTGTGAGC |
| 5240 | CTCACACCTGTCCTTCTCA | TGAGAAGGACAGGTGTGAG |
| 5241 | TCACACCTGTCCTTCTCAG | CTGAGAAGGACAGGTGTGA |
| 5242 | CACACCTGTCCTTCTCAGG | CCTGAGAAGGACAGGTGTG |
| 5243 | ACACCTGTCCTTCTCAGGC | GCCTGAGAAGGACAGGTGT |
| 5244 | CACCTGTCCTTCTCAGGCT | AGCCTGAGAAGGACAGGTG |
| 5245 | ACCTGTCCTTCTCAGGCTG | CAGCCTGAGAAGGACAGGT |
| 5246 | CCTGTCCTTCTCAGGCTGG | CCAGCCTGAGAAGGACAGG |
| 5247 | CTGTCCTTCTCAGGCTGGC | GCCAGCCTGAGAAGGACAG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 5248 | TGTCCTTCTCAGGCTGGCA | TGCCAGCCTGAGAAGGACA |
| 5249 | GTCCTTCTCAGGCTGGCAT | ATGCCAGCCTGAGAAGGAC |
| 5250 | TCCTTCTCAGGCTGGCATC | GATGCCAGCCTGAGAAGGA |
| 5251 | CCTTCTCAGGCTGGCATCT | AGATGCCAGCCTGAGAAGG |
| 5252 | CTTCTCAGGCTGGCATCTC | GAGATGCCAGCCTGAGAAG |
| 5253 | TTCTCAGGCTGGCATCTCC | GGAGATGCCAGCCTGAGAA |
| 5254 | TCTCAGGCTGGCATCTCCC | GGGAGATGCCAGCCTGAGA |
| 5255 | CTCAGGCTGGCATCTCCCC | GGGGAGATGCCAGCCTGAG |
| 5256 | TCAGGCTGGCATCTCCCCC | GGGGGAGATGCCAGCCTGA |
| 5257 | CAGGCTGGCATCTCCCCCA | TGGGGGAGATGCCAGCCTG |
| 5258 | AGGCTGGCATCTCCCCCAC | GTGGGGGAGATGCCAGCCT |
| 5259 | GGCTGGCATCTCCCCCACC | GGTGGGGGAGATGCCAGCC |
| 5260 | GCTGGCATCTCCCCCACCC | GGGTGGGGGAGATGCCAGC |
| 5261 | CTGGCATCTCCCCCACCCT | AGGGTGGGGGAGATGCCAG |
| 5262 | TGGCATCTCCCCCACCCTG | CAGGGTGGGGGAGATGCCA |
| 5263 | GGCATCTCCCCCACCCTGT | ACAGGGTGGGGGAGATGCC |
| 5264 | GCATCTCCCCCACCCTGTG | CACAGGGTGGGGGAGATGC |
| 5265 | CATCTCCCCCACCCTGTGC | GCACAGGGTGGGGGAGATG |
| 5266 | ATCTCCCCCACCCTGTGCC | GGCACAGGGTGGGGGAGAT |
| 5267 | TCTCCCCCACCCTGTGCCC | GGGCACAGGGTGGGGGAGA |
| 5268 | CTCCCCCACCCTGTGCCCC | GGGGCACAGGGTGGGGGAG |
| 5269 | TCCCCCACCCTGTGCCCCT | AGGGGCACAGGGTGGGGGA |
| 5270 | CCCCCACCCTGTGCCCCTT | AAGGGGCACAGGGTGGGGG |
| 5271 | CCCCACCCTGTGCCCCTTT | AAAGGGGCACAGGGTGGGG |
| 5272 | CCCACCCTGTGCCCCTTTT | AAAAGGGGCACAGGGTGGG |
| 5273 | CCACCCTGTGCCCCTTTTC | GAAAAGGGGCACAGGGTGG |
| 5274 | CACCCTGTGCCCCTTTTCA | TGAAAAGGGGCACAGGGTG |
| 5275 | ACCCTGTGCCCCTTTTCAT | ATGAAAAGGGGCACAGGGT |
| 5276 | CCCTGTGCCCCTTTTCATG | CATGAAAAGGGGCACAGGG |
| 5277 | CCTGTGCCCCTTTTCATGG | CCATGAAAAGGGGCACAGG |
| 5278 | CTGTGCCCCTTTTCATGGT | ACCATGAAAAGGGGCACAG |
| 5279 | TGTGCCCCTTTTCATGGTA | TACCATGAAAAGGGGCACA |
| 5280 | GTGCCCCTTTTCATGGTAC | GTACCATGAAAAGGGGCAC |
| 5281 | TGCCCCTTTTCATGGTACC | GGTACCATGAAAAGGGGCA |
| 5282 | GCCCCTTTTCATGGTACCA | TGGTACCATGAAAAGGGGC |
| 5283 | CCCCTTTTCATGGTACCAG | CTGGTACCATGAAAAGGGG |
| 5284 | CCCTTTTCATGGTACCAGG | CCTGGTACCATGAAAAGGG |
| 5285 | CCTTTTCATGGTACCAGGC | GCCTGGTACCATGAAAAGG |
| 5286 | CTTTTCATGGTACCAGGCC | GGCCTGGTACCATGAAAAG |
| 5287 | TTTTCATGGTACCAGGCCC | GGGCCTGGTACCATGAAAA |
| 5288 | TTTCATGGTACCAGGCCCG | CGGGCCTGGTACCATGAAA |
| 5289 | TTCATGGTACCAGGCCCGC | GCGGGCCTGGTACCATGAA |
| 5290 | TCATGGTACCAGGCCCGCA | TGCGGGCCTGGTACCATGA |
| 5291 | CATGGTACCAGGCCCGCAC | GTGCGGGCCTGGTACCATG |
| 5292 | ATGGTACCAGGCCCGCACT | AGTGCGGGCCTGGTACCAT |
| 5293 | TGGTACCAGGCCCGCACTG | CAGTGCGGGCCTGGTACCA |
| 5294 | GGTACCAGGCCCGCACTGG | CCAGTGCGGGCCTGGTACC |
| 5295 | GTACCAGGCCCGCACTGGG | CCCAGTGCGGGCCTGGTAC |
| 5296 | TACCAGGCCCGCACTGGGG | CCCCAGTGCGGGCCTGGTA |
| 5297 | ACCAGGCCCGCACTGGGGG | CCCCCAGTGCGGGCCTGGT |
| 5298 | CCAGGCCCGCACTGGGGGC | GCCCCCAGTGCGGGCCTGG |
| 5299 | CAGGCCCGCACTGGGGGCA | TGCCCCCAGTGCGGGCCTG |
| 5300 | AGGCCCGCACTGGGGGCAA | TTGCCCCCAGTGCGGGCCT |
| 5301 | GGCCCGCACTGGGGGCAAT | ATTGCCCCCAGTGCGGGCC |
| 5302 | GCCCGCACTGGGGGCAATT | AATTGCCCCCAGTGCGGGC |
| 5303 | CCCGCACTGGGGGCAATTG | CAATTGCCCCCAGTGCGGG |
| 5304 | CCGCACTGGGGGCAATTGA | TCAATTGCCCCCAGTGCGG |
| 5305 | CGCACTGGGGGCAATTGAC | GTCAATTGCCCCCAGTGCG |
| 5306 | GCACTGGGGGCAATTGACT | AGTCAATTGCCCCCAGTGC |
| 5307 | CACTGGGGGCAATTGACTT | AAGTCAATTGCCCCCAGTG |
| 5308 | ACTGGGGGCAATTGACTTC | GAAGTCAATTGCCCCCAGT |
| 5309 | CTGGGGGCAATTGACTTCC | GGAAGTCAATTGCCCCCAG |
| 5310 | TGGGGGCAATTGACTTCCT | AGGAAGTCAATTGCCCCCA |
| 5311 | GGGGGCAATTGACTTCCTC | GAGGAAGTCAATTGCCCCC |
| 5312 | GGGGCAATTGACTTCCTCC | GGAGGAAGTCAATTGCCCC |
| 5313 | GGGCAATTGACTTCCTCCA | TGGAGGAAGTCAATTGCCC |
| 5314 | GGCAATTGACTTCCTCCAA | TTGGAGGAAGTCAATTGCC |
| 5315 | GCAATTGACTTCCTCCAAT | ATTGGAGGAAGTCAATTGC |
| 5316 | CAATTGACTTCCTCCAATC | GATTGGAGGAAGTCAATTG |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 5317 | AATTGACTTCCTCCAATCC | GGATTGGAGGAAGTCAATT |
| 5318 | ATTGACTTCCTCCAATCCC | GGGATTGGAGGAAGTCAAT |
| 5319 | TTGACTTCCTCCAATCCCC | GGGGATTGGAGGAAGTCAA |
| 5320 | TGACTTCCTCCAATCCCCA | TGGGGATTGGAGGAAGTCA |
| 5321 | GACTTCCTCCAATCCCCAC | GTGGGGATTGGAGGAAGTC |
| 5322 | ACTTCCTCCAATCCCCACT | AGTGGGGATTGGAGGAAGT |
| 5323 | CTTCCTCCAATCCCCACTC | GAGTGGGGATTGGAGGAAG |
| 5324 | TTCCTCCAATCCCCACTCC | GGAGTGGGGATTGGAGGAA |
| 5325 | TCCTCCAATCCCCACTCCT | AGGAGTGGGGATTGGAGGA |
| 5326 | CCTCCAATCCCCACTCCTC | GAGGAGTGGGGATTGGAGG |
| 5327 | CTCCAATCCCCACTCCTCC | GGAGGAGTGGGGATTGGAG |
| 5328 | TCCAATCCCCACTCCTCCG | CGGAGGAGTGGGGATTGGA |
| 5329 | CCAATCCCCACTCCTCCGA | TCGGAGGAGTGGGGATTGG |
| 5330 | CAATCCCCACTCCTCCGAG | CTCGGAGGAGTGGGGATTG |
| 5331 | AATCCCCACTCCTCCGAGA | TCTCGGAGGAGTGGGGATT |
| 5332 | ATCCCCACTCCTCCGAGAC | GTCTCGGAGGAGTGGGGAT |
| 5333 | TCCCCACTCCTCCGAGACC | GGTCTCGGAGGAGTGGGGA |
| 5334 | CCCCACTCCTCCGAGACCC | GGGTCTCGGAGGAGTGGGG |
| 5335 | CCCACTCCTCCGAGACCCA | TGGGTCTCGGAGGAGTGGG |
| 5336 | CCACTCCTCCGAGACCCAG | CTGGGTCTCGGAGGAGTGG |
| 5337 | CACTCCTCCGAGACCCAGG | CCTGGGTCTCGGAGGAGTG |
| 5338 | ACTCCTCCGAGACCCAGGA | TCCTGGGTCTCGGAGGAGT |
| 5339 | CTCCTCCGAGACCCAGGAG | CTCCTGGGTCTCGGAGGAG |
| 5340 | TCCTCCGAGACCCAGGAGA | TCTCCTGGGTCTCGGAGGA |
| 5341 | CCTCCGAGACCCAGGAGAC | GTCTCCTGGGTCTCGGAGG |
| 5342 | CTCCGAGACCCAGGAGACA | TGTCTCCTGGGTCTCGGAG |
| 5343 | TCCGAGACCCAGGAGACAA | TTGTCTCCTGGGTCTCGGA |
| 5344 | CCGAGACCCAGGAGACAAA | TTTGTCTCCTGGGTCTCGG |
| 5345 | CGAGACCCAGGAGACAAAC | GTTTGTCTCCTGGGTCTCG |
| 5346 | GAGACCCAGGAGACAAACA | TGTTTGTCTCCTGGGTCTC |
| 5347 | AGACCCAGGAGACAAACAG | CTGTTTGTCTCCTGGGTCT |
| 5348 | GACCCAGGAGACAAACAGC | GCTGTTTGTCTCCTGGGTC |
| 5349 | ACCCAGGAGACAAACAGCC | GGCTGTTTGTCTCCTGGGT |
| 5350 | CCCAGGAGACAAACAGCCC | GGGCTGTTTGTCTCCTGGG |
| 5351 | CCAGGAGACAAACAGCCCT | AGGGCTGTTTGTCTCCTGG |
| 5352 | CAGGAGACAAACAGCCCTT | AAGGGCTGTTTGTCTCCTG |
| 5353 | AGGAGACAAACAGCCCTTC | GAAGGGCTGTTTGTCTCCT |
| 5354 | GGAGACAAACAGCCCTTCC | GGAAGGGCTGTTTGTCTCC |
| 5355 | GAGACAAACAGCCCTTCCT | AGGAAGGGCTGTTTGTCTC |
| 5356 | AGACAAACAGCCCTTCCTT | AAGGAAGGGCTGTTTGTCT |
| 5357 | GACAAACAGCCCTTCCTTG | CAAGGAAGGGCTGTTTGTC |
| 5358 | ACAAACAGCCCTTCCTTGG | CCAAGGAAGGGCTGTTTGT |
| 5359 | CAAACAGCCCTTCCTTGGG | CCCAAGGAAGGGCTGTTTG |
| 5360 | AAACAGCCCTTCCTTGGGG | CCCCAAGGAAGGGCTGTTT |
| 5361 | AACAGCCCTTCCTTGGGGA | TCCCCAAGGAAGGGCTGTT |
| 5362 | ACAGCCCTTCCTTGGGGAA | TTCCCCAAGGAAGGGCTGT |
| 5363 | CAGCCCTTCCTTGGGGAAA | TTTCCCCAAGGAAGGGCTG |
| 5364 | AGCCCTTCCTTGGGGAAAC | GTTTCCCCAAGGAAGGGCT |
| 5365 | GCCCTTCCTTGGGGAAACT | AGTTTCCCCAAGGAAGGGC |
| 5366 | CCCTTCCTTGGGGAAACTT | AAGTTTCCCCAAGGAAGGG |
| 5367 | CCTTCCTTGGGGAAACTTG | CAAGTTTCCCCAAGGAAGG |
| 5368 | CTTCCTTGGGGAAACTTGG | CCAAGTTTCCCCAAGGAAG |
| 5369 | TTCCTTGGGGAAACTTGGG | CCCAAGTTTCCCCAAGGAA |
| 5370 | TCCTTGGGGAAACTTGGGA | TCCCAAGTTTCCCCAAGGA |
| 5371 | CCTTGGGGAAACTTGGGAA | TTCCCAAGTTTCCCCAAGG |
| 5372 | CTTGGGGAAACTTGGGAAT | ATTCCCAAGTTTCCCCAAG |
| 5373 | TTGGGGAAACTTGGGAATC | GATTCCCAAGTTTCCCCAA |
| 5374 | TGGGGAAACTTGGGAATCA | TGATTCCCAAGTTTCCCCA |
| 5375 | GGGGAAACTTGGGAATCAT | ATGATTCCCAAGTTTCCCC |
| 5376 | GGGAAACTTGGGAATCATT | AATGATTCCCAAGTTTCCC |
| 5377 | GGAAACTTGGGAATCATTC | GAATGATTCCCAAGTTTCC |
| 5378 | GAAACTTGGGAATCATTCT | AGAATGATTCCCAAGTTTC |
| 5379 | AAACTTGGGAATCATTCTG | CAGAATGATTCCCAAGTTT |
| 5380 | AACTTGGGAATCATTCTGG | CCAGAATGATTCCCAAGTT |
| 5381 | ACTTGGGAATCATTCTGGC | GCCAGAATGATTCCCAAGT |
| 5382 | CTTGGGAATCATTCTGGCT | AGCCAGAATGATTCCCAAG |
| 5383 | TTGGGAATCATTCTGGCTT | AAGCCAGAATGATTCCCAA |
| 5384 | TGGGAATCATTCTGGCTTA | TAAGCCAGAATGATTCCCA |
| 5385 | GGGAATCATTCTGGCTTAA | TTAAGCCAGAATGATTCCC |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 5386 | GGAATCATTCTGGCTTAAA | TTTAAGCCAGAATGATTCC |
| 5387 | GAATCATTCTGGCTTAAAC | GTTTAAGCCAGAATGATTC |
| 5388 | AATCATTCTGGCTTAAACA | TGTTTAAGCCAGAATGATT |
| 5389 | ATCATTCTGGCTTAAACAA | TTGTTTAAGCCAGAATGAT |
| 5390 | TCATTCTGGCTTAAACAAC | GTTGTTTAAGCCAGAATGA |
| 5391 | CATTCTGGCTTAAACAACA | TGTTGTTTAAGCCAGAATG |
| 5392 | ATTCTGGCTTAAACAACAC | GTGTTGTTTAAGCCAGAAT |
| 5393 | TTCTGGCTTAAACAACACC | GGTGTTGTTTAAGCCAGAA |
| 5394 | TCTGGCTTAAACAACACCT | AGGTGTTGTTTAAGCCAGA |
| 5395 | CTGGCTTAAACAACACCTC | GAGGTGTTGTTTAAGCCAG |
| 5396 | TGGCTTAAACAACACCTCC | GGAGGTGTTGTTTAAGCCA |
| 5397 | GGCTTAAACAACACCTCCT | AGGAGGTGTTGTTTAAGCC |
| 5398 | GCTTAAACAACACCTCCTC | GAGGAGGTGTTGTTTAAGC |
| 5399 | CTTAAACAACACCTCCTCC | GGAGGAGGTGTTGTTTAAG |
| 5400 | TTAAACAACACCTCCTCCT | AGGAGGAGGTGTTGTTTAA |
| 5401 | TAAACAACACCTCCTCCTG | CAGGAGGAGGTGTTGTTTA |
| 5402 | AAACAACACCTCCTCCTGC | GCAGGAGGAGGTGTTGTTT |
| 5403 | AACAACACCTCCTCCTGCT | AGCAGGAGGAGGTGTTGTT |
| 5404 | ACAACACCTCCTCCTGCTG | CAGCAGGAGGAGGTGTTGT |
| 5405 | CAACACCTCCTCCTGCTGC | GCAGCAGGAGGAGGTGTTG |
| 5406 | AACACCTCCTCCTGCTGCT | AGCAGCAGGAGGAGGTGTT |
| 5407 | ACACCTCCTCCTGCTGCTC | GAGCAGCAGGAGGAGGTGT |
| 5408 | CACCTCCTCCTGCTGCTCA | TGAGCAGCAGGAGGAGGTG |
| 5409 | ACCTCCTCCTGCTGCTCAC | GTGAGCAGCAGGAGGAGGT |
| 5410 | CCTCCTCCTGCTGCTCACT | AGTGAGCAGCAGGAGGAGG |
| 5411 | CTCCTCCTGCTGCTCACTC | GAGTGAGCAGCAGGAGGAG |
| 5412 | TCCTCCTGCTGCTCACTCC | GGAGTGAGCAGCAGGAGGA |
| 5413 | CCTCCTGCTGCTCACTCCC | GGGAGTGAGCAGCAGGAGG |
| 5414 | CTCCTGCTGCTCACTCCCG | CGGGAGTGAGCAGCAGGAG |
| 5415 | TCCTGCTGCTCACTCCCGC | GCGGGAGTGAGCAGCAGGA |
| 5416 | CCTGCTGCTCACTCCCGCT | AGCGGGAGTGAGCAGCAGG |
| 5417 | CTGCTGCTCACTCCCGCTG | CAGCGGGAGTGAGCAGCAG |
| 5418 | TGCTGCTCACTCCCGCTGA | TCAGCGGGAGTGAGCAGCA |
| 5419 | GCTGCTCACTCCCGCTGAG | CTCAGCGGGAGTGAGCAGC |
| 5420 | CTGCTCACTCCCGCTGAGC | GCTCAGCGGGAGTGAGCAG |
| 5421 | TGCTCACTCCCGCTGAGCC | GGCTCAGCGGGAGTGAGCA |
| 5422 | GCTCACTCCCGCTGAGCCC | GGGCTCAGCGGGAGTGAGC |
| 5423 | CTCACTCCCGCTGAGCCCA | TGGGCTCAGCGGGAGTGAG |
| 5424 | TCACTCCCGCTGAGCCCAC | GTGGGCTCAGCGGGAGTGA |
| 5425 | CACTCCCGCTGAGCCCACT | AGTGGGCTCAGCGGGAGTG |
| 5426 | ACTCCCGCTGAGCCCACTC | GAGTGGGCTCAGCGGGAGT |
| 5427 | CTCCCGCTGAGCCCACTCT | AGAGTGGGCTCAGCGGGAG |
| 5428 | TCCCGCTGAGCCCACTCTA | TAGAGTGGGCTCAGCGGGA |
| 5429 | CCCGCTGAGCCCACTCTAC | GTAGAGTGGGCTCAGCGGG |
| 5430 | CCGCTGAGCCCACTCTACT | AGTAGAGTGGGCTCAGCGG |
| 5431 | CGCTGAGCCCACTCTACTG | CAGTAGAGTGGGCTCAGCG |
| 5432 | GCTGAGCCCACTCTACTGC | GCAGTAGAGTGGGCTCAGC |
| 5433 | CTGAGCCCACTCTACTGCC | GGCAGTAGAGTGGGCTCAG |
| 5434 | TGAGCCCACTCTACTGCCC | GGGCAGTAGAGTGGGCTCA |
| 5435 | GAGCCCACTCTACTGCCCC | GGGGCAGTAGAGTGGGCTC |
| 5436 | AGCCCACTCTACTGCCCCA | TGGGGCAGTAGAGTGGGCT |
| 5437 | GCCCACTCTACTGCCCCAG | CTGGGGCAGTAGAGTGGGC |
| 5438 | CCCACTCTACTGCCCCAGC | GCTGGGGCAGTAGAGTGGG |
| 5439 | CCACTCTACTGCCCCAGCT | AGCTGGGGCAGTAGAGTGG |
| 5440 | CACTCTACTGCCCCAGCTC | GAGCTGGGGCAGTAGAGTG |
| 5441 | ACTCTACTGCCCCAGCTCC | GGAGCTGGGGCAGTAGAGT |
| 5442 | CTCTACTGCCCCAGCTCCG | CGGAGCTGGGGCAGTAGAG |
| 5443 | TCTACTGCCCCAGCTCCGT | ACGGAGCTGGGGCAGTAGA |
| 5444 | CTACTGCCCCAGCTCCGTT | AACGGAGCTGGGGCAGTAG |
| 5445 | TACTGCCCCAGCTCCGTTT | AAACGGAGCTGGGGCAGTA |
| 5446 | ACTGCCCCAGCTCCGTTTC | GAAACGGAGCTGGGGCAGT |
| 5447 | CTGCCCCAGCTCCGTTTCT | AGAAACGGAGCTGGGGCAG |
| 5448 | TGCCCCAGCTCCGTTTCTA | TAGAAACGGAGCTGGGGCA |
| 5449 | GCCCCAGCTCCGTTTCTAC | GTAGAAACGGAGCTGGGGC |
| 5450 | CCCCAGCTCCGTTTCTACC | GGTAGAAACGGAGCTGGGG |
| 5451 | CCCAGCTCCGTTTCTACCA | TGGTAGAAACGGAGCTGGG |
| 5452 | CCAGCTCCGTTTCTACCAC | GTGGTAGAAACGGAGCTGG |
| 5453 | CAGCTCCGTTTCTACCACC | GGTGGTAGAAACGGAGCTG |
| 5454 | AGCTCCGTTTCTACCACCG | CGGTGGTAGAAACGGAGCT |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 5455 | GCTCCGTTTCTACCACCGC | GCGGTGGTAGAAACGGAGC |
| 5456 | CTCCGTTTCTACCACCGCA | TGCGGTGGTAGAAACGGAG |
| 5457 | TCCGTTTCTACCACCGCAT | ATGCGGTGGTAGAAACGGA |
| 5458 | CCGTTTCTACCACCGCATC | GATGCGGTGGTAGAAACGG |
| 5459 | CGTTTCTACCACCGCATCC | GGATGCGGTGGTAGAAACG |
| 5460 | GTTTCTACCACCGCATCCT | AGGATGCGGTGGTAGAAAC |
| 5461 | TTTCTACCACCGCATCCTC | GAGGATGCGGTGGTAGAAA |
| 5462 | TTCTACCACCGCATCCTCA | TGAGGATGCGGTGGTAGAA |
| 5463 | TCTACCACCGCATCCTCAC | GTGAGGATGCGGTGGTAGA |
| 5464 | CTACCACCGCATCCTCACT | AGTGAGGATGCGGTGGTAG |
| 5465 | TACCACCGCATCCTCACTG | CAGTGAGGATGCGGTGGTA |
| 5466 | ACCACCGCATCCTCACTGG | CCAGTGAGGATGCGGTGGT |
| 5467 | CCACCGCATCCTCACTGGG | CCCAGTGAGGATGCGGTGG |
| 5468 | CACCGCATCCTCACTGGGC | GCCCAGTGAGGATGCGGTG |
| 5469 | ACCGCATCCTCACTGGGCT | AGCCCAGTGAGGATGCGGT |
| 5470 | CCGCATCCTCACTGGGCTC | GAGCCCAGTGAGGATGCGG |
| 5471 | CGCATCCTCACTGGGCTCA | TGAGCCCAGTGAGGATGCG |
| 5472 | GCATCCTCACTGGGCTCAC | GTGAGCCCAGTGAGGATGC |
| 5473 | CATCCTCACTGGGCTCACT | AGTGAGCCCAGTGAGGATG |
| 5474 | ATCCTCACTGGGCTCACTG | CAGTGAGCCCAGTGAGGAT |
| 5475 | TCCTCACTGGGCTCACTGC | GCAGTGAGCCCAGTGAGGA |
| 5476 | CCTCACTGGGCTCACTGCA | TGCAGTGAGCCCAGTGAGG |
| 5477 | CTCACTGGGCTCACTGCAG | CTGCAGTGAGCCCAGTGAG |
| 5478 | TCACTGGGCTCACTGCAGG | CCTGCAGTGAGCCCAGTGA |
| 5479 | CACTGGGCTCACTGCAGGC | GCCTGCAGTGAGCCCAGTG |
| 5480 | ACTGGGCTCACTGCAGGCA | TGCCTGCAGTGAGCCCAGT |
| 5481 | CTGGGCTCACTGCAGGCAT | ATGCCTGCAGTGAGCCCAG |
| 5482 | TGGGCTCACTGCAGGCATG | CATGCCTGCAGTGAGCCCA |
| 5483 | GGGCTCACTGCAGGCATGC | GCATGCCTGCAGTGAGCCC |
| 5484 | GGCTCACTGCAGGCATGCT | AGCATGCCTGCAGTGAGCC |
| 5485 | GCTCACTGCAGGCATGCTG | CAGCATGCCTGCAGTGAGC |
| 5486 | CTCACTGCAGGCATGCTGA | TCAGCATGCCTGCAGTGAG |
| 5487 | TCACTGCAGGCATGCTGAA | TTCAGCATGCCTGCAGTGA |
| 5488 | CACTGCAGGCATGCTGAAC | GTTCAGCATGCCTGCAGTG |
| 5489 | ACTGCAGGCATGCTGAACA | TGTTCAGCATGCCTGCAGT |
| 5490 | CTGCAGGCATGCTGAACAA | TTGTTCAGCATGCCTGCAG |
| 5491 | TGCAGGCATGCTGAACAAG | CTTGTTCAGCATGCCTGCA |
| 5492 | GCAGGCATGCTGAACAAGG | CCTTGTTCAGCATGCCTGC |
| 5493 | CAGGCATGCTGAACAAGGG | CCCTTGTTCAGCATGCCTG |
| 5494 | AGGCATGCTGAACAAGGGG | CCCCTTGTTCAGCATGCCT |
| 5495 | GGCATGCTGAACAAGGGGC | GCCCCTTGTTCAGCATGCC |
| 5496 | GCATGCTGAACAAGGGGCC | GGCCCCTTGTTCAGCATGC |
| 5497 | CATGCTGAACAAGGGGCCT | AGGCCCCTTGTTCAGCATG |
| 5498 | ATGCTGAACAAGGGGCCTC | GAGGCCCCTTGTTCAGCAT |
| 5499 | TGCTGAACAAGGGGCCTCC | GGAGGCCCCTTGTTCAGCA |
| 5500 | GCTGAACAAGGGGCCTCCA | TGGAGGCCCCTTGTTCAGC |
| 5501 | CTGAACAAGGGGCCTCCAA | TTGGAGGCCCCTTGTTCAG |
| 5502 | TGAACAAGGGGCCTCCAAC | GTTGGAGGCCCCTTGTTCA |
| 5503 | GAACAAGGGGCCTCCAACC | GGTTGGAGGCCCCTTGTTC |
| 5504 | AACAAGGGGCCTCCAACCT | AGGTTGGAGGCCCCTTGTT |
| 5505 | ACAAGGGGCCTCCAACCTT | AAGGTTGGAGGCCCCTTGT |
| 5506 | CAAGGGGCCTCCAACCTTC | GAAGGTTGGAGGCCCCTTG |
| 5507 | AAGGGGCCTCCAACCTTCT | AGAAGGTTGGAGGCCCCTT |
| 5508 | AGGGGCCTCCAACCTTCTG | CAGAAGGTTGGAGGCCCCT |
| 5509 | GGGGCCTCCAACCTTCTGC | GCAGAAGGTTGGAGGCCCC |
| 5510 | GGGCCTCCAACCTTCTGCC | GGCAGAAGGTTGGAGGCCC |
| 5511 | GGCCTCCAACCTTCTGCCC | GGGCAGAAGGTTGGAGGCC |
| 5512 | GCCTCCAACCTTCTGCCCT | AGGGCAGAAGGTTGGAGGC |
| 5513 | CCTCCAACCTTCTGCCCTC | GAGGGCAGAAGGTTGGAGG |
| 5514 | CTCCAACCTTCTGCCCTCC | GGAGGGCAGAAGGTTGGAG |
| 5515 | TCCAACCTTCTGCCCTCCT | AGGAGGGCAGAAGGTTGGA |
| 5516 | CCAACCTTCTGCCCTCCTG | CAGGAGGGCAGAAGGTTGG |
| 5517 | CAACCTTCTGCCCTCCTGC | GCAGGAGGGCAGAAGGTTG |
| 5518 | AACCTTCTGCCCTCCTGCC | GGCAGGAGGGCAGAAGGTT |
| 5519 | ACCTTCTGCCCTCCTGCCA | TGGCAGGAGGGCAGAAGGT |
| 5520 | CCTTCTGCCCTCCTGCCAA | TTGGCAGGAGGGCAGAAGG |
| 5521 | CTTCTGCCCTCCTGCCAAA | TTTGGCAGGAGGGCAGAAG |
| 5522 | TTCTGCCCTCCTGCCAAAA | TTTTGGCAGGAGGGCAGAA |
| 5523 | TCTGCCCTCCTGCCAAAAG | CTTTTGGCAGGAGGGCAGA |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X - 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 5524 | CTGCCCTCCTGCCAAAAGA | TCTTTTGGCAGGAGGGCAG |
| 5525 | TGCCCTCCTGCCAAAAGAT | ATCTTTTGGCAGGAGGGCA |
| 5526 | GCCCTCCTGCCAAAAGATC | GATCTTTTGGCAGGAGGGC |
| 5527 | CCCTCCTGCCAAAAGATCT | AGATCTTTTGGCAGGAGGG |
| 5528 | CCTCCTGCCAAAAGATCTG | CAGATCTTTTGGCAGGAGG |
| 5529 | CTCCTGCCAAAAGATCTGG | CCAGATCTTTTGGCAGGAG |
| 5530 | TCCTGCCAAAAGATCTGGG | CCCAGATCTTTTGGCAGGA |
| 5531 | CCTGCCAAAAGATCTGGGG | CCCCAGATCTTTTGGCAGG |
| 5532 | CTGCCAAAAGATCTGGGGA | TCCCCAGATCTTTTGGCAG |
| 5533 | TGCCAAAAGATCTGGGGAG | CTCCCCAGATCTTTTGGCA |
| 5534 | GCCAAAAGATCTGGGGAGT | ACTCCCCAGATCTTTTGGC |
| 5535 | CCAAAAGATCTGGGGAGTG | CACTCCCCAGATCTTTTGG |
| 5536 | CAAAAGATCTGGGGAGTGT | ACACTCCCCAGATCTTTTG |
| 5537 | AAAAGATCTGGGGAGTGTG | CACACTCCCCAGATCTTTT |
| 5538 | AAAGATCTGGGGAGTGTGA | TCACACTCCCCAGATCTTT |
| 5539 | AAGATCTGGGGAGTGTGAG | CTCACACTCCCCAGATCTT |
| 5540 | AGATCTGGGGAGTGTGAGG | CCTCACACTCCCCAGATCT |
| 5541 | GATCTGGGGAGTGTGAGGA | TCCTCACACTCCCCAGATC |
| 5542 | ATCTGGGGAGTGTGAGGAG | CTCCTCACACTCCCCAGAT |
| 5543 | TCTGGGGAGTGTGAGGAGA | TCTCCTCACACTCCCCAGA |
| 5544 | CTGGGGAGTGTGAGGAGAG | CTCTCCTCACACTCCCCAG |
| 5545 | TGGGGAGTGTGAGGAGAGG | CCTCTCCTCACACTCCCCA |
| 5546 | GGGGAGTGTGAGGAGAGGG | CCCTCTCCTCACACTCCCC |
| 5547 | GGGAGTGTGAGGAGAGGGT | ACCCTCTCCTCACACTCCC |
| 5548 | GGAGTGTGAGGAGAGGGTG | CACCCTCTCCTCACACTCC |
| 5549 | GAGTGTGAGGAGAGGGTGG | CCACCCTCTCCTCACACTC |
| 5550 | AGTGTGAGGAGAGGGTGGC | GCCACCCTCTCCTCACACT |
| 5551 | GTGTGAGGAGAGGGTGGCA | TGCCACCCTCTCCTCACAC |
| 5552 | TGTGAGGAGAGGGTGGCAT | ATGCCACCCTCTCCTCACA |
| 5553 | GTGAGGAGAGGGTGGCATC | GATGCCACCCTCTCCTCAC |
| 5554 | TGAGGAGAGGGTGGCATCA | TGATGCCACCCTCTCCTCA |
| 5555 | GAGGAGAGGGTGGCATCAG | CTGATGCCACCCTCTCCTC |
| 5556 | AGGAGAGGGTGGCATCAGG | CCTGATGCCACCCTCTCCT |
| 5557 | GGAGAGGGTGGCATCAGGA | TCCTGATGCCACCCTCTCC |
| 5558 | GAGAGGGTGGCATCAGGAG | CTCCTGATGCCACCCTCTC |
| 5559 | AGAGGGTGGCATCAGGAGC | GCTCCTGATGCCACCCTCT |
| 5560 | GAGGGTGGCATCAGGAGCT | AGCTCCTGATGCCACCCTC |
| 5561 | AGGGTGGCATCAGGAGCTG | CAGCTCCTGATGCCACCCT |
| 5562 | GGGTGGCATCAGGAGCTGC | GCAGCTCCTGATGCCACCC |
| 5563 | GGTGGCATCAGGAGCTGCT | AGCAGCTCCTGATGCCACC |
| 5564 | GTGGCATCAGGAGCTGCTC | GAGCAGCTCCTGATGCCAC |
| 5565 | TGGCATCAGGAGCTGCTCA | TGAGCAGCTCCTGATGCCA |
| 5566 | GGCATCAGGAGCTGCTCAG | CTGAGCAGCTCCTGATGCC |
| 5567 | GCATCAGGAGCTGCTCAGG | CCTGAGCAGCTCCTGATGC |
| 5568 | CATCAGGAGCTGCTCAGGC | GCCTGAGCAGCTCCTGATG |
| 5569 | ATCAGGAGCTGCTCAGGCT | AGCCTGAGCAGCTCCTGAT |
| 5570 | TCAGGAGCTGCTCAGGCTT | AAGCCTGAGCAGCTCCTGA |
| 5571 | CAGGAGCTGCTCAGGCTTG | CAAGCCTGAGCAGCTCCTG |
| 5572 | AGGAGCTGCTCAGGCTTGG | CCAAGCCTGAGCAGCTCCT |
| 5573 | GGAGCTGCTCAGGCTTGGC | GCCAAGCCTGAGCAGCTCC |
| 5574 | GAGCTGCTCAGGCTTGGCG | CGCCAAGCCTGAGCAGCTC |
| 5575 | AGCTGCTCAGGCTTGGCGG | CCGCCAAGCCTGAGCAGCT |
| 5576 | GCTGCTCAGGCTTGGCGGA | TCCGCCAAGCCTGAGCAGC |
| 5577 | CTGCTCAGGCTTGGCGGAG | CTCCGCCAAGCCTGAGCAG |
| 5578 | TGCTCAGGCTTGGCGGAGG | CCTCCGCCAAGCCTGAGCA |
| 5579 | GCTCAGGCTTGGCGGAGGG | CCCTCCGCCAAGCCTGAGC |
| 5580 | CTCAGGCTTGGCGGAGGGA | TCCCTCCGCCAAGCCTGAG |
| 5581 | TCAGGCTTGGCGGAGGGAG | CTCCCTCCGCCAAGCCTGA |
| 5582 | CAGGCTTGGCGGAGGGAGC | GCTCCCTCCGCCAAGCCTG |
| 5583 | AGGCTTGGCGGAGGGAGCG | CGCTCCCTCCGCCAAGCCT |
| 5584 | GGCTTGGCGGAGGGAGCGG | CCGCTCCCTCCGCCAAGCC |
| 5585 | GCTTGGCGGAGGGAGCGGC | GCCGCTCCCTCCGCCAAGC |
| 5586 | CTTGGCGGAGGGAGCGGCA | TGCCGCTCCCTCCGCCAAG |
| 5587 | TTGGCGGAGGGAGCGGCAT | ATGCCGCTCCCTCCGCCAA |
| 5588 | TGGCGGAGGGAGCGGCATG | CATGCCGCTCCCTCCGCCA |
| 5589 | GGCGGAGGGAGCGGCATGG | CCATGCCGCTCCCTCCGCC |
| 5590 | GCGGAGGGAGCGGCATGGG | CCCATGCCGCTCCCTCCGC |
| 5591 | CGGAGGGAGCGGCATGGGC | GCCCATGCCGCTCCCTCCG |
| 5592 | GGAGGGAGCGGCATGGGCG | CGCCCATGCCGCTCCCTCC |

TABLE 1-continued cDNA Human Hairless 19-mer Target Sequences and
Complement Referenced to NM_005144-
*Homo sapiens* hairless homolog (mouse) (HR),
transcript variant 1, complete mRNA (1-5699 bp).
(SEQ ID NO: for Sense equals (2X − 1) SEQ ID
NO: for Antisense equals (2X), (e.g. where
X = 1 Sense has SEQ ID NO: 1 and Antisense
has SEQ ID NO: 2)

| X | Sense (5'-3') | Antisense (5'-3') |
|---|---|---|
| 5593 | GAGGGAGCGGCATGGGCGA | TCGCCCATGCCGCTCCCTC |
| 5594 | AGGGAGCGGCATGGGCGAT | ATCGCCCATGCCGCTCCCT |
| 5595 | GGGAGCGGCATGGGCGATG | CATCGCCCATGCCGCTCCC |
| 5596 | GGAGCGGCATGGGCGATGT | ACATCGCCCATGCCGCTCC |
| 5597 | GAGCGGCATGGGCGATGTC | GACATCGCCCATGCCGCTC |
| 5598 | AGCGGCATGGGCGATGTCA | TGACATCGCCCATGCCGCT |
| 5599 | GCGGCATGGGCGATGTCAC | GTGACATCGCCCATGCCGC |
| 5600 | CGGCATGGGCGATGTCACT | AGTGACATCGCCCATGCCG |
| 5601 | GGCATGGGCGATGTCACTC | GAGTGACATCGCCCATGCC |
| 5602 | GCATGGGCGATGTCACTCA | TGAGTGACATCGCCCATGC |
| 5603 | CATGGGCGATGTCACTCAG | CTGAGTGACATCGCCCATG |
| 5604 | ATGGGCGATGTCACTCAGC | GCTGAGTGACATCGCCCAT |
| 5605 | TGGGCGATGTCACTCAGCC | GGCTGAGTGACATCGCCCA |
| 5606 | GGGCGATGTCACTCAGCCC | GGGCTGAGTGACATCGCCC |
| 5607 | GGCGATGTCACTCAGCCCC | GGGGCTGAGTGACATCGCC |
| 5608 | GCGATGTCACTCAGCCCCT | AGGGGCTGAGTGACATCGC |
| 5609 | CGATGTCACTCAGCCCCTT | AAGGGGCTGAGTGACATCG |
| 5610 | GATGTCACTCAGCCCCTTC | GAAGGGGCTGAGTGACATC |
| 5611 | ATGTCACTCAGCCCCTTCC | GGAAGGGGCTGAGTGACAT |
| 5612 | TGTCACTCAGCCCCTTCCC | GGGAAGGGGCTGAGTGACA |
| 5613 | GTCACTCAGCCCCTTCCCG | CGGGAAGGGGCTGAGTGAC |
| 5614 | TCACTCAGCCCCTTCCCGG | CCGGGAAGGGGCTGAGTGA |
| 5615 | CACTCAGCCCCTTCCCGGT | ACCGGGAAGGGGCTGAGTG |
| 5616 | ACTCAGCCCCTTCCCGGTC | GACCGGGAAGGGGCTGAGT |
| 5617 | CTCAGCCCCTTCCCGGTCC | GGACCGGGAAGGGGCTGAG |
| 5618 | TCAGCCCCTTCCCGGTCCG | CGGACCGGGAAGGGGCTGA |
| 5619 | CAGCCCCTTCCCGGTCCGC | GCGGACCGGGAAGGGGCTG |
| 5620 | AGCCCCTTCCCGGTCCGCC | GGCGGACCGGGAAGGGGCT |
| 5621 | GCCCCTTCCCGGTCCGCCC | GGGCGGACCGGGAAGGGGC |
| 5622 | CCCCTTCCCGGTCCGCCCG | CGGGCGGACCGGGAAGGGG |
| 5623 | CCCTTCCCGGTCCGCCCGC | GCGGGCGGACCGGGAAGGG |
| 5624 | CCTTCCCGGTCCGCCCGCT | AGCGGGCGGACCGGGAAGG |
| 5625 | CTTCCCGGTCCGCCCGCTT | AAGCGGGCGGACCGGGAAG |
| 5626 | TTCCCGGTCCGCCCGCTTC | GAAGCGGGCGGACCGGGAA |
| 5627 | TCCCGGTCCGCCCGCTTCC | GGAAGCGGGCGGACCGGGA |
| 5628 | CCCGGTCCGCCCGCTTCCC | GGGAAGCGGGCGGACCGGG |
| 5629 | CCGGTCCGCCCGCTTCCCT | AGGGAAGCGGGCGGACCGG |
| 5630 | CGGTCCGCCCGCTTCCCTC | GAGGGAAGCGGGCGGACCG |
| 5631 | GGTCCGCCCGCTTCCCTCC | GGAGGGAAGCGGGCGGACC |
| 5632 | GTCCGCCCGCTTCCCTCCT | AGGAGGGAAGCGGGCGGAC |
| 5633 | TCCGCCCGCTTCCCTCCTT | AAGGAGGGAAGCGGGCGGA |
| 5634 | CCGCCCGCTTCCCTCCTTC | GAAGGAGGGAAGCGGGCGG |
| 5635 | CGCCCGCTTCCCTCCTTCA | TGAAGGAGGGAAGCGGGCG |
| 5636 | GCCCGCTTCCCTCCTTCAT | ATGAAGGAGGGAAGCGGGC |
| 5637 | CCCGCTTCCCTCCTTCATG | CATGAAGGAGGGAAGCGGG |
| 5638 | CCGCTTCCCTCCTTCATGA | TCATGAAGGAGGGAAGCGG |
| 5639 | CGCTTCCCTCCTTCATGAT | ATCATGAAGGAGGGAAGCG |
| 5640 | GCTTCCCTCCTTCATGATT | AATCATGAAGGAGGGAAGC |
| 5641 | CTTCCCTCCTTCATGATTT | AAATCATGAAGGAGGGAAG |
| 5642 | TTCCCTCCTTCATGATTTC | GAAATCATGAAGGAGGGAA |
| 5643 | TCCCTCCTTCATGATTTCC | GGAAATCATGAAGGAGGGA |
| 5644 | CCCTCCTTCATGATTTCCA | TGGAAATCATGAAGGAGGG |
| 5645 | CCTCCTTCATGATTTCCAT | ATGGAAATCATGAAGGAGG |
| 5646 | CTCCTTCATGATTTCCATT | AATGGAAATCATGAAGGAG |
| 5647 | TCCTTCATGATTTCCATTA | TAATGGAAATCATGAAGGA |
| 5648 | CCTTCATGATTTCCATTAA | TTAATGGAAATCATGAAGG |
| 5649 | CTTCATGATTTCCATTAAA | TTTAATGGAAATCATGAAG |
| 5650 | TTCATGATTTCCATTAAAG | CTTTAATGGAAATCATGAA |
| 5651 | TCATGATTTCCATTAAAGT | ACTTTAATGGAAATCATGA |
| 5652 | CATGATTTCCATTAAAGTC | GACTTTAATGGAAATCATG |
| 5653 | ATGATTTCCATTAAAGTCT | AGACTTTAATGGAAATCAT |
| 5654 | TGATTTCCATTAAAGTCTG | CAGACTTTAATGGAAATCA |
| 5655 | GATTTCCATTAAAGTCTGT | ACAGACTTTAATGGAAATC |
| 5656 | ATTTCCATTAAAGTCTGTT | AACAGACTTTAATGGAAAT |
| 5657 | TTTCCATTAAAGTCTGTTG | CAACAGACTTTAATGGAAA |
| 5658 | TTCCATTAAAGTCTGTTGT | ACAACAGACTTTAATGGAA |
| 5659 | TCCATTAAAGTCTGTTGTT | AACAACAGACTTTAATGGA |
| 5660 | CCATTAAAGTCTGTTGTTT | AAACAACAGACTTTAATGG |
| 5661 | CATTAAAGTCTGTTGTTTT | AAAACAACAGACTTTAATG |

TABLE 1-continued cDNA Human Hairless 19-mer Target Sequences and Complement Referenced to NM_005144- *Homo sapiens* hairless homolog (mouse) (HR), transcript variant 1, complete mRNA (1-5699 bp). (SEQ ID NO: for Sense equals (2X − 1) SEQ ID NO: for Antisense equals (2X), (e.g. where X = 1 Sense has SEQ ID NO: 1 and Antisense has SEQ ID NO: 2)

| X | Sense (5'-3') | Antisense (5'-3') |
|---|---|---|
| 5662 | ATTAAAGTCTGTTGTTTTG | CAAAACAACAGACTTTAAT |
| 5663 | TTAAAGTCTGTTGTTTTGT | ACAAAACAACAGACTTTAA |
| 5664 | TAAAGTCTGTTGTTTTGTG | CACAAAACAACAGACTTTA |

TABLE 2

Human and Mouse Hairless Polymorphisms

| Gene | mRNA (bp) | Accession number | Position (nt) | From/To | Comments |
|---|---|---|---|---|---|
| Human Hairless | 5699 | NM_005144 | 867 | C/A | *Homo sapiens* hairless homolog (mouse) (HR), transcript variant 1, mRNA |
|  |  |  | 1330 | T/G |  |
|  |  |  | 1677 | C/T |  |
|  |  |  | 1686 | C/T |  |
|  |  |  | 2437 | C/A |  |
|  |  |  | 2491 | G/A |  |
|  |  |  | 2671 | G/A |  |
|  |  |  | 2672 | C/T |  |
|  |  |  | 2786 | T/C |  |
|  |  |  | 3058 | T/C |  |
|  |  |  | 3064 | A/G |  |
|  |  |  | 3208 | C/T |  |
|  |  |  | 3253 | G/A |  |
|  |  |  | 3340 | G/A |  |
|  |  |  | 3695 | C/T |  |
|  |  |  | 3812 | A/T |  |
|  |  |  | 3851 | C/T |  |
|  |  |  | 3854 | C/T |  |
|  |  |  | 4545 | A/G |  |
|  |  |  | 4715 | C/G |  |
|  |  |  | 4820 | C/A |  |
| Mouse hairless | 5599 | NM_021877 | 402 | A/G | *Mus musculus* hairless (hr), mRNA |
|  |  |  | 535 | C/A |  |
|  |  |  | 1603 | G/A |  |
|  |  |  | 1681 | A/G |  |
|  |  |  | 1895 | C/T |  |
|  |  |  | 2251 | G/A |  |
|  |  |  | 2482 | T/C |  |
|  |  |  | 2569 | T/C |  |
|  |  |  | 2917 | T/C |  |
|  |  |  | 3232 | C/T |  |
|  |  |  | 3371 | A/T |  |
|  |  |  | 3610 | C/A |  |
|  |  |  | 4065 | T/G |  |

TABLE 3

Exemplary siRNA target sequences in mammalian hairless mRNAs (shown as cDNA sequences)

| Start | Sequence | Region |
|---|---|---|
| Mouse (*Mus musculus*) hairless (hr), mRNA, NM_021877 | | |
| 2023 | GCAGGAGACACCGGAGACAATCATA (SEQ ID NO: 11373) | ORF |
| 2495 | GGACTCTTCAACACCCACTGGAGAT (SEQ ID NO: 11374) | ORF |

TABLE 3-continued

Exemplary siRNA target sequences in mammalian hairless mRNAs (shown as cDNA sequences)

| Start | Sequence | Region |
|---|---|---|
| 2713 | CCAAGTCTGGGCCAAGTTTGACATT (SEQ ID NO: 11375) | ORF |
| 2831 | CCACAACCTTCCTGCAATGGAGATT (SEQ ID NO: 11376) | ORF |
| 2844 | GCAATGGAGATTCCAATCGGACCAA (SEQ ID NO: 11377) | ORF |
| 3042 | CCAGTGATGACCGCATTACCAACAT (SEQ ID NO: 11378) | ORF |
| 3085 | GCAGGTAGTAGAACGGAAGATCCAA (SEQ ID NO: 11379) | ORF |
| 3750 | CCTGGTATCGAGCACAGAAAGATTT (SEQ ID NO: 11380) | ORF |
| 4068 | GCACAATCAGTGTCACTCAGCACTT (SEQ ID NO: 11381) | ORF |
| *Homo sapiens* hairless homolog (mouse) (HR), transcript variant 1, mRNA, NM_005144 | | |
| 2151 | GCGGAACCTGGGTTGTTTGGCTTAA (SEQ ID NO: 11382) | ORF |
| 2831 | GGACACATCGATAGGGAACAAGGAT (SEQ ID NO: 11383) | ORF |
| 3626 | CCCAACTCCACAACCTTCCTGCAAT (SEQ ID NO: 11384) | ORF |
| 3796 | GCCATGAGCGAATACACATGGCCTT (SEQ ID NO: 11385) | ORF |
| 4092 | CCTGTGTTGGTGTCAGGGATCCAAA (SEQ ID NO: 11386) | ORF |
| Rat (*Rattus norvegicus*) hairless (hr) mRNA, NM-024364 | | |
| 913 | CCAAGATTCTAGAGCGAGCTCCCTT (SEQ ID NO: 11387) | ORF |
| 2045 | GGATTCCTGTGCCACTTCTGAGGAA (SEQ ID NO: 11388) | ORF |
| 2601 | CCACAACTTTCCTGCAATGGAGATT (SEQ ID NO: 11389) | ORF |
| 2614 | GCAATGGAGATTCCAATCGGACCAA (SEQ ID NO: 11390) | ORF |
| 2729 | GCTGCTAGCCTCTACAGCTGTCAAA (SEQ ID NO: 11391) | ORF |
| 2765 | GCATGAGCGGATTCACATGGCCTTT (SEQ ID NO: 11392) | ORF |
| 2812 | CCAGTGATGACCGCATTACCAACAT (SEQ ID NO: 11393) | ORF |
| 2855 | GCAGGTAGTAGAACGGAAGATCCAA (SEQ ID NO: 11394) | ORF |
| 3520 | CCTGGTACCGAGCACAGAAAGATTT (SEQ ID NO: 11395) | ORF |
| 3838 | GCACAATCAGTGTCACTCAGCACTT (SEQ ID NO: 11396) | ORF |

TABLE 3-continued

Exemplary siRNA target sequences in mammalian hairless mRNAs (shown as cDNA sequences)

| Start | Sequence | Region |
|---|---|---|
| Monkey (*Macaca mulatto*) hairless mRNA, complete cds, AF_361864 | | |
| 1152 | GCACTCGGAGCAGTTTGAATGTCCA (SEQ ID NO: 11397) | ORF |
| 1344 | GGACACATCGATAGGGAACAAGGAG (SEQ ID NO: 11398) | ORF |
| 2025 | GCACCAGGTCTGGGTCAAGTTTGAT (SEQ ID NO: 11399) | ORF |
| 2172 | CCACAGGACCAAGAGCATCAAAGAG (SEQ ID NO: 113400) | ORF |
| 2605 | CCTGTGTTGGTGTCAGGGATCCAAA (SEQ ID NO: 11401) | ORF |
| Pig (*Sus scrofa*) hairless mRNA, partical cds, AY279972 | | |
| 490 | CAGATATGGGCAGCCTATGGTGTGA (SEQ ID NO: 11402) | ORF |
| 918 | CCTGGTAAGCACAGTGAGCATCACT (SEQ ID NO: 11403) | ORF |
| 921 | GGTAAGCACAGTGAGCATCACTCAG (SEQ ID NO: 11404) | ORF |
| 926 | GCACAGTGAGCATCACTCAGCACTT (SEQ ID NO: 11405) | ORF |
| 927 | CACAGTGAGCATCACTCAGCACTTC (SEQ ID NO: 11406) | ORF |
| Sheep (*Ovis aries*) hairless mRNA, partial cds, AY130969 | | |
| 366 | GGATCCTGAGCATAATGGTGGCCAT (SEQ ID NO: 11407) | ORF |
| 1140 | GCTTACTCGACACTCTGAGCAGTTT (SEQ ID NO: 11408) | ORF |
| 1798 | GGACTGTTCAATACCCACTGGAGAT (SEQ ID NO: 11409) | ORF |
| 1967 | CCCAGTTTGTCTCCAGTCAGCCTTT (SEQ ID NO: 11410) | ORF |
| 2016 | CCAGGTCTGGGTCAAGTTTGACATT (SEQ ID NO: 11411) | ORF |

TABLE 4

Human hairless target/siRNA sequences human hairless NM_005144

| Loop: | 475-615 |
|---|---|
| Loop: | 651-752 |
| Loop: | 951-1137 |
| Loop: | 1968-2183 |
| Loop: | 2348-2568 |
| Loop: | 2769-2806 |
| Loop: | 3024-3365 |
| Loop: | 3069-3277 |
| Loop: | 4577-4698 |
| Loop: | 3605-3724 |
| Loop: | 4861-5079 |
| Loop: | 310-436 |
| Loop: | 1953-2248 |
| Loop: | 919-1265 |
| Loop: | 4286-4465 |
| Loop: | 2373-2555 |
| Loop: | 4853-5284 |
| Loop: | 1916-2288 |
| Loop: | 2739-2863 |
| Loop: | 4874-5043 |
| Loop: | 3047-3318 |
| Loop: | 959-1123 |
| Loop: | 4477-4534 |
| Loop: | 871-1302 |
| Loop: | 4325-4459 |
| Loop: | 4913-5029 |
| Loop: | 940-1166 |
| Loop: | 1946-2277 |
| Loop: | 4086-4199 |
| Loop: | 5093-5247 |

TABLE 5

Mouse hairless target/siRNA sequences mouse hairless NM_021877

| Loop: | 318-523 |
|---|---|
| Loop: | 2422-2459 |
| Loop: | 1870-1913 |
| Loop: | 5010-5089 |
| Loop: | 3614-3736 |
| Loop: | 20-23 |
| Loop: | 1048-1390 |
| Loop: | 1122-1304 |
| Loop: | 3434-3550 |
| Loop: | 3257-3337 |
| Loop: | 4272-4504 |
| Loop: | 3009-3024 |
| Loop: | 4879-4967 |
| Loop: | 668-845 |
| Loop: | 4050-4222 |
| Loop: | 1702-1800 |
| Loop: | 3364-3567 |
| Loop: | 1015-1029 |
| Loop: | 4730-4780 |
| Loop: | 1712-1792 |
| Loop: | 4540-4566 |
| Loop: | 4070-4135 |
| Loop: | 1220-1260 |
| Loop: | 3579-3701 |
| Loop: | 445-459 |
| Loop: | 3491-3516 |
| Loop: | 205-238 |
| Loop: | 1691-1926 |
| Loop: | 2320-2337 |
| Loop: | 896-951 |
| Loop: | 2212-2244 |
| Loop: | 5156-5179 |
| Loop: | 2850-3948 |
| Loop: | 1141-1201 |
| Loop: | 2588-2648 |
| Loop: | 403-518 |
| Loop: | 3370-3407 |
| Loop: | 412-510 |
| Loop: | 4517-4594 |
| Loop: | 659-871 |
| Loop: | 1087-1103 |
| Loop: | 1600-1624 |
| Loop: | 4389-4461 |
| Loop: | 3423-3561 |
| Loop: | 713-812 |
| Loop: | 176-302 |
| Loop: | 1073-1336 |
| Loop: | 675-837 |
| Loop: | 4395-4417 |
| Loop: | 1082-1316 |
| Loop: | 4152-4215 |
| Loop: | 2877-2944 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08329667B2). An electronic copy of the "Sequence Listing" will also be available from the USPTO upon request and payment of the fee set forth in 37 CFR 1.19(b)(3).

What is claimed is:

1. A method of removing hair from an area of a human, comprising:
   (A) first synchronizing hair growth cycles for hair follicles in said area, wherein said synchronization is accomplished by:
      (i) twice pulling the hair from said follicles; or
      (ii) administering a follicle growth inducer to said area; and
   (B) subsequently applying to said area a double stranded nucleic acid molecule comprising:
      (i) a sense sequence corresponding to 19-29 contiguous nucleotides of SEQ ID NO: 11412; and
      (ii) an antisense sequence complementary thereto, wherein said double stranded nucleic acid molecule inhibits expression of human hairless protein, whereby hair growth in said area is inhibited.

2. The method of claim 1, wherein inhibition of hair growth in said area persists at least one month.

3. The method of claim 1, wherein said double stranded nucleic acid comprises at least one 3'-overhang.

4. The method of claim 3, wherein said 3'-overhang is a 2- or 3'-base overhang.

5. The method of claim 3, wherein said 3'-overhang comprises at least one deoxynucleotide.

6. The method of claim 1, wherein at least one strand of said double stranded nucleic acid comprises at least one nucleotide analog or internucleotidic linkage different from unmodified RNA.

7. The method of claim 1, wherein said sense sequence comprises SEQ ID NO:11329.

8. The method of claim 1, wherein said sense sequence and said antisense sequence each comprises 19 complementary nucleotides and 1 to 3 non-complementary 3'-nucleotides.

9. The method of claim 1, wherein said sense sequence and said antisense sequence each comprises 20 complementary nucleotides and 1 to 3 non-complementary 3'-nucleotides.

10. The method of claim 1, wherein said sense sequence and said antisense sequence each comprises 21 complementary nucleotides and 1 to 3 non-complementary 3'-nucleotides.

11. The method of claim 1, wherein said sense sequence and said antisense sequence each comprises 22 complementary nucleotides and 1 to 3 non-complementary 3'-nucleotides.

12. The method of claim 1, wherein said sense sequence and said antisense sequence each comprises 23 complementary nucleotides and 1 to 3 non-complementary 3'-nucleotides.

13. The method of claim 1, wherein said sense sequence and said antisense sequence each comprises 24 complementary nucleotides and 1 to 3 non-complementary 3'-nucleotides.

14. The method of claim 1, wherein said sense sequence and said antisense sequence each comprises 25 complementary nucleotides and 1 to 3 non-complementary 3'-nucleotides.

15. The method of claim 1, wherein said sense sequence and said antisense sequence each comprises 26 complementary nucleotides and 1 to 3 non-complementary 3'-nucleotides.

16. The method of claim 1, wherein said sense sequence and said antisense sequence each comprises 27 complementary nucleotides and 1 to 3 non-complementary 3'-nucleotides.

17. The method of claim 1, wherein said sense sequence and said antisense sequence each comprises 28 complementary nucleotides and 1 to 3 non-complementary 3'-nucleotides.

18. A method for removing hair from an area of a mammal, comprising:
   (A) synchronizing hair growth cycles for hair follicles in said area, wherein said synchronization is accomplished by:
      (i) twice pulling the hair from said follicles; or
      (ii) administering a follicle growth inducer to said area; and
   (B) subsequently applying to said area a double stranded nucleic acid molecule comprising:
      (i) a sense sequence corresponding to 19-29 contiguous nucleotides of SEQ ID NO: 11412 and
      (ii) an antisense sequence complementary thereto, wherein said double stranded nucleic acid molecule inhibits hairless mRNA translation.

19. The method of claim 18, wherein said mammal is a human.

20. The method of claim 18, wherein inhibition of hair growth in said area persists at least one month.

21. The method of claim 18, wherein said double stranded nucleic acid comprises at least one 3'-overhang.

22. The method of claim 21 wherein said 3'-overhang is a 2- or 3'-base overhang.

23. The method of claim 22 wherein said 3'-overhang comprises at least one deoxynucleotide.

24. The method of claim 18, wherein at least one strand of said double stranded nucleic acid comprises at least one nucleotide analog or internucleotidic linkage different from unmodified RNA.

25. The method of claim 18, wherein said sense sequence comprises SEQ ID NO:11329.

26. The method of claim 18, wherein said sense sequence and said antisense sequence each comprises 19 complementary nucleotides and 1 to 3 non-complementary 3'-nucleotides.

27. The method of claim 18, wherein said sense sequence and said antisense sequence each comprises 20 complementary nucleotides and 1 to 3 non-complementary 3'-nucleotides.

28. The method of claim 18, wherein said sense sequence and said antisense sequence each comprises 21 complementary nucleotides and 1 to 3 non-complementary 3'-nucleotides.

29. The method of claim 18, wherein said sense sequence and said antisense sequence each comprises 22 complementary nucleotides and 1 to 3 non-complementary 3'-nucleotides.

30. The method of claim 18, wherein said sense sequence and said antisense sequence each comprises 23 complementary nucleotides and 1 to 3 non-complementary 3'-nucleotides.

31. The method of claim 18, wherein said sense sequence and said antisense sequence each comprises 24 complementary nucleotides and 1 to 3 non-complementary 3'-nucleotides.

32. The method of claim 18, wherein said sense sequence and said antisense sequence each comprises 25 complementary nucleotides and 1 to 3 non-complementary 3'-nucleotides.

33. The method of claim 18, wherein said sense sequence and said antisense sequence each comprises 26 complementary nucleotides and 1 to 3 non-complementary 3'-nucleotides.

34. The method of claim 18, wherein said sense sequence and said antisense sequence each comprises 27 complementary nucleotides and 1 to 3 non-complementary 3'-nucleotides.

35. The method of claim 18, wherein said sense sequence and said antisense sequence each comprises 28 complementary nucleotides and 1 to 3 non-complementary 3'-nucleotides.

36. A method of inhibiting expression of hairless protein in an area of a mammal, comprising:
   (A) first synchronizing hair growth cycles for hair follicles in said area, wherein said synchronization is accomplished by:
      (i) twice pulling the hair from said follicles; or
      (ii) administering a follicle growth inducer to said area; and
   (B) subsequently applying to said area a double stranded nucleic acid molecule comprising:
      (i) a sense sequence corresponding to 19-29 contiguous nucleotides of SEQ ID NO: 11412; and
      (ii) an antisense sequence complementary thereto.

37. A method for treating a human desirous of losing hair in an area, comprising:
   (A) first synchronizing hair growth cycles for hair follicles in said area, wherein said synchronization is accomplished by:
      (i) twice pulling the hair from said follicles; or
      (ii) administering a follicle growth inducer to said area; and
   (B) subsequently applying to said area a double stranded nucleic acid molecule comprising:
      (i) a sense sequence corresponding to 19-29 contiguous nucleotides of SEQ ID NO: 11412; and
      (ii) an antisense sequence complementary thereto.

* * * * *